United States Patent [19]
Audia et al.

[11] Patent Number: 5,670,514
[45] Date of Patent: Sep. 23, 1997

[54] COMPOSITIONS FOR INHIBITING BONE LOSS

[75] Inventors: James E. Audia; Blake L. Neubauer, both of Indianapolis, Ind.

[73] Assignee: Eli Lilly and Company, Indianapolis, Ind.

[21] Appl. No.: 625,567

[22] Filed: Mar. 28, 1996

Related U.S. Application Data

[62] Division of Ser. No. 438,420, May 10, 1995, Pat. No. 5,550,134.

[51] Int. Cl.⁶ .................. A61K 31/44; A61K 31/445; A61K 31/40; A61K 31/185
[52] U.S. Cl. .................. 514/298; 514/324; 514/333; 514/422; 514/428; 514/443; 514/578; 514/296
[58] Field of Search .................. 514/298, 324, 514/422, 428, 443, 333, 578, 296

[56] References Cited

U.S. PATENT DOCUMENTS 5,239,075  8/1993  Audia et al. .................. 546/110

OTHER PUBLICATIONS

Anderson, et al., *Proc. Natl. Acad. Sci. USA*, 87:3640 (1990).
Anderson, et al., *Nature*, 354:159–61 (1991).
Matzkin, et al., *Clinical Endocrinol.*, 37:432–436 (1992).

*Primary Examiner*—Theodore J. Criares
*Attorney, Agent, or Firm*—James J. Sales; David E. Boone

[57] ABSTRACT

The present invention provides methods of inhibiting bone loss in mammals via the administration to a mammal in need of such treatment an effective amount of a compound from a series of benzoquinolin-3-ones. Such compounds also are sequentially or concurrently coadministered with a bone antiresorptive agent or a bone anabolic agent.

5 Claims, No Drawings

COMPOSITIONS FOR INHIBITING BONE LOSS

This application is a division, of application Ser. No. 08/438,420 filed May 10, 1995, now U.S. Pat. No. 5,550,134.

The present invention relates to the fields of pharmacology and pharmaceutical chemistry, and provides methods for inhibiting the loss of bone in humans.

The mechanism of bone loss is not well understood, but in practical effect, the disorder arises from an imbalance in the formation of new healthy bone and the resorption of old bone, skewed toward a net loss of bone tissue. This bone loss includes a decrease in both mineral content and protein matrix components of the bone, and leads to an increased fracture rate of, predominantly, femoral bones and bones in the forearm and vertebrae. These fractures, in turn, lead to an increase in general morbidity, a marked loss of stature and mobility, and, in many cases, an increase in mortality resulting from complications.

Bone loss occurs in a wide range of subjects including post-menopausal women, patients who have undergone hysterectomy, patients who are undergoing or have undergone long-term administration of corticosteroids, patients suffering from Cushing's syndrome, and patents having gonadal dysgenesis.

Unchecked, bone loss can lead to osteoporosis, a major debilitating disease whose prominent feature is the loss of bone mass (decreased density and enlargement of bone spaces) without a reduction in bone volume, producing porosity and fragility.

One of the most common types of osteoporosis is found in post-menopausal women affecting an estimated 20 to 25 million women in the United States alone. A significant feature of post-menopausal osteoporosis is the large and rapid loss of bone mass due to the cessation of estrogen production by the ovaries. Indeed, data clearly support the ability of estrogens to limit the progression of osteoporotic bone loss, and estrogen replacement is a recognized treatment for postmenopausal osteoporosis in the United States and many other countries. Although the administration of estrogens have beneficial effects on bone when given even at very low levels, long-term estrogen therapy has been implicated in a variety of disorders such as an increase in the risk of uterine and breast cancer, causing many women to avoid this treatment. Recently suggested therapeutic regimens which seek to lessen the cancer risk, such as administering combinations of progestogen and estrogen, cause the patient to experience regular withdrawal bleeding which is unacceptable to most older women. Concerns over the significant undesirable effects associated with estrogen therapy, and the limited ability of estrogens to reverse existing bone loss, support the need to develop alternative therapy for bone loss that generates the desirable effects on bone but does not cause undesirable effects.

Attempts to fill this need by the use of compounds commonly known as antiestrogens, which interact with the estrogen receptor, have had limited success, perhaps due to the fact that these compounds generally display a mixed agonist/antagonist effect. That is, although these compounds can antagonize estrogen interaction with the receptor, the compounds themselves may cause estrogenic responses in those tissues having estrogen receptors. Therefore, some antiestrogens, when administered alone, are subject to the same adverse effects associated with estrogen therapy.

Accordingly, the present invention provides methods for inhibiting the loss of bone without the associated adverse effects of hormone replacement therapy, and thus, serves an an effective acceptable treatment for osteoporosis. The primary pharmaceutical agents used for the methods of the present invention are known to inhibit the activity of the enzyme 5α-reductase (5AR), such inhibition demonstrating the ability of these agents to inhibit bone loss in humans. The inhibition of bone loss contemplated by the present methods includes both medical therapeutic and/or prophylactic treatment, as appropriate.

For some time, the enzyme 5α-reductase (5AR) has been known to be important in the physiological mechanisms related to testosterone and 5α-dihydrotestosterone. It is known that 5α-dihydrotestosterone is an extremely potent androgen and it has been known or suspected that it is involved in the mechanisms of benign prostatic hyperplasia and male pattern baldness among other disorders and diseases. One 5AR inhibitor, finasteride, is now approved in the United States and other countries for the treatment of benign prostatic hyperplasia.

Recently, it has been found that there are at least two 5AR isozymes in the human, Andersson, et al., *Proc. Natl. Acad. Sci. USA*, 87:3640–44 (1990); Andersson, et al., *Nature*, 354, 159–61 (1991). The isozymes, usually called Type I and Type II, exhibit differences in their biochemical properties, genetics, and pharmacology. Both isozymes are now the subject of considerable research and it has been found that Type I is more prevalent in the scalp, and that Type II is more prevalent in the prostate.

It has been discovered that Type I 5AR is the form of the enzyme which is active in one of the processes which affect the formation/resorption of bone. By inhibiting the enzymatic activity of Type I 5-α-reductase, bone loss is inhibited via a plurality of biological pathways. Thus, it is now possible to provide methods of inhibiting bone loss, particularly in humans via the methods of the present invention.

The present invention, therefore, provides a method for inhibiting bone loss, particularly in humans, via the administration of a 5AR inhibiting compound of formula I below.

Because one of the biological pathways of inhibiting the activity of Type 5AR in bone results in an anabolic response (an increase in the bone-forming protein matrix) it would also be beneficial to coadminister, either concurrently or sequentially, an antiresorption compound. Thus, the present invention also provides a method of inhibiting bone loss via the coadministration of a Type I 5AR inhibiting compound of formula I below and a bone antiresorption pharmaceutical agent.

Furthermore, the inhibition of Type I 5AR results in an increase in available testosterone which is a known precursor to estradiol. Increased indigenous estradiol levels will contribute to the inhibition of bone resorption, but it would be beneficial to coadminister, either concurrently or sequentially, an additional bone anabolic agent such as parathyroid hormone (PTH) or an analog thereof. Thus, the present invention further provides a method of inhibiting bone loss via the coadministration of a Type I 5AR inhibiting compound of formula I below and a bone anabolic agent.

One aspect of the present invention provides a method for inhibiting bone loss comprising administering to a mammal in need of treatment an effective amount of a compound of formula I

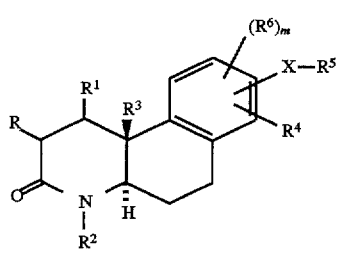

wherein
- R and $R^1$ both represent hydrogen or combine to form a bond;
- $R^2$ represents hydrogen or $C_1-C_3$ alkyl;
- $R^3$ represents hydrogen, methyl or ethyl; either $R^4$ and X—$R^5$ have the following definitions, $(R^6)_m$ is absent, and $R^3$ does not represent hydrogen; or $(R^6)_m$ has the following definition, $R^4$ and X—$R^5$ are absent, and $R^3$ does not represent ethyl;
- $R^4$ and —X—$R^5$ each occupies one of the 7-, 8- and 9-positions;
- $R^4$ represents hydrogen, halo, methyl or ethyl;
- X represents $C_1-C_4$ alkyl, $C_2-C_4$ alkenyl, $C_2-C_4$ alkynyl, a bond, —SO—, —SO$_2$—, —CO—Y—(CH$_2$)$_n$—, —Y—CO—(CH$_2$)$_n$, —CO—, —Z—(CH$_2$)$_n$—, or —SO$_3$—; wherein X groups which are not symmetrical may be in either orientation;
- y represents —S—, —O—, or —NH—;
- Z represents —O— or —S—;
- n represents 0–3;
- $R^5$ represents phenyl, naphthalenyl, pyridinyl, pyrazinyl, pyridazinyl, pyrimidinyl, anthracenyl, acenaphthalenyl, thiazolyl, benzimidazolyl, indazolyl, thiophenyl, phenanthrenyl, quinolinyl, fluorenyl, isoquinolinyl, indanyl, benzopyranyl, indolyl, benzisoquinolinyl, benzindolyl, benzothiazolyl, benzothiophenyl, quinoxalinyl, benzoxazolyl, tetrazolyl, naphthothiazolyl, quinazolinyl, thiazolopyridinyl, pyridazinoquinazolinyl, benzisothiazolyl, benzodioxolyl, benzodioxinyl, diphenylmethyl or triphenylmethyl;
- the above $R^5$ groups are unsubstituted or substituted with 1–3 groups chosen from the group consisting of halo, trifluoromethyl, trifluoroethoxy, $C_1-C_4$ alkyl, trifluoromethoxy, hydroxy, $C_1-C_3$ alkoxy, nitro, $C_1-C_3$ alkylthio, $C_1-C_6$ alkanoyl, phenyl, oxo, phenoxy, phenylthio, $C_1-C_3$ alkylsulfinyl, $C_1-C_3$ alkylsulfonyl, cyano, amino, $C_1-C_3$ alkylamino, diphenylmethylamino, triphenylmethylamino, benzyloxy, benzylthio, (mono-halo, nitro or CF$_3$) benzyl(oxy or thio), di($_1$-C$_3$ alkyl, $C_3-C_6$ cycloalkyl, or $C_4-C_8$ cycloalkylalkyl)amino, (mono-$C_1-C_3$ alkyl, $C_1-C_3$ alkoxy or halo)-(phenyl, phenoxy, phenylthio, phenylsulfonyl or phenoxysulfonyl), $C_2-C_6$ alkanoylamino, benzoylamino, diphenylmethylamino ($C_1-C_3$ alkyl), aminocarbonyl, $C_1-C_3$ alkylaminocarbonyl, di($C_1-C_3$ alkyl)aminocarbonyl, halo-$C_1-C_6$ alkanoyl, aminosulfonyl, $C_1-C_3$ alkylaminosulfonyl, di($C_1-C_3$ alkyl)aminosulfonyl, phenyl(oxy or thio)($C_1-C_3$ alkyl), (halo, $C_1-C_3$ alkyl or $C_1-C_3$ alkoxy)phenyl(oxy or thio)($C_1-C_3$ alkyl), benzoyl, or (amino, $C_1-C_3$ alkylamino or di($C_1-C_3$ alkyl)amino)($C_1-C_3$ alkyl);
- or an above $R^5$ group is substituted with a morpholino ($C_1-C_3$ alkyl) group, a phenyl($C_1-C_3$ alkyl)piperidinyl group, a phenyl($C_1-C_3$ alkyl)-piperidinylaminocarbonyl group, a $C_2-C_6$ alkanoylaminothiophenyl group, or a (amino, $C_1-C_3$ alkylamino or di($C_1-C_3$ alkyl)amino) naphthalenylsulfonylamino group;
- or $R^5$ is a perhalophenyl group;
- m represents 1–2;
- $R^6$ represents hydrogen, halogen, NO$_2$, cyano, CF$_3$, $C_1-C_3$ alkyl, $C_1-C_6$ alkoxy, carboxy, $C_1-C_6$ alkoxycarbonyl, amino, $C_1-C_4$ alkylamino, $C_1-C_4$ dialkylamino, amido, $C_1-C_4$ alkylamido, $C_1-C_4$ dialkylamido, mercapto, $C_1-C_6$ alkylthio, $C_1-C_6$ alkylsulfinyl, $C_1-C_6$ alkylsulfonyl, or a group —A—$R^7$ where A represents $C_1-C_6$ alkylene, $C_2-C_6$ alkenylene or $C_2-C_6$ alkynylene; and $R^7$ represents halogen, hydroxy, CF$_3$, $C_1-C_6$ alkoxy, carboxy, $C_1-C_6$ alkoxycarbonyl, amino, $C_1-C_4$ alkylamino, $C_1-C_4$ dialkylamino, amido, $C_1-C_4$ alkylamido, $C_1-C_4$ dialkylamido, $C_1-C_4$ alkylsulfonylamino, aminosulfonyl or $C_1-C_4$ alkylaminosulfonyl;

or a pharmaceutically acceptable salt thereof.

Another aspect of the present invention provides the above-described method, and further comprises the coadministration of an antiresorptive agent and/or an anabolic agent.

Throughout the present document, all temperatures will be described in degrees Celsius and all expressions of concentration, percentage and proportion will be expressed in weight units, except for mixtures of solvents, which will be described in volume units, unless otherwise stated.

References to compounds of formula I in this document include the pharmaceutically acceptable salts of such compounds, unless otherwise stated.

The Compounds

The compounds of Formula I wherein X—$R^5$ and $R^4$ are absent, and $(R^6)_m$ represents certain groups, and compound A as well, have been disclosed in U.S. Pat. No. 5,239,075 and European Patent Office Publication 0532100. That U.S. patent is herein incorporated by reference and the reader should refer to it for the description, synthesis and biological activities of that group of compounds.

The compounds wherein $(R^6)_m$ is absent and X—$R^5$ and $R^4$ are as described above, have not previously been published, and so that group of compounds will be described in full.

The various positions on the benzo[f]quinoline ring are indicated below.

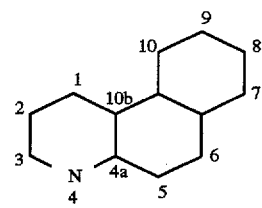

The spatial configuration of the group $R^3$ at 10b and the hydrogen atom at 4a are required, and the synthetic methods for obtaining that configuration will be shown. The reader will understand that most of the compounds can exist in two stereochemical forms, or even more depending on the nature of the $R^5$ group, and that all stereochemical forms are included in the present invention. In some of the compounds prepared or described below, single enantiomers are prepared in pure form and are identified by (+) or (−) nomenclature. In other cases, the mixture of enantiomers is prepared.

(Compounds where $R^4$ and $X—R^5$ are absent)

These compounds, as well as compound A, are well disclosed in U.S. Pat. No. 5,239,075, and so only some discussion of the compounds which are particularly preferred for the present methods is necessary here.

A preferred group of such compounds includes those of formula I wherein:

R and $R^1$ are hydrogen;

$R^6$ is halogen, $CF_3$, $C_1$–$C_6$ alkyl, $C_1$–$C_4$ alkoxy or —A—$R^7$ where A is $C_1$–$C_4$ alkylene and $R^7$ is $C_1$–$C_4$ alkoxy-carbonyl.

A more preferable group of such compounds includes those wherein:

$R^2$ is hydrogen or methyl;

R and $R^1$ are hydrogen;

$R^6$ is halogen, $CF_3$ or $C_1$–$C_4$ alkyl.

Particularly preferred such compounds are as follows:

(−)-(4aR)-(10bR)-8-chloro-4-methyl-1,2,3,4,4a,5,6,10b-octahydrobenzo[f]quinolin-3-one (+)-(4aR)-(10bR)-8-chloro-4,10b-dimethyl-1,2,3,4,4a,5,6,10b-octahydrobenzo[f]quinolin-3-one 8-chloro-4,10b-dimethyl-1,2,3,4,4a,5,6,10b-octahydrobenzo[f]quinolin-3-one (+)-(4aR)-(10bR)-8,9-dichloro-4,10b-dimethyl-1,2,3,4,4a,5,6,10b-octahydrobenzo[f]quinolin-3-one (Compounds where $(R^6)_m$ is absent)

The groups $R^4$ and $X—R^5$ may occupy either the 7, 8, or 9-position.

The term "halo" includes chloro, bromo and fluoro.

The various alkyl groups, such as $C_1$–$C_3$ alkyl, $C_1$–$C_4$ alkyl and the like include groups such as methyl, ethyl, propyl, isopropyl, t-butyl, butyl and isobutyl. When such groups link other portions of a molecule, they are bivalent and the location of the linkages will be indicated in the chemical name.

Alkenyl and alkynyl groups constitute linking groups which are bivalent and are bonded to two other groups. For example, $C_2$–$C_4$ alkenyl includes 2-propenyl, 3-butenyl and 2-butenyl; and $C_2$–$C_4$ alkynyl includes, for example, ethynyl, 2-propynyl, 2-butynyl and iso-2-butynyl.

The groups $C_1$–$C_6$ alkanoyl and $C_2$–$C_6$ alkanoyl include such groups as formyl, acetyl, propionyl, isobutyryl, 2-ethylpropionyl and hexanoyl. The group $C_3$–$C_6$ cycloalkyl includes cyclopropyl, cyclobutyl, cyclopentyl and cyclohexyl, and the group $C_4$–$C_8$ cycloalkylalkyl includes, for example, cyclopropylmethyl, cyclohexylethyl, cyclobutylbutyl and cyclohexylmethyl.

Terms such as $C_1$–$C_3$ alkoxy, $C_1$–$C_3$ alkylsulfonyl, benzylthio, phenoxy, and $C_1$–$C_3$ alkylamino refer to the indicated alkyl, benzyl or the like group linked to an oxygen atom, sulfur atom, sulfonyl group or amino group as indicated.

Terms such as halo-$C_1$–$C_6$ alkanoyl, halophenyl or $C_1$–$C_3$ alkylphenyl refer so the indicated basic group having substituted on it 1, 2, or 3 halo or $C_1$–$C_3$ alkyl groups as may be described in the individual case.

The term perhalophenyl refers to a phenyl group which is fully substituted at all available positions with halogen atoms.

The compounds of formula I all have the benzo[f] quinoline nucleus, on the phenyl ring of which is substituted a cyclic group, frequently an arylcyclic group, which is linked to the benzoquinoline through the X linker, which in many cases is simply a bond. The $R^5$ groups may be substituted with additional organic groups, and may bear as many as three of the indicated substituent groups. Multiple substituents may all be the same, as, for example, 2,3,5-trifluorophenyl, or may be different, such as, for example, 3,5-bis(t-butyl)-4-hydroxyphenyl. The specifically named compounds which appear below in this document will further illustrate the contemplated X, $R^5$ and substituent groups.

The X groups which are not symmetrical may be in either orientation on the molecule; for example, the atom Z of the group —Z—$(CH_2)_n$— may be adjacent either to $R^5$ or to the phenyl ring of the nucleus of formula I.

The cyclic $R^5$ groups may take any permissible orientation. For example, the following specific $R^5$ groups are contemplated.

phenyl
2-quinolinyl
4-quinolinyl
7-quinolinyl
1-isoquinolinyl
3-isoquinolinyl
8-isoquinolinyl
2-quinoxalinyl
5-quinoxalinyl
7-quinoxalinyl
2-benzothiazolyl
4-benzothiazolyl
6-benzothiazolyl
7-1H-indazolyl
3-1H-indazolyl
5-2H-indazolyl
2-2H-indazolyl
7-2H-indazolyl
4-3H-indazolyl
3-3H-indazolyl
1-indolyl
3-indolyl
3-2H-indolyl
2-3H-indolyl
6-2H-indolyl
4-3H-indolyl
2-benzoxazolyl
5-benzoxazolyl
3-1,2-benzisothiazolyl
5-1,2-benzisothiazolyl
7-2,1-benzisothiazolyl
4-2,1-benzisothiazolyl
2-pyridinyl
4-pyridinyl
3-pyridazinyl
5-pyridazinyl
2-pyrazinyl
5-pyrazinyl
2-naphtho[2,3-d]thiazolyl
8-naphtho[2,3-d]thiazolyl
6-naphtho[2,3-d]thiazolyl
1-naphtho[2,1-d]thiazolyl
5-naphtho[2,1-d]thiazolyl 2-naphtho[1,2-d]thiazolyl
6-naphtho[1,2-d]thiazolyl
1-naphthalenyl
2-naphthalenyl
2-thienyl
3-thienyl
1-anthracenyl
10-anthracenyl
6-anthracenyl
1-phenanthrenyl
4-phenanthrenyl
9-phenanthrenyl
1-3H-fluorenyl
3-3H-fluorenyl
9-3H-fluorenyl
1-fluorenyl
5-fluorenyl
1-acenaphthalenyl
5-acenaphthalenyl
diphenylmethyl
triphenylmethyl
2-thiazolyl
4-thiazolyl
2-benzimidazolyl
6-benzimidazolyl
1-indanyl
4-indanyl
3-2H-1-benzopyranyl
7-2H-1-benzopyranyl
2-chromanyl
5-chromanyl
4-4H-1-benzopyranyl
8-4H-1-benzopyranyl
3-5H-1-benzopyranyl
5-5H-1-benzopyranyl
1-benz[g]isoquinolinyl
5-benz[g]isoquinolinyl
8-benz[g]isoquinolinyl
4-benz[h]isoquinolinyl
10-benz[h]isoquinolinyl
2-benz[f]isoquinolinyl
6-benz[f]isoquinolinyl
3-1H-benz[de]isoquinolinyl
9-1H-benz[de]isoquinolinyl
4-4H-benz[de]isoquinolinyl
6-4H-benz[de]isoquinolinyl
1-1H-benz[t]indolyl
4-1H-benz[f]indolyl
2-3H-benz[f]indolyl
7-3H-benz[f]indolyl
2-pyrimidinyl
5-pyrimidinyl
1-3H-carbazolyl
5-3H-carbazolyl
3-4aH-carbazolyl
4a-4aH-carbazolyl
2-8aH-carbazolyl
7-8aH-carbazolyl
8-carbazolyl
4-carbazolyl
2-1H-benz[g]indolyl
6-1H-benz[g]indolyl
3-3H-benz[g]indolyl
9-3H-benz[g]indolyl
1-1H-benz[e]indolyl
5-1H-benz[e]indolyl
3-3H-benz[e]indolyl
7-3H-benz[e]indolyl
2-benz[cd]indolyl
5-benz[cd]indolyl
2-1-benzothiophenyl
5-1-benzothiophenyl
1-2-benzothiophenyl
7-2-benzothiophenyl
5-1H-tetrazolyl
1-1H-tetrazolyl
5-2H-tetrazolyl
2-quinazolinyl
6-quinazolinyl
2-thiazolo[4,5-b]pyridinyl
6-thiazolo[4,5-b]pyridinyl
7-thiazolo[5,4-b]pyridinyl
4-thiazolo[4,5-c]pyridinyl
6-thiazolo[4,5-c]pyridinyl
3-5H-thiazolo[3,2-a]pyridinyl
8-5H-thiazolo[3,2-a]pyridinyl
2-7H-thiazolo[3,2-a]pyridinyl
7-7H-thiazolo[3,2-a]pyridinyl
3-3H-thiazolo[3,4-a]pyridinyl
5-3H-thiazolo[3,4-a]pyridinyl
10-10H-pyridazino[3,2-b]quinazolinyl
4-10H-pyridazino[3,2-b]quinazolinyl
8-10H-pyridazino[3,2-b]quinazolinyl
3-3H-1,2-benzodioxolyl
5-3H-1,2-benzodioxolyl
2-1,3-benzodioxolyl
7-1,2-benzodioxolyl
2-1,4-benzodioxinyl
6-1,4-benzodioxinyl Linking X groups, besides the alkyl, alkenyl and alkynyl groups, include the following, for example. The groups are named as they appear in the generic formula, but it will be understood that the groups may, in fact, be oriented in either direction.

acetylthio
sulfinyl
sulfonyl
oxycarbonyl
propoxycarbonyl
methylthiocarbonyl
butyrylamino
propionyloxy
ethylaminocarbonyl carbonyl
oxy
thio
methoxy
propylthio
a bond
oxysulfonyl The cyclic R⁵ groups may be substituted with a variety of substituent groups, as set out in general in formula I. To assure that the reader fully understands the nature of those substituent groups, a representative group of them will be named as follows:

chloro
bromo
fluoro
trifluoromethyl
methyl
isopropyl
s-butyl
trifluoromethoxy
hydroxy
methoxy
isopropoxy
nitro
methylthio
ethylthio
formyl
acetyl
propionyl
pentanoyl
2,2-dimethylbutyryl
phenyl
oxo
phenoxy
phenylthio
methylsulfinyl
propylsulfinyl
ethylsulfonyl
isopropylsulfonyl
cyano
amine
methylamino
propylamino
diphenylmethylamino
triphenylmethylamino
benzyloxy
benzylthio
3-chlorobenzyloxy
4-fluorobenzylthio
2-nitrobenzyloxy
3-trifluoromethylbenzylthio
dimethylamino
diethylamino
di(isopropyl)amino
bis(cyclopropyl)amino
bis(cyclohexyl)amino
methyl(cyclohexyl)amine
bis(cyclohexylmethyl)amine
propyl(cyclopentylethyl)amino
cyclopentyl(cyclopropylpropyl)amino
3-methylphenyl
2-propylphenoxy
4-ethylphenylthio
3-isopropylphenylsulfonyl
4-methoxyphenyl
2-ethoxyphenoxysulfonyl
3-ethoxyphenylthio
4-chlorophenyl
4-bromophenylthio
3-fluorophenoxysulfonyl
acetylamino
propionylamino
pentanoylamino
2-ethylpropionylamino
benzoylamino
diphenylmethylaminomethyl
3-(diphenylmethylamino)propyl
aminocarbonyl
methylaminocarbonyl
isopropylaminocarbonyl
dimethylaminocarbonyl
ethyl(isopropyl)aminocarbonyl
chloroacetyl
3-bromopropionyl
4,4,4-trifluorobutyryl
3-chloro-2-methylbutyryl
3,4-dichlorohexanoyl
aminosulfonyl
methylaminosulfonyl
isopropylaminosulfonyl
diethylaminosulfonyl
methyl(propyl)aminosulfonyl
phenoxymethyl
2-phenylthioethyl
2-phenoxypropyl
3-chlorophenylthiomethyl
2-(3,4-difluorophenoxy)ethyl
2-(2-methoxy-4-propylphenoxy)ethyl
3-(3,5-diethoxyphenoxy)propyl
3-(4-chloro-3-ethoxyphenylthio)propyl
2,6-dichloro-4-propylphenylthiomethyl
benzoyl
aminomethyl
2-aminoisopropyl
methylaminomethyl
2-ethylaminoethyl
3-(ethylamino)propyl
dimethylaminomethyl
ethyl(isopropyl)aminomethyl
3-(ethyl(propyl)amino)propyl
morpholinylmethyl
2-morpholinylpropyl
3-phenylmethyl-1-piperidinyl 4-(2-phenylpropyl)-1-piperidinyl
2-phenylmethyl-1-piperidinylaminocarbonyl
4-(3-phenylpropyl)-1-piperidinylaminocarbonyl
3-acetylamino-5-thiophenyl
2-hexanoylamino-4-thiophenyl
3-butyrylamino-4-thiophenyl
8-amino-2-naphthalenylsulfonylamino
2-methylamino-1-naphthalenylsulfonylamino
5-isopropylamino-2-naphthalenylsulfonylamino
4-dimethylamino-2-naphthalenylsulfonylamino
3-methyl(propyl)amino-1-naphthalenylsulfonylamino
perfluorophenyl
perbromophenyl While all of the compounds described by formula I are important in the concept of the present invention, certain groups of those compounds constitute preferred aspects of the invention. The following table sets out a number of such preferred groups of the compounds wherein $(R^6)_m$ is absent, the use of each of which constitutes a preferred aspect of the invention. It will be understood that the reader can combine groups of preferred aspects listed in the following table to produce additional more limited or more comprehensive preferred aspects.

a) R and $R^1$ both represent hydrogen;
b) $R^3$ represents methyl;
c) $R^2$ represents $C_1$–$C_3$ alkyl;
d) $R^2$ represents $C_1$–$C_2$ alkyl;
e) $R^2$ represents methyl;
f) $R^2$ represents methyl or hydrogen;
g) $R^4$ represents hydrogen;
h) $R^4$ represents hydrogen, halo or methyl;
i) X represents alkyl, alkenyl or alkynyl;
j) X represents a bond;
k) X represents a bond or a sulfur atom;
l) X represents —SO—, —SO$_2$—, or —SO$_3$—;
m) X represents —CO— or —CO—Y—(CH$_2$)$_n$—;
n) X represents —Z—(CH$_2$)$_n$—, alkyl or —CO—;
o) X represents a bond, —Z—(CH$_2$)$_n$—, alkyl or —CO—;
p) X represents a sulfur atom;
q) Y represents —O— or —S—;
r) Y represents —NH—;
s) n represents 0 or 1;
t) n represents 2 or 3;
u) n represents 0;
v) Z represents —S—;
w) $R^5$ represents phenyl or naphthalenyl;
x) $R^5$ represents pyridinyl, pyrazinyl, pyridazinyl or pyrimidinyl;
y) $R^5$ represents anthracenyl, phenanthrenyl, fluorenyl or acenaphthalenyl;
z) $R^5$ represents thiazolyl, thiophenyl or tetrazolyl;
aa) $R^5$ represents benzimidazolyl, indanyl, indolyl or indazolyl;
ab) $R^5$ represents quinolinyl, isoquinolinyl, quinoxalinyl or quinazolinyl;
ac) $R^5$ represents benzopyranyl, benzothiazolyl, benzothiophenyl or benzisothiazolyl;
ad) $R^5$ represents benzothiazolyl;
ae) $R^5$ represents benzoxazolyl, benzodioxolyl, or benzodioxinyl;
af) $R^5$ represents benzisoquinolyl, benzindolyl, naphthothiazolyl, thiazolopyridinyl or pyridazinoquinazolinyl;
ag) $R^5$ represents diphenylmethyl or triphenylmethyl.

Further preferred classes of compounds are also important in the practice of the present invention. A particularly preferred class of compounds includes those wherein $R^2$ represents methyl or hydrogen, particularly methyl; X represents a bond, a methylthio group, a sulfur atom, or an ethyl or ethenyl group, particularly a bond or a sulfur atom; $R^5$ represents phenyl, naphthalenyl, isoquinolinyl, indolyl, benzothiazolyl, pyridinyl, indazolyl, thiazolonaphthalenyl, quinolinyl or diphenylmethyl; and the $R^5$ group is unsubstituted or substituted with 1–3, particularly 1, groups chosen from the group consisting of halo, trifluoromethoxy, trifluoroethoxy, trifluoromethyl, $C_1$–$C_3$ alkyl, methoxy, nitro, phenyl, toluenesulfonyl, and pivaloylamino.

A further preferred class of compounds of the present invention includes those described in the paragraph immediately above, and, in addition, those wherein X represents propyl, aminocarbonylmethyl, methoxycarbonyl and oxycarbonyl; $R^5$ represents thiophenyl, fluorenyl, indanyl, quinoxalinyl, pyridazinyl, thiazolopyridinyl, and benzisoquinolinyl; and the $R^5$ group is unsubstituted or substituted with 1–3, particularly 1, groups chosen from the group consisting of hydroxy, $C_1$–$C_4$ alkyl, oxo, benzyloxy, phenoxymethyl and benzylpiperidinyl.

As described in formula I, the invention includes pharmaceutically acceptable salts of the compounds defined by the above formula. Although generally neutral, a particular compound of this invention can possess a sufficiently acidic, a sufficiently basic, or both functional groups, and accordingly react with any of a number of nontoxic inorganic bases, and nontoxic inorganic and organic acids, to form a pharmaceutically acceptable salt. Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from nontoxic inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate. The potassium and sodium salt forms are particularly preferred.

Thus, the groups $R^4$ and $X-R^5$ include a numbers of substitutions each of which may be placed at the 7, 8 or 9-position of the nucleus of formula I. All such substituents are easily understandable by the chemist, but a number of the contemplated substituent arrangements will be mentioned for the convenience of the reader.

8-(6-phenoxysulfonyl-4-quinolinyloxy)

7-chloro-8-(3-chloromethyl-7-quinolinylthio)

7-[2-(3-phenoxy-6-isoquinolinylaminocarbonyl)ethyl]

9-fluoro-7-(1-methoxycarbonyl-4-isoquino-linylmethyl)

8-[3-(5-bromo-t-butyl-3-quinoxalinyl)propyl]

8-fluoro-7-[3-(8-butylthio-2-quinoxalinyl )-3-propynyl]

7-(3-phenyl-1,2-benzisothiazol-5-yloxycarbonyl)

8-bromo-9-(5-hexyloxysulfonylbenzoxazol-2-ylthio)

9-methyl-7-(6-trifluoromethyl-2,1-benzisothiazol-3-yl)

7-(3-isopropoxycarbonylaminopyridinyl-2-ylmethyl)

9-chloro-8-(7-hydroxy-4-benzothiazolylthio)

7-(4-isopentoxycarbonyl-1H-indazol-4-yloxy)

7-ethyl-9-[3-(6-[2-ethyl-5-methylphenoxysulfonyl]-1H-indazol-3-yl)-2 -propynyl]

9-[2-(6-ethoxycarbonyl-2H-indazol-2-yloxy)ethyl]

8-[2-(3-fluoro-2H-indazol-6-yl)ethoxy]

8-chloro-7-(3-trifluoromethoxy-3H-indazol-4-ylthiocarbonylmethyl)

7-[2-(5-propoxy-4-[4-fluorophenoxy]-3H-indazol-7-ylthio)ethyl]

8-ethyl-7-[4-(4-[3-chlorophenoxysulfonyl]-2-indolyl)butyl]

8-[3-(7-methoxy-4-[2,3-dichloropropoxycarbonylamino] 2-indolyloxy]propyl

7-[2-(5-[4-fluoro-3-methylphenoxysulfonyl]-2H-indol-4-yl)ethylcarbonylthio]

8-methyl-7-[3-(6-chloro-2-[3-chloro-5-ethylphenoxyethyl]-2H-indole-3-yl)-2-butynyl]

Synthesis

The synthesis of the compounds wherein $R^4$ and $X-R^5$ are absent is clearly explained with numerous examples in U.S. Pat. No. 5,239,075, and the reader is referred thereto.

Synthesis of the compounds of formula I wherein $(R^6)_m$ is absent may proceed in various ways, depending in large part on the identity of the group $-X-R^5$. It is very often advantageous to form the benzo[f]quinoline nucleus without the $-X-R^5$ group, and to add that group in a separate step, thus providing a convergent synthesis. In such a case, the $-X-R^5$ group of the compound of formula I is replaced by a leaving group, preferably a bromine atom, when the benzo[f]quinoline nucleus is prepared. Since the $R^4$ group of the nucleus is small, it may be in place throughout the synthesis. Thus, an important intermediate is the following compound of formula II.

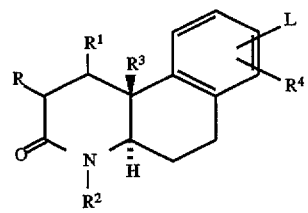

wherein L represents a leaving group, preferably bromo.

Synthesis of Nucleus

A series of synthetic methods for the preparation of intermediates of formula II was taught by Audia et al. in U.S. Pat. No. 5,239,075, issued Aug. 24, 1993. That patent is incorporated by reference herein, and the reader readily will understand the synthetic methods taught by it.

A preferred method for preparing the intermediates of formula II wherein $(R^6)_m$ is absent is the heteroannulation carried out by reacting an enamine of the formula

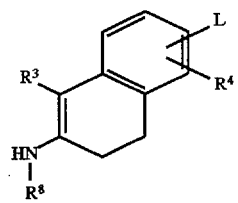

with an activated acrylate, particularly acryloyl chloride, acrylic anhydride, or acryloyl toluenesulfonate or methanesulfonate. The group $R^8$ in the above intermediate is a chiral directing group, in order to obtain the correct enantiomer of the intermediate of formula II. The most preferred $R^8$ group is (R)-(+)-1-phenylethyl. This process is taught in general by EPO Publication 0564193.

The product of the heteroannulation just described is of the formula

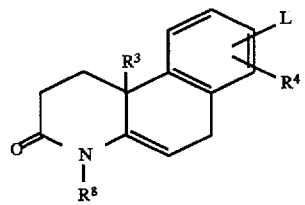

and the double bond at the 4a,5-position must be reduced in a second step. The reduction is readily carried out under mild conditions with chemical reducing agents such as borohydrides. Cyanoborohydride is preferred; the reduction may be carried out, for example, in formic acid under ambient conditions. More conveniently, the reduction step may be combined with the removal of the $R^8$ group, by reaction with trifluoroacetic acid in a reaction medium containing or consisting of triethylsilane at reduced temperature in the range of from about −40° to 0°.

The above heteroannulation is carried out under mild process conditions. In most instances it will be found that excellent yields are obtained in short periods of time at temperatures in the range of ambient. For example, temperatures from about 0° to about 150° are used, and reaction times in the range from a few minutes to a few hours are sufficient. Preferable reaction temperatures are in the range from about −20° to about ambient temperature, and most preferably the reactants are combined at very low temperatures in the range of −20° to −80°, and the reaction mixture is allowed to warm slowly to ambient temperature while the reaction occurs. The reaction mixture may be a biphasic mixture of a convenient organic solvent and an aqueous solution of a mild base. For example, solvents may include haloalkanes, ethers, including tetrahydrofuran, and nitriles including acetonitrile. Preferred mild bases are alkali metal carbonates and bicarbonates; more highly basic reagents, such as alkali and alkaline earth metal hydroxides and the like may be used, but the bicarbonates are usually preferred.

One-Pot Nucleus Process

A particularly preferred method of synthesis of a key intermediate of formula II proceeds according to the following scheme.

An intermediate of the formula

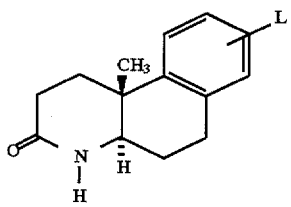

V wherein L is bromo, and is located at the 7-, 8- or 9-position is prepared by reacting a compound of the formula

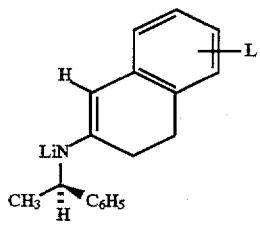

VI with methyl iodide in an ether solvent to prepare a compound of the formula

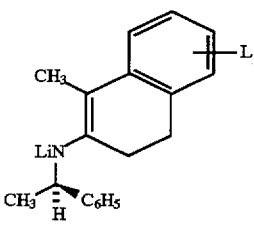

VII combining acrylic anhydride or acryloyl chloride with the reaction mixture comprising the compound of formula VII to prepare a compound of the formula

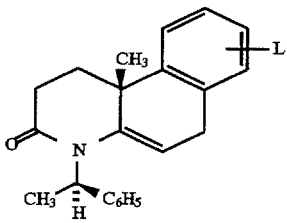

VIII quenching the reaction with sodium bicarbonate, evaporating the organic solution comprising the compound of formula VIII; and combining the residue comprising the compound of formula VIII with a trialkylsilane and trifluoroacetic acid in the absence of a solvent to prepare the compound of formula V.

The starting material of formula VI is prepared most conveniently by a modification of a process shown in European Patent Publication 0564193. A substituted 2-tetralone, having the desired L substituent on the unsaturated ring, is reacted with (R)-(+)-phenethylamine to prepare the intermediate of the formula

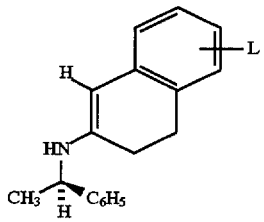

The reaction is conveniently carried out at elevated temperature, particularly the reflux temperature, in toluene in the presence of a strong acid such as p-toluenesulfonic acid. Water must be removed as it is formed in this reaction, and the absence of water being formed is an indication of completion of the reaction. A slight excess of phenethylamine, such as about 1.05–1.10 equivalents, should be used. Alternatively, tetrahydrofuran (THF) may be used as the solvent, and it is particularly convenient in that case to use molecular sieves to dehydrate the reaction mixture, using at least twice the weight of molecular sieves compared to the amount of water which will be released by the process.

The above phenethylamino compound is lithiated to prepare the starting material of formula VI. The reaction may be carried out with, for example, n-butyllithium or with lithium diisopropylamide (LDA). When the reaction is carried out, as is preferred, with LDA, the best results are obtained if the LDA is freshly generated from diisopropylamine and n-butyllithium immediately before use in the process. A substantial excess, about 15–25%, of LDA should be used for best results.

The LDA reaction is best carried out in THF at a low temperature in the range of about −100° to about 0°, preferably about −78° to about −10°. The phenethylamino compound need not be purified or isolated, but the first reaction mixture should be evaporated under vacuum and the residue taken up in THF. It is preferred to add the phenethylamino material, in solution, to a solution of LDA in cold tetrahydrofuran; the opposite manner of addition is operable but provides lower yields. The reaction may be carried out in quite short periods of time, less than one hour in general.

The lithio compound of formula VI is difficult to isolate and purify, and so it should be introduced into the process as a solution in the lithiation reaction mixture.

In the first step of the present process, the lithio compound of formula VI is reacted with methyl iodide to provide the compound of formula VII. It is advisable to use about 15–25% of excess methyl iodide, and to carry out the process in an ester solvent, such as diethyl ether, methyl butyl ether or, preferably, THF. The reaction is very rapid at low temperatures in the range of about −100° to about −50°, most preferably, about −80° to about −60°. Reaction times in the range of from about a few minutes to about one hour are adequate, and a 20-minute reaction time is often preferred.

If the compound of formula VI is in the form of the reaction mixture from lithiation with LDA, and the reaction mixture therefore contains the residual diisopropylamine, that amine must be neutralized before further reaction of the compound of formula VII. Most conveniently, the methyl iodide mixture is allowed to warm to a temperature close to 0°, and a sufficient amount of methanesulfonic acid is added to neutralize the diisopropylamine. Other strong acids may be used, but methanesulfonic acid is particularly convenient because the resulting methanesulfonate salt of diisopropylamine is only slightly soluble and therefore may be easily removed by simple filtration or centrifugation.

The reaction mixture comprising the compound of formula VII is combined with acrylic anhydride or acryloyl chloride to initiate the aza-annulation reaction which forms the compound of formula VIII. It is best to generate the acrylic anhydride, the preferred reagent, immediately before use by the reaction of acryloyl chloride and acrylic acid, using triethylamine and a stabilizer, such as hydroquinone and butylated hydroxytoluene, in THF.

The aza-annulation is best carried out by adding the acrylic anhydride or acryloyl chloride at a very low temperature, such as from about −100° to about −70°, and allowing the mixture to warm very slowly with stirring to a temperature in the range of about −20° to about 0°, or even up to about 10°–20°. A period of 12–15 hours is not too much for that period of time. When the reaction has gone as far toward completion as is desired, the reaction is quenched by addition of sodium bicarbonate. It is preferred to use from about 1.5 to about 4 equivalents of base, most preferably about 2 equivalents. The base may be added as a solution, for example, in water or in an aqueous solvent such as water/dimethylaminopyridine, but it is preferred to add the base in solid form. The reaction mixture is stirred with the quenching base for a brief period, and then the mixture is filtered, the volatiles are removed, and the solvent may be replaced with an ether solvent, preferably diethyl ether, and the organic solution may then be worked up by washing with aqueous base and aqueous acid, and perhaps with additional purification steps such as a wash with a saturated salt solution. If such work up steps are used, the solution is then dehydrated and evaporated under vacuum to obtain the non-volatile portions of the reaction mixture, containing the final intermediate of formula VIII. On the other hand, the residue from the quenched reaction mixture may be carried on without work up if desired.

The residue from the aza-annulation step is cooled, and a chilled mixture of a trialkylsilane and trifluoroacetic acid is added. The addition should take place at a low temperature in the range of from about −40° to about 0°, and no other solvent is used. A large quantity of trifluoroacetic acid, in the range of about 10–50 equivalents, most preferably about 20–30 equivalents is used. The preferred trialkylsilane is triethylsilane, although trimethylsilane, tripropylsilane and the like may also be used. A substantial excess of trialkylsilane, in the range of about 5–20 equivalents, most preferably about 7–15 equivalents is used. The mixture is stirred for about 10–20 hours while it is allowed to warm slowly to about 30°, and then the mixture is slowly heated to an elevated temperature, preferably the reflux temperature, and is stirred at that temperature for a few hours, such as about 2–6 hours to complete the formation of the compound of formula V.

The residue containing the intermediate of formula V is dissolved, preferably in a haloalkane such as dichloromethane, washed with base, such as aqueous sodium bicarbonate, and concentrated under vacuum. The residue is thoroughly washed with, for example, an ether solvent which may often preferably be diethyl ether to obtain the purified desired compound of formula V.

Further details of the process will be shown below as Preparations.

It will be understood that the principles of the above process may be applied to compounds of the present invention other than the specific intermediates shown. So long as the $R^4$ and X—$R^5$ substituents, or the $(R^6)_m$ substituents, of the compound to be prepared are stable under the reaction conditions, particularly the exposure to LDA, those substituents may be placed on the starting tetralone and carried through the steps of the process to prepare the complete compound of formula I in a single linked process, although the one-pot aspect of the above process may not be possible with such starting materials.

Alkylation Process

It is necessary in the synthesis to alkylate the nucleus to add the $R^2$ substituent, if one is desired. U.S. Pat. No. 5,239,075 shows such alkylation by reaction with an alkyl iodide in the presence of a very strong base such as sodium hydride, a conventional process step. Similar alkylations are shown below in the presence of, preferably, potassium t-butoxide in t-butanol as solvent.

The present invention also provides a superior and preferred process for alkylating certain benzoquinolinone compounds which include many of the compounds of the present invention, and also many of the compounds previously disclosed in U.S. Pat. No. 5,239,075. The process allows particularly economical and ready alkylation of the N-4 position of the molecule without the necessity to use unusually strong bases such as potassium t-butoxide and the like. The compounds which are prepared by the present alkylation process are of the formula

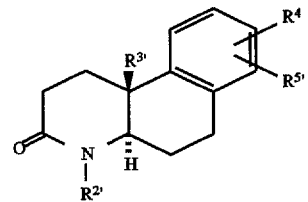

wherein $R^{2'}$ is methyl, ethyl or n-propyl;

$R^{3'}$ is hydrogen or methyl;

$R^4$ is hydrogen, halo, methyl or ethyl;

$R^{5'}$ is halo, nitro, cyano, $C_1$–$C_6$ alkyl, trifluoromethyl or $C_1$–$C_6$ alkoxy;

or $R^{5'}$ is a group —A—$R^7$ wherein A is $C_1$–$C_6$ alkyl, $C_2$–$C_6$ alkenyl, or $C_2$–$C_6$ alkynyl; and $R^7$ is halo, trifluoromethyl, or $C_1$–$C_6$ alkoxy;

or $R^{5'}$ is a group —X'—$R^9$ wherein X' is $C_1$–$C_4$ alkyl, $C_2$–$C_4$ alkenyl, $C_2$–$C_4$ alkynyl or a bond;

and $R^9$ is phenyl, naphthalenyl, pyridinyl, pyrazinyl, pyridazinyl, pyrimidinyl, anthracenyl, acenaphthalenyl, thiazolyl, benzimidazolyl, indazolyl, thiophenyl, phenanthrenyl, quinolinyl, fluorenyl, isoquinolinyl, indanyl, benzopyranyl, indolyl, benzisoquinolinyl, benzindolyl, benzothiazolyl, benzothiophenyl, quinoxalinyl, benzoxazolyl, tetrazolyl, naphthothiazolyl, quinazolinyl, thiazolopyridinyl, pyridazinoquinazolinyl, benzisothiazolyl, benzodioxolyl, benzodioxinyl, diphenylmethyl or triphenylmethyl;

the above $R^9$ groups are unsubstituted or substituted with 1–3 groups chosen from the group consisting of halo, trifluoromethyl, trifluoroethoxy, $C_1$–$C_4$ alkyl, trifluoromethoxy, hydroxy, $C_1$–$C_3$ alkoxy, nitro, $C_1$–$C_3$ alkylthio, $C_1$–$C_6$ alkanoyl, phenyl, oxy, phenoxy, phenylthio, $C_1$–$C_3$ alkylsulfonyl, cyano, benzyloxy, benzylthio, (mono-halo, nitro or trifluoromethyl) benzyl(oxy or thio), (mono-$C_1$–$C_3$ alkyl, $C_1$–$C_3$ alkoxy or halo)-(phenyl, phenoxy, phenylthio, phenylsulfonyl or phenoxysulfonyl), halo-$C_1$–$C_6$ alkanoyl, phenyl(oxy or thio)($C_1$–$C_3$ alkyl), (halo, $c_1$–$c_3$ alkyl or $C_1$–$C_3$ alkoxy)phenyl(oxy or thio)($C_1$–$C_3$ alkyl), or benzoyl;

or an above $R^9$ group is substituted with a morpholino ($C_1$–$C_3$ alkyl) group, or a phenyl($C_1$–$C_3$ alkyl) piperidinyl group;

or $R^9$ is a perhalophenyl group; the process comprises reacting a compound of the formula

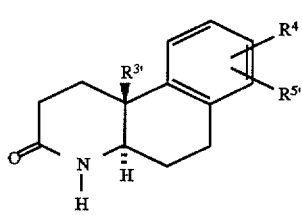

with methyl, ethyl or n-propyl iodide in a reaction mixture comprising an organic solvent chosen from the group consisting of tetrahydrofuran, dimethoxyethane, diethoxyethane and methyl t-butyl ether, and aqueous sodium or potassium hydroxide.

The compounds prepared by the alkylation process are among those which have been described in full above, or have been described in full in the above-mentioned patent. No additional description of the products is necessary. Similarly, the starting materials of Formula B have also been thoroughly described, and they are prepared by the general methods of preparation described in this document or in U.S. Pat. No. 5,239,075.

The present process itself is readily carried out, and is distinguished by both particularly effective alkylation, under mild and easily controlled conditions, and by particularly easy isolation of the products. Frequently, prior art alkylations of similar types required the use of phase transfer catalysts to isolate the products in satisfactory yield and purity, but it has been found that the products of the present alkylations are isolated by simple crystallization.

Certain aspects of the alkylation process are preferred and will be mentioned below specifically. It will be understood that the following aspects arm each important individually, and also that preferred aspects may be combined to create further, more limited or more expansive, preferred aspects.

a) $R^{2'}$ is methyl and the compound of formula B is reacted with methyl iodide;

b) $R^{2'}$ is methyl or ethyl and the compound of formula B is reacted with methyl or ethyl iodide;

c) $R^{3'}$ is hydrogen;

d) $R^{3'}$ is methyl;

e) $R^4$ is hydrogen;

f) $R^{5'}$ is halo;

g) the organic solvent is tetrahydrofuran;

h) the hydroxide is sodium hydroxide;

i) the concentration of the aqueous sodium or potassium hydroxide is near saturation.

The alkylation process is carried out in conventional chemical plant equipment, preferably at ambient pressure and at moderate temperatures. It is preferably begun by slurrying the starting material of formula B in the organic solvent at a temperature near ambient, such as from about 0° to about 50°, more preferably from about 15° to about 25°. The most preferred organic solvent is tetrahydrofuran (THF), and it is preferred to use about 5–15 liters of solvent per kilogram of starting material; more preferable solvent volume is about 10 liters per kilogram. The alkyl iodide is then added as neat liquid. A substantial excess of alkyl iodide is preferably used, such as about 1.2–1.8 equivalents based on the starting material, most preferably about 1.5 equivalents.

The aqueous sodium or potassium hydroxide is then added, still at about ambient temperature, in an amount of about 1–4 liters per kilogram of starting material. The quantity of aqueous base is somewhat dependent on the concentration of the base and the choice of sodium or potassium hydroxide; when the most preferred base, 50% sodium hydroxide, is used, the most preferred amount of it is about 2 liters per kilogram of starting material. Then the reaction mixture, consisting of solid material slurried in two liquid phases, is warmed to about 25°–65° with vigorous agitation and the reaction is allowed to proceed at about constant temperature with constant agitation. The preferred reaction temperature is about 35°–40°. As the reaction proceeds toward completion, the solid starting material and alkyl iodide will dissolve and react, so the disappearance of solids is a crude indication of completion. The reaction may be followed by high pressure liquid chromatography (HPLC) on C-18 silica gel column, eluting with 1:1 acetonitrile:aqueous buffer (5% ammonium acetate) and monitoring at 220 nanometers.

When the reaction has gone as far as is desired toward completion, the mixture is cooled to about ambient and the aqueous layer is separated and discarded.

The preferred purification and isolation procedure proceeds by diluting the organic layer with water, and neutralizing it with aqueous mineral acid. Then the solution is distilled until the vapor temperature rises to about 69°–80°, removing most of the THF. Slow cooling to about 5° over a period of about 1–14 hours crystallizes the product, which needs only washing with water and drying to be ready for use as an intermediate or as a pharmaceutical.

The alkylation process provides product in the same stereochemical form as the starting material, in satisfactory purity for the pharmaceutical industry, and in yields of or above 90% when operated according to the preferred manners.

The following Examples further explain the process and provide details which will be of use to the skilled reader.

EXAMPLE 1

(4aR)-(10bR)-8-chloro-4-methyl-1,2,3,4,4a,5,6,10b-octahydrobenzo[f]quinolin-3-one To a 1-liter flask equipped with a condenser and a stirrer were added 470 mL of THF, 18.7 g of methyl iodide and 47 g of (4aR)-(10bR)-8-chloro-1,2,3,4,4a,5,6,10b-octahydrobenzo[f]quinolin-3-one, and stirring was begun at ambient temperature. To the mixture was added 100 ml of 50% aqueous sodium hydroxide in one portion, and gentle heating was begun. The temperature was raised as high as 41° and was then gradually lowered to 29° at the end of 16 hours of stirring. HPLC liquid chromatography, eluting with 1:1 acetonitrile:aqueous buffer (5% ammonium acetate) and monitoring at 220 nanometers, then showed that all the starting material had been consumed and the aqueous layer was removed. The organic layer was concentrated to an oil under vacuum, and the residue was dissolved in ethyl acetate. The solution was washed with brine, and the organic layer was washed with 200 mL of water twice, and was dried over magnesium sulfate and evaporated under vacuum while heptane was added portionwise as the ethyl acetate was removed. A total of 500 mL of heptane was added, and the product began to crystallize when about half of it had been added. The slurry was concentrated to about 300 ml, and filtered, and the solids were washed with heptane and dried in vacuum at 40°–50° to obtain 47.03 g of product, m.p. 97°–99°, of 98.7% purity.

The following example shows an advantageous manner of isolating the product of the present alkylation.

EXAMPLE 1A (4aR)-(10bR)-8-chloro-4-methyl-1,2,3,4,4a,5,6,10b-octahydrobenzo[f]quinolin-3-one Two hundred L of THF was added to a reactor, and 24.6 kg of (4aR)-(10bR)-8-chloro-1,2,3,4,4a,5,6,10b-octahydrobenzo[f] quinolin-3-one was added. Then 35 kg of methyl iodide was added, rinsed in with 10 L of THF. A 79.6 kg portion of 50% aqueous sodium hydroxide was added in 13 minutes at 15°–25°, rinsed in with 40 L of THF. The mixture was stirred at 36°–39° for 13 hours, and was then cooled to 15°–25°. The layers were allowed to separate, and the water/THF phase was neutralized to pH 7 with hydrochloric acid and heated to reflux. Distillate was removed until the temperature reached 77°. A total of 154 kg of water was added from time to time. The solution was cooled over 3 hours to 3°–10°, and was then stirred vigorously at that temperature until solids began to form. Then the slurry was stirred gently at constant temperature for 3 hours. The slurry was filtered, and the vessel and filter cake were washed with cold water. The cake was air dried at 25°–35° for 75 hours to obtain 27.3 kg of the desired product, potency 85.1% by liquid chromatographic analysis.

EXAMPLE 2

(4aR)-(10bR)-8-chloro-4-ethyl-1,2,3,4,4a,5,6,10b-octahydrobenzo[f]quinolin-3-one A 9.4 g portion of (4aR)-(10bR)-8-chloro-1,2,3,4,4a,5,6,10b-octahydrobenzo[f]quinolin-3-one was combined in a flask with 94 ml of THF, 20 mL of 50% aqueous sodium hydroxide and 9.36 g of ethyl iodide, and was stirred at reflux, about 66°, for about 16 hours. The mixture was cooled to ambient temperature, and the layers were separated. The organic layer was evaporated to an oil, which was dissolved in ethyl acetate and extracted three times with 100 mL portions of water. It was then dried and evaporated to half its volume while heptane was added in portions. The resulting white crystalline product was filtered, washed with heptane and dried under vacuum at 25° to obtain 3.15 g of the desired product, m.p. 108°–110°.

Analysis calculated for $C_{15}H_{18}ClNO$: C, 68.54; H. 6.83; N. 5.54 Found: C, 68.50; H. 6.88; N, 5.31

Mass spec. (f.d.): M+263

EXAMPLE 3

(4aR)-(10bR)-8-chloro-4-ethyl-1,2,3,4,4a,5,6,10b-octahydrobenzo[f]quinolin-3-one A 9.4 g portion of (4aR)-(10bR)-8-chloro-1,2,3,4,4a,5,6, 10b-octahydrobenzo[f]quinolin-3-one was combined with 150 mL of THF, 20 mL of 50% aqueous sodium hydroxide and 12.5 g of ethyl iodide in a flask, and was warmed with stirring to about 37°. Stirring at approximately constant temperature was continued for about 72 hours and the reaction was worked up as described above in Example 2 to obtain 3.88 g of the desired product, m.p. 108°–110°. The product was found to be 98.6% pure by HPLC, eluting with 1:1 acetonitrile:aqueous buffer (5% ammonium acetate) and monitoring at 220 nanometers.

EXAMPLE 4

(4aR)-(10bR)-8-chloro-4-propyl-1,2,3,4,4a,5,6,10b-octahydrobenzo[f]quinolin-3-one A 2.35 g portion of (4aR)-(10bR)-8-chloro-1,2,3,4,4a,5, 6,10b-octahydrobenzo[f]quinolin-3-one was slurried in 40 mL of THF and 5 mL of 50% aqueous sodium hydroxide, and 3.4 g of propyl iodide was added. The mixture was heated to about 60°, and the mixture was stirred at that temperature for about 22 hours. Workup was carried out by separating the organic layer and evaporating it to dryness, and adding water and ethyl acetate. The organic layer was separated, washed twice with water, dried, filtered and evaporated under vacuum to obtain 710 mg of white crystalline product, found to be of about 90% purity. It was then purified by silica gel flash chromatography, eluting with ethyl acetate, to obtain 510 mg of purified product, m.p. 110°–11°, of 98.98% purity, by HPLC, eluting with 1:1 acetonitrile:aqueous buffer (5% ammonium acetate) and monitoring at 220 nanometers.

Analysis calculated for $C_{16}H_{20}NClO$: C, 69,18; H, 7.26; N, 5.04 Found: C, 68.92; H, 7.09; N, 5.15

If a product of formula I having an isopropyl $R^2$ group is desired, alkylation of the intermediate of formula VIII may be accomplished with isopropyl iodide, using sodium hydride as an activating agent and operating the reaction in a solvent of the group mentioned just above at an elevated temperature such as the reflux temperature.

Frequently a final stage intermediate such as that of formula VIII is produced in a racemic form as a mixture of the two trans-4a-10b isomers. Such an isomeric mixture may be converted to substantially pure desired enantiomers by a process clearly explained in U.S. Pat. No. 5,239,075, which proceeds by opening the piperidinone ring with a strong acid such as methanesulfonic acid, preparing a chiral salt with (−)-(R,R)-di-p-toluyltartaric acid, and separating the desired enantiomeric form of the salt as typically is done in such resolutions. The salt is then sprung with aqueous base and the piperidinone ring is reclosed by simple heating.

Oxidation

Another operation which may be carried out on the nucleus of the compounds of the present invention is oxidation to provide the compounds wherein R and $R^1$ represent a bond. Such oxidations are conveniently carried out by reaction with an oxidizing agent such as 2,3-dichloro-5,6-dicyano-1,4-benzoquinone (DDQ) in the presence of bis (trimethylsilyl) trifluoromethyl acetamide, preferably in dioxane as solvent. The oxidations are carried out at elevated temperature, such as the reflux temperature or from about 50° to about 150°, and preferably the reaction mixtures are stirred at about ambient temperature for a period of time before heating is begun. Further, information about such oxidations can be found below in the Examples.

Leaving Groups

In the course of preparing compounds having various X—$R^5$ groups, it is necessary or convenient to provide nucleus compounds having corresponding leaving groups or reactive groups. For example, compounds having carboxy, thio, hydroxy, amino, formyl and $B(OH)_2$ groups are needed for various syntheses and are readily prepared, as is demonstrated below, for example, in the Preparations. Such compounds are preferably prepared from compounds having

X—R⁵ Groups

Various processes are conveniently used for placing the X—R⁵ groups on the benzoquinolinone nucleus; the choice of processes is primarily dependent on the nature of the X group. Where the X group is merely a bond, a preferred process is dependent on palladium mediated boron chemistry. In one preferred process, a benzoquinolinone nucleus compound having a bromine atom as the L substituent is reacted with an intermediate which constitutes the R⁵ substituent group with a boronic acid (B(OH)₂) at the point of attachment to the benzoquinolinone nucleus. The reaction is conveniently carried out in the presence of a catalytic amount of tetrakis (triphenylphosphine) palladium, in a basic reaction mixture including, for example, aqueous sodium carbonate or triethylamine. The preferred solvent is an ether such as THF or dimethoxyethane (DME), and the reactions go cleanly at elevated temperatures such as the reflux temperature or from about 50° to about 100°. A useful variation on the above process is carried out using an ester of boronic acid as the intermediate, such as a diethylborane. The examples show illustrations of such syntheses.

Similarly, compounds having a bond as the X group may be synthesized by the palladium mediated reaction of a bromine-substituted compound providing the R⁵ group with a boronic acid-substituted benzoquinolinone nucleus.

Still another method for preparing compounds having no X group is to react a halo-substituted nucleus compound of formula IV with a compound comprising the desired R⁵ group, substituted with a tri-n-butylstannyl group at the point of attachment. Such reactions are carried out in the presence of a small amount of bis(triphenylphosphine) palladium halide at high temperatures such as from about 60° to about 120°. A solvent such as acetonitrile may be used, and the reaction should be carried out in inert gas atmosphere.

Another particularly important group of compounds of formula I are those wherein X is a sulfur atom. Such groups are conveniently prepared by at least two main processes. In one process, a halo-substituted benzoquinolinone nucleus compound is reacted with a disulfide of the formula R⁵—S—S—R⁵. For example, if a benzylthio substituent is to be provided, the disulfide would be dibenzyldisulfide. The reactions go readily at ambient temperature after combining the reactants at a very low temperature, such as from about −50° to about −100°, in an ether solvent in the presence of a very strong base, particularly a combination of methyl-lithium and t-butyl-lithium. The reactions are rapid and may be carried out in 1 hour or, at most, a few hours. Another method of synthesis of thiosubstituted compounds, which avoids the use of very low temperatures, is one where either the nucleus or the compound providing the R⁵ group is substituted with an SH group and the other is substituted with a bromine, chlorine or iodine atom. Such reactions are carried out at ambient or moderately elevated temperatures, such as from about 50° to about 100°, in a high-boiling solvent such as dimethyl-formamide and in a basic reaction medium. Such bases as potassium carbonate, sodium bicarbonate, triethylamine and other moderately strong bases are adequate. Numerous examples of such syntheses are shown below.

Similarly, when the group X is an oxygen atom, the compounds are conveniently prepared by reactions where one of the nucleus and the R⁵ group—providing compound carries a halogen atom, and the other carries a hydroxy group. As usual with such reactions, basic conditions and moderately elevated temperatures, such as were just described, are adequate to provide reasonably prompt and clean production of the desired compound of formula I.

Compounds wherein X is an oxyalkyl or thioalkyl group are prepared from a nucleus compound having a formyl or formylalkyl L substituent, which material is prepared, as shown below, by reaction of a halo-substituted nucleus compound with dimethylformamide in the presence of a very strong base, to prepare the formyl substituted compound. It is reduced to form a hydroxymethyl group, which is converted to a haloalkyl group, and finally reacted with an SH or OH-substituted compound providing the R⁵ group.

The group of compounds of formula I where X is alkyl, alkenyl or alkynyl are made, in general, by processes where a halo-substituted nucleus compound is reacted with a compound providing the X—R⁵ group, in the presence of a 9-borabicyclo [3.3.1]nonane alkyl compound (generated in situ by treatment of the appropriate alkene with 9-borabicyclo[3.3.1]nonane (9-BBN)) or of a bis(tri-substituted-phosphine)palladium compound, at a high temperature in an inert atmosphere. Solvents such as dimethyl-formamide may be used, and a basic environment provided by triethylamine or the like is appropriate. Temperatures in the range of from about 80° to about 140° may be used for long periods of time up to as much as 24 hours. The resulting compounds may be hydrogenated in conventional manners to reduce them from alkynes to alkenes or from alkenes to alkyls.

Another method of synthesis of alkyl-linked compounds may be carried out by reacting the halo-substituted benzoquinoline nucleus compound with a very strong base, preferably a combination of methyllithium and t-butyllithim, and then adding an aldehyde or ketone providing the desired X—R⁵ substituent. For example, an example below shows the preparation of a compound wherein X is a bond and R⁵ is diphenylmethyl by such a reaction of benzophenone. Such reactions should be carried out at low temperature, warming to ambient or slightly elevated temperature, preferably in an ether solvent.

Compounds of formula I wherein X is a carbonyl group, an ester group or a carboxamide are prepared in manners following the general processes for synthesis of such compounds. For example, a compound where X is a carboxamide may conveniently be prepared by reacting a halo-substituted benzoquinolinone nucleus compound with an isocyanate carrying the desired R⁵ group. Such reactions are carried out in ether solvents, frequently preferably THF, in the presence of methyllithium/t-butyllithium at low temperatures.

Another method for synthesis of carbonyl-substituted compounds is to react an aldehyde with a halo-substituted nucleus compound, to provide a hydroxymethyl-substituted intermediate. Such a reaction is carried out in the presence of methyllithium/t-butyllithium at low temperatures, again in an ethereal solvent by preference. The hydroxymethyl intermediate is oxidized, as with Jones reagent under the usual conditions for such reactions, to prepare the desired compound where X is a carbonyl group.

The benzoquinolinone intermediate having a carboxy substituent on the phenyl ring, the preparation of which is shown below as a Preparation, is conveniently used to prepare compounds where X incorporates an ester or amide linkage, by conventional esterification reactions with alcohols, or amide preparations with amines. All of the conventional reaction conditions are applicable, such as the use of carbonyldiimidazole as an initiator, or oxalyl chloride/dimethylformamide. When an X group incorporates an alkylene chain together with an ester or amide linkage, appropriate starting materials including the alkylene chain are used as a chemist would anticipate.

On the other hand, when the X group comprises an amide linkage where the nitrogen is linked to the benzoquinolinone, the amino-substituted intermediate prepared below is conveniently reacted with, for example, a carbonyl halide carrying the desired $R^5$ group under the conventional reaction conditions. Again, small alkylene groups may be incorporated as desired to make up any of the possible X groups in the contemplation of the present invention.

For example, an unsaturated alkyl-substituted nucleus compound, prepared as discussed above, may be oxidatively cleaved to form the corresponding carboxyalkyl compound. Oxidizing agents such as periodates are commonly used for such transformation and may be used in these instances. The carboxy compound is then esterified or amidated in the usual manner to prepare the desired alkyl-ester or alkyl-amide X group.

It will be understood that the above discussions of esters include thioesters where the group Y represents a sulfur atom, as well as the more commonly used esters.

Finally, numerous transformations are or may be carried out on $R^5$ groups, to transform one compound of the present invention to another compound. For example, a compound where the $R^5$ group is substituted with a functional group such as alkanoyl, especially formyl, may be reacted with an amine to prepare the corresponding aminoalkyl-substituted compound. Compounds having, for example, nitro groups may be reduced to form the corresponding amino-substituted compounds, and amino-substituted compounds may be reacted with ketones or aldehydes in the presence of reducing agents, or by subsequent reduction, to prepare the corresponding compounds wherein the $R^5$ group is substituted with alkyl amino.

Further information about the preparation of compounds of the present invention is to be found in the following Preparations and Examples, which, while certainly not intended to limit the present invention, are illustrative of the processes by which all of the compounds are prepared.

The first group of Preparations below illustrate the preferred synthesis of the benzoquinolinone nucleus compounds which process was described in detail above.

Preparation 1

(R)-6-bromo-2-(1-phenylethylamino)-3,4-dihydronaphthalene, lithium salt

6-Bromo-2-tetralone, (45.0 g, 200 mmol uncorrected, potency of 90%, 0.90 equiv, corrected) was refluxed with (R)-(+)-phenethylamine (26.6 g, 220 mmol, 1.10 equiv, p-toluenesulfonic acid (160 mg, 0.84 mmol, 0.004 equiv), and toluene (600 mL) in a 2000-mL round bottom flask fitted with a water separator. Reflux was continued until a water-free distillate was observed and then approximately 250 mL of toluene was collected over about 2 to 3 hours. The mixture was cooled to approximately 30°–35° and concentrated under house vacuum.

The residue above, containing the enamine intermediate, was dissolved in tetrahydrofuran (THF, 480 g, 540 mL) and cooled below −50°. This solution of the enamine was added via cannula to a solution of lithium diisopropylamide (LDA, 1.15 equiv) at −50° to −60° over 5 minutes. The solution was warmed to −5° over 20 minutes and then recooled to −75° affording a 0.125M solution of the lithium salt starting material. Proceed immediately to next step—unstable intermediate.

Preparation 2

(4aR)-10bR)-8-bromo-10b-methyl-1,2,3,4,4a,5,6,10b-octahydrobenzo[f]quinolin-3-one
Step A—Methyl Iodide Methyl iodide (14.4 mL, 230 mmol, 1.15 equiv.) was added via syringe to the reaction mixture from Preparation 1 at −75° to −70° over 3 minutes. This solution was warmed to −5° in 20 minutes and then treated with methanesulfonic acid (24.8 g, 16.8 mL, 1.3 equiv.) affording a solution of the desired enamine admixed with diisopropylamine methanesulfonate as a slightly soluble, off-white precipitate, which was then removed by filtration.
Step B—Aza-Annulation The reaction mixture solution from the above step was treated with acryloyl chloride (1.7 equiv.) at −75° in one portion over about 5 minutes. The mixture was then allowed to warm to −8° over 15 hours. The reaction was quenched by pouring into sodium bicarbonate (60 g in 240 mL of water at 5° to 7°, 15 minutes addition time, 20 minutes stir, pH should be basic). Dimethylaminopyridine (0.01 equiv, 2 mmol, 244 mg) was added and the mixture stirred another hour. The mixture was concentrated under vacuum (10°–25°, initial volume 2000 mL; final volume 400 mL) and methylene chloride (400 mL) was added and the organic phase was washed with aqueous sulfuric acid (1.0N, two 100 mL portions, pH 1–3) and sodium bicarbonate (1.0N, 50 mL, pH 9). The organic extracts were dried and clarified by filtration over approximately 20 g of 4 Å molecular sieves. The mixture was concentrated under vacuum to a total weight of 129.6 g.
Step C—Reduction-Cleavage To about 103 g of the above residue were added 37 mL of triethylsilane and 46 mL of trifluoroacetic acid at 25°. After 1.5 hours reduction was approximately 50% complete. After an additional 12 hours the reduction was complete by TLC. The mixture was then refluxed for 2.5 hours. The mixture was allowed to cool and was concentrated in vacuo to approximately 25 g. The residue above was dissolved in 400 mL of methylene chloride, washed with aqueous sodium hydroxide (enough for pH 11) and concentrated under vacuum. This concentrate was then treated with diethyl ether (approximately 5 volumes at 22° then 0° for several hours). The mixture was filtered and rinsed with several small portions of ether affording the desired product after drying as a crystalline, white solid (yield=approximately 60% based on purity of bromotetralone).

Analysis by reverse phase high performance liquid chromatography on a Waters NOVA-PAK instrument, C-18 3.9×150 mm column, eluting with 2 ml/min. of 25% aqueous acetonitrile containing 1% ammonium acetate, operating the detector at 220 nm.

Potency: 91.2%

Related substances: 6.8%

Anal Calcd for $C_{14}H_{16}NOBr$: C, 57.16; H, 5.48; N, 4.76; Br, 27.16 Found: C, 55.08; H, 5.43; N, 4:30; Br, 27.78

$^{13}C$ NMR (CDCl$_3$): 21.60, 24.62, 28.24, 29.48, 33.15, 36.90, 57.28, 121.03, 127.42, 130.09, 132.86, 137.51, 143.26, 173.62

1H NMR (CDCl$_3$): 1.18(s, 3H)

α589 nm-90°

α365 nm-302° ee%>98%, determined by chromatography on a Chiracel-OD instrument and 1 mL/min, 40°, eluting with 10% isopropanol in hexane and operating the detector at 220 nm.

Preparation 3 acrylic anhydride

Two hundred fifty ml of tetrahydrofuran was added to a 1 liter jacketed flask with stir bar and nitrogen purge, and 250 mg of butylated hydroxytoluene, 250 mg of hydroquinone and 25.3 g of triethylamine were added. The solution was cooled to 0°, and to it was added 18.0 g of acrylic acid over a 2 minute period. The solution was cooled again to 0°, and 22.6 g of acryloyl chloride was added over a 10 minute period. It is important to maintain the addition rate constant during the acryloyl chloride addition. Maintaining the jacket temperature at 0° and continuing the nitrogen purge, the solution was stirred for 1 hour, and then it was filtered in a vacuum filter and the cake was washed with 50 ml of additional tetrahydrofuran.

Preparation 4

(R)-6-chloro-2-(1-phenylethylamino)-3,4-dihydronaphthalene, lithium salt

6-Chloro-2-tetralone (4.51 g, 25 mmol) was reacted with 3.32 g of (R)-(+)-phenethylamine and 20 mg of p-toluenesulfonic acid. The reaction was carried out as shown in Preparation 1 above in 100 mL of toluene, and when the reaction was complete the mixture was concentrated under vacuum and the residue was dissolved in 70 mL of tetrahydrofuran. The solution was cooled to −50° to −60°, and was added quickly to a solution of 1.15 equivalents of lithium diisopropylamide in 122 mL of tetrahydrofuran at −70° to −65°. The solution was allowed to warm to −20° for 20 minutes, and was then quickly recooled to −75°.

Preparation 5

(4aR)-(10bR)-8-chloro-10b-methyl-1,2,3,4,4a,5,6,10b-octahydrobenzo[f]quinolin-3-one To the cold solution from Preparation 4, was added 1.15 equivalents of methyl iodide, and the mixture was allowed to warm to −5° over a 15 minute period with continued good stirring. Then 1.3 equiv. of methanesulfonic acid was added to the mixture over a 5 minute period.

That mixture was vigorously stirred for 10 minutes at −5°, and was then cooled again to −75°. To it was added in one portion, 2.4 equiv. of acrylic anhydride, with continued stirring, and the mixture was allowed to warm from −75° to 15° over a period of 13 hours.

The resulting reaction mixture was poured into a well stirred solution of aqueous sodium bicarbonate (2 g/200 mL at 20°) and 100 mg of dimethylaminopyridine. After two hours of stirring at ambient temperature, most of the volatiles were removed under vacuum, and 130 mL of methylene chloride was added. The mixture was washed with 50 mL of 1N hydrochloric acid, and then with aqueous sodium bicarbonate, and the organic phase was dried and concentrated to a white foam (10.37 g).

The foam was placed in a flask in a ice bath and was treated with 40 mL triethylsilane and 60 mL of trifluoroacetic acid for 15 hours at 0° and was then held for four days at 25°. The volatiles were removed under vacuum, and the colorless oil was decanted from the solid product. The residue was dissolved in 200 mL of methylene chloride and washed with saturated aqueous sodium bicarbonate. The extracts were dried with 4A molecular sieves and evaporated. The residue was washed with 76 mL of diethyl ether to obtain 3.87 g of the desired product as a white solid admixed with a small amount of isomeric material.

MS=249, 251 (M+, M+2)

IR (CHCl$_3$)=3396, 1662 cm$^{-1}$.

Anal Calcd for C$_{14}$H$_{16}$NOCl: C, 67.33; H, 6.46; N, 5.61; Cl, 14.20 Found: C, 66.57; H, 6.43; N, 5.40; Cl, 13.91

$^1$H NMR (CDCl$_3$ 500 MHz): 1.16(s, 3H), 3.54(dxd, 1H),

UV (MeOH): γ205 (21000), 271(600), 280(600)

The following group of examples illustrates the preparation of compounds where X is a sulfur atom by reactions with disulfides.

EXAMPLE 5

(+)-(4aR)-(10bR)-8-(4-chlorophenylthio)-10b-methyl-1,2,3,4,4a,5,6,10b-octahydrobenzo[f]quinolin-3-one To a 3-necked 125 ml flask was added 50 ml of THF and 500 mg of (4aR)-(10bR)-8-bromo-10b-methyl-1,2,3,4,4a,5,6,10b-octahydrobenzo[f]quinolin-3-one at ambient temperature. The solution was cooled to −75°, and to it was added dropwise 1.7 ml of methyllithium in diethyl ether. The mixture was stirred for 15 minutes, and then 3.4 ml of t-butyllithium (1.7M in pentane) was added and the temperature rose to −70°. The mixture was stirred for 5 minutes and then 1.95 g of bis(4-chlorophenyl) disulfide dissolved in 10 ml of THF was added in portions. The reaction mixture was stirred for 20 minutes at −75° and then was allowed to warm to ambient temperature. It was acidified with 1N hydrochloric acid, and was diluted with 300 ml of ethyl acetate. The organic solution was washed successively with 1N hydrochloric acid, 10% sodium carbonate solution, water and brine, and was then dried and concentrated under vacuum to obtain 2 g of a yellow oil. The oil was purified by chromatography over silica gel, eluting with a solvent beginning with 2% methanol in dichloromethane and going to 3% methanol/dichloromethane. The product-containing fractions were evaporated to obtain 540 mg of foam, which was crystallized from ethyl acetate to obtain 453 mg of purified product. mp 169°–172° FDMS: m/e=357. α[D]$_{589}$=+83.91, α[D]$_{365}$=+293.47 (methanol).

| Analysis | Calculated | Found |
|---|---|---|
| C | 67.12 | 67.33 |
| H | 5.63 | 5.82 |
| N | 3.91 | 3.78 |

EXAMPLE 6

(+)-(4aR)-(10bR)-8-(4-methylphenylthio)-10b-methyl-1,2,3,4,4a,5,6,10b-octahydrobenzo[f]quinolin-3-one A 549 mg portion of the same intermediate used in Example 5 was reacted with 1.84 g of bis(4-methylphenyl) disulfide under conditions as described in Example 5 to obtain 481 mg of the desired product. mp 209°–212° FDMS: m/e=337. α[D]$_{589}$=+85.00, α[D]$_{365}$=+309.00 (chloroform).

| Analysis | Calculated | Found |
|---|---|---|
| C | 74.74 | 75.00 |
| H | 6.87 | 6.94 |
| N | 4.15 | 4.10 |

EXAMPLE 7

(+)-(4aR)-(10bR)-8-(2-chorophenyl)-10b-methyl-1,2,3,4,4a,5,6,10b-octahydrobenzo[f]quinolin-3-one A 910 mg portion of the same starting material used in Example 5 was reacted with 3.6 g of bis(2-chorophenyl) disulfide as described in Example 5 to obtain 790 mg of the desired product. mp 890°–191° FDMS: m/e=357. α[D]$_{589}$= +80.66, α[D]$_{365}$=+281.3 (chloroform).

| Analysis | Calculated | Found |
|---|---|---|
| C | 67.12 | 67.30 |
| H | 5.63 | 5.52 |
| N | 3.91 | 3.99 |

EXAMPLE 8

(+)-(4aR)-(10bR)-8-(3-chlorophenylthio)-10b-methyl-1,2,3,4,4a,5,6,10b-octahydrobenzo[f]quinolin-3-one A 930 mg portion of the same starting material as in Example 5 was reacted with 3.6 g of bis(3-chlorophenyl)-disulfide as described in Example 5 to obtain 810 mg of the desired product. mp 186°–187°. FDMS: m/e=357. α[D]$_{589}$= +80.5, α[D]$_{365}$=+292.6 (chloroform).

| Analysis | Calculated | Found |
|---|---|---|
| C | 67.12 | 67.41 |
| H | 5.63 | 5.82 |
| N | 3.91 | 3.88 |

EXAMPLE 9

(+)-(4aR)-(10bR)-8-(2-methylphenylthio)-10b-methyl-1,2,3,4,4a,5,6,10b-octahydrobenzo [f]quinolin-3-one A 620 mg portion of the same starting material used in Example 5 was reacted with 2.1 g of bis(2-methylpheny) disulfide to obtain 490 mg of the desired product, using conditions as described in Example 5 above. mp 192°, 196°–199° FDMS: m/e=337. α[D]$_{589}$=+87.8, α[D]$_{365}$=+310.3 (chloroform).

| Analysis | Calculated | Found |
|---|---|---|
| C | 74.74 | 74.46 |
| H | 6.87 | 6.90 |
| N | 4.15 | 3.90 |

EXAMPLE 10

(+)-(4aR)-(10bR)-8-(3-methylphenylthio)-10b-methyl-1,2,3,4,4a,5,6,10b-octahydrobenzo[f]quinolin-3-one A 620 mg portion of the same starting material used in Example 5 was reacted with 2.1 g of bis(3-methylphenyl) disulfide under the conditions of Example 5 to obtain 480 mg of the desired product. mp 189°–191° FDMS: m/e=337. α[D]$_{589}$=+87.8, α[D]$_{365}$=+316.5 (chloroform).

| Analysis | Calculated | Found |
|---|---|---|
| C | 74.74 | 75.02 |
| H | 6.87 | 6.90 |
| N | 4.15 | 4.34 |

EXAMPLE 11

(+)-(4aR)-(10bR)-8-(1-naphthylthio)-10b-methyl-1,2,3,4,4a,5,6,10b-octahydrobenzo[f]quinolin-3-one A 630 mg portion of the same starting material used in Example 5 was reacted with 2.73 g of bis(1-naphthyl) disulfide under the conditions of Example 5 to obtain 555 mg of the desired product. mp 199°–201° FDMS: m/e=373. α[D]$_{589}$=+76.7, α[D]$_{365}$=+238.6 (chloroform).

| Analysis | Calculated | Found |
|---|---|---|
| C | 77.18 | 76.96 |
| H | 6.21 | 6.12 |
| N | 3.75 | 3.64 |

EXAMPLE 12

(+)-(4aR)-(10bR)-8-(2-methoxyphenylthio)-10b-methyl-1,2,3,4,4a,5,6,10b-octahydrobenzo[f]quinolin-3-one A 700 mg portion of the same starting material used in Example 5 was reacted with 2.65 g of bis(2-methoxyphenyl) disulfide under the conditions of Example 5 to obtain 580 mg of the desired product. mp 176°–179° FDMS: m/e=353. α[D]$_{589}$=+80.4, α[D]$_{365}$=+287.9 (chloroform).

| Analysis | Calculated | Found |
|---|---|---|
| C | 71.36 | 71.64 |
| H | 6.56 | 6.46 |
| N | 3.96 | 3.72 |

EXAMPLE 13

(+)-(4aR)-(10bR)-8-(4-methoxyphenylthio)-10b-methyl-1,2,3,4,4a,5,6,10b-octahydrobenzo[f]quinolin-3-one A 700 mg portion of the same starting material used in Example 5 was reacted with 2.65 g of bis(4-methoxyphenyl) disulfide under the conditions of Example 5 to obtain 630 mg of the desired product. mp 194°–196° FDMS: m/e=353. α[D]$_{589}$=86.2, α[D]$_{365}$=+309.4 (chloroform).

| Analysis | Calculated | Found |
|---|---|---|
| C | 71.36 | 71.21 |
| H | 6.56 | 6.51 |
| N | 3.96 | 3.71 |

EXAMPLE 14

(+)-(4aR)-(10bR)-8-(4-fluorophenylthio)-10b-methyl-1,2,3,4,4a,5,6,10b-octahydrobenzo[f]quinolin-3-one A 700 mg portion of the same starting material used in Example 5 was reacted with 2.4 g of bis(4-fluorophenyl) disulfide under the conditions of Example 5 to obtain 600 mg of the desired product. mp 179°–181° FDMS: m/e=341. α[D]$_{589}$=+88.9, α[D]$_{365}$=+313.2 (chloroform).

| Analysis | Calculated | Found |
|---|---|---|
| C | 70.35 | 70.07 |
| H | 5.90 | 5.85 |
| N | 4.10 | 3.83 |

EXAMPLE 15

(4aR)-(10bR)-8-(3-methoxyphenylthio)-10b-methyl-1,2,3,4,4a,5,6,10b-octahydrobenzo[f]quinolin-3-one A 700 mg portion of the same starting material used in Example 5 was reacted with 2.65 g of bis(3-methoxyphenyl) disulfide under the conditions of Example 5 to obtain 650 mg of the desired product. mp 154.5°–155.5° FDMS: m/e=353.

| Analysis | Calculated | Found |
|---|---|---|
| C | 71.36 | 71.29 |
| H | 6.56 | 6.56 |
| N | 3.96 | 3.91 |

EXAMPLE 16

(+)-(4aR)-(10bR)-8-(3-fluorophenylthio)-10b-methyl-1,2,3,4,4a,5,6,10b-octahydrobenzo [f]quinolin-3-one A 700 mg portion of the same starting material used in Example 5 was reacted with 2.4 g of bis(3-fluorophenyl) disulfide under the conditions of Example 5 to obtain 600 mg of the desired product. mp 154°–156° FDMS: m/e=341. $\alpha[D]_{589}$=+84.8, $\alpha[D]_{365}$=+300.6 (chloroform).

| Analysis | Calculated | Found |
|---|---|---|
| C | 70.35 | 70.38 |
| H | 5.90 | 5.96 |
| N | 4.10 | 4.09 |

EXAMPLE 17

(+)-(4aR)-(10bR)-8-(2-fluorophenylthio)-10b-methyl-1,2,3,4,4a,5,6,10b-octahydrobenzo[f]quinolin-3-one A 700 mg portion of the same starting material used in Example 5 was reacted with 2.4 g of bis(2-fluorophenyl) disulfide under the conditions of Example 5 to obtain 640 mg of the desired product. mp 196°–198° FDMS: m/e=341. $\alpha[D]_{589}$=+84.2, $\alpha[D]_{365}$=+300.8 (chloroform).

| Analysis | Calculated | Found |
|---|---|---|
| C | 70.35 | 70.24 |
| H | 5.90 | 5.95 |
| N | 4.10 | 3.97 |

EXAMPLE 18

(4aR)-(10bR)-8-(3-quinolinylthio)-10b-methyl-1,2,3,4,4a,5,6,10b-octahydrobenzo[f]quinolin-3-one A 750 mg portion of the same starting material used in Example 5 was reacted with 3.27 g of bis(3-quinolinyl)-disulfide under the conditions of Example 5 to obtain 340 mg of the desired product. mp 168°–170° FDMS: m/e=374.

| Analysis | Calculated | Found |
|---|---|---|
| C | 73.76 | 73.56 |
| H | 5.92 | 5.96 |
| N | 7.48 | 7.36 |

EXAMPLE 19

(4aR)-(10bR)-8-(2-quinolinylthio)-10b-methyl-1,2,3,4,4a,5,6,10b-octahydrobenzo[f]quinolin-3-one A 750 mg portion of the same starting material used in Example 5 was reacted with 3.27 g of bis(2-quinolinyl)-disulfide under the conditions of Example 5 to obtain 560 mg of the desired product. mp 2200°–222° FDMS: m/e=374.

| Analysis | Calculated | Found |
|---|---|---|
| C | 73.76 | 73.56 |
| H | 5.92 | 5.92 |
| N | 7.48 | 7.40 |

EXAMPLE 20

(+)-(4aR)-(10bR)-8-(8-quinolinylthio)-10b-methyl-1,2,3,4,4a,5,6,10b-octahydrobenzo[f]quinolin-3-one A 750 mg portion of the same starting material used in Example 5 was reacted with 3.27 g of bis(8-quinolinyl)-disulfide to obtain 375 mg of the desired product. mp>260° FDMS: m/e=374. $\alpha[D]_{589}$=+71.6, $\alpha[D]_{365}$=absorbance (chloroform).

| Analysis | Calculated | Found |
|---|---|---|
| C | 73.76 | 73.61 |
| H | 5.92 | 5.99 |
| N | 7.48 | 7.46 |

EXAMPLE 21

(4aR)-(10bR)-8-(2-pyridinylthio)-10b-methyl-1,2,3,4,4a,5,6,10b-octahydrobenzo[f]quinolin-3-one A 750 mg portion of the same starting material used in Example 5 was reacted with 2.25 g of bis(2-pyridinyl)-disulfide as described in Example 5 to obtain 530 mg of the desired product. mp 223°–225° FDMS: m/e=324.

| Analysis | Calculated | Found |
|---|---|---|
| C | 70.34 | 70.09 |
| H | 6.21 | 6.24 |
| N | 8.63 | 8.57 |

EXAMPLE 22

(4aR)-(10bR)-8-phenylthio-10b-methyl-1,2,3,4,4a,5,6,10b-octahydrobenzo[f]quinolin-3-one A 500 mg portion of the same starting material used in Example 5 was reacted with 414 g of diphenyldisulfide as described in Example 5 to obtain 351 mg of the desired product. mp 183°–185° FDMS: m/e=323.

| Analysis | Calculated | Found |
|---|---|---|
| C | 74.27 | 73.99 |
| H | 6.54 | 6.68 |
| N | 4.33 | 4.53 |

EXAMPLE 23

(4aR)-(10bR)-8-benzylthio-10b-methyl-1,2,3,4,4a,5,6,10b-octahydrobenzo[f]quinolin-3-one A 501 mg portion of the same starting material used in Example 5 was reacted with 1.0 g of dibenzyldisulfide substantially as described in Example 5 to obtain 329 mg of the desired product. mp 172°–174° FDMS: m/e=337. $\alpha[D]_{589}$=80.84 (c=0.57 in chloroform).

| Analysis | Calculated | Found |
|---|---|---|
| C | 74.74 | 74.49 |
| H | 6.87 | 6.85 |
| N | 4.15 | 4.18 |

The following group of examples demonstrates syntheses which a bromine-substituted benzoquinolinone nucleus compound is reacted with a compound having a boronic acid leaving group and providing the $R^5$ group, where X is a bond.

EXAMPLE 24

(+)-(4aR)-(10bR)-4-methyl-8-(4-chloro-3-trifluoromethyl-phenyl)-10b-methyl-1,2,3,4,4a,5,6,10b-octahydrobenzo[f]-quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine) palladium (0) (23 mg, 0.02 mmol), 4-chloro-3-trifluoromethylphenylboronic acid (175 mg, 0.78 mmol), 0.65 mL of 2M aq. sodium carbonate solution and 2 mL of THF, fitted with a reflux condenser, and the stirred mixture was heated at 80°, under nitrogen, for 16 h. The mixture was cooled, diluted with chloroform (50 mL) and washed with brine (2×25 mL). The combined organic extracts were dried over sodium sulfate, concentrated, and purified by silica gel chromatography (ethyl acetate eluent), to give 188 mg (71%) of the title compound as a white solid. mp 134°–137°. FDMS: m/e=407. $\alpha[D]_{589}$=+59.74 (c=1.02, chloroform).

| Analysis | Calculated | Found |
|---|---|---|
| C | 64.79 | 64.78 |
| H | 5.19 | 5.23 |
| N | 3.43 | 3.65 |

EXAMPLE 25

(+)-(4aR)-(10bR)-4-methyl-8-(3-chloro-4-hydroxyphenyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine) palladium (0) (23 mg, 0.02 mmol), 3-chloro-4-hydroxyphenylboronic acid (134 mg, 0.7 mmol), 0.65 mL of 2M sodium carbonate solution and 2 mL of THF, fitted with a reflux condenser, and the stirred mixture was heated at 80°, under nitrogen, for 24 h. The mixture was cooled, diluted with chloroform (50 mL) and washed with brine (2×25 mL). The combined organic extracts were dried over sodium sulfate, concentrated, and purified by silica gel chromatography (ethyl acetate eluent), to give 139 mg (61%) of the title compound as a white solid. mp 245°. FDMS: m/e=355. $\alpha[D]_{589}$=+17.62 (c=1.02, chloroform).

| Analysis | Calculated | Found |
|---|---|---|
| C | 70.88 | 70.74 |

| Analysis | Calculated | Found |
|---|---|---|
| H | 6.23 | 6.27 |
| N | 3.94 | 4.10 |

EXAMPLE 26

(+)-(4aR)-(10bR)-4-methyl-8-(2,3-difluorophenyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine) palladium (0) (23 mg, 0.02 mmol), 2,3-difluorophenylboronic acid (123 mg, 0.78 mmol), 0.65 mL of 2M sodium carbonate solution and 2 mL of THF, fitted with a reflux condenser, and the stirred mixture was heated at 80°, under nitrogen, for 16 h. Additional palladium reagent was added, and the mixture was heated for an additional 16 h. The mixture was cooled, diluted with chloroform (75 mL) and washed with brine (2 ×25 mL). The combined organic extracts were dried over sodium sulfate, concentrated, and purified by silica gel chromatography (ethyl acetate eluent) to give 111 mg (50%) of the title compound as a white solid. mp 147°–148°. FDMS: m/e=341 $\alpha[D]_{589}$=+70.44 (c=1.08, chloroform).

| Analysis | Calculated | Found |
|---|---|---|
| C | 73.88 | 73.79 |
| H | 6.20 | 6.27 |
| N | 4.10 | 4.16 |

EXAMPLE 27

(+)-(4aR)-(10bR)-4-methyl-8-(3,4-difluorophenyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine) palladium (0) (23 mg, 0.02 mmol), 3,4-difluorophenylboronic acid (123 mg, 0.78 mmol), 0.65 mL of 2M sodium carbonate solution and 2 mL of THF, fitted with a reflux condenser, and the slurred mixture was heated at 80°, under nitrogen, for 24 h. Additional palladium reagent and boronic acid was added, and the mixture was heated for an additional 24 h. The mixture was cooled, diluted with chloroform (75 mL) and washed with brine (2×25 mL). The combined organic extracts were dried over sodium sulfate, concentrated, and purified by silica gel chromatography (ethyl acetate eluent) to give 130 mg (58%) of the title compound as a white solid. mp 143°–148°. FDMS: m/e=341 $\alpha[D]_{589}$=+65.12 (c=0.97, chloroform).

| Analysis | Calculated | Found |
|---|---|---|
| C | 73.88 | 73.90 |
| H | 6.20 | 6.21 |
| N | 4.10 | 3.86 |

EXAMPLE 28

(+)-(4aR)-(10bR)-4-methyl-8-(3-fluoro-4-hydroxyphenyl)-10b-methyl-1,2,3,4,4a,5,6,10b-octahydrobenzo[f]quinolin-3-one A 15 mL round bottom flask was charged with (+)-(4aR)
-(10bR)-4-methyl-8-bromo-10b-methyl-1,2,3,4,4a,5,6,10b-
octahydrobenzo[f]quinolin-3-one (200 mg, 0.65 mmol), tetrakis (triphenylphosphine) palladium (0) (23 mg, 0.02 mmol), 3-fluoro-4-hydroxyphenylboronic acid (122 mg, 0.78 mmol), 0.65 mL of 2M sodium carbonate solution and 2 mL of THF, fitted with a reflux condenser, and the stirred mixture was heated at 80°, under nitrogen, for 16 h. The mixture was cooled, diluted with chloroform (50 mL) and washed with brine (2×50 mL). The combined organic extracts were dried over sodium sulfate, concentrated, and purified by silica gel chromatography (ethyl acetate eluent), to give 111 mg (50%) of the title compound as a white solid. mp>240° C. FDMS: m/e=339. $\alpha[D]_{589}$=+11.21 (c=1.07, chloroform).

| Analysis | Calculated | Found |
|---|---|---|
| C | 74.31 | 74.12 |
| H | 6.53 | 6.53 |
| N | 4.13 | 3.88 |

EXAMPLE 29

(+)-(4aR)-(10bR)-4-methyl-8-(3,4-ethylenedioxyphenyl)
-10b-methyl-1,2,3,4,4a,5,6,10b-octahydrobenzo[f]quinolin-3-one A 15 mL round bottom flask was charged with (+)-(4aR)
-(10bR)-4-methyl-8-bromo-10b-methyl-1,2,3,4,4a,5,6,10b-
octahydrobenzo[f]quinolin-3-one (200 mg, 0.65 mmol), tetrakis (triphenylphosphine) palladium (0) (23 mg, 0.02 mmol), 3,4-ethylenedioxyphenylboronic acid (140 mg, 0.78 mmol), 0.65 mL of 2M sodium carbonate solution and 2 mL of THF, fitted with a reflux condenser, and the stirred mixture was heated at 80°, under nitrogen, for 24 h. The mixture was cooled, diluted with chloroform (50 mL) and washed with brine (2×25 mL). The combined organic extracts were dried over sodium sulfate, concentrated, and purified by silica gel chromatography (ethyl acetate eluent), to give 189 mg (80%) of the title compound as an amorphous solid. mp 183°–189°. FDMS: m/e=363. $\alpha[D]_{589}$=+80.77 (c=1.04, chloroform).

| Analysis | Calculated | Found |
|---|---|---|
| C | 76.01 | 75.75 |
| H | 6.93 | 6.89 |
| N | 3.85 | 3.62 |

EXAMPLE 30

(+)-(4aR)-(10bR)-4-methyl-8-(3,5-di[t-butyl]-4-hydroxyphenyl)-10b-methyl-1,2,3,4,4a,5,6,10b-octahydrobenzo[f]-quinolin-3-one A 15 mL round bottom flask was charged with (+)-(4aR)
-(10bR)-4-methyl-8-bromo-10b-methyl-1,2,3,4,4a,5,6,10b-
octahydrobenzo[f]quinolin-3-one (200 mg, 0.65 mmol), tetrakis (triphenylphosphine) palladium (0) (23 mg, 0.02 mmol), 3,5-di(t-butyl)-4-hydroxyphenylboronic acid (195 mg, 0.78 mmol), 0.65 mL of 2M sodium carbonate solution and 2 mL of THF, fitted with a reflux condenser, and the stirred mixture was heated at 80°, under nitrogen, for 16 h. The mixture was cooled, diluted with chloroform (50 mL) and washed with brine (2×25 mL). The combined organic extracts were dried over sodium sulfate, concentrated, and purified by silica gel chromatography (ethyl acetate eluent), to give 170 mg (58%) of the title compound as a white solid. mp>265°. FDMS: m/e=433 $\alpha[D]_{589}$=+46.45 (c=1.00, chloroform).

| Analysis | Calculated | Found |
|---|---|---|
| C | 80.33 | 78.52 |
| H | 9.06 | 9.01 |
| N | 3.23 | 2.69 |

EXAMPLE 31

(+)-(4aR)-(10bR)-4-methyl-8-(2-trifluoromethyl-4-fluoro-phenyl)-10b-methyl-1,2,3,4,4a,5,6,10b-octahydrobenzo[f]-quinolin-3-one A 15 mL round bottom flask was charged with (+)-(4aR)
-(10bR)-4-methyl-8-bromo-10b-methyl-1,2,3,4,4a,5,6,10b-
octahydrobenzo[f]quinolin-3-one (200 mg, 0.65 mmol), tetrakis (triphenylphosphine) palladium (0) (23 mg, 0.02 mmol), 2-trifluoromethyl-4-fluorophenylboronic acid (162 mg, 0.78 mmol), 0.65 mL of 2M sodium carbonate solution and 2 mL of THF, fitted with a reflux condenser, and the stirred mixture was heated at 80°, under nitrogen, for 24 h. The mixture was cooled, diluted with chloroform (75 mL) and washed with brine (2×25 mL). The combined organic extracts were dried over sodium sulfate, concentrated, and purified by silica gel chromatography (ethyl acetate eluent), to give 96 mg (38%) of the title compound as an amorphous foam. mp 70°. FDMS: m/e=391. $\alpha[D]_{589}$=+55.81 (c=0.60, chloroform).

| Analysis | Calculated | Found |
|---|---|---|
| C | 67.51 | 66.97 |
| H | 5.41 | 5.31 |
| N | 3.58 | 3.07 |

EXAMPLE 32

(+)-(4aR)-(10bR)-4-methyl-8-(1-[4-t-butylcarbonylamino]-naphthyl)-10b-methyl-1,2,3,4,4a,5,6,10b-octahydrobenzo [f]-quinolin-3-one A 15 mL round bottom flask was charged with (+)-(4aR)
-(10bR)-4-methyl-8-bromo-10b-methyl-1,2,3,4,4a,5,6,10b-
octahydrobenzo[f]quinolin-3-one (200 mg, 0.65 mmol), tetrakis (triphenylphosphine) palladium (0) (23 mg, 0.02 mmol), 4-(t-butylcarbonylamino)-1-naphthylboronic acid (211 mg, 0.78 mmol), 0.65 mL of 2M sodium carbonate solution and 2 mL of THF, fitted with a reflux condenser, and the stirred mixture was heated at 80°, under nitrogen, for 24 h. Additional palladium reagent and boronic acid was added, and the mixture was heated for an additional 24 h. The mixture was cooled, diluted with dichloromethane (75 mL) and washed with brine (2×25 mL). The combined organic extracts were dried over sodium sulfate, concentrated, and purified by silica gel chromatography (ethyl acetate eluent), to give 239 mg (81%) of the title compound as an amorphous solid. mp>260°. FDMS: m/e=454. $\alpha[D]_{589}$=+46.85 (c=0.51, chloroform).

| Analysis | Calculated | Found |
|---|---|---|
| C | 79.26 | 80.39 |
| H | 7.54 | 7.87 |
| N | 6.16 | 5.82 |

EXAMPLE 33

(+)-(4aR)-(10bR)-4-methyl-8-(2-chloro-5-trifluoromethylphenyl)-10b-methyl-1,2,3,4,4a,5,6,10b-octahydrobenzo[f]-quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis(triphenylphosphine) palladium (0) (23 mg, 0.02 mmol), 2-chloro-5-trifluoromethylphenylboronic acid (175 mg, 0.78 mmol), 0.65 mL of 2M sodium carbonate solution and 2 mL of THF, fitted with a reflux condenser, and the stirred mixture was heated at 80°, under nitrogen, for 24 h. The mixture was cooled, diluted with chloroform (50 mL) and washed with brine (2×25 mL). The combined organic extracts were dried over sodium sulfate, concentrated, and purified by silica gel chromatography (ethyl acetate eluent), to give 170 mg (64%) of the title compound as an oil. FDMS: m/e=407. α[D]$_{589}$=+49.42 (c=0.58, chloroform).

| Analysis | Calculated | Found |
|---|---|---|
| C | 64.79 | 65.65 |
| H | 5.19 | 5.39 |
| N | 3.43 | 3.75 |

EXAMPLE 34

(+)-(4aR)-(10bR)-4-methyl-8-(3-t-butylcarboxamidophenyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine) palladium (0) (23 mg, 0.02 mmol), 3-(t-butylcarboxamido)phenylboronic acid (172 mg, 0.78 mmol), 0.65 mL of 2M sodium carbonate solution and 2 mL of THF, fitted with a reflux condenser, and the stirred mixture was heated at 80°, under nitrogen, for 24 h. The mixture was cooled, diluted with chloroform (75 mL) and washed with brine (2×25 mL). The combined organic extracts were dried over sodium sulfate, concentrated, and purified by silica gel chromatography (ethyl acetate eluent), to give 213 mg (81%) of the title compound as a waxy solid. FDMS: m/e=404. α[D]$_{589}$=+54.34 (c=0.45, chloroform).

| Analysis | Calculated | Found |
|---|---|---|
| C | 77.19 | 77.45 |
| H | 7.97 | 7.93 |
| N | 6.92 | 6.64 |

EXAMPLE 35

(+)-(4aR)-(10bR)-4-methyl-8-(2-[1-diethylcarboxamido]-naphthyl)-10b-methyl-1,2,3,4,4a,5,6,10b-octahydrobenzo[f]-quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis(triphenylphosphine) palladium (0) (23 mg, 0.02 mmol), 1-(diethylcarboxamido)-2-naphthylboronic acid (211 mg, 0.78 mmol), 0.65 mL of 2M sodium carbonate solution and 2 mL of THF, fitted with a reflux condenser, and the stirred mixture was heated at 80°, under nitrogen, for 24 h. The mixture was cooled, diluted with chloroform (75 mL) and washed with brine (2×25 mL). The combined organic extracts were dried over sodium sulfate, concentrated, and purified by silica gel chromatography (ethyl acetate eluent), to give 240 mg (81%) of the title compound as a white solid. mp 208°–211°. FDMS: m/e=454. α[D]$_{589}$=+49.37 (c=0.51, chloroform).

| Analysis | Calculated | Found |
|---|---|---|
| C | 79.26 | 77.29 |
| H | 7.54 | 7.57 |
| N | 6.16 | 6.11 |

EXAMPLE 36

(+)-(4aR)-(10bR)-4-methyl-8-(4-hydroxy-3-methoxyphenyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine) palladium (0) (23 mg, 0.02 mmol), 4-hydroxy-3-methoxyphenylboronic acid (131 mg, 0.78 mmol), 0.65 mL of 2M sodium carbonate solution and 2 mL of THF, fitted with a reflux condenser, and the stirred mixture was heated at 80°, under nitrogen, for 24 h. The mixture was cooled, diluted with chloroform (75 mL) and washed with brine (2×25 mL). The combined organic extracts were dried over sodium sulfate, concentrated, and purified by silica gel chromatography (ethyl acetate eluent), to give 91 mg (40%) of the title compound as a white solid. mp 247°–250°. FDMS: m/e=351. α[D]$_{589}$=+79.51 (c=0.75, chloroform).

| Analysis | Calculated | Found |
|---|---|---|
| C | 75.19 | 75.13 |
| H | 7.17 | 7.24 |
| N | 3.99 | 3.97 |

EXAMPLE 37

(+)-(4aR)-(10bR)-4-methyl-8-(4-t-butylcarbonylaminophenyl)-10b-methyl-1,2,3,4,4a,5,6,10b-octahydrobenzo [f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine) palladium (0) (50 mg, 0.04 mmol), 4-t-butylcarbonylaminophenylboronic acid (172 mg, 0.78 mmol), 0.65 mL of 2M sodium carbonate solution and 2 mL of THF, fitted with a reflux condenser, and the stirred mixture was heated at 80°, under nitrogen, for 24 h. The mixture was cooled, diluted with chloroform (50 mL) and washed with brine (2×25 mL). The combined organic extracts were dried over sodium sulfate, concentrated, and purified by silica gel chromatography (ethyl acetate eluent), to give 104 mg (40% of the title compound as a brown solid.

mp>265° C. FDMS: m/e=404. α[D]$_{589}$=+49.42 (c=0.56, chloroform).

| Analysis | Calculated | Found |
|---|---|---|
| C | 77.19 | 76.92 |
| H | 7.97 | 8.07 |
| N | 6.92 | 6.73 |

EXAMPLE 38

(+)-(4aR)-(10bR)-4-methyl-8-(2-fluorophenyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mg, 0.65 mmol), tetrakis (triphenylphosphine) palladium (0) (23 mg, 0.02 mmol), 2-fluorophenylboronic acid (109 mg, 0.78 mmol), 0.65 mL of 2M sodium carbonate solution and 2 mL of THF, fitted with a reflux condenser, and the stirred mixture was heated at 80°, under nitrogen, for 16 h. The mixture was cooled, diluted with chloroform (75 mL) and washed with brine (2×25 mL). The combined organic extracts were dried over sodium sulfate, concentrated, and purified by silica gel chromatography (ethyl acetate eluent) to give 172 mg (82%) of the title compound as a foam. mp 142°–150°. FDMS: m/e=323. α[D]$_{589}$=+77.89 (c=0.69, chloroform).

| Analysis | Calculated | Found |
|---|---|---|
| C | 77.99 | 78.09 |
| H | 6.86 | 6.95 |
| N | 4.33 | 4.30 |

EXAMPLE 39

(+)-(4aR)-(10bR)-4-methyl-8-(2-methoxyphenyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine) palladium (0) (23 mg, 0.02 mmol), 2-methoxyphenylboronic acid (119 mg, 0.78 mmol), 0.65 mL of 2M sodium carbonate solution and 2 mL of THF, fitted with a reflux condenser, and the stirred mixture was heated at 80°, under nitrogen, for 24 h. The mixture was cooled, diluted with chloroform (50 mL) and washed with brine (2×25 mL). The combined organic extracts were dried over sodium sulfate, concentrated, and purified by silica gel chromatography (EtOAc eluent), to give 160 mg (73%) of the title compound as a white solid. mp 152°–156°. FDMS: m/e=335. α[D]$_{589}$=+77.45 (c=0.64, chloroform).

| Analysis | Calculated | Found |
|---|---|---|
| C | 78.77 | 78.53 |
| H | 7.51 | 7.25 |
| N | 4.18 | 4.35 |

EXAMPLE 40

(+)-(4aR)-(10bR)-4-methyl-8-(2-methylphenyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine) palladium (0) (23 mg, 0.02 mmol), 2-methylphenylboronic acid (106 mg, 0.78 mmol), 0.65 mL of 2M sodium carbonate solution and 2 mL of THF, fitted with a reflux condenser, and the stirred mixture was heated at 80°, under nitrogen, for 24 h. The mixture was cooled, diluted with chloroform (75 mL) and washed with brine (2×25 mL). The combined organic extracts were dried over sodium sulfate, concentrated, and purified by silica gel chromatography (ethyl acetate eluent), to give 146 mg (70%) of the title compound as an amorphous solid. mp 82°–87°. FDMS: m/e=319. α[D]$_{589}$=+63.96 (c=0.35, chloroform).

| Analysis | Calculated | Found |
|---|---|---|
| C | 82.72 | 82.63 |
| H | 7.89 | 7.95 |
| N | 4.38 | 4.10 |

EXAMPLE 41

(+)-(4aR)-(10bR)-4-methyl-8-(2-chlorophenyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine) palladium (0) (23 mg, 0.02 mmol), 2-chlorophenylboronic acid (122 mg, 0.78 mmol), 0.65 mL of 2M sodium carbonate solution and 2 mL of THF, fitted with a reflux condenser, and the stirred mixture was heated at 80°, under nitrogen, for 24 h. The mixture was cooled, diluted with chloroform (75 mL) and washed with brine (2×25 mL). The combined organic extracts were dried over sodium sulfate, concentrated, and purified by silica gel chromatography (ethyl acetate eluent), to give 186 mg (84%) of the title compound as an amorphous foam. mp 111°–120°. FDMS: m/e=339. α[D]$_{589}$=+56.86 (c=0.64, chloroform).

| Analysis | Calculated | Found |
|---|---|---|
| C | 74.22 | 74.50 |
| H | 6.52 | 6.46 |
| N | 4.12 | 3.82 |

EXAMPLE 42

(+)-(4aR)-(10bR)-4-methyl-8-(3,4-dimethoxyphenyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis(triphenylphosphine) palladium (0) (23 mg, 0.02 mmol), 3,4-dimethoxyphenylboronic acid (142 mg, 0.78 mmol), 0.65 mL of 2M sodium carbonate solution and 2 mL of THF, fitted with a reflux condenser, and the stirred mixture was heated at 80°, under nitrogen, for 24 h. The mixture was cooled, diluted with chloroform (75 mL) and washed with brine (2×25 mL). The combined organic extracts were dried over sodium sulfate, concentrated, and purified by silica gel chromatography (ethyl acetate eluent), to give 171 mg (72%) of the title compound as an amorphous foam. mp 108°–112°. FDMS: m/e=365. α[D]$_{589}$=+73.75 (c=0.56, chloroform).

| Analysis | Calculated | Found |
|---|---|---|
| C | 75.59 | 75.88 |
| H | 7.45 | 7.57 |
| N | 3.83 | 3.85 |

EXAMPLE 43

(+)-(4aR)-(10bR)-4-methyl-8-(2-trifluoromethylphenyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine) palladium (0) (23 mg, 0.02 mmol), 2-trifluoromethylphenylboronic acid (148 mg, 0.78 mmol), 0.65 mL of 2M sodium carbonate solution and 2 mL of THF, fitted with a reflux condenser, and the stirred mixture was heated at 80°, under nitrogen, for 24 h. The mixture was cooled, diluted with $CHCl_3$ (75 mL) and washed with brine (2×25 mL). The combined organic extracts were dried over sodium sulfate, concentrated, and purified by silica gel chromatography (ethyl acetate eluent), to give 201 mg (83%) of the title compound as an oil. FDMS: m/e=373. $\alpha[D]_{589}$=+60.00 (c=0.36, chloroform).

| Analysis | Calculated | Found |
|---|---|---|
| C | 70.76 | 70.55 |
| H | 5.94 | 7.97 |
| N | 3.75 | 3.49 |

EXAMPLE 44

(+)-(4aR)-(10bR)-4-methyl-8-(3-fluorophenyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine) palladium (0) (23 mg, 0.02 mmol), 3-fluorophenylboronic acid (109 mg, 0.78 mmol), 0.65 mL of 2M sodium carbonate solution and 2 mL of THF, fitted with a reflux condenser, and the stirred mixture was heated at 80°, under nitrogen, for 18 h. The mixture was cooled, diluted with chloroform (75 mL) and washed with brine (2×25 mL). The combined organic extracts were dried over sodium sulfate, concentrated, and purified by silica gel chromatography (ethyl acetate eluent), to give 177 mg (84%) of the title compound as an amorphous foam. mp 116°–120°. FDMS: m/e=323. $\alpha[D]_{589}$=+81.84 (c=0.47, chloroform).

| Analysis | Calculated | Found |
|---|---|---|
| C | 77.99 | 77.69 |
| H | 6.86 | 6.85 |
| N | 4.33 | 4.11 |

EXAMPLE 45

(+)-(4aR)-(10bR)-8-(3-quinolinyl)-10b-methyl-1,2,3,4,4a,-5,6,10b-octahydrobenzo[f]quinolin-3-one A 15 mL round bottom flask was charged with (+)-(4aR)-(10bR)-10b-methyl-1,2,3,4,4a,-5,6,10b-octahydrobenzo[f] quinolin-3-one-8-boronic acid (168 mg, 0.65 mmol) (prepared in Prep. 9 below), tetrakis (triphenylphosphine)-palladium(0) (23 mg, 0.02 mmol), 3-bromoquinoline (135 mg, 0.65 mmol), 0.65 mL of 2M sodium carbonate and 2 mL of THF, fitted with a reflux condenser, and the stirred mixture was heated at 80°, under nitrogen, for 24 h. The mixture was cooled, diluted with chloroform (75 mL) and washed with brine (2×25 mL). The combined organic extracts were dried over sodium sulfate, concentrated, and purified by silica gel chromatography (5% methanol/ethyl acetate eluent) to give 141 mg (63%) of the title compound as a white solid. mp 265°–266°. FDMS: m/e=342. $\alpha[D]_{589}$=+88.70 (c=0.84, chloroform)

EXAMPLE 46

(+)-(4aR)-(10bR)-4-methyl-8-(4-fluoro-3-trifluoromethyl-phenyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine) palladium (0) (23 mg, 0.02 mmol), 4-fluoro-3-trifluoromethylphenylboronic acid (162 mg, 0.78 mmol), 0.65 mL of 2M sodium carbonate solution and 2 mL of THF, fitted with a reflux condenser, and the stirred mixture was heated at 80°, under nitrogen, for 18 h. The mixture was cooled, diluted with chloroform (75 mL) and washed with brine (2×25 mL). The combined organic extracts were dried over sodium sulfate, concentrated, and purified by silica gel chromatography (ethyl acetate eluent) to give 110 mg (43%) of the title compound as an amorphous foam. FDMS: m/e=323. $\alpha[D]_{589}$=+51.47 (c=0.52, chloroform).

| Analysis | Calculated | Found |
|---|---|---|
| C | 67.51 | 67.80 |
| H | 5.41 | 5.46 |
| N | 3.58 | 3.32 |

EXAMPLE 47

(+)-(4aR)-10bR)-4-methyl-8-(4-methoxyphenyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,5,10b-octahydrobenzo[f]quinolin-3-one (200 mg, 0.65 mmol), tetrakis (triphenylphosphine) palladium (0) (23 mg, 0.02 mmol), 4-methoxyphenylboronic acid (119 mg, 0.78 mmol), 0.65 mL of 2M sodium carbonate solution and 1.5 mL of toluene, fitted with a reflux condenser, and the stirred mixture was heated at 80°, under nitrogen, for 16 h. The mixture was cooled, diluted with dichloromethane (75 mL) and washed with brine (2×25 mL). The combined organic extracts were dried over sodium sulfate, concentrated, and purified by silica gel chromatography (ethyl acetate eluent), followed by recrystallization from ethyl acetate to give 173 mg (79%) of the title compound as a white solid. mp 150°. FDMS: m/e=335. $\alpha[D]_{589}$=+73.82 (c=1.01, methanol).

| Analysis | Calculated | Found |
|---|---|---|
| C | 78.77 | 78.49 |
| H | 7.51 | 7.44 |
| N | 4.18 | 4.43 |

EXAMPLE 48

(+)-(4aR)-(10bR)-4-methyl-8-(3-methoxyphenyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine) palladium (0) (23 mg, 0.02 mmol), 3-methoxyphenylboronic acid (119 mg, 0.78 mmol), 0.65 mL of 2M sodium carbonate solution and 1.5 mL of toluene fitted with a reflux condenser, and the stirred mixture was heated at 80°, under nitrogen, for 24 h The mixture was cooled, diluted with dichloromethane (75 mL) and washed with brine (2×25 mL). The combined organic extracts were dried over sodium sulfate, concentrated, and purified by silica gel chromatography (ethyl acetate eluent) to give 144 mg (66%) of the title compound as a white solid. mp 140°. FDMS: m/e=335. $\alpha[D]_{589}$=+77.45 (c=1.02, chloroform).

| Analysis | Calculated | Found |
|---|---|---|
| C | 78.77 | 78.53 |
| H | 7.51 | 7.50 |
| N | 4.18 | 3.92 |

EXAMPLE 49

(+)-(4aR)-10bR)-4-methyl-8-phenyl-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine) palladium (0) (23 mg, 0.02 mmol), phenylboronic acid (95 mg, 0.78 mmol), 0.65 mL of 2M sodium carbonate solution and 2 mL of toluene, fitted with a reflux condenser, and the stirred mixture was heated at 80°, under nitrogen, for 24 h. The mixture was cooled, diluted with dichloromethane (75 mL) and washed with brine (2×25 mL). The combined organic extracts were dried over sodium sulfate, concentrated, and purified by silica gel chromatography (ethyl acetate eluent), followed by recrystallization from ethyl acetate, to give 139 mg (70%) of the title compound as a white solid. mp 155°. FDMS: m/e=305.

| Analysis | Calculated | Found |
|---|---|---|
| C | 82.59 | 82.79 |
| H | 7.59 | 7.59 |
| N | 4.59 | 4.39 |

EXAMPLE 50

(+)-(4aR)-(10bR)-4-methyl-8-(4-chlorophenyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine) palladium (0) (23 mg, 0.02 mmol), 4-chlorophenylboronic acid (122 mg, 0.78 mmol), 0.65 mL of 2M sodium carbonate solution and 2 mL of toluene, fitted with a reflux condenser, and the stirred mixture was heated at 80°, under nitrogen, for 16h. The mixture was cooled, diluted with dichloromethane (75 mL) and washed with brine (2×25 mL). The combined organic extracts were dried over sodium sulfate, concentrated, and purified by silica gel chromatography (ethyl acetate eluent) followed by recrystallization from ethyl acetate, to give 166 mg (75%) of the title compound as a white solid. mp 192°. FDMS: m/e=339. $\alpha[D]_{589}$=+76.14 (c=1.00, chloroform).

| Analysis | Calculated | Found |
|---|---|---|
| C | 74.22 | 74.17 |
| H | 6.52 | 6.68 |
| N | 4.12 | 3.97 |

EXAMPLE 51

(+)-(4aR)-(10bR )-4-methyl-8-(4-methylphenyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine) palladium (0) (23 mg, 0.02 mmol), 4-methylphenylboronic acid (106 mg, 0.78 mmol), 0.65 mL of 2M sodium carbonate solution and 2 mL of toluene, fitted with a reflux condenser, and the stirred mixture was heated at 80°, under nitrogen, for 17 h. The mixture was cooled, diluted with dichloromethane (75 mL) and washed with brine (2×25 mL). The combined organic extracts were dried over sodium sulfate, concentrated, and purified by silica gel chromatography (ethyl acetate eluent), followed by recrystallization from ethyl acetate, to give 150 mg (72%) of the title compound as a white solid. mp 178°. FDMS: m/e=319. $\alpha[D]_{589}$=+77.14 (c=1.00, chloroform).

| Analysis | Calculated | Found |
|---|---|---|
| C | 82.72 | 82.66 |
| H | 7.89 | 7.95 |
| N | 4.38 | 4.20 |

EXAMPLE 52

(+)-(4aR)-(10bR)-4-methyl-8-(3,5-dichlorophenyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine) palladium (0) (23 mg, 0.02 mmol), 3,5-dichlorophenylboronic acid (149 mg, 0.78 mmol), 0.65 mL of 2M sodium carbonate solution and 1.5 mL of toluene, fitted with a reflux condenser, and the stirred mixture was heated at 80°, under nitrogen, for 24 h. The mixture was cooled, diluted with dichloromethane (75 mL) and washed with brine (2×25 mL). The combined organic extracts were dried over sodium sulfate, concentrated, and purified by silica gel chromatography (ethyl acetate eluent), followed by recrystallization from ethyl acetate to give 145 mg (60%) of the title compound as a white solid. mp 172°. FDMS: m/e=374 $\alpha[D]_{589}$=+70.91 (c=0.55, chloroform).

| Analysis | Calculated | Found |
|---|---|---|
| C | 67.39 | 67.43 |
| H | 5.65 | 5.67 |
| N | 3.74 | 3.65 |

EXAMPLE 53

(+)-(4aR)-(10bR)-4-methyl-8-(1-naphthyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b- octahydrobenzo[f]quinolin-3-one (200 mg, 0.65 mmol), tetrakis (triphenylphosphine) palladium (0) (23 mg, 0.02 mmol), 1-naphthylboronic acid 134 mg, 0.78 mmol), 0.65 mL of 1M sodium hydroxide solution and 2 mL of benzene, fitted with a reflux condenser, and the stirred mixture was heated at 80°, under nitrogen, for 24 h. The mixture was cooled, diluted with dichloromethane (75 mL) and washed with brine (2×25 mL). The combined organic extracts were dried over sodium sulfate, concentrated, and purified by silica gel chromatography (ethyl acetate eluent), followed by recrystallization from ethyl acetate to give 116 mg (50%) of the title compound as a white solid. mp 159°. FDMS: m/e=355. $\alpha[D]_{589}$=+60.00 (c=0.50, chloroform).

| Analysis | Calculated | Found |
|---|---|---|
| C | 84.47 | 84.73 |
| H | 7.09 | 7.08 |
| N | 3.94 | 3.89 |

EXAMPLE 54

(+)-(4aR)-(10bR)-4-methyl-8-(3-pyridyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine) palladium (0) (30 mg, 0.03 mmol), tetrabutylammonium bromide (17 mg, 0.05 mmol), diethyl(3-pyridyl)borane (148 mg, 0.98 mmol), powdered potassium hydroxide (85 mg, 1.4 mmol) and 3 mL of DME, fitted with a reflux condenser, and the stirred mixture was heated at 80°, under nitrogen, for 24 h. The mixture was cooled, diluted with water (15 mL), extracted with 10% methanol in dichloromethane (2×50 mL) and washed with brine (2×25 mL). The combined organic extracts were dried over sodium sulfate, concentrated, and purified by silica gel chromatography (ethyl acetate eluent), to give 112 mg (56%) of the title compound as a white solid. mp 135°. FDMS: m/e=306.

| Analysis | Calculated | Found |
|---|---|---|
| C | 78.40 | 78.37 |
| H | 7.24 | 7.37 |
| N | 9.14 | 9.14 |

EXAMPLE 55

(+)-(4aR)-(10bR)-4-methyl-8-(3-biphenyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine) palladium (0) (23 mg, 0.02 mmol), 3-biphenylboronic acid (154 mg, 0.78 mmol), 0.65 mL of 2M sodium carbonate solution and 2 mL of toluene, fitted with a reflux condenser, and the stirred mixture was heated at 80°, under nitrogen, for 24 h. The mixture was cooled, diluted with dichloromethane/ether (3:1, 75 mL) and washed with brine (2×25 mL). The combined organic extracts were dried over sodium sulfate, concentrated, and purified by silica gel chromatography (ethyl acetate eluent), to give 176 mg (71%) of the title compound as a white solid. mp 131°. FDMS: m/e=381. $\alpha[D]_{589}$=+71.15 (c=0.53, CHCl$_3$).

| Analysis | Calculated | Found |
|---|---|---|
| C | 85.00 | 84.77 |
| H | 7.13 | 7.31 |
| N | 3.67 | 3.46 |

EXAMPLE 56

(+)-(4aR)-(10bR)-4-methyl-8-(4-phenoxyphenyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine) palladium (0) (23 mg, 0.02 mmol), 4-phenoxyphenylboronic acid (167 mg, 0.78 mmol), 0.65 mL of 2M sodium carbonate solution and 2 mL of toluene, fitted with a reflux condenser, and the stirred mixture was heated at 80°, under nitrogen, for 24 h. The mixture was cooled, diluted with chloroform (75 mL) and washed with brine (2×25 mL). The combined organic extracts were dried over sodium sulfate, concentrated, and purified by silica gel chromatography (ethyl acetate eluent), to give 206 mg (80%) of the title compound as a white solid. mp 148°–150°. FDMS: m/e=397. $\alpha[D]_{589}$=+64.51 (c=0.62, chloroform).

| Analysis | Calculated | Found |
|---|---|---|
| C | 81.58 | 81.47 |
| H | 6.85 | 8.83 |
| N | 3.52 | 3.60 |

EXAMPLE 57

(+)-(4aR)-(10bR)-4-methyl-8-(3-formylphenyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine) palladium (0) (23 mg, 0.02 mmol), 3-formylphenylboronic acid (117 mg, 0.78 mmol), 0.65 mL of 2M sodium carbonate solution and 2 mL of toluene, fitted with a reflux condenser, and the stirred mixture was heated at 80°, under nitrogen for 24 h. The mixture was cooled, diluted with dichloromethane (75 mL) and washed with brine (2×25 mL). The combined organic extracts were dried over sodium sulfate, concentrated, and purified by silica gel chromatography (ethyl acetate eluent), to give 141 mg (65%) of the title compound as a white solid. mp 163°. FDMS: m/e=333.

| Analysis | Calculated | Found |
|---|---|---|
| C | 79.25 | 79.16 |
| H | 6.95 | 6.99 |
| N | 4.20 | 3.92 |

EXAMPLE 58

(+)-(4aR)-(10bR)-4-methyl-8-(3-formyl-4-hydroxyphenyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b- octahydrobenzo[f]quinolin-3-one (200 mg, 0.65 mmol), tetrakis(triphenylphosphine) palladium (0) (23 mg, 0.02 mmol), 3-formyl-4-hydroxyphenylboronic acid (129 mg, 0.78 mmol), 0.65 mL of 2M sodium carbonate solution and 2 mL of toluene, fitted with a reflux condenser, and the stirred mixture was heated at 80°, under nitrogen, for 24 h. Additional palladium reagent and boronic acid was added, and the mixture was heated for an additional 24 h. The mixture was cooled, diluted with dichloromethane (75 mL) and washed with brine (2×25 mL). The combined organic extracts were dried over sodium sulfate, concentrated, and purified by silica gel chromatography (ethyl acetate eluent), followed by recrystallization from ethyl acetate, to give 85 mg (37%) of the title compound as a white solid. mp 184°–187°. FDMS: m/e=349.

| Analysis | Calculated | Found |
|---|---|---|
| C | 75.62 | 75.86 |
| H | 6.63 | 6.72 |
| N | 4.01 | 3.87 |

EXAMPLE 59

(+)-(4aR)-(10bR)-4-methyl-8-(4-dimethylaminophenyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine) palladium (0) (23 mg, 0.02 mmol), 4-dimethylaminophenylboronic acid (129 mg, 0.78 mmol), 0.65 mL of 2M sodium carbonate solution and 2 mL of toluene, fitted with a reflux condenser, and the stirred mixture was heated at 80°, under nitrogen, for 17 h. The mixture was cooled, diluted with dichloromethane 75 mL) and washed with brine (2×25 mL). The combined organic extracts were dried over sodium sulfate, concentrated, and purified by silica gel chromatography (ethyl acetate eluent), no give 119 mg (53%) of the title compound as an amorphous foam. mp 197°–202°. FDMS: m/e=348. α[D]$_{589}$=+76.84 (c=0.95, chloroform).

| Analysis | Calculated | Found |
|---|---|---|
| C | 78.27 | 77.92 |
| H | 8.10 | 8.12 |
| N | 8.04 | 7.84 |

EXAMPLE 60

(+)-(4aR)-(10bR)-4-methyl-8-(2-[6-hydroxy]naphthyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine) palladium (0) (50 mg, 0.04 mmol), 6-hydroxy-2-naphthylboronic acid (147 mg, 0.78 mmol), 0.65 mL of 2M sodium carbonate solution and 2 mL of toluene, fitted with a reflux condenser, and the stirred mixture was heated at 80°, under nitrogen, for 24 h. Additional palladium reagent and boronic acid was added, and the mixture was heated for an additional 24 h. The mixture was cooled, diluted with dichloromethane (75 mL) and washed with brine (2×25 mL). The aqueous layer was acidified with 5N hydrochloric acid, and extracted with dichloromethane. The combined organic extracts were dried over sodium sulfate, concentrated, and purified by silica gel chromatography (ethyl acetate eluent) to give 47 mg (20%) of the title compound as a white solid. mp >260° (decomp.) FDMS: m/e=371.

| Analysis | Calculated | Found |
|---|---|---|
| C | 80.83 | 79.84 |
| H | 6.78 | 6.73 |
| N | 3.77 | 3.25 |

EXAMPLE 61

(+)-(4aR)-(10bR)-4-methyl-8-(9-anthracenyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine) palladium (0) (23 mg, 0.02 mmol), 9-anthracenylboronic acid (159 mg, 0.78 mmol), 0.65 mL of sodium carbonate and 2 mL of toluene, fitted with a reflux condenser, and the stirred mixture was heated at 80°, under nitrogen, for 48 h. The mixture was cooled, diluted with chloroform (75 mL) and washed with brine (2×25 mL). The combined organic extracts were dried over sodium sulfate, concentrated, and purified by silica gel chromatography (EtOAc eluent) to give 112 mg (43%) of the title compound as an amorphous solid. mp 95°–110°. FDMS: m/e=405. α[D]$_{589}$=+45.73 (c=0.66, chloroform).

| Analysis | Calculated | Found |
|---|---|---|
| C | 85.89 | 84.93 |
| H | 6.71 | 6.55 |
| N | 3.45 | 3.01 |

EXAMPLE 62

(+)-(4aR)-(10bR)-4-methyl-8-(2-[6-benzyloxy]naphthyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine) palladium (0) (23 mg, 0.02 mmol), 6-benzyloxy-2-naphthylboronic acid (200 mg, 0.72 mmol), 0.65 mL of 2M sodium carbonate solution and 2 mL of toluene, fitted with a reflux condenser, and the stirred mixture was heated at 80°, under nitrogen, for 24 h. Additional palladium reagent and boronic acid was added, and the mixture was heated for an additional 24 h. The mixture was cooled, diluted with dichloromethane (75 mL) and washed with brine (2×25 mL). The combined organic extracts were dried over sodium sulfate, concentrated, and purified by silica gel chromatography (ethyl acetate eluent), followed by recrystallization from ethyl acetate, to give 73 mg (24%) of the title compound as a white solid. mp 173°–176° FDMS: m/e=361. α[D]$_{589}$=+66.07 (c=0.56, chloroform).

| Analysis | Calculated | Found |
|---|---|---|
| C | 83.26 | 83.50 |
| H | 6.77 | 6.84 |
| N | 3.03 | 3.03 |

EXAMPLE 63

(+)-(4aR)-(10bR)-4-methyl-8-(3-chlorophenyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine) palladium (0) (23 mg, 0.02 mmol), 3-chlorophenylboronic acid (122 mg, 0.78 mmol), 0.65 mL of 2M sodium carbonate solution and 1.5 mL of toluene, fitted with a reflux condenser, and the stirred mixture was heated at 80°, under nitrogen, for 24 h. The mixture was cooled, diluted with dichloromethane (75 mL) and washed with brine (2×25 mL). The combined organic extracts were dried over sodium sulfate, concentrated, and purified by silica gel chromatography (ethyl acetate eluent), to give 164 mg (74%) of the title compound as an amorphous foam. mp 158°–65°. FDMS: m/e=339. $\alpha[D]_{589}$=+74.90 (c=1.00, methanol).

| Analysis | Calculated | Found |
|---|---|---|
| C | 74.22 | 73.95 |
| H | 6.52 | 6.51 |
| N | 4.12 | 4.89 |

EXAMPLE 64

(+)-(4aR)-(10bR)-4-methyl-8-(1-[4-fluoro]naphthyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine) palladium (0) (23 mg, 0.02 mmol), 4-fluoro-1-naphthylboronic acid (148 mg, 0.78 mmol), triethylamine (0.2 mL, 1.3 mmol), and 2 mL of DME, fitted with a reflux condenser, and the stirred mixture was heated at 80°, under nitrogen, for 24 h. The mixture was cooled, diluted with dichloromethane (75 mL) and washed with brine (2×25 mL). The combined organic extracts were dried over sodium sulfate, concentrated, and purified by silica gel chromatography (ethyl acetate eluent), to give 188 mg (77%) of the title compound as an amorphous foam. mp 115°–125°. FDMS: m/e=373. $\alpha[D]_{589}$=+60.78 (c=1.02, chloroform).

| Analysis | Calculated | Found |
|---|---|---|
| C | 80.40 | 78.80 |
| H | 6.48 | 6.35 |
| N | 3.75 | 3.41 |

EXAMPLE 65

(+)-(4aR)-(10bR)-4-methyl-8-(1-[4-methyl]naphthyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis(triphenylphosphine) palladium (0) (23 mg, 0.02 mmol), 4-methyl-1-naphthylboronic acid (145 mg, 0.78 mmol), triethylamine (0.2 mL, 1.3 mmol), and 2 mL of dimethyl ether, fitted with a reflux condenser, and the stirred mixture was heated at 80°, under nitrogen, for 24 h. The mixture was cooled, diluted with dichloromethane (75 mL) and washed with brine (2×25 mL). The combined organic extracts were dried over sodium sulfate, concentrated, and purified by silica gel chromatography (ethyl acetate eluent), followed by recrystallization from diethyl ether to give 36 mg (15%) of the title compound as a white solid. mp 175°–178°. FDMS: m/e=369. $\alpha[D]_{589}$=+63.81 (c=1.05, chloroform).

| Analysis | Calculated | Found |
|---|---|---|
| C | 84.51 | 84.73 |
| H | 7.36 | 7.44 |
| N | 3.79 | 3.54 |

EXAMPLE 66

(+)-(4aR)-(10bR)-4-methyl-8-(5-acenaphthenyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin- 3-one (200 mg, 0.65 mmol), tetrakis (triphenylphosphine) palladium (0) (23 mg, 0.02 mmol), 5-acenaphtheneboronic acid (154 mg, 0.78 mmol), 0.20 mL of triethylamine and 2 mL of DME, fitted with a reflux condenser, and the stirred mixture was heated at 80°, under nitrogen, for 24 h. The mixture was cooled, diluted with chloroform (75 mL) and washed with brine (2×25 mL). The combined organic extracts were dried over sodium sulfate, concentrated, and purified by silica gel chromatography (ethyl acetate eluent) to give 170 mg (69%) of the title compound as a white solid. mp>200° (decomp.) FDMS: m/e=381 $\alpha[D]_{589}$=+61.47 (c=0.84, chloroform).

| Analysis | Calculated | Found |
|---|---|---|
| C | 85.00 | 85.24 |
| H | 7.13 | 7.17 |
| N | 3.67 | 3.51 |

EXAMPLE 67

(+)-(4aR)-(10bR)-4-methyl-8-(9-phenanthrenyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine) palladium (0) (23 mg, 0.02 mmol), 9-phenanthreneboronic acid (173 mg, 0.78 mmol), triethylamine (0.2 mL, 1.3 mmol), and 2 mL of dimethyl ether, fitted with a reflux condenser, and the stirred mixture was heated at 80°, under nitrogen, for 24 h. The mixture was cooled, diluted with chloroform (75 mL) and washed with brine (2×25 mL). The combined organic extracts were dried over sodium sulfate, concentrated, and purified by silica gel chromatography (ethyl acetate eluent), to give 80 mg (30%) of the title compound as a white solid. mp 218°–220°.

FDMS: m/e=405. α[D]$_{589}$=+63.01 (c=0.98, chloroform).

| Analysis | Calculated | Found |
|---|---|---|
| C | 85.89 | 86.06 |
| H | 6.71 | 6.83 |
| N | 3.45 | 3.39 |

EXAMPLE 68

(+)-(4aR-(10bR)-4-methyl-8-(4-[N-propyl, N-cyclopropylmethylamino]-1-naphthyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine)palladium(0) (23 mg, 0.02 mmol), 4-(N-propyl, N-cyclopropylmethylamino)-1-naphthyl-boronic acid (249 mg, 0.78 mmol), 1.8 mL of 2M sodium carbonate solution and 2 mL of THF, fitted with a reflux condenser, and the stirred mixture was heated at 80°, under nitrogen, for 24 h. The mixture was cooled, diluted with chloroform (75 mL) and washed with brine (2×50 mL). The combined organic extracts were dried over sodium sulfate, concentrated, and purified by silica gel chromatography (ethyl acetate eluent), to give 193 mg (64%) of the title compound as an oil. FDMS: m/e=466. α[D]$_{589}$=+50.52 (c=0.95, chloroform).

EXAMPLE 69

(+)-(4aR)-(10bR)-4-methyl-8-(2,3-dimethylphenyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine)palladium(0) (23 mg, 0.02 mmol), 2,3-dimethylphenylboronic acid (117 mg, 0.78 mmol), 0.65 mL of 2M sodium carbonate solution and 2 mL of THF, fitted with a reflux condenser, and the stirred mixture was heated at 80°, under nitrogen, for 24 h. The mixture was cooled, diluted with chloroform (50 mL) and washed with brine (2×50 mL). The combined organic extracts were dried over sodium sulfate, concentrated, and purified by silica gel chromatography (ethyl acetate eluent), to give 55 mg (25 %) of the title compound as an amorphous solid. mp 133°–140°. FDMS: m/e=333. α[D]$_{589}$=+61.90 (c=1.05, methanol).

| Analysis | Calculated | Found |
|---|---|---|
| C | 82.84 | 82.64 |
| H | 8.16 | 8.07 |
| N | 4.20 | 4.15 |

EXAMPLE 70

(+)-(4aR)-(10bR)-4-methyl-8-(3,4-methylenedioxyphenyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis(triphenylphosphine)palladium(0) (23 mg, 0.02 mmol), 3,4-methylenedioxyphenyl boronic acid (131 mg, 0.78 mmol), 0.65 mL of 2M sodium carbonate solution and 2 mL of THF, fitted with a reflux condenser, and the stirred mixture was heated at 80°, under nitrogen, for 24 h. The mixture was cooled, diluted with chloroform (50 mL) and washed with brine (2×25 mL). The combined organic extracts were dried over sodium sulfate, concentrated, and purified by silica gel chromatography (ethyl acetate eluent), to give 130 mg (57%) of the title compound as an amorphous solid. mp 146°–152°. FDMS: m/e=349. α[D]$_{589}$=+67.92 (c=1.06, chloroform).

| Analysis | Calculated | Found |
|---|---|---|
| C | 75.62 | 75.46 |
| H | 6.63 | 6.77 |
| N | 4.01 | 3.80 |

EXAMPLE 71

(+)-(4aR)-(10bR)-4-methyl-8-(2-naphthyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine)palladium(0) (23 mg, 0.02 mmol), 2-naphthylboronic acid (168 mg, 0.98 mmol), 0.65 mL of 2M sodium carbonate solution and 2 mL of THF, fitted with a reflux condenser, and the stirred mixture was heated at 80° for 16 h. The mixture was cooled, diluted with chloroform (75 mL) and washed with brine (2×25 mL). The combined organic extracts were dried over sodium sulfate, concentrated, and purified by silica gel chromatagraphy (ethyl acetate eluent) to give 126 mg (55%) of the title compound as a white solid. mp 221°–223°. FDMS: m/e=355. α[D]$_{589}$=+73.58 (C=1.06, chloroform).

| Analysis | Calculated | Found |
|---|---|---|
| C | 84.47 | 84.63 |
| H | 7.09 | 7.06 |
| N | 3.94 | 3.93 |

EXAMPLE 72

(+)-(4aR)-(10bR)-4-methyl-8-(1-[2-methyl]naphthyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine)palladium(0) (23 mg, 0.02 mmol), 2-methyl-1-naphthylboronic acid (182 mg, 0.98 mmol), 0.65 mL of 2M sodium carbonate solution and 2 mL of THF, fitted with a reflux condenser, and the stirred mixture was heated at 80°, under nitrogen, for 24 h. The mixture was cooled, diluted with chloroform (50 mL) and washed with brine (2×50 mL). The combined organic extracts were dried over sodium sulfate, concentrated, and purified by silica gel chromatography (ethyl acetate eluent), to give 104 mg (44%) of the title compound as a white solid. mp 196°–200°. FDMS: m/e=369. α[D]$_{589}$=+54.72 (c=1.06, chloroform).

| Analysis | Calculated | Found |
|---|---|---|
| C | 84.51 | 84.27 |
| H | 7.36 | 7.42 |
| N | 3.79 | 3.93 |

EXAMPLE 73

(+)-(4aR)-(10bR)-4-methyl-8-(2,3-dichlorophenyl)-10b-methyl-1,2,3,4,4a,5,6,10b-octahydrobenzo[f]quinolin-3-one A 15 mL round bottom flask was charged with (+)-(4aR)-g(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine)palladium(0) (23 mg, 0.02 mmol), 2,3-dichlorophenylboronic acid (187 mg, 0.98 mmol), 0.65 mL of 2M sodium carbonate solution and 2 mL of THF, fitted with a reflux condenser, and the stirred mixture was heated at 80°, under nitrogen, for 16 h. The mixture was cooled, diluted with chloroform (50 mL) and washed with brine (2×50 mL). The combined organic extracts were dried over sodium sulfate, concentrated, and purified by silica gel chromatography (ethyl acetate eluent), to give 193 mg (79%) of the title compound as an off-white solid. mp 131°–134°. FDMS: m/e=373 $\alpha[D]_{589}$=+81.02 (c=1.05, chloroform).

| Analysis | Calculated | Found |
|---|---|---|
| C | 67.39 | 68.46 |
| H | 5.65 | 5.70 |
| N | 3.74 | 3.75 |

EXAMPLE 74

(+)-(4aR)-(10bR)-4-methyl-8-(2-[N,N-diethylcarboxamido]-phenyl)-10b-methyl-1,2,3,4,4a,5,6,10b-octahydrobenzo[f]-quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenytphosphine)palladium(0) (23 mg, 0.02 mmol), 2-(N,N-diethylcarboxamido)phenylboronic acid (218 mg, 0.98 mmol), 0.65 mL of 2M sodium carbonate solution and 2 mL of THF, fitted with a reflux condenser, and the stirred mixture was heated at 80°, under nitrogen, for 24 h. The mixture was cooled, diluted with chloroform (50 mL) and washed with brine (2×25 mL). The combined organic extracts were dried over sodium sulfate, concentrated, and purified by silica gel chromatography (ethyl acetate eluent), to give 180 mg (68%) of the title compound as a white solid. mp 147°–149°. FDMS: m/e=404 $\alpha[D]_{589}$=+56.86 (c=1.02, chloroform).

| Analysis | Calculated | Found |
|---|---|---|
| C | 77.19 | 76.99 |
| H | 7.97 | 8.05 |
| N | 6.92 | 6.87 |

EXAMPLE 75

(+)-(4aR)-(10bR)-4-methyl-8-(4-t-butylphenyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine)palladium(0) (23 mg, 0.02 mmol), 4-t-butylphenylboronic acid (139 mg, 0.78 mmol), 0.65 mL of 2M sodium carbonate solution and 2 mL of THF, fitted with a reflux condenser, and the stirred mixture was heated at 80°, under nitrogen, for 16 h. The mixture was cooled, diluted with chloroform (50 mL) and washed with brine (2×25 mL). The combined organic extracts were dried over sodium sulfate, concentrated, and purified by silica gel chromatography (ethyl acetate eluent), to give 163 mg (69%) of the title compound as an amorphous solid. mp 141°–147°. FDMS: m/e=361 $\alpha[D]_{589}$=+67.88 (c=1.05, chloroform).

| Analysis | Calculated | Found |
|---|---|---|
| C | 83.06 | 83.34 |
| H | 8.64 | 8.72 |
| N | 3.87 | 3.76 |

EXAMPLE 76

(+)-(4aR)-(10bR)-4-methyl-8-(4-n-butylphenyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine)palladium(0) (23 mg, 0.02 mmol), 4-n-butylphenylboronic acid (139 mg, 0.78 mmol), 0.65 mL of 2M sodium carbonate solution and 2 mL of THF, fitted with a reflux condenser, and the stirred mixture was heated at 80°, under nitrogen, for 24 h. The mixture was cooled, diluted with chloroform (75 mL) and washed with brine (2×25 mL). The combined organic extracts were dried over sodium sulfate, concentrated, and purified by silica gel chromatography (ethyl acetate eluent), to give 180 mg (77%) of the title compound as a white solid. mp 102°–108°. FDMS: m/e=361. $\alpha[D]_{589}$=+68.70 (c=1.05, chloroform).

| Analysis | Calculated | Found |
|---|---|---|
| C | 83.06 | 82.98 |
| H | 8.64 | 8.73 |
| N | 3.87 | 3.64 |

EXAMPLE 77

(+)-(4aR)-(10bR)-4-methyl-8-(3,4-dichlorophenyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine)palladium(0) (23 mg, 0.02 mmol), 3,4-dichlorophenylboronic acid (149 mg, 0.78 mmol), 0.65 mL of 2M sodium carbonate solution and 2 mL of THF, fitted with a reflux condenser, and the stirred mixture was heated at 80°, under nitrogen, for 16 h. The mixture was cooled, diluted with chloroform (75 mL) and washed with brine (2×25 mL). The combined organic extracts were dried over sodium sulfate, concentrated, and purified by silica gel chromatography (ethyl acetate eluent) to give 156 mg (64%) of the title compound as a foam. mp 129°–135°. FDMS: m/e=374. $\alpha[D]_{589}$=+68.66 (c=1.03, chloroform).

| Analysis | Calculated | Found |
|---|---|---|
| C | 67.39 | 68.37 |
| H | 5.65 | 5.81 |
| N | 3.74 | 3.63 |

EXAMPLE 78

(+)-(4aR)-(10bR)-4-methyl-8-(4-trifluoromethoxyphenyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine)palladium(0) (23 mg, 0.02 mmol), 4-trifluoromethoxyphenylboronic acid (161 mg, 0.78 mmol), 0.65 mL of 2M sodium carbonate solution and 2 mL of THF, fitted with a reflux condenser, and the stirred mixture was healed at 80°, under nitrogen, for 24 h. The mixture was cooled, diluted with chloroform (50 mL) and washed with brine (2×25 mL). The combined organic extracts were dried over sodium sulfate, concentrated, and purified by silica gel chromatography (ethyl acetate eluent), to give 137 mg (56%) of the title compound as a waxy solid. FDMS: m/e=389. $\alpha[D]_{589}$=+48.95 (c=0.96, chloroform).

EXAMPLE 79

(+)-(4aR)-(10bR)-4-methyl-8-(4-trifluoromethylphenyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine)palladium(0) (23 mg, 0.02 mmol), 4-trifluoromethylphenylboronic acid (148 mg, 0.78 mmol), 0.65 mL of 2M sodium carbonate solution and 2 mL of THF, fitted with a reflux condenser, and the stirred mixture was heated at 80°, under nitrogen, for 16 h. The mixture was cooled, diluted with chloroform (50 mL) and washed with brine (2×25 mL). The combined organic extracts were dried over sodium sulfate, concentrated, and purified by silica gel chromatography (ethyl acetate eluent), to give 137 mg (56%) of the title compound as a white solid. mp 86°–89°. FDMS: m/e=373 $\alpha[D]_{589}$=+28.90 (c =1.04, chloroform).

| Analysis | Calculated | Found |
|---|---|---|
| C | 70.76 | 70.96 |
| H | 5.94 | 6.00 |
| N | 3.75 | 3.09 |

EXAMPLE 80

(+)-(4aR)-(10bR)-4-methyl-8-(3-trifluoromethylphenyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine)palladium(0) (23 mg, 0.02 mmol), 3-trifluoromethylphenylboronic acid (148 mg, 0.78 mmol), 0.65 mL of 2M sodium carbonate solution and 2 mL of THF, fitted with a reflux condenser, and the stirred mixture was heated at 80°, under nitrogen, for 24 h. The mixture was cooled, diluted with chloroform (75 mL) and washed with brine (2×25 mL). The combined organic extracts were dried over sodium sulfate, concentrated, and purified by silica gel chromatography (ethyl acetate eluent), to give 180 mg (77%) of the title compound as an amorphous foam. mp 64°–87°. FDMS: m/e=373. $\alpha[D]_{589}$=+64.42 (c=1.04, chloroform).

| Analysis | Calculated | Found |
|---|---|---|
| C | 70.76 | 71.04 |
| H | 5.94 | 5.98 |
| N | 3.75 | 3.48 |

EXAMPLE 81

(+)-(4aR)-(10bR)-4-methyl-8-(2-[6-methoxy]naphthyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine)palladium(0) (23 mg, 0.02 mmol), 6-methoxynaphthyl-2-boronic acid (158 mg, 0.78 mmol), 0.65 mL of 2M sodium carbonate solution and 2 mL of THF fitted with a reflux condenser, and the stirred mixture was heated at 80°, under nitrogen, for 17 h. The mixture was cooled, diluted with chloroform (75 mL) and washed with brine (2×25 mL). The combined organic extracts were dried over sodium sulfate, concentrated, and purified by silica gel chromatography (ethyl acetate eluent), to give 233 mg (93%) of the title compound as a white solid. mp 216°–2°. FDMS: m/e=385. $\alpha[D]_{589}$=+59.64 (c=0.97, chloroform).

| Analysis | Calculated | Found |
|---|---|---|
| C | 81.01 | 80.72 |
| H | 7.06 | 6.99 |
| N | 3.63 | 3.57 |

EXAMPLE 82

(+)-(4aR)-(10bR)-4-methyl-8-(2-benzothienyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine)palladium(0) (23 mg, 0.02 mmol), 2-benzothiopheneboronic acid (140 mg, 0.78 mmol), 0.65 mL of 2M sodium carbonate solution and 2 mL of toluene, fitted with a reflux condenser, and the stirred mixture was heated at 80°, under nitrogen, for 17 h. The mixture was cooled, diluted with chloroform (75 mL) and washed with brine (2×25 mL). The combined organic extracts were dried over sodium sulfate, concentrated, and purified by silica gel chromatography (70% ethyl acetate/ hexanes eluent), to give 190 mg (81%) of the title compound as a white solid. mp 247°–250°. FDMS: m/e=361. $\alpha[D]_{589}$=+93.33 (c=0.36, chloroform).

| Analysis | Calculated | Found |
|---|---|---|
| C | 76.42 | 76.29 |
| H | 6.41 | 6.37 |
| N | 3.87 | 3.68 |

EXAMPLE 83

(+)-(4aR)-(10bR)-4-methyl-8-(3,5-dimethylphenyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine)palladium(0) (23 mg, 0.02 mmol), 3,5-dimethylphenylboronic acid (117 mg, 0.78 mmol), 0.65 mL of 2M sodium carbonate solution, 1.5 mL of toluene, and 1 mL of methanol, fitted with a reflux condenser, and the stirred mixture was healed at 80°, under nitrogen, for 24 h. The mixture was cooled, diluted with dichloromethane (75 mL) and washed with brine (2×25 mL). The combined organic extracts were dried over sodium sulfate, concentrated, and purified by silica gel chromatography (ethyl acetate eluent), to give 186 mg (86%) of the title compound as a white solid. mp 129°–130°. FDMS: m/e =333. $\alpha[D]_{589}$=+73.31 (c=1.00, chloroform).

| Analysis | Calculated | Found |
|---|---|---|
| C | 82.84 | 82.59 |
| H | 8.16 | 8.08 |
| N | 4.20 | 4.01 |

EXAMPLE 84

(+)-(4aR)-(10bR)-4-methyl-8-(4-biphenyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine)palladium(0) (23 mg, 0.02 mmol), 4-biphenylboronic acid (154 mg, 0.78 mmol) ,0.65 mL of 2M sodium carbonate solution, 1.5 mL of toluene, and 1 mL of methanol, fitted with a reflux condenser, and the stirred mixture was heated at 80°, under nitrogen, for 24 h. The mixture was cooled, diluted with dichloromethane (75 mL) and washed with brine (2×25 mL). The combined organic extracts were dried over sodium sulfate, concentrated, and purified by silica gel chromatography (ethyl acetate eluent), to give 178 mg (72%) of the title compound as a white solid. mp 206°–207°. FDMS: m/e =381. $\alpha[D]_{589}$=+63.93 (c=1.01, chloroform).

| Analysis | Calculated | Found |
|---|---|---|
| C | 85.00 | 84.51 |
| H | 7.13 | 6.85 |
| N | 3.67 | 3.37 |

EXAMPLE 85

(+)-(4aR)-(10bR)-4-methyl-8-(4-fluorophenyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine)palladium(0) (23 mg, 0.02 mmol), 4-fluorophenylboronic acid (109 mg, 0.78 mmol), 0.65 mL of 2M sodium carbonate solution, 1.5 mL of toluene, and 1 mL of methanol, fitted with a reflux condenser, and the stirred mixture was heated at 80°, under nitrogen, for 24 h. The mixture was cooled, diluted with dichloromethane (75 mL) and washed with brine (2×25 mL). The combined organic extracts were dried over sodium sulfate, concentrated, and purified by silica gel chromatography (ethyl acetate eluent), to give 140 mg (67%) of the title compound as a white solid. mp 121°–122°. FDMS: m/e= 323. $\alpha[D]_{589}$=+79.46 (c=0.99, chloroform).

| Analysis | Calculated | Found |
|---|---|---|
| C | 77.99 | 77.70 |
| H | 6.86 | 6.85 |
| N | 4.33 | 4.25 |

EXAMPLE 86

(+)-(4aR)-(10bR)-4-methyl-8-(3-nitrophenyl)-10b-methyl-1,2,3,4,4a,5,6,10b-octanydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine)palladium(0) (23 mg, 0.02 mmol), 3-nitrophenylboronic acid (130 mg, 0.78 mmol), 0.65 mL of 2M sodium carbonate solution, 1.5 mL of toluene, and 1 mL of methanol, fitted with a reflux condenser, and the stirred mixture was heated at 80°, under nitrogen, for 24 h. The mixture was cooled, diluted with dichloromethane (75 mL) and washed with brine (2×25 mL). The combined organic extracts were dried over sodium sulfate, concentrated, and purified by silica gel chromatography (ethyl acetate eluent), to give 159 mg (70%) of the title compound as a tan solid. mp 181°–183°. FDMS: m/e=350. $\alpha[D]_{589}$=+80.70 (c=1.04, chloroform).

| Analysis | Calculated | Found |
|---|---|---|
| C | 71.98 | 71.85 |
| H | 6.33 | 6.22 |
| N | 7.99 | 7.71 |

EXAMPLE 87

(+)-(4aR)-(10bR)-4-methyl-8-(3,5-bis[trifluoromethyl]phenyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine)palladium(0) (23 mg, 0.02 mmol), 3,5-bis(trifluoromethyl)phenylboronic acid (213 mg, 0.78 mmol), 0.65 mL of 2M sodium carbonate solution, 1.5 mL of toluene, and 1 mL of methanol, fitted with a reflux condenser, and the stirred mixture was heated at 80°, under nitrogen, for 24 h. The mixture was cooled, diluted with dichloromethane (75 mL) and washed with brine (2×25 mL). The combined organic extracts were dried over sodium sulfate, concentrated, and purified by silica gel chromatography (ethyl acetate eluent), to give 194 mg (68%) of the title compound as a white solid. mp 110°–112°. FDMS: m/e=441

α[D]₅₈₉=+80.70 (c=1.05, methanol).

| Analysis | Calculated | Found |
|---|---|---|
| C | 62.58 | 62.43 |
| H | 4.79 | 4.81 |
| N | 3.17 | 3.40 |

EXAMPLE 88

(+)-(4aR)-(10bR)-4-methyl-8-(3-chloro-4-fluorophenyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine)palladium(0) (23 mg, 0.02 mmol), 3-chloro-4-fluorophenylboronic acid (136 mg, 0.78 mmol), 0.65 mL of 2M sodium carbonate solution, 1.5 mL of toluene, and 1 mL of methanol, fitted with a reflux condenser, and the stirred mixture was heated at 80°, under nitrogen, for 24 h. The mixture was cooled, diluted with dichloromethane (75 mL) and washed with brine (2×25 mL). The combined organic extracts were dried over sodium sulfate, concentrated, and purified by silica gel chromatography (ethyl acetate eluent), to give 170 mg (73%) of the title compound as a white solid. mp 114°–116°. FDMS: m/e= 357. α[D]₅₈₉=+86.00 (c=1.00, methanol).

| Analysis | Calculated | Found |
|---|---|---|
| C | 70.48 | 70.35 |
| H | 5.91 | 6.00 |
| N | 3.91 | 3.95 |

EXAMPLE 89

(+)-(4aR)-(10bR)-4-methyl-8-(4-[4-ethoxy]biphenyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine)palladium(0) (23 mg, 0.02 mmol), 4-(4-ethoxy)biphenylboronic acid (189 mg, 0.78 mmol), 0.65 mL of 2M sodium carbonate solution, 1.5 mL of toluene, and 1 mL of methanol, fitted with a reflux condenser, and the stirred mixture was heated at 80°, under nitrogen, for 24 h. The mixture was cooled, diluted with dichloromethane (75 mL) and washed with brine (2×25 mL). The combined organic extracts were dried over sodium sulfate, concentrated, and purified by silica gel chromatography (ethyl acetate eluent), to give 166 mg (60%) of the title compound as a white solid. mp 177°–179°. FDMS: m/e= 425. α[D]₅₈₉=+66.30 (c=1.03, chloroform).

| Analysis | Calculated | Found |
|---|---|---|
| C | 81.85 | 81.64 |
| H | 7.34 | 7.12 |
| N | 3.29 | 3.57 |

EXAMPLE 90

(+)-(4aR)-(10bR)-4-methyl-8-(3-aminophenyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine)palladium(0) (23 mg, 0.02 mmol), 3-aminophenylboronic acid hemisulfate (181 mg, 0.78 mmol), 1.0 mL of 2M sodium carbonate solution, 1.5 mL of toluene, and 1 mL of methanol, fitted with a reflux condenser, and he stirred mixture was heated at 80°, under nitrogen, for 24 h. The mixture was cooled, diluted with dichloromethane (75 mL) and washed with brine (2×25 mL). The combined organic extracts were dried over sodium sulfate, concentrated, and purified by silica gel chromatography (ethyl acetate eluent), to give 170 mg (82%) of the title compound as a tan solid. mp 230°–231° (decomp.) FDMS: m/e=320. α[D]₅₈₉=+80.00 (c=1.05, methanol).

| Analysis | Calculated | Found |
|---|---|---|
| C | 78.71 | 78.99 |
| H | 7.55 | 7.55 |
| N | 8.74 | 9.12 |

EXAMPLE 91

(+)-(4aR)-(10bR)-4-methyl-8-[3-([5-dimethylamino-1-naphthyl]sulfonylamino)phenyl]-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (83 mg, 0.27 mmol), tetrakis (triphenylphosphine)palladium(0) (23 mg, 0.02 mmol), 3-dansylaminophenylboronic acid (99 mg, 0.27 mmol), 0.3 mL of 2M sodium carbonate solution, 0.5 mL of toluene, and 0.1 mL of methanol, fitted with a reflux condenser, and the stirred mixture was heated at 80°, under nitrogen, for 24 h. The mixture was cooled, diluted with dichloromethane (75 mL) and washed with brine (2×25 mL). The combined organic extracts were dried over sodium sulfate, concentrated, and purified by silica gel chromatography (ethyl acetate eluent), to give 94 mg (63%) of the title compound as a yellow solid. mp 130°–140° (decomp.) FDMS: m/e=553. α[D]₅₈₉=+3.01 (c=1.03 methanol).

EXAMPLE 92

(+)-(4aR)-(10bR)-8-(1-naphthyl)-10b-methyl-1,2,3,4,4a,-5,6,10b-octahydrobenzo[f]quinolin-3-one A 15 mL round bottom flask was charged with (+)-(4aR)-(10bR)-8-bromo-10b-methyl-1,2,3,4,4a,5,6,10b-octahydrobenzo[f]quinolin-3-one (500 mg, 1.70 mmol), tetrakis(triphenylphosphine)palladium(0) (80 mg, 0.07 mmol), 1-napthylboronic acid (439 mg, 2.55 mmol), 2.4 mL of 2M sodium carbonate and 4 mL of toluene, fitted with a reflux condenser, and the stirred mixture was heated at 80°, under nitrogen, for 24 h. The mixture was cooled, diluted with dichloromethane (200 mL) and washed with brine (2×50 mL). The combined organic extracts were dried over sodium sulfate, concentrated, and purified by silica gel chromatography (0–50% methanol/ethyl acetate eluent gradient) to give 405 mg (70%) of the title compound as a white solid. mp 247°–248°. FDMS: m/e=341. α[D]₅₈₉=+1.93 (c=1.04, methanol).

EXAMPLE 93

(+)-(4aR)-(10bR)-8-(3-nitrophenyl)-10b-methyl-1,2,3,4,4a,-5,6,10b-oczahydrobenzo[f]quinolin-3-one A 15 mL round bottom flask was charged with (+)-(4aR)-(10bR)-8-bromo-10b-methyl-1,2,3,4,4a,5,6,10b-octahydrobenzo[f]quinolin-3-one (500 mg, 1.70 mmol), tetrakis(triphenylphosphine)palladium(0) (80 mg, 0.07 mmol), 3-nitrophenylboronic acid (426 mg, 2.55 mmol), 2.4 mL of 2M sodium carbonate and 4 mL of toluene, fitted with a reflux condenser, and the stirred mixture was heated at 80°, under nitrogen, for 24 h. The mixture was cooled, diluted with dichloromethane (200 mL) and washed with brine (2×50 mL). The combined organic extracts were dried over sodium sulfate, concentrated, and purified by silica gel chromatography (ethyl acetate eluent) to give 456 mg (80%) of the title compound as a white solid. mp 223°–225°. FDMS: m/e=336. $\alpha[D]_{589}$=+45.63 (c=1.03, methanol).

EXAMPLE 94

(+)-(4aR)-(10bR)-4-methyl-8-(2,4-dichlorophenyl)-10b-methyl-1,2,3,4,4a,5,6,10b-octahydrobenzo[f]quinolin-3-one A 15 mL round bottom flask was charged with (+)-(4aR)-(10bR)-4-methyl-8-bromo-10b-methyl-1,2,3,4,4a,5,6,10b-octahydrobenzo[f]quinolin-3-one (200 mg, 0.65 mmol), tetrakis (triphenylphosphine)palladium(0) (23 mg, 0.02 mmol), 2,4-dichlorophenylboronic acid (149 mg, 0.78 mmol), 0.65 mL of 2M sodium carbonate solution and 1.5 mL of toluene fitted with a reflux condenser, and the stirred mixture was heated at 80°, under nitrogen, for 24 h. The mixture was cooled, diluted with dichloromethane (75 mL) and washed with brine (2×25 mL). The combined organic extracts were dried over sodium sulfate, concentrated, and purified by silica gel chromatography (ethyl acetate eluent), followed by recrystallization from ethyl acetate to give 157 mg (65%) of the title compound as an amorphous foam. mp 45°–48°. FDMS: m/e=374.

| Analysis | Calculated | Found |
|---|---|---|
| C | 67.39 | 66.95 |
| H | 5.65 | 5.43 |
| N | 3.74 | 3.82 |

The following group of examples illustrate alkylations, other than the preferred alkylations of Examples 1–4 above, which provide modifications of the benzoquinolinone nucleus.

EXAMPLE 95

(+)-(4aR)-(10bR) -4,10b-dimethyl-8-(4-chlorophenylthio)-1,2,3,4,-4a,5,6,10b-octahydrobenzo[f]quinolin-3-one A 350 mg portion of (4aR)-(10bR)-10b-methyl-8-(4-chlorophenylthio)-1,2,3,4,4a,5,6,10b-octahydrobenzo[f]-quinolin-3-one was slurried in 14 ml of t-butanol in a nitrogen-blanketed flask, and 0.2 ml of a 25 mg/ml aqueous solution of methyl iodide was added, followed by 330 mg of potassium t-butoxide. The mixture was stirred at ambient temperature for 5 hours, and then the reaction mixture was poured into water, and the mixture was extracted twice with ethyl acetate. The combined organic layers were washed with water and with brine, dried over sodium sulfate and concentrated under vacuum to obtain an oil, which was purified by silica gel chromatography on a Chromatotron (Harrison Research Co.), using dichloromethane containing from 1% to 3% of methanol as the eluent. The product-containing fractions were combined and concentrated under vacuum to obtain 330 mg of solid, which was crystallized from heptane/ethyl acetate to obtain 254 mg of the desired product. mp 122°–124° FDMS: m/e=371. $\alpha[D]_{589}$=+60.2, $\alpha[D]_{365}$=+262.55 (chloroform).

| Analysis | Calculated | Found |
|---|---|---|
| C | 67.82 | 68.05 |
| H | 5.96 | 6.00 |
| N | 3.77 | 3.89 |

EXAMPLE 96

(+)-(4aR)-(10bR)-4,10b-dimethyl-8-(4-methylphenylthio)-1,2,3,4,4a,5,6,10b-octahydrobenzo[f]quinolin-3-one Following the process of Example 95 a 390 mg portion of (4aR)-10bR)-10b-methyl-8-(4-methylphenylthio)-1,2,3,4,4a,5,6,10b-octahydrobenzo[f]quinolin-3-one was methylated to obtain 280 mg of the desired product. mp 154°–156° FDMS: m/e=351. $\alpha[D]_{589}$=+76.6, $\alpha[D]_{365}$=+282.53 (chloroform).

| Analysis | Calculated | Found |
|---|---|---|
| C | 75.17 | 74.95 |
| H | 7.17 | 7.25 |
| N | 3.99 | 4.17 |

EXAMPLE 97

(+)-(4aR)-(10bR) -4,10b-dimethyl-8-(phenylsulfonyl)-1,2,3,4,-4a,5,6,10b-octahydrobenzo[f]quinolin-3-one A 200 mg portion of (4aR)-(10bR)-10b-methyl-8-(phenylsulfonyl)-1,2,3,4,4a,5,6,10b-octahydrobenzo[f]-quinolin-3-one was methylated with methyl iodide to obtain 144 mg of the desired product. mp 165°–167° FDMS: m/e=369. $\alpha[D]_{589}$=+76.2, $\alpha[D]_{365}$=+269.7 (chloroform).

| Analysis | Calculated | Found |
|---|---|---|
| C | 68.27 | 68.44 |
| H | 6.27 | 6.39 |
| N | 3.79 | 3.69 |

EXAMPLE 98

(+)-(4aR)-(10bR)-4,10b-dimethyl-8-(2-naphthylthio)-1,2,3,4,-4a,5,6,10b-octahydrobenzo[f]quinolin-3-one A 282 mg portion of (4aR)-(10bR)-10b-methyl-8-(2-naphthylthio)-1,2,3,4,4a,5,6,10b-octahydrobenzo[f] quinolin-3-one was methylated with methyl iodide following the process of Example 95 to obtain 137 mg of the desired product. mp 138°–139.5° FDMS: m/e=387. $\alpha[D]_{589}$=+69.6, $\alpha[D]_{365}$=+261.4 (chloroform).

| Analysis | Calculated | Found |
|---|---|---|
| C | 77.48 | 77.28 |
| H | 6.50 | 6.63 |
| N | 3.61 | 3.71 |

EXAMPLE 99

(+)-(4aR)-(10bR)-4,10b-dimethyl-8-(2-chlorophenylthio)-1,2,3,4,-4a,5,6,10b-octahydrobenzo[f]quinolin-3-one The process of Example 95 was used to methylate 620 mg of (4aR)-(10bR)-10b-methyl-8-(2-chlorophenylthio)-1,2,3,4,4a,5,6,10b-octahydrobenzo[f]quinolin-3-one, to obtain 420 mg of the desired product. mp 123°–125° FDMS: m/e=371. α[D]$_{589}$=+76.0, α[D]$_{365}$=+255.3 (chloroform).

| Analysis | Calculated | Found |
|---|---|---|
| C | 67.82 | 67.87 |
| H | 5.96 | 5.97 |
| N | 3.77 | 3.94 |

EXAMPLE 100

(+)-(4aR)-(10bR)-4,10b-dimethyl-8-(3-chlorophenylthio)-1,2,3,4,-4a,5,6,10b-octahydrobenzo[f]quinolin-3-one A 612 mg portion of (4aR)-(10bR)-10b-methyl-8-(3-chlorophenylthio)-1,2,3,4,4a,5,6,10b-octahydrobenzo[f]-quinolin-3-one was methylated with methyl iodide substantially as shown in Example 95. Attempts at crystallization of the product were unsuccessful, so it was characterized as an opaque colorless oil, 525 mg. FDMS: m/e=371. α[D]$_{589}$=+72.9, α[D]$_{365}$=+265.2 (chloroform).

| Analysis | Calculated | Found |
|---|---|---|
| C | 67.82 | 67.60 |
| H | 5.96 | 5.91 |
| N | 3.77 | 3.86 |

EXAMPLE 101

(+)-(4aR)-(10bR)-4,10b-dimethyl-8-(2-methylphenylthio)-1,2,3,4,-4a,5,6,10b-octahydrobenzo[f]quinolin-3-one A 390 mg portion of (4aR)-(10bR)-10b-methyl-8-(2-methylphenylthio)-1,2,3,4,4a,5,6,10b-octahydrobenzo[f]-quinolin-3-one was methylated substantially as shown in Example 95 above, to obtain 330 mg of the desired product. mp 105°–106° FDMS: m/e=351. α[D]$_{589}$=+77.0, α[D]$_{365}$=+282.8 (chloroform).

| Analysis | Calculated | Found |
|---|---|---|
| C | 75.17 | 75.46 |
| H | 7.17 | 7.34 |
| N | 3.98 | 3.95 |

EXAMPLE 102

(+)-(4aR)-(10bR)-4,10b-dimethyl-8-(3-methylphenylthio)-1,2,3,4,-4a,5,6,10b-octahydrobenzo[f]quinolin-3-one A 380 mg portion of (4aR)-(10bR)-10b-methyl-8-(3-methylphenylthio)-1,2,3,4,4a,5,6,10b-octahydrobenzo[f]-quinolin-3-one was methylated as shown in Example 95 above to obtain 290 mg of the desired product. mp 103°–104° FDMS: m/e=351. α[D]$_{589}$=+80.3, α[D]$_{365}$=+292.2 (chloroform).

| Analysis | Calculated | Found |
|---|---|---|
| C | 75.17 | 75.40 |
| H | 7.17 | 7.19 |
| N | 3.98 | 3.98 |

EXAMPLE 103

(+)-(4aR)-(10bR)-4,10b-dimethyl-8-(1-naphthylthio)-1,2,3,4,-4a,5,6,10b-octahydrobenzo[f]quinolin-3-one A 390 mg portion of (4aR)-(10bR)-10b-methyl-8-(1-naphthylthio)-1,2,3,4,4a,5,6,10b-octahydrobenzo[f]quinolin-3-one was methylated as described in Example 95 above to obtain 300 mg of the desired product. mp 161°–162° FDMS: m/e=387. α[D]$_{589}$=+65.2, α[D]$_{365}$=+248.4 (chloroform).

| Analysis | Calculated | Found |
|---|---|---|
| C | 77.48 | 77.64 |
| H | 6.50 | 6.54 |
| N | 3.61 | 3.54 |

EXAMPLE 104

(+)-(4aR)-(10bR)-4,10b-dimethyl-8-(2-methoxyphenylthio)-1,2,3,4,-4a,5,6,10b-octahydrobenzo[f]quinolin-3-one A 430 mg portion of (4aR)-(10bR)-10b-methyl-8-(2-methoxyphenylthio)-1,2,3,4,4a,5,6,10b-octahydrobenzo[f]-quinolin-3-one was methylated substantially as described in Example 95 above to obtain 300 mg of the desired product. mp 166°–167.5° FDMS: m/e=367. α[D]$_{589}$=+72.7, α[D]$_{365}$=+265.1 (chloroform).

| Analysis | Calculated | Found |
|---|---|---|
| C | 71.90 | 71.98 |
| H | 6.86 | 6.64 |
| N | 3.81 | 3.67 |

EXAMPLE 105

(+)-(4aR)-(10bR)-4,10b-dimethyl-8-(4-methoxyphenylthio)-1,2,3,4,-4a,5,6,10b-octahydrobenzo[f]quinolin-3-one A 480 mg portion of (4aR)-10bR)-10b-methyl-8-(4-methoxyphenylthio)-1,2,3,4,4a,5,6,10b-octahydrobenzo[f]-quinolin-3-one was methylated as described in Example 95 to obtain 400 mg of the desired product. mp 150°–151° FDMS: m/e=367. α[D]$_{589}$=+74.1, α[D]$_{365}$=+276.8 (chloroform).

| Analysis | Calculated | Found |
|---|---|---|
| C | 71.90 | 71.95 |
| H | 6.86 | 6.64 |
| N | 3.81 | 3.85 |

EXAMPLE 106

(4aR)-(10bR)-4,10b-dimethyl-8-(3-quinolinylthio)-1,2,3,4,-4a,5,6,10b-octahydrobenzo[f]quinolin-3-one A 256 mg portion of (4aR)-(10bR)-10b-methyl-8-(3-quinolinylthio)-1,2,3,4,4a,5,6,10b-octahydrobenzo[f]quinolin-3-one was methylated according to the process of Example 95 to obtain 255 mg of the desired product, as an amorphous solid. FDMS: m/e=388.

| Analysis | Calculated | Found |
|---|---|---|
| C | 74.19 | 73.94 |
| H | 6.23 | 6.41 |
| N | 7.21 | 7.13 |

EXAMPLE 107

(+)-(4aR)-(10bR)-4,10b-dimethyl-8-(2-quinolinylthio)-1,2,3,4,-4a,5,6,10b-octahydrobenzo[f]quinolin-3-one A 420 mg portion of (4aR)-(10bR)-10b-methyl-8-(2-quinolinylthio)-1,2,3,4,4a,5,6,10b-octahydrobenzo[f]quinolin-3-one was methylated as described in Example 95 to obtain 300 mg of the desired product. mp 175°–177° FDMS: m/e=388. $\alpha[D]_{589}$=+65.9, $\alpha[D]_{365}$=absorbance (chloroform).

| Analysis | Calculated | Found |
|---|---|---|
| C | 74.19 | 74.01 |
| H | 6.23 | 6.10 |
| N | 7.21 | 7.39 |

EXAMPLE 108

(+)-(4aR)-(10bR)-4,10b-dimethyl-8-(2-fluorophenylthio)-1,2,3,4,-4a,5,6,10b-octahydrobenzo[f]quinolin-3-one A 490 mg portion of (4aR)-(10bR)-10b-methyl-8-(2-fluorophenylthio)-1,2,3,4,4a,5,6,10b-octahydrobenzo[f]quinolin-3-one was methylated substantially according to the process of Example 95 to obtain 490 mg of the desired product, which was not crystalline. mp 100°–103° FDMS: m/e=354. $\alpha[D]_{589}$=+76.5, $\alpha[D]_{365}$=+273.6 (chloroform).

| Analysis | Calculated | Found |
|---|---|---|
| C | 70.96 | 71.21 |
| H | 6.24 | 6.32 |
| N | 3.94 | 4.16 |

EXAMPLE 109

(+)-(4aR)-(10bR)-4,10b-dimethyl-8-(3-fluorophenylthio)-1,2,3,4,-4a,5,6,10b-octahydrobenzo[f]quinolin-3-one A 460 mg portion of (4aR)-(10bR)-10b-methyl-8-(3-flurophenylthio)-1,2,3,4,4a,5,6,10b-octahydrobenzo[f]quinolin-3-one was methylated according to the process of Example 95 to obtain 430 mg of the desired product in the form of an oil. FDMS: m/e=355. $\alpha[D]_{589}$=+76.5, $\alpha[D]_{365}$=+275.2 (chloroform).

| Analysis | Calculated | Found |
|---|---|---|
| C | 70.96 | 71.11 |
| H | 6.24 | 6.32 |
| N | 3.94 | 3.98 |

EXAMPLE 110

(4aR)-(10bR)-4,10b-dimethyl-8-(8-quinolinylthio)-1,2,3,4,-4a,5,6,10b-octahydrobenzo[f]quinolin-3-one A 305 mg portion of (4aR)-(10bR)-10b-methyl-8-(8-quinolinylthio)-1,2,3,4,4a,5,6,10b-octahydrobenzo[f]quinolin-3-one was methylated substantially according to the process of Example 95 to obtain 114 mg of the desired product. mp 241°–242° FDMS: m/e=388.

| Analysis | Calculated | Found |
|---|---|---|
| C | 74.19 | 73.98 |
| H | 6.23 | 6.15 |
| N | 7.21 | 7.18 |

EXAMPLE 111

(+)-(4aR)-(10bR)-4,10b-dimethyl-8-(2-pyridinylthio)-1,2,3,4,-4a,5,6,10b-octahydrobenzo[f]quinolin-3-one Four hundred mg of (4aR)-(10bR)-10b-methyl-8-(2-pyridinylthio)-1,2,3,4,4a,5,6,10b-octahydrobenzo[f]quinolin-3-one was methylated substantially according to the process of Example 95 to obtain 330 mg of the desired product. mp 174°–176° FDMS: m/e=338. $\alpha[D]_{589}$=+79.8, $\alpha[D]_{365}$=+288.7 (chloroform).

| Analysis | Calculated | Found |
|---|---|---|
| C | 70.97 | 70.70 |
| H | 6.55 | 6.74 |
| N | 8.28 | 8.06 |

EXAMPLE 112

(4aR)-(10bR)-4,10b-dimethyl-8-(2-benzothiazolylthio)-1,2,3,4,4a,5,6,10b-octahydrobenzo[f]quinolin-3-one A 170 mg portion of (4aR)-(10bR)-10b-methyl-8-(2-benzothiazolylthio)-1,2,3,4,4a,5,6,10b-octahydrobenzo[f]quinolin-3-one was alkylated with methyl iodide substantially according to the process of Example 95 to obtain 84 mg of the desired product. mp 188°–189° FDMS: m/e=394.

| Analysis | Calculated | Found |
|---|---|---|
| C | 66.97 | 66.73 |
| H | 5.62 | 5.65 |
| N | 7.10 | 6.87 |

EXAMPLE 113

(4aR)-(10bR)-4,10b-dimethyl-8-(1-isoquinolinylthio)-1,2,3,4,-4a,5,6,10b-octahydrobenzo[f]quinolin-3-one A 140 mg portion of (4aR)-(10bR)-10b-methyl-8-(1-isoquinolinylthio)-1,2,3,4,4a,5,6,10b-octahydrobenzo[f]quinolin-3-one was methylated substantially according to the process of Example 95 to obtain 90 mg of the desired product. mp 196°–199° FDMS: m/e=388.

| Analysis | Calculated | Found |
|---|---|---|
| C | 74.19 | 74.08 |
| H | 6.23 | 6.41 |
| N | 7.21 | 7.45 |

EXAMPLE 114

(4aR)-(10bR)-4,10b-dimethyl-8-(4-isoquinolinylthio)-1,2,3,4,-4a,5,6,10b-octahydrobenzo[f]quinolin-3-one A 300 mg portion of (4aR)-(10bR)-10b-methyl-8-(4-isoquinolinylthio)-1,2,3,4,4a,5,6,10b-octahydrobenzo[f]-quinolin-3-one was alkylated substantially according to the process of Example 95 to obtain 140 mg of the desired product. mp 161°–163° FDMS: m/e=388.

| Analysis | Calculated | Found |
|---|---|---|
| C | 74.19 | 74.05 |
| H | 6.23 | 6.18 |
| N | 7.21 | 7.47 |

EXAMPLE 115

(+)-(4aR)-(10bR)-4,10b-dimethyl-8-(4-pyridinylthio)-1,2,3,4,-4a,5,6,10b-octahydrobenzo[f]quinolin-3-one A 390 mg portion of (4aR)-(10bR)-10b-methyl-8-(4-pyridinylthio)-1,2,3,4,4a,5,6,10b-octahydrobenzo[f]-quinolin-3-one was methylated substantially according to the process of Example 95 to obtain 228 mg of the desired product. mp 157°–158° FDMS: m/e=338. $\alpha[D]_{589}$=+77.5, $\alpha[D]_{365}$=absorbance (chloroform).

| Analysis | Calculated | Found |
|---|---|---|
| C | 70.97 | 71.25 |
| H | 6.55 | 6.27 |
| N | 8.28 | 8.27 |

EXAMPLE 116

(4aR)-(10bR)-4,10b-dimethyl-8-phenylthio-1,2,3,4,-4a,5,6,10b-octahydrobenzo[f]quinolin-3-one Potassium t-butoxide (0.22 g, 1.9 mmol) was added to 5 mL of t-butanol in a 25 mL round bottom flask. The (4aR)-(10bR)-10b-methyl-8-phenylthio-1,2,3,4,4a,5,6,10b-octahydrobenzo[f]-quinolin-3-one, (0.183 g, 0.566 mmol) was added followed by methyl iodide while cooling briefly in an ice bath. The mixture was allowed to stir at room temperature for 18 h before diluting with ethyl acetate and filtering to remove inorganics. Filtrate was concentrated in vacuo to give a oil which was triturated in hexane/diethyl ether to facilitate crystallization. Recrystallization from ethyl acetate/hexane gave 0.90 g of white crystals: mp 109°–112°. FD MS 337 M +. Calcd for $C_{21}H_{23}N_1O_1S_1$.

| Analysis | Calculated | Found |
|---|---|---|
| C | 74.74 | 74.55 |
| H | 6.87 | 6.79 |
| N | 4.15 | 4.35 |

EXAMPLE 117

(+)-(4aR)-(10bR)-4-methyl-8-(1-naphthyl)-10b-methyl-3,4,4a,5,6,10b-hexahydrobenzo[f]quinolin-3-one A 15 mL round bottom flask was charged with (+)-(4aR)-(10bR)-8-(1-naphthyl)-10b-methyl-3,4,4a,5,6,10b-hexahydrobenzo[f]quinolin-3-one (22 mg, 0.065 mmol), 0.20 mL of t-butanol, and potassium t-butoxide (22 mg, 0.19 mmol). Methyl iodide (0.012 mL, 0.19 mmol) was added and the mixture was stirred at room temperature for 4 h. The mixture was diluted with ethyl acetate, and purified by silica gel chromatography (ethyl acetate eluent) to give 16 mg (70%) of the title compound as a yellow solid, upon trituration from diethyl ether/hexanes. mp 172°–173°. FDMS: m/e=353.

| Analysis | Calculated | Found |
|---|---|---|
| C | 84.92 | 84.70 |
| H | 6.56 | 6.29 |
| N | 3.96 | 3.55 |

EXAMPLE 118

(+)-(4aR)-(10bR)-4-methyl-8-(3-nitrophenyl)-10b-methyl-3,4,4a,5,6,10b-hexahydrobenzo[f]quinolin-3-one A 15 mL round bottom flask was charged with (+)-(4aR)-(10bR)-8-(3-nitrophenyl)-10b-methyl-3,4,4a,5,6,10b-hexahydrobenzo[f]quinolin-3-one (12 mg, 0.034 mmol), 0.10 mL of t-butanol, and potassium t-butoxide (12 mg, 0.10 mmol). Methyl iodide (0.006 mL, 0.10 mmol) was added and the mixture was stirred at room temperature for 4 h. The mixture was diluted with ethyl acetate, and purified by silica gel chromatography (ethyl acetate eluent) to give 9 mg (75%) of the title compound as a white solid, upon trituration from diethyl ether/hexanes. mp 175°–177°. FDMS: m/e=348.

EXAMPLE 119

(+)-(4aR)-(10bR)-4-methyl-8-(4-nitrophenyl)-10b-methyl-1,2,3,4,4a, 5,6,10b-octahydrobenzo[f]quinolin-3-one A 15 mL round bottom flask was charged with (+)-(4aR)-(10bR)-8-(4-nitrophenyl)-10b-methyl-1,2,3,4,4a,-5,6,10b-octahydrobenzo[f]quinolin-3-one (14 mg, 0.04 mmol), 0.10 mL of t-butanol, and potassium t-butoxide (14 mg, 0.12 mmol). Methyl iodide (0.03 mL, 0.08 mmol) was added and the mixture was stirred at room temperature for 4 h. The mixture was diluted with ethyl acetate, and purified by silica gel chromatography (ethyl acetate eluent) to give 10 mg (70%) of the title compound as a white solid. mp 59°–60°. FDMS: m/e=350.

EXAMPLE 120

(+)-(4aR)-(10bR)-4-methyl-8-(4-methylthiophenyl)-10b-methyl-1,2,3,4,4a,5,6,10b-octahydrobenzo[f]quinolin-3-one A 15 mL round bottom flask was charged with (+)-(4aR)-(10bR)-8-(4-methylthiophenyl)-10b-methyl-1,2,3,4,4a,5,6,10b-octahydrobenzo[f]quinolin-3-one (20 mg, 0.06 mmol), 0.10 mL of t-butanol, and potassium t-butoxide (20 mg, 0.18 mmol). Methyl iodide (0.011 mL, 0.18 mmol) was added and the mixture was stirred at room temperature for 4 h. The mixture was diluted with ethyl acetate, and purified by silica gel chromatography (ethyl acetate eluent) to give 15 mg (72%) of the title compound as a white solid. mp 115°–117°. FDMS: m/e=351.

EXAMPLE 121

(+)-(4aR)-(10bR)-4-methyl-8-(4-cyanophenyl)-10b-methyl-1,2,3,4,4a,5,6,10b-octahydrobenzo[f]quinolin-3-one A 15 mL round bottom flask was charged with (+)-(4aR)-(10bR)-8-(4-cyanophenyl)-10b-methyl-1,2,3,4,4a,-5,6,10b-octahydrobenzo[f]quinolin-3-one (24 mg, 0.08 mmol), 0.20 mL of t-butanol, and potassium t-butoxide (26 mg, 0.24 mmol). Methyl iodide (0.014 mL, 0.24 mmol) was added and the mixture was stirred at room temperature for 4 h. The mixture was diluted with ethyl acetate, and purified by silica gel chromatography (ethyl acetate eluent) to give 20 mg (80%) of the title compound as a white solid. mp 148°–150°. FDMS: m/e=330.

| Analysis | Calculated | Found |
|---|---|---|
| C | 79.97 | 79.77 |
| H | 6.71 | 6.63 |
| N | 8.48 | 8.69 |

EXAMPLE 122

(+)-(4aR)-(10bR)-4-methyl-8-(4-[isopropylcarbonyl]phenyl)-10b-methyl-1,2,3,4,4a,5,6,10b-octahydrobenzo[f]quinolin-3-one A 15 mL round bottom flask was charged with (+)-(4aR)-(10bR)-8-(4-acetylphenyl)-10b-methyl-1,2,3,4,4a,-5,6,10b-octahydrobenzo[f]quinolin-3-one (33 mg, 0.10 mmol), 0.25 mL of t-butanol, and potassium t-butoxide (33 mg, 0.33 mmol). Methyl iodide (0.019 mL, 0.33 mmol) was added and the mixture was stirred at room temperature for 4 h. The mixture was diluted with ethyl acetate, and purified by silica gel chromatography (ethyl acetate eluent) to give 20 mg (54%) of the title compound as a white solid. mp 101°–103°. FDMS: m/e=375.

EXAMPLE 123

(+)-(4aR)-(10bR)-4-methyl-8-(4-methylsulfonamidophenyl)-10b-methyl-1,2,3,4,4a,5,6,10b-octahydrobenzo[f]quinolin-3-one A 15 mL round bottom flask was charged with (+)-(4aR)-(10bR)-8-(4-sulfonamidophenyl)-10b-methyl-1,2,3,4,4a,-5,6,10b-octahydrobenzo[f]quinolin-3-one (33 mg, 0.09 mmol), 0.20 mL of t-butanol, and potassium t-butoxide (30 mg, 0.27 mmol). Methyl iodide (0.017 mL, 0.27 mmol) was added and the mixture was stirred at room temperature for 4 h. The mixture was diluted with ethyl acetate, and purified by silica gel chromatography (ethyl acetate eluent) to give 20 mg (56%) of the title compound as an oil. FDMS: m/e=398.

EXAMPLE 124

(+)-(4aR)-(10bR)-4-methyl-8-(2-nitrophenyl)-10b-methyl-1,2,3,4,4a,5,6,10b-octahydrobenzo[f]quinolin-3-one A 15 mL round bottom flask was charged with (+)-(4aR)-(10bR)-8-(2-nitrophenyl)-10b-methyl-1,2,3,4,4a,-5,6,10b-octahydrobenzo[f]quinolin-3-one (60 mg, 0.18 mmol), 0.3 mL of t-butanol, and potassium t-butoxide (60 mg, 0.54 mmol). Methyl iodide (0.034 mL, 0.54 mmol) was added and the mixture was stirred at room temperature for 4 h. The mixture was diluted with ethyl acetate, and purified by silica gel chromatography (ethyl acetate eluent) to give 50 mg (80%) of the title compound as a white solid. mp 130°–131°. FDMS: m/e=350.

EXAMPLE 125

(+)-(4aR)-(10bR)-4-methyl-8-(2-cyanophenyl)-10b-methyl-1,2,3,4,4a,5,6,10b-octahydrobenzo[f]quinolin-3-one A 15 mL round bottom flask was charged with (+)-(4aR)-(10bR)-8-(2-cyanophenyl)-10b-methyl-1,2,3,4,4a,-5,6,10b-octahydrobenzo[f]quinolin-3-one (55 mg, 0.17 mmol), 0.4 mL of t-butanol, and potassium t-butoxide (58 mg, 0.51 mmol). Methyl iodide (0.034 mL, 0.54 mmol) was added and the mixture was stirred at room temperature for 4 h. The mixture was diluted with ethyl acetate, and purified by silica gel chromatography (ethyl acetate eluent) to give 50 mg (87%) of the title compound as a white solid. mp 54°–55°. FDMS: m/e=330. $\alpha[D]_{589}$=+74.33 (c=0.36, chloroform).

EXAMPLE 126

(+)-(4aR)-(10bR)-4-methyl-8-(2-[5-(phenoxymethyl)thienyl])-10b-methyl-1,2,3,4,4a,5,6,10b-octahydrobenzo[f]quinolin-3-one A 15 mL round bottom flask was charged with (+)-(4aR)-(10bR)-8-(2-[5-(phenoxymethyl)thienyl])-10b-methyl-1,2,3,4,4a,5,6,10b-octahydrobenzo[f]quinolin-3-one (70 mg, 0.17 mmol), 0.4 mL of t-butanol, and potassium t-butoxide (58 mg, 0.51 mmol). Methyl iodide (0.034 mL, 0.54 mmol) was added and the mixture was stirred at room temperature for 4 h. The mixture was diluted with ethyl acetate, and purified by silica gel chromatography (ethyl acetate eluent) to give 65 mg (90%) of the title compound as a white solid. mp 149°–151°. FDMS: m/e=417 $\alpha[D]_{589}$=+68.50 (c=0.89, chloroform).

EXAMPLE 127

(+)-(4aR)-(10bR)-4-methyl-8-(2-methylthiophenyl)-10b-methyl-1,2,3,4,4a,5,6,10b-octahydrobenzo[f]quinolin-3-one A 15 mL round bottom flask was charged with (+)-(4aR)-(10bR)-8-(2-methylthiophenyl)-10b-methyl-1,2,3,4,4a,-5,6,10b-octahydrobenzo[f]quinolin-3-one (55 mg, 0.16 mmol), 0.4 mL of t-butanol, and potassium t-butoxide (55 mg, 0.48 mmol). Methyl iodide (0.031 mL, 0.48 mmol) was added and the mixture was stirred at room temperature for 4 h. The mixture was diluted with ethyl acetate, and purified by silica gel chromatography (ethyl acetate eluent) to give 15 mg (26%) of the title compound as an oil. FDMS: m/e=351.

EXAMPLE 128

(+)-(4aR)-(10bR)-4-methyl-8-(2,4,5-trifluorophenyl)-10b-methyl-1,2,3,4,4a,5,6,10b-octahydrobenzo[f]quinolin-3-one A 15 mL round bottom flask was charged with (+)-(4aR)-(10bR)-8-(2,4,5-trifluorophenyl)-10b-methyl-1,2,3,4,4a,5,6,10b-octahydrobenzo[f]quinolin-3-one (43 mg, 0.12 mmol), 0.3 mL of t-butanol, and potassium t-butoxide (42 mg, 0.36 mmol). Methyl iodide (0.023 mL, 0.36 mmol) was added and the mixture was stirred at room temperature for 4 h. The mixture was diluted with ethyl acetate, and purified by silica gel chromatography (ethyl acetate eluent) to give 40 mg (89%) of the title compound as a foam. FDMS: m/e=359.

EXAMPLE 129

(+)-(4aR)-(10bR)-4-methyl-8-(2-[5-(4-fluorophenoxymethyl)-thienyl])-10b-methyl-1,2,3,4,4a,5,6,10b-octahydrobenzo[f]-quinolin-3-one A 15 mL round bottom flask was charged with (+)-(4aR)-)10bR)8-(2-[5-(4-fluorophenoxymethyl)thienyl])-10b-methyl-1,2,3,4,4a,5,6,10b-octahydrobenzo[f]quinolin-3-one (47 mg, 0.11 mmol), 0.3 mL of t-butanol, and potassium t-butoxide (38 mg, 0.33 mmol). Methyl iodide (0.021 mL, 0.33 mmol) was added and the mixture was stirred at room temperature for 4 h. The mixture was diluted with ethyl acetate, and purified by silica gel chromatography (ethyl acetate eluent) to give 35 mg (71%) of the title compound as a white solid. mp 136°–138°. FDMS: m/e=435 $\alpha[D]_{589}$=+63.40 (c=0.74, chloroform).

EXAMPLE 130

(+)-(4aR)-(10bR)-4-methyl-8-(2,3,5-trifluorophenyl)-10b-methyl-1,2,3,4,4a,5,6,10b-octahydrobenzo[f]quinolin-3-one A 15 mL round bottom flask was charged with (+)-(4aR)-(10bR)-8-(2,3,5-trifluorophenyl)-10b-methyl-1,2,3,4,4a,5,6,10b-octahydrobenzo[f]quinolin-3-one (35 mg, 0.10 mmol), 0.3 mL of t-butanol, and potassium t-butoxide (34 mg, 0.30 mmol). Methyl iodide (0.019 mL, 0.30 mmol) was added and the mixture was stirred at room temperature for 4 h. The mixture was diluted with ethyl acetate, and purified by silica gel chromatography (ethyl acetate eluent) to give 30 mg (83%) of the title compound as a foam. FDMS: m/e=359.

EXAMPLE 131

(+)-(4aR)-(10bR)-4-methyl-8-(2-fluorenyl)-10b-methyl-1,2,3,4,4a,5,6,10b-octahydrobenzo[f]quinolin-3-one A 15 mL round bottom flask was charged with (+)-(4aR)-(10bR)-8-(2-fluorenyl)-10b-methyl-1,2,3,4,4a,5,6,10b-octahydrobenzo[f]quinolin-3-one (31 mg, 0.08 mmol), 0.2 mL of butanol, and potassium t-butoxide (27 mg, 0.24 mmol). Methyl iodide (0.015 mL, 0.24 mmol) was added and the mixture was stirred at room temperature for 4 h. The mixture was diluted with ethyl acetate, and purified by silica gel chromatography (ethyl acetate eluent) to give 26 mg (82%) of the title compound as an off-white solid. mp 175° (decomp). FDMS: m/e=393.

EXAMPLE 132

(+)-(4aR)-(10bR)-4-methyl-8-(3-[2,5-dichlororo]thienyl)-10b-methyl-1,2,3,4,4a,5,6,10b-octahydrobenzo[f]quinolin-3-one A 15 mL round bottom flask was charged with (+)-(4aR)-(10bR)-8-(3-[2,5-dichloro]thienyl)-10b-methyl-1,2,3,4,4a,5,6,10b-octahydrobenzo[f]quinolin-3-one (49 mg, 0.13 mmol), 0.4 mL of t-butanol, and potassium t-butoxide (45 mg, 0.39 mmol). Methyl iodide (0.025 mL, 0.39 mmol) was added and the mixture was stirred at room temperature for 4 h. The mixture was diluted with ethyl acetate, and purified by silica gel chromatography (ethyl acetate eluent) to give 35 mg (69%) of the title compound as an oil. FDMS: m/e=379.

EXAMPLE 133

(+)-(4aR)-(10bR)-4-methyl-8-(4-nitro-2-trifluoromethylphenyl)-10b-methyl-1,2,3,4,4a,5,6,10b-octahydrobenzo[f]-quinolin-3-one A 15 mL round bottom flask was charged with (+)-(4aR)-(10bR)-8-(4-nitro-2-trifluoromethylphenyl)-10b-methyl-1,2,3,4,4a,5,6,10b-octahydrobenzo[f]quinolin-3-one (48 mg, 0.12 mmol), 0.3 mL of t-butanol, and potassium t-butoxide (40 mg, 0.36 mmol). Methyl iodide (0.022 mL, 0.36 mmol) was added and the mixture was stirred at room temperature for 4 h. The mixture was diluted with ethyl acetate, and purified by silica gel chromatography (ethyl acetate eluent) to give 35 mg (70%) of the title compound as a white solid. mp 128°–130°. FDMS: m/e=418.

EXAMPLE 134

(+)-(4aR)-(10bR)-4-methyl-8-(2-nitro-4-trifluoromethylphenyl)-10b-methyl-1,2,3,4,4a,5,6,10b-octahydrobenzo[f]-quinolin-3-one A 15 mL round bottom flask was charged with (+)-(4aR)-(10bR)-8-(2-nitro-4-trifluoromethylphenyl)-10b-methyl-1,2,3,4,4a,5,6,10b-octahydrobenzo[f]quinolin-3-one (48 mg, 0.12 mmol), 0.3 mL of t-butanol, and potassium t-butoxide (40 mg, 0.36 mmol). Methyl iodide (0.022 mL, 0.36 mmol) was added and the mixture was stirred at room temperature for 4 h. The mixture was diluted with ethyl acetate, and purified by silica gel chromatography (ethyl acetate eluent) to give 38 mg (76%) of the title compound as an off-white solid. mp 55°–57°. FDMS: m/e =418. $\alpha[D]_{589}$=+60.50 (c=0.16, methanol).

EXAMPLE 135

(+)-(4aR)-(10bR)-4-methyl-8-(4-chloro-2,3,5,6-tetrafluoro-phenyl)-10b-methyl-1,2,3,4,4a,5,6,10b-octahydrobenzo[f]-quinolin-3-one A 15 mL round bottom flask was charged with (+)-(4aR)-(10bR)-8-(4-chloro-2,3,5,6-tetrafluorophenyl)-10b-methyl-1,2,3,4,4a,5,6,10b-octahydrobenzo[f]quinolin-3-one (43 mg, 0.12 mmol), 0.3 mL of t-butanol, and potassium t-butoxide (40 mg, 0.36 mmol). Methyl iodide (0.022 mL, 0.36 mmol) was added and the mixture was stirred at room temperature for 4 h. The mixture was diluted with ethyl acetate, and purified by silica gel chromatography (ethyl acetate eluent) to give 30 mg (66%) of the title compound as an off-white solid. mp 150°–151°. FDMS: m/e=412 $a[D]_{589}$=+68.57 (c=0.12, chloroform).

| analysis: | calculated | found |
| --- | --- | --- |
| C | 61.25 | 61.04 |
| H | 4.41 | 4.53 |
| N | 3.40 | 3.22 |

EXAMPLE 136

(4aR)-(10bR)-8-benzylthio-4,10b-dimethyl-1,2,3,4,4a,5,6,10b-octahydrobenzo[f]quinolin-3-one A 275.2 mg portion of (4aR)-(10bR)-10b-methyl-8-benzylthio-1,2,3,4,4a,5,6,10b-octahydrobenzo[f]quinolin-3-one was methylated substantially according to the process of Example 95. This material was purified on a Chromatotron (2 mm plate, eluted with 3% methanol/chloroform) followed by recrystallization from ethyl acetate to give 150 mg of the desired white solid (52% yield). mp 137°–138°. FDMS: m/e=351. $\alpha[D]_{589}$=59.44 (c=0.36 in methanol).

| Analysis | Calculated | Found |
| --- | --- | --- |
| C | 75.17 | 75.90 |
| H | 7.17 | 7.34 |
| N | 3.99 | 4.03 |

EXAMPLE 137

(4aR)-(10bR)-8-phenylthiomethyl-4,10b-dimethyl-1,2,3,4,-4a,5,6,10b-octahydrobenzo[f]quinolin-3-one A 157 mg portion of (4aR)-(10bR)-10b-methyl-8-phenylthiomethyl-1,2,3,4,4a,5,6,10b-octahydrobenzo[f]-quinolin-3-one was methylated substantially according to the process of Example 95. This material was purified on a Chromatotron (2 mm plate, eluted with ethyl acetate) to give 134 mg of the desired white solid (82% yield). mp 144°–146°. FDMS: m/e=351. $\alpha[D]_{589}$=78.54 (c=0.5 in methanol).

| Analysis | Calculated | Found |
|---|---|---|
| C | 75.17 | 74.92 |
| H | 7.17 | 7.27 |
| N | 3.98 | 4.19 |

EXAMPLE 138

(4aR)-(10bR)-8-(2-benzothiazole)thiomethyl-4,10b-dimethyl-1,2,3,4,4a,5,6,10b-octahydrobenzo[f]quinolin-3-one A 202 mg portion of (4aR)-(10bR)-10b-methyl-8-(2-benzothiazole)thiomethyl-1,2,3,4,4a,5,6,10b-octahydrobenzo[f]quinolin-3-one was methylated substantially according to the process of Example 95. This material was purified on a Chromatotron (2 mm plate, eluted with ethyl acetate) to give 158 mg of the desired white solid (76% yield). mp 182°–184°. FDMS: m/e=408. $\alpha[D]_{589}$=67.31 (c=0.5 in methanol).

| Analysis | Calculated | Found |
|---|---|---|
| C | 67.61 | 67.74 |
| H | 5.92 | 6.03 |
| N | 6.86 | 6.98 |

EXAMPLE 139

(4aR)-(10bR)-8-diphenylmethyl-4,10b-dimethyl-1,2,3,4,-4a,5,6,10b-octahydrobenzo[f]quinolin-3-one A 109 mg portion of (4aR)-(10bR)-10b-methyl-8-diphenylmethyl-1,2,3,4,4a,5,6,10b-octahydrobenzo[f]quinolin-3-one was methylated substantially according to the process of Example 95 above to obtain 109 mg of crude product, which was purified by chromatography as shown in Example 95 followed by recrystallization to obtain 33 mg of the desired product. mp 145°–146°. FDMS: m/e=396. $\alpha[D]_{589}$=58.93 (c=0.5 in chloroform).

The following group of examples demonstrate oxidations which provide hexahydroquinolinones in which the groups R and $R^1$ represent a bond.

EXAMPLE 140

(+)-(4aR)-(10bR)-8-(1-naphthyl)-10b-methyl-3,4,4a,5,6,10b-hexahydrobenzo[f]quinolin-3-one To a suspension of (+)-(4aR)-(10bR)-8-(1-naphthyl)-10b-methyl-1,2,3,4,4a,5,6,10b-octahydrobenzo[f]-quinolin-3-one (295 mg, 0.865 mmol, in 3.5 mL of 1,4-dioxane was added DDQ (216 mg, 1.1 equiv.) followed by bistrimethyl-silyltrifluoromethyl acetamide (998 mg, 4.5 equiv.), and the solution was stirred at room temperature for 2 h, then heated at 100° for 20 h. The mixture was cooled to room temperature, diluted with ethyl acetate, and washed with 2M sodium hydroxide. The organic phase was washed with brine, dried over sodium sulfate, concentrated and chromatographed on silica gel (ethyl acetate eluent) to give, after trituration from ether/hexanes, 60 mg (20%) of the title compound as a white solid. mp 199°–201° (decomp.) FDMS m/e=339. $\alpha[D]_{589}$=+35.98 (c=0.67, chloroform).

| Analysis | Calculated | Found |
|---|---|---|
| C | 84.92 | 84.72 |
| H | 6.24 | 5.98 |
| N | 4.13 | 3.85 |

EXAMPLE 141

(+)-(4aR)-(10bR)-8-(3-nitrophenyl)-10b-methyl-3,4,4a,5,6,10b-hexahydrobenzo[f]quinolin-3-one To a suspension of (+)-(4aR)-(10bR)-8-(3-nitrophenyl)-10b-methyl-1,2,3,4,4a,5,6,10b-octahydrobenzo[f]-quinolin-3-one (264 mg, 0.786 mmol), in 3.0 mL of 1,4-dioxane was added DDQ (196 mg, 1.1 equiv.) followed by bistrimethyl-silyltrifluoromethyl acetamide (911 mg, 4.5 equiv.), and the solution was stirred at room temperature for 2 h, then heated at 100° for 20 h. The mixture was cooled to room temperature, diluted with ethyl acetate, and washed with 2M sodium hydroxide. The organic phase was washed with brine, dried over sodium sulfate, concentrated and chromatographed on silica gel (ethyl acetate eluent) to give, after trituration from ether/hexanes, 55 mg (21%) of the title compound as an orange solid. mp 205°–206°. FDMS m/e= 334. $\alpha[D]_{589}$=+57.23 (c=0.66, chloroform).

| Analysis | Calculated | Found |
|---|---|---|
| C | 71.84 | 71.47 |
| H | 5.43 | 5.49 |
| N | 8.38 | 7.96 |

EXAMPLE 142

(+)-(4aR)-(10bR)-8-(3-isoquinolinyl)-10b-methyl-3,4,4a,5,6,10b-hexahydrobenzo[f]quinolin-3-one To a suspension of (+)-(4aR)-(10bR)-8-(3-isoquinolinyl)-10b-methyl-1,2,3,4,4a,5,6,10b-octahydrobenzo[f]quinolin-3-one (80 mg, 0.230 mmol), in 1.0 mL of 1,4-dioxane was added DDQ (58 mg, 1.1 equiv.) followed by bistrimethyl-silyltrifluoromethyl acetamide (270 mg, 4.5 equiv.), and the solution was stirred at room temperature for 2 h, then heated at 100° for 20 h. The mixture was cooled to room temperature, diluted with ethyl acetate, and washed with 2M sodium hydroxide. The organic phase was washed with brine, dried over sodium sulfate, concentrated and chromatographed on silica gel (ethyl acetate eluent) to give, after trituration from ether/hexanes, 18 mg (24%) of the title compound as a white solid. mp 248° (decomp.) FDMS m/e=340.

Preparation 6

(4aR)-(10bR)-8-formyl-10b-methyl-1,2,3,4,4a,5,6,10b-octahydrobenzo[f]quinolin-3-one Methyllithium (1.5 mL, 2.1 mmol of a 1.4M solution in diethyl ether) was added to (4aR)-(10bR)-8-bromo-10b-methyl-1,2,3,4,-4a,5,6,10b-octahydrobenzo[f]quinolin-3-one (0.500 g, 1.7 mmol) in 25 mL of anhydrous THF which had been cooled in a dry ice/isopropanol bath under nitrogen, and was stirred for 15 min before addition of t-butyllithium (2.0 mL, 3.4 mmol of a 1.7M solution in pentane). After 30 min, dimethylformamide (0.4 mL) was added, and the mixture was allowed to warm to 0°, and additional dimethylformamide (0.2 mL) was added. The ice bath was removed and the reaction was quenched with 1N hydrochloric acid to make pH=2, and then the mixture was extracted with 10% isopropanol/chloroform. The combined organic extracts were washed well with water, dried over sodium sulfate, and evaporated. The resulting product was slurried in diethyl ether before recrystallizing from 50% ethyl acetate/hexane to give off-white crystals: mp 185°–189°. FD MS 243M +; Calcd for $C_{15}H_{17}N_1O_2$: C, 74.05; H, 7.04; N, 5.76. Found: C, 73.85; H, 7.11; N, 5.91.

Preparation 7

(4aR)-(10bR)-8-carboxy-10b-methyl-1,2,3,4,4a,5,6,10b-octahydrobenzo[f]quinolin-3-one In a flame-dried 3-neck round bottom flask equipped with magnetic stirrer and nitrogen inlet was dissolved (4aR)-(10bR)-8-bromo-10b-methyl-1,2,3,4,4a,5,6,10b-octahydrobenzo[f]quinoline-3-one (500 mg, 1.7 mmol). The solution was cooled to −78° and treated with ethereal methyllithium (1.7 mL, 1.4M, 2.4 mmol) added dropwise over 2 min. After further stirring for 15 min., a solution of t-butyllithium (2.9 mL, 1.7M in pentane, 5.0 mmol) was added dropwise. Following complete addition, the suspension was treated with excess carbon dioxide, (generated from dry ice, dried by passage through calcium sulfate) added subsurface for 2 min. The mixture was allowed to warm to ambient temperature and was acidified with 1N aqueous hydrochloric acid. The mixture was extracted with 10% isopropanol/-chloroform and the organic phase dried over anhydrous magnesium sulfate. Removal of solvent under reduced pressure afforded the crude product (520 mg) contaminated with pivalic acid. Trituration with ethyl acetate afforded product (322 mg) as a white powder (mp>320°) m/e 259.

| Analysis | Calculated | Found |
|---|---|---|
| C | 69.48 | 69.51 |
| H | 6.61 | 6.63 |
| N | 5.40 | 5.18 |

EXAMPLE 143

(+)-(4aR)-(10bR)-4-methyl-8-(phenylcarboxamido)-10b-methyl-1,2,3,4,4a,5,6,10b-octahydrobenzo[f]quinolin-3-one A 50 mL round bottom flask was charged with (+)-(4aR)-(10bR)-4-methyl-8-carboxy-10b-methyl-1,2,3,4,4a,-5,6,10b-octahydrobenzo[f]quinolin-3-one (100 mg, 0.37) and 2 mL of benzene. Oxalyl chloride (1.1 mmol) was added dropwise via syringe to the stirred mixture, followed by a catalytic amount of dimethylformamide (one drop). Allowed to stir at room temperature for 25 min, then removed volatiles in vacuo. Added 1 mL of THF, followed by a solution of aniline and pyridine (4 eq) in 1 mL of THF to the acid chloride solution at 0°. Allowed to warm to room temperature. Diluted with 50 mL of chloroform, and washed with 1N hydrochloric acid (2×25 mL), 10% aq. sodium bicarbonate (2×25 mL), water, (2×25 mL), and brine (2×25 mL). The combined organic extracts were dried over sodium sulfate, concentrated and chromatographed on silica (ethyl acetate eluent), to give 24 mg (19%) of the title compound as an amorphous yellow foam. FDMS: m/e=348.

EXAMPLE 144

(+)-(4aR)-(10bR)-4-methyl-8-benzyloxycarbonyl-10b-methyl-1,2,3,4,4a,5,6,10b-octahydrobenzo[f]quinolin-3-one A 50 mL round bottom flask was charged with (+)-(4aR)-(10bR)-4-methyl-8-carboxy-10b-methyl-1,2,3,4,4a,-5,6,10b-octahydrobenzo[f]quinolin-3-one (100 mg, 0.37) and 2 mL of benzene. Oxalyl chloride (1.1 mmol) was added dropwise via syringe to the stirred mixture, followed by a catalytic amount of dimethylformamide (one drop). The mixture was allowed to stir at room temperature for 25 min, and then the volatiles were removed in vacuo. One mL of THF was added, followed by a solution of benzyl alcohol and pyridine (4 eq) in 1 mL of THF at 0°. It was then allowed to warm to room temperature, diluted with 50 mL of chloroform, and washed with 0.1N hydrochloric acid (2×25 mL), 10% sodium bicarbonate (2×25 mL), water, (2×25 mL), and brine (2×25 mL). The combined organic extracts were dried over sodium sulfate, concentrated and chromatographed on silica (ethyl acetate eluent), to give 11 mg (8%) of the title compound as an amorphous yellow foam. FDMS: m/e=349.

EXAMPLE 145

(+)-(4aR)-(10bR)-4-methyl-8-phenoxycarbonyl-10b-methyl-1,2,3,4,4a,5,6,10b-octahydrobenzo[f]quinolin-3-one A 50 mL round bottom flask was charged with (+)-(4aR)-(10bR)-4-methyl-8-carboxy-10b-methyl-1,2,3,4,4a,-5,6,10b-octahydrobenzo[f]quinolin-3-one (300 mg, 1.10 mmol) and 6 mL of benzene. Oxalyl chloride (3.3 mmol) was added dropwise via syringe to the stirred mixture, followed by a catalytic amount of dimethylformamide (two drops). It was allowed to stir at room temperature for 75 min. and then the volatiles were removed in vacuo. Four mL of THF was added, followed by a solution of phenol and pyridine (4 eq) in 2 mL of THF at 0°. It was allowed to warm to room temperature, diluted with 50 mL of ethyl acetate, and washed with 0.1N hydrochloric acid (2×25 mL), 10% sodium bicarbonate (2×25 mL), water, (2×25 mL), and brine (2×25 mL). The combined organic extracts were dried over sodium sulfate, concentrated and chromatographed on silica (0–2% methanol/dichloromethane gradient eluent), followed by additional chromatography (80% ethyl acetate/hexanes eluent) to give 43 mg (11%) of the title compound as a yellow solid. mp 194°–196°. FDMS: m/e=349. α[D]$_{589}$=+78.53 (c=1.00, chloroform).

| Analysis | Calculated | Found |
|---|---|---|
| C | 75.52 | 75.44 |
| H | 6.63 | 6.74 |
| N | 4.01 | 4.00 |

EXAMPLE 146

(+)-(4aR)-(10bR)-4-methyl-8-(benzylcarboxamido)-10b-methyl-1,2,3,4,4a,5,6,10b-octahydrobenzo[f]quinolin-3-one A 50 mL round bottom flask was charged with (+)-(4aR)-(10bR)-4-methyl-8-carboxy-10b-methyl-1,2,3,4,4a,-5,6,10b-octahydrobenzo[f]quinolin-3-one (100 mg, 0.37) and 2 mL of benzene. Oxalyl chloride (1.1 mmol) was added dropwise via syringe to the stirred mixture, followed by a catalytic amount of dimethylformamide (one drop). The mixture was stirred at room temperature for 25 min, and then the volatiles were removed in vacuo. One mL of THF was added, followed by a solution of benzylamine and pyridine (4 eq) in 1 mL of THF at 0°. It was allowed to warm to room temperature, diluted with 50 mL of chloroform, and washed with 1N hydrochloric acid (2×25 mL), 10% aq. sodium bicarbonate (2×25 mL), water, (2×25 mL), and brine (2×25 mL). The combined organic extracts were dried over sodium sulfate, concentrated and chromatographed on silica (ethyl acetate eluent), to give 40 mg (30%) of the title compound as an amorphous brown foam. FDMS: m/e=362.

EXAMPLE 147

(4aR)-(10bR)-4,10b-dimethyl-8-diphenylmethoxycarbonyl-1,2,3,4,4a,5,6,10b-octahydrobenzo[f]quinolin-3-one Under an atmosphere of nitrogen, 100 mg of 4,10b-dimethyl-8-carboxy-1,2,3,4,4a,5,6,10b-octahydrobenzo[f]-quinolin-3-one and 66 mg of 1,1'-carbonyldiimidazole were dissolved in 5 mL of anhydrous dimethylformamide and stirred for 1 h. Then 74 mg of benzhydrol was added, and the reaction was stirred for 18 hours, still at ambient temperature. The volatiles were then removed under high vacuum, and the residue was dissolved in 50 mL of dichloromethane and washed with 40 mL of 1N hydrochloric acid, with two 40 mL portions of saturated aqueous sodium bicarbonate, and finally with 40 mL of brine. The organic layer was dried with sodium sulfate, filtered and evaporated under vacuum to give 141 mg of impure product, which was purified by chromatography on silica gel, eluting with ethyl acetate to obtain 91 mg (57%) of the desired product. An analytical sample was recrystallized from ethyl acetate/water. mp 130°–131°. FDMS: m/e=439.

| Analysis | Calculated | Found |
|---|---|---|
| C | 79.24 | 79.49 |
| H | 6.65 | 6.57 |
| N | 3.19 | 3.28 |

EXAMPLE 148

(4aR)-(10bR)-4,10b-dimethyl-8-diphenylmethylcarboxamido-1,2,3,4,4a,5,6,10b-octahydrobenzo[f]quinolin-3-one A 150 mg portion of 4,10b-dimethyl-8-carboxy-1,2,3,4, 4a,5,6,10b-octahydrobenzo[f]-quinolin-3-one and 97.9 mg of 1,1'-carbonyldiimidazole were dissolved in 4 mL of dry dimethylformamide. The reaction was stirred under nitrogen for 4 h at ambient temperature, and then 108 µl of diphenylmethylamine was then added to the solution, and it was stirred for 36 h more. The mixture was then evaporated under high vacuum, and the residue was taken in chloroform and washed with 1N hydrochloric acid, twice with saturated aqueous sodium bicarbonate, and finally with brine. The organic layer was then dried, filtered and evaporated under vacuum to recover 246 mg of impure product. That product was purified on a Chromatotron, eluting with ethyl acetate. The product-containing fraction was recrystallized from ethyl acetate/hexane to obtain 94 mg (40%) of the desired product. mp 210°–211° FDMS: m/e=438.

| Analysis | Calculated | Found |
|---|---|---|
| C | 79.42 | 79.27 |
| H | 6.89 | 6.99 |
| N | 6.39 | 6.42 |

The following preparation and example illustrates syntheses of compounds making use of an SH-substituted benzoquinolinone nucleus compound.

Preparation 8

(+)-(4aR)-(10bR)-4-methyl-8-mercapto-10b-methyl-1,2, 3,4,4a,-5,6,10b-octahydrobenzo[f]quinolin-3-one To a solution of (+)-(4aR)-(10bR)-8-bromo-10b-methyl-1,2,3,4,4a,5,6,10b-octahydrobenzo[f]quinolin-3-one (5.88 g, 20 mmol) in 300 mL of anhydrous THF was added methyllithium (158 mL, 1.4M solution in diethyl ether at –78°. The mixture was allowed to stir at –78° for 20 min, then t-butyllithium (26 mL, 1.7M in pentane) was added. The mixture was stirred for an additional 90 min, and N,N-diisopropylthiuram disulfide (14.1 g, 40 mmol) in 80 mL of anhydrous THF was added at –78°. The mixture was stirred for 15 min, the cold bath was removed, and the mixture was allowed to warm to room temperature. To the mixture was added 100 mL of 1N hydrochloric acid, the organic phase was separated and washed with 1N hydrochloric acid (200 mL), 10% sodium bicarabonate (2×200 mL), and brine (2×200 mL). The organic layer was dried over sodium sulfate, concentrated, and purified by silica gel chromatography (100% ethyl acetate-5% methanol/ethyl acetate eluent gradient) to give 6.14 g (79%) of material which was dissolved in 61 mL of t-butanol, and potassium t-butoxide (7.42 g, 62.8 mmol) was added. The mixture was allowed to stir at room temp for 30 min (became homogeneous), cooled to 0°, and methyl iodide (62.8 mmol in 10 mL of t-butanol) was added dropwise via addition funnel. The cold bath was removed and the mixture was allowed to stir at room temperature for 16 h. The mixture was then diluted with 300 mL of ethyl acetate, the organic phase was separated, washed with brine, dried over sodium sulfate and concentrated to give 6.08 g (96%) of (+)-(4aR) -10bR)-4-methyl-8-([N,N-diisopropyl]thiuramyl)-1,2,3,4, 4a,5,6,1b-octahydrobenzo[f]-quinolin-3-one as a white solid. mp 181°–182°. FDMS m/e=404. $\alpha[D]_{589}$=+72.11 (c=0.21, chloroform).

| Analysis | Calculated | Found |
|---|---|---|
| C | 65.30 | 65.11 |
| H | 7.97 | 7.96 |
| N | 6.92 | 7.07 |

The above thiuram (6.08 g, 15.0 mmol) was dissolved in 250 mL of trifluoroacetic acid and heated at 72° for 16 h. The solution was cooled, the volatiles were removed via rotary evaporator, the resulting oil was dissolved in chloroform, and the organic layer was washed with 10% sodium bicarabonate solution (2×200 mL) followed by brine (2×200 mL). The organic extract was dried over sodium sulfate, and concentrated to give 3.80 g (96%) of the title 8-mercapto compound as oil, used directly without further purification. FDMS m/e=261.

EXAMPLE 149

(+)-(4aR)-(10bR)-4-methyl-8-(2-thiazoylthio)-10b-methyl-1,2,3,4,4a,5,6,10b-octahydrobenzo[f]quinolin-3-one A 15 mL round bottom flask was charged with (+)-(4aR) -(10bR)-4-methyl-8-mercapto-10b-methyl-1,2,3,4,4a,-5,6, 10b-octahydrobenzo[f]quinolin-3-one (100 mg, 0.38 mmol), potassium carbonate (158 mg, 1.14 mmol), 2-bromothiazole (75 mg, 0.46 mmol) and 1 mL of anhydrous dimethylformamide, fitted with a reflux condenser, and the stirred mixture was heated at 60°, under nitrogen, for 18 h. The mixture was cooled, diluted with ethyl acetate (75 mL) and washed with brine (2×25 mL). The combined organic extracts were dried over sodium sulfate, concentrated, and purified by silica gel chromatography (ethyl acetate eluent) to give 30 mg (23%) of the title compound as an amorphous solid. mp 140°–142°. FDMS: m/e=344.

| Analysis | Calculated | Found |
|---|---|---|
| C | 62.76 | 62.52 |
| H | 5.85 | 5.96 |
| N | 8.13 | 7.93 |

EXAMPLE 150

(+)-(4aR)-(10bR)-4-methyl-8-(2-benzoxazolylthio)-10b-methyl-1,2,3,4,4a,5,6,10b-octahydrobenzo[f]quinolin-3-one A 15 mL round bottom flask was charged with (+)-(4aR)-(10bR)-4-methyl-8-mercapto-10b-methyl-1,2,3,4,4a,-5,6,10b-octahydrobenzo[f]quinolin-3-one (100 mg, 0.38 mmol), potassium carbonate (158 mg, 1.14 mmol), 2-chlorobenzoxazole (71 mg, 0.46 mmol) and 1.5 mL of anhydrous dimethylformamide, fitted with a reflux condenser, and the stirred mixture was heated at 60°, under nitrogen, for 18 h. The mixture was cooled, diluted with ethyl acetate (75 mL) and washed with brine (2×25 mL). The combined organic extracts were dried over sodium sulfate, concentrated, and purified by silica gel chromatography (ethyl acetate eluent) to give 65 mg (45%) of the title compound as an amorphous foam. FDMS: m/e=378.

| Analysis | Calculated | Found |
|---|---|---|
| C | 69.82 | 67.82 |
| H | 5.86 | 6.55 |
| N | 7.40 | 7.15 |

EXAMPLE 151

(+)-(4aR)-(10bR)-4-methyl-8-(2-pyrimidinylthio)-10b-methyl-1,2,3,4,4a,5,6,10b-octahydrobenzo[f]quinolin-3-one A 15 mL round bottom flask was charged with (+)-(4aR)-(10bR)-4-methyl-8-mercapto-10b-methyl-1,2,3,4,4a,-5,6,10b-octahydrobenzo[f]quinolin-3-one (100 mg, 0.38 mmol), potassium carbonate (158 mg, 1.14 mmol), 2-chloropyrimidine (53 mg, 0.46 mmol) and 1 mL of anhydrous dimethylformamide, fitted with a reflux condenser, and the stirred mixture was heated at 60°, under nitrogen, for 18 h. The mixture was cooled, diluted with ethyl acetate (75 mL) and washed with brine (2×25 mL). The combined organic extracts were dried over sodium sulfate, concentrated, and purified by silica gel chromatography (ethyl acetate eluent) to give 30 mg (23%) of the title compound as an oil. FDMS: m/e=339.

| Analysis | Calculated | Found |
|---|---|---|
| C | 67.23 | 67.55 |
| H | 6.24 | 5.88 |
| N | 12.38 | 12.25 |

EXAMPLE 152

(+)-(4aR)-(10bR)-4-methyl-8-(2-pyrazinylthio)-10b-methyl-1,2,3,4,4a,5,6,10b-octahydrobenzo[f]quinolin-3-one A 15 mL round bottom flask was charged with (+)-(4aR)-(10bR)-4-methyl-8-mercapto-10b-methyl-1,2,3,4,4a,-5,6,10b-octahydrobenzo[f]quinolin-3-one (100 mg, 0.38 mmol), potassium carbonate (158 mg, 1.14 mmol), 2-chloropyrazine (53 mg, 0.46 mmol) and 1 mL of anhydrous dimethylformamide, fitted with a reflux condenser, and the stirred mixture was heated at 60°, under nitrogen, for 18 h. The mixture was cooled, diluted with ethyl acetate (75 mL) and washed with brine (2×25 mL). The combined organic extracts were dried over sodium sulfate, concentrated, and purified by silica gel chromatography (80% ethyl acetate/hexanes eluent) to give 63 mg (49%) of the title compound as an off white solid. mp 94°–95°. FDMS: m/e=339. $\alpha[D]_{589}$=+88.14 (c=0.92, chloroform).

| Analysis | Calculated | Found |
|---|---|---|
| C | 67.23 | 67.26 |
| H | 6.24 | 6.04 |
| N | 12.38 | 11.90 |

EXAMPLE 153

(+)-(4aR)-(10bR)-4-methyl-8-(2-quinoxalinylthio)-10b-methyl-1,2,3,4,4a,5,6,10b-octahydrobenzo[f]quinolin-3-one A 15 mL round bottom flask was charged with (+)-(4aR)-(10bR)-4-methyl-8-mercapto-10b-methyl-1,2,3,4,4a,-5,6,10b-octahydrobenzo[f]quinolin-3-one (100 mg, 0.38 mmol), potassium carbonate (158 mg, 1.14 mmol), 2-chloroquinoxaline (76 mg, 0.46 mmol) and 1.5 mL of anhydrous dimethyl formamide, fitted with a reflux condenser, and the stirred mixture was heated at 60°, under nitrogen, for 18 h. The mixture was cooled, diluted with ethyl acetate (75 mL) and washed with brine (2×25 mL). The combined organic extracts were dried over sodium sulfate, concentrated, and purified by silica gel chromatography (80% ethyl acetate/hexanes eluent) to give 82 mg (55%) of the title compound as an amorphous foam. FDMS: m/e=589. $\alpha[D]_{589}$=+68.96 (c=0.81, chloroform).

EXAMPLE 154

(+)-(4aR)-(10bR)-4-methyl-8-(2-[3-phenyl]tetrazoylthio)-10b-methyl-1,2,3,4,4a,5,6,10b-octahydrobenzo[f]quinolin-3-one A 15 mL round bottom flask was charged with (+)-(4aR)-(10bR)-4-methyl-8-mercapto-10b-methyl-1,2,3,4,4a,-5,6,10b-octahydrobenzo[f]quinolin-3-one (100 mg, 0.38 mmol), potassium carbonate (158 mg, 1.14 mmol), 2-chloro-3-phenyltetrazole (83 mg, 0.46 mmol) and 1 mL of anhydrous dimethylformamide, fitted with a reflux condenser, and the stirred mixture was heated at 60°, under nitrogen, for 18 h. The mixture was cooled, diluted with ethyl acetate (75 mL) and washed with brine (2×25 mL). The combined organic extracts were dried over sodium sulfate, concentrated, and purified by silica gel chromatography (ethyl acetate eluent) to give 81 mg (53%) of the title compound as a white solid. mp 128°–130°. FDMS: m/e=405. $\alpha[D]_{589}$=+69.47 (c=0.57, chloroform).

| Analysis | Calculated | Found |
|---|---|---|
| C | 65.16 | 65.35 |
| H | 5.72 | 5.85 |
| N | 17.27 | 17.08 |

EXAMPLE 155

(+)-(4aR)-(10bR)-4-methyl-8-(2-[5-trifluoromethyl]pyridyl-thio)-10b-methyl-1,2,3,4,4a,5,6,10b-octahydrobenzo[f]-quinolin-3-one A 15 mL round bottom flask was charged with (+)-(4aR)-(10bR)-4-methyl-8-mercapto-10b-methyl-1,2,3,4,4a,-5,6,10b-octahydrobenzo[f]quinolin-3-one (100 mg, 0.38 mmol), potassium carbonate (158 mg, 1.14 mmol), 2-chloro-5-trifluoromethylpyridine (84 mg, 0.46 mmol) and 1.5 mL of anhydrous dimethylformamide, fitted with a reflux condenser, and the stirred mixture was heated at 60°, under nitrogen, for 18 h. The mixture was cooled, diluted with ethyl acetate (75 mL) and washed with brine (2×25 mL). The combined organic extracts were dried over sodium sulfate, concentrated, and purified by silica gel chromatography (ethyl acetate eluent) to give 90 mg (58%) of the title compound as an amorphous solid. mp 134°–140°. FDMS: m/e=406. $\alpha[D]_{589}$=+76.80 (c=0.42, chloroform).

| Analysis | Calculated | Found |
|---|---|---|
| C | 62.05 | 61.89 |
| H | 5.21 | 5.31 |
| N | 6.89 | 6.72 |

EXAMPLE 156

(+)-(4aR)-(10bR)-4-methyl-8-(3-indazolylthio)-10b-methyl-1,2,3,4,4a,5,6,10b-octahydrobenzo[f]quinolin-3-one A 15 mL round bottom flask was charged with (+)-(4aR)-(10bR)-4-methyl-8-mercapto-10b-methyl-1,2,3,4,4a,-5,6,10b-octahydrobanzo[f]quinolin-3-one (100 mg, 0.38 mmol), potassium carbonate (158 mg, 1.14 mmol), 1-(t-butoxycarbonyl)-3-chloroindazole (116 mg, 0.46 mmol) and 1 mL of anhydrous dimethylformamide, fitted with a reflux condenser, and the stirred mixture was heated at 60°, under nitrogen, for 18 h. The mixture was cooled, diluted with ethyl acetate (75 mL) and washed with brine (2×25 mL). The combined organic extracts were dried over sodium sulfate, concentrated, and purified by silica gel chromatography (ethyl acetate eluent) to give 60 mg (16%) of the title compound as an oil. FDMS: m/e=377.

EXAMPLE 157

(+)-(4aR)-(10bR)-4-methyl-8-(2-[4-isopropyl]benzothiazolyl-thio)-10b-methyl-1,2,3,4,4a,5,6,10b-octahydrobenzo[f]quinolin-3-one A 15 mL round bottom flask was charged with (+)-(4aR)-(10bR)-4-methyl-8-mercapto-10b-methyl-1,2,3,4,4a,-5,6,10b-octahydrobenzo[f]quinolin-3-one (100 mg, 0.38 mmol), potassium carbonate (158 mg, 1.14 mmol), 2-chloro-4-isopropylbenzothiazole (161 mg, 0.76 mmol) and 1 mL of anhydrous dimethylformamide, fitted with a reflux condenser, and the stirred mixture was heated at 60°, under nitrogen, for 18 h. The mixture was cooled, diluted with ethyl acetate (75 mL) and washed with brine (2×25 mL). The combined organic extracts were dried over sodium sulfate, concentrated, and purified by silica gel chromatography (ethyl acetate eluent) to give 57 mg (34%) of the title compound as an amorphous solid. mp 166°–170°. FDMS: m/e=436.

| Analysis | Calculated | Found |
|---|---|---|
| C | 68.77 | 68.56 |
| H | 6.46 | 6.29 |
| N | 6.42 | 6.36 |

EXAMPLE 158

(+)-(4aR)-(10bR)-4-methyl-8-(6-chloro-2-benzothiazolylthio)-10b-methyl-1,2,3,4,4a,5,6,10b-octahydrobenzo[f]quinolin-3-one A 15 mL round bottom flask was charged with (+)-(4aR)-(10bR)-4-methyl-8-mercapto-10b-methyl-1,2,3,4,4a,-5,6,10b-octahydrobenzo[f]quinolin-3-one (100 mg, 0.38 mmol), potassium carbonate (158 mg, 1.14 mmol), 2,6-dichlorobenzothiazole (155 mg, 0.76 mmol) and 1.5 mL of anhydrous dimethylformamide, fitted with a reflux condenser, and the stirred mixture was heated at 60°, under nitrogen, for 18 h. The mixture was cooled, diluted with ethyl acetate (75 mL) and washed with brine (2×25 mL). The combined organic extracts were dried over sodium sulfate, concentrated, and purified by silica gel chromatography (ethyl acetate eluent) to give 86 mg (53%) of the title compound as an amorphous solid. mp 156°–162°. FDMS: m/e =429. $\alpha[D]_{589}$=+63.53 (c=0.66, chloroform).

| Analysis | Calculated | Found |
|---|---|---|
| C | 61.60 | 60.89 |
| H | 4.93 | 5.35 |
| N | 6.53 | 6.10 |

EXAMPLE 159

(+)-(4aR)-(10bR)-4-methyl-8-(4-methyl-2-benzothiazolylthio)-10b-methyl-1,2,3,4,4a,5,6,10b-octahydrobenzo[f]quinolin-3-one A 15 mL round bottom flask was charged with (+)-(4aR)-(10bR)-4-methyl-8-mercapto-10b-methyl-1,2,3,4,4a,-5,6,10b-octahydrobenzo[f]quinolin-3-one (100 mg, 0.38 mmol), potassium carbonate (158 mg, 1.14 mmol), 2-chloro-4-methylbenzothiazole (84 mg, 0.46 mmol) and 1 mL of anhydrous dimethylformamide, fitted with a reflux condenser, and the stirred mixture was heated at 60°, under nitrogen, for 18 h. The mixture was cooled, diluted with ethyl acetate (75 mL) and washed with brine (2×25 mL). The combined organic extracts were dried over sodium sulfate, concentrated, and purified by silica gel chromatography (ethyl acetate eluent) to give 66 mg (43%) of the title compound as an amorphous solid. mp 134°–142°. FDMS: m/e =408. $\alpha[D]_{589}$=+62.80 (c=0.74, chloroform).

| Analysis | Calculated | Found |
|---|---|---|
| C | 67.61 | 67.14 |
| H | 5.92 | 6.11 |
| N | 6.86 | 6.63 |

EXAMPLE 160

(+)-(4aR)-(10bR)-4-methyl-8-(5-nitro-2-benzothiazolylthio)-10b-methyl-1,2,3,4,4a,5,6,10b-octahydrobenzo[f]quinolin-3-one A 15 mL round bottom flask was charged with (+)-(4aR)-(10bR)-4-methyl-8-mercapto-10b-methyl-1,2,3,4,4a,-5,6,10b-octahydrobenzo[f]quinolin-3-one (100 mg, 0.38 mmol), potassium carbonate (158 mg, 1.14 mmol), 2-chloro-5-nitrobenzothiazole (99 mg, 0.46 mmol) and 1 mL of anhydrous dimethylformamide, fitted with a reflux condenser, and the stirred mixture was heated at 60°, under nitrogen, for 18 h. The mixture was cooled, diluted with ethyl acetate (75 mL) and washed with brine (2×25 mL). The combined organic extracts were dried over sodium sulfate, concentrated, and purified by silica gel chromatography (ethyl acetate eluent) to give 97 mg (58%) of the title compound as an amorphous solid. mp 96°–100°. FDMS: m/e=439. $\alpha[D]_{589}$=+61.35 (c=0.64, chloroform).

| Analysis | Calculated | Found |
|---|---|---|
| C | 60.12 | 59.85 |
| H | 4.82 | 5.09 |
| N | 9.56 | 9.35 |

EXAMPLE 161

(+)-(4aR)-(10bR)-4-methyl-8-(6-methoxy-2-benzothiazolylthio)-10b-methyl-1,2,3,4,4a,5,6,10b-octahydrobenzo[f]quinolin-3-one A 15 mL round bottom flask was charged with (+)-(4aR)-(10bR)-4-methyl-8-mercapto-10b-methyl-1,2,3,4,4a,-5,6,10b-octahdrobenzo[f]quinolin-3-one (100 mg, 0.38 mmol), potassium carbonate (158 mg, 1.14 mmol), 2-chloro-6-methoxy-benzothiazole (92 mg, 0.46 mmol) and 1.5 mL of anhydrous dimethylformamide, fitted with a reflux condenser, and the stirred mixture was heated at 60°, under nitrogen, for 18 h. The mixture was cooled, diluted with ethyl acetate (75 mL) and washed with brine (2×25 mL). The combined organic extracts were dried over sodium sulfate, concentrated, and purified by silica gel chromatography (ethyl acetate eluent) to give 76 mg (47%) of the title compound as an amorphous solid. mp 102°–107°. FDMS: m/e =424. $\alpha[D]_{589}$=+64.29 (c=0.71, chloroform).

| Analysis | Calculated | Found |
|---|---|---|
| C | 65.07 | 64.81 |
| H | 5.70 | 5.98 |
| N | 6.60 | 6.40 |

EXAMPLE 162

(+)-(4aR)-(10bR)-4-methyl-8-(4-fluoro-2-benzothiazolylthio)-10b-methyl-1,2,3,4,4a,5,6,10b-octahydrobenzo[f]quinolin-3-one A 15 mL round bottom flask was charged with (+)-(4aR)-(10bR)-4-methyl-8-mercapto-10b-methyl-1,2,3,4,4a,-5,6,10b-octahydrobenzo[f]quinolin-3-one (100 mg, 0.38 mmol), potassium carbonate (158 mg, 1.14 mmol), 2-chloro-4-fluoro benzothiazole (86 mg, 0.46 mmol and 1 mL of anhydrous dimethylformamide, fitted with a reflux condenser, and the stirred mixture was heated at 60°, under nitrogen, for 48 h. The mixture was cooled, diluted with ethyl acetate (75 mL) and washed with brine (2×25 mL). The combined organic extracts were dried over sodium sulfate, concentrated, and purified by silica gel chromatography (80% ethyl acetate/hexanes eluent) to give 91 mg (58%) of the title compound as an amorphous solid. mp 140°–145°. FDMS: m/e=412. $\alpha[D]_{589}$=+70.06 (c=0.52, chloroform).

| Analysis | Calculated | Found |
|---|---|---|
| C | 64.05 | 64.29 |
| H | 5.13 | 5.21 |
| N | 6.79 | 6.97 |

EXAMPLE 163

(+)-(4aR)-(10bR)-4-methyl-8-2-naphtho<1,2-d>-thiazolylthio)-10b-methyl-1,2,3,4,4a,5,6,10b-octahydrobenzo[f]-quinolin-3-one A 15 mL round bottom flask was charged with (+)-(4aR)-(10bR)-4-methyl-8-mercapto-10b-methyl-1,2,3,4,4a,-5,6,10b-octahydrobenzo[f]quinolin-3-one (100 mg, 0.38 mmol), potassium carbonate (158 mg, 1.14 mmol), 2-chloronaphtho<1,2-d>thiazole (101 mg, 0.46 mmol) and 1.5 mL of anhydrous dimethylformamide, fitted with a reflux condenser, and the stirred mixture was heated at 60°, under nitrogen, for 48 h. The mixture was cooled, diluted with ethyl acetate (75 mL) and washed with brine (2×25 mL). The combined organic extracts were dried over sodium sulfate, concentrated, and purified by silica gel chromatography (80% ethyl acetate/hexanes eluent) to give 94 mg (56%) of the title compound as an amorphous solid. mp 179°–184°. FDMS: m/e=444. $\alpha[D]_{589}$=+60.59 (c=0.67, chloroform).

| Analysis | Calculated | Found |
|---|---|---|
| C | 70.24 | 69.95 |
| H | 5.44 | 5.50 |
| N | 6.30 | 6.16 |

EXAMPLE 164

(+)-(4aR)-(10bR)-4-methyl-8-(4-chloro-2-benzothiazolylthio)-10b-methyl-1,2,3,4,4a,5,6,10b-octahydrobenzo[f]quinolin-3-one A 15 mL round bottom flask was charged with (+)-(4aR)-(10bR)-4-methyl-8-mercapto-10b-methyl-1,2,3,4,4a,-5,6,10b-octahydrobenzo[f]quinolin-3-one (100 mg, 0.38 mmol), potassium carbonate (158 mg, 1.14 mmol), 2,4-dichlorobenzo-thiazole (94 mg, 0.46 mmol/and 1 mL of anhydrous dimethyl formamide, fitted with a reflux condenser, and the stirred mixture was heated at 60°, under nitrogen, for 48 h. The mixture was cooled, diluted with ethyl acetate (75 mL) and washed with brine (2×25 mL). The combined organic extracts were dried over sodium sulfate, concentrated, and purified by silica gel chromatography (80% ethyl acetate/hexanes eluent) to give 80 mg (49%) of the title compound as an amorphous solid. mp 207°–209°. FDMS: m/e=429 $\alpha[D]_{589}$=+63.86 (c=0.57, chloroform).

| Analysis | Calculated | Found |
|---|---|---|
| C | 61.60 | 61.80 |
| H | 4.93 | 5.13 |
| N | 6.53 | 6.45 |

EXAMPLE 165

(+)-(4aR)-(10bR)-4-methyl-8-(5,6-dichloro-2-benzothiazolyl-thio)-10b-methyl-1,2,3,4,4a,5,6,10b-octahydrobenzo[f]-quinolin-3-one A 15 mL round bottom flask was charged with (+)-(4aR)-(10bR)-4-methyl-8-mercapto-10b-methyl-1,2,3,4,4a,-5,6,10b-octahydrobenzo[f]quinolin-3-one (100 mg, 0.38 mmol), potassium carbonate (158 mg, 1.14 mmol), 2,5,6-trichloro benzothiazole (110 mg, 0.46 mmol) and 1 mL of anhydrous dimethylformamide, fitted with a reflux condenser, and the stirred mixture was heated at 60°, under nitrogen, for 18 h. The mixture was cooled, diluted with ethyl acetate (75 mL) and washed with brine (2×25 mL). The combined organic extracts were dried over sodium sulfate, concentrated, and purified by silica gel chromatography (80% ethyl acetate/hexanes eluent) to give 54 mg (31%) of the title compound as an amorphous foam. FDMS: m/e=463.

EXAMPLE 166

(+)-(4aR)-(10bR)-4-methyl-8-5-nitro-2-pyridinylthio)-10b-methyl-1,2,3,4,4a,5,6,10b-octahydrobenzo[f]quinolin-3-one A 15 mL round bottom flask was charged with (+)-(4aR)-(10bR)-4-methyl-8-mercapto-10b-methyl-1,2,3,4,4a,-5,6,10b-octahydrobenzo[f]quinolin-3-one (100 mg, 0.38 mmol), potassium carbonate (158 mg, 1.14 mmol), 2-bromo-5-nitropyridine (93 mg, 0.46 mmol) and 1.5 mL of anhydrous dimethylformamide, fitted with a reflux condenser, and the stirred mixture was heated at 60°, under nitrogen, for 18 h. The mixture was cooled, diluted with ethyl acetate (75 mL) and washed with brine (2×25 mL). The combined organic extracts were dried over sodium sulfate, concentrated, and purified by silica gel chromatography (80% ethyl acetate/hexanes eluent) to give 106 mg (73%) of the title compound as an amorphous foam. mp 188°–191°. FDMS: m/e=383. α[D]$_{589}$=+57.07 (c=0.68, chloroform).

| Analysis | Calculated | Found |
|---|---|---|
| C | 62.64 | 62.09 |
| H | 5.52 | 5.76 |
| N | 10.96 | 10.40 |

EXAMPLE 167

(+)-(4aR)-(10bR)-4-methyl-8-(3-nitro-2-pyridinylthio)-10b-methyl-1,2,3,4,4a,5,6,10b-octahydrobenzo[f]quinolin-3-one A 15 mL round bottom flask was charged with (+)-(4aR)-(10bR)-4-methyl-8-mercapto-10b-methyl-1,2,3,4,4a,-5,6,10b-octahydrobenzo[f]quinolin-3-one (100 mg, 0.38 mmol), potassium carbonate (158 mg, 1.14 mmol), 2-chloro-3-nitropyridine (73 mg, 0.46 mmol) and 1.5 mL of anhydrous dimethylformamide, fitted with a reflux condenser, and the stirred mixture was heated at 60°, under nitrogen, for 18 h. The mixture was cooled, diluted with ethyl acetate (75 mL) and washed with brine (2×25 mL). The combined organic extracts were dried over sodium sulfate, concentrated, and purified by silica gel chromatography (90% ethyl acetate/hexanes eluent) to give 95 mg (65%) of the title compound as an amorphous foam. mp 80°–84°. FDMS: m/e=383. α[D]$_{589}$=+73.78 (c=0.49, chloroform).

EXAMPLE 168

(+)-(4aR)-(10bR)-4-methyl-8-(6-nitro-2-quinolinylthio)-10b-methyl-1,2,3,4,4a,5,6,10b-octahydrobenzo[f]quinolin-3-one A 15 mL round bottom flask was charged with (+)-(4aR)-(10bR)-4-methyl-8-mercapto-10b-methyl-1,2,3,4,4a,-5,6,10b-octahydrobenzo[f]quinolin-3-one (100 mg, 0.38 mmol), potassium carbonate (96 mg, 1.14 mmol), 2-chloro-6-nitroquinoline (96 mg, 0.46 mmol) and 1.5 mL of anhydrous dimethylformamide, fitted with a reflux condenser, and the stirred mixture was heated at 60°, under nitrogen, for 18 h. The mixture was cooled, diluted with ethyl acetate (75 mL) and washed with brine (2×25 mL). The combined organic extracts were dried over sodium sulfate, concentrated, and purified by silica gel chromatography (ethyl acetate eluent) to give 88 mg (53%) of the title compound as a tan solid. mp 195°–196°. FDMS: m/e=433. α[D]$_{589}$=+64.56 (c =0.78, chloroform).

| Analysis | Calculated | Found |
|---|---|---|
| C | 66.49 | 66.25 |
| H | 5.35 | 5.51 |
| N | 9.69 | 9.41 |

EXAMPLE 169

(+)-(4aR)-(10bR)-4-methyl-8-(5-nitro-2-quinolinylthio)-10b-methyl-1,2,3,4,4a,5,6,10b-octahydrobenzo[f]quinolin-3-one A 15 mL round bottom flask was charged with (+)-(4aR)-(10bR)-4-methyl-8-mercapto-10b-methyl-1,2,3,4,4a,5,6,10b-octahydrobenzo[f]quinolin-3-one (31 mg, 0.12 mmol), potassium carbonate (158 mg, 1.14 mmol), 2-chloro-5-nitroquinoline (30 mg, 0.14 mmol) and 1 mL of anhydrous dimethylformamide, fitted with a reflux condenser, and the stirred mixture was heated at 60°, under nitrogen, for 18 h. The mixture was cooled, diluted with ethyl acetate (75 mL) and washed with brine (2×25 mL). The combined organic extracts were dried over sodium sulfate, concentrated, and purified by silica gel chromatography (ethyl acetate eluent) to give 29 mg (56%) of the title compound as an amorphous foam. mp 149°–154°. FDMS: m/e=433. α[D]$_{589}$=+60.00 (c=0.10, chloroform).

EXAMPLE 170

(+)-(4aR)-(10bR)-4-methyl-8-(8-nitro-2-quinolinylthio)-10b-methyl-1,2,3,4,4a,5,6,10b-octahydrobenzo[f]quinolin-3-one A 15 mL round bottom flask was charged with (+)-(4aR)-(10bR)-4-methyl-8-mercapto-10b-methyl-1,2,3,4,4a,-5,6,10b-octahydrobenzo[f]quinolin-3-one (100 mg, 0.38 mmol), potassium carbonate (158 mg, 1 14 mmol), 2-chloro-8-nitroquinoline (96 mg, 0.46 mmol) and 1.5 mL of anhydrous dimethylformamide, fitted with a reflux condenser, and the stirred mixture was heated at 60°, under nitrogen, for 48 h. The mixture was cooled, diluted with ethyl acetate (75 mL) and washed with brine (2×25 mL). The combined organic extracts were dried over sodium sulfate, concentrated, and purified by silica gel chromatography (80–100% ethyl acetate/hexanes eluent) to give 90 mg (55%) of the title compound as a solid. mp 199°–200°. FDMS: m/e=433. α[D]$_{589}$=+76.80 (c=0.42, chloroform).

| Analysis | Calculated | Found |
|---|---|---|
| C | 66.49 | 66.28 |
| H | 5.35 | 5.52 |
| N | 9.69 | 9.47 |

EXAMPLE 171

(+)-(4aR)-(10bR)-4-methyl-8-(6-phenyl-3-pyridazinylthio)-10b-methyl-1,2,3,4,4a,5,6,10b-octahydrobenzo[f]quinolin-3-one A 15 mL round bottom flask was charged with (+)-(4aR)-(10bR)-4-methyl-8-mercapto-10b-methyl-1,2,3,4,4a,-5,6,10b-octahydrobenzo[f]quinolin-3-one (100 mg, 0.38 mmol), potassium carbonate (158 mg, 1.14 mmol), 3-chloro-6-phenyl-pyridazine (88 mg, 0.46 mmol) and 1.5 mL of anhydrous dimethylformamide, fitted with a reflux condenser, and the stirred mixture was heated at 60°, under nitrogen, for 48 h. The mixture was cooled, diluted with ethyl acetate (75 mL) and washed with brine (2×25 mL). The combined organic extracts were dried over sodium sulfate, concentrated, and purified by silica gel chromatography (ethyl acetate eluent) to give 77 mg (49%) of the title compound as an amorphous solid. mp 199°–200°. FDMS: m/e=415. α[D]$_{589}$=+67.26 (c=0.63, chloroform).

| Analysis | Calculated | Found |
|---|---|---|
| C | 72.26 | 72.06 |
| H | 6.06 | 6.21 |
| N | 10.11 | 9.93 |

EXAMPLE 172

(+)-(4aR)-(10bR)-4-methyl-8-(2-phenyl-4-quinazolinylthio)-10b-methyl-1,2,3,4,4a,5,6,10b-octahydrobenzo[f]quinolin-3-one A 15 mL round bottom flask was charged with (+)-(4aR)-(10bR)-4-methyl-8-mercapto-10b-methyl-1,2,3,4,4a,-5,6,10b-octahydrobenzo[f]quinolin-3-one (100 mg, 0.38 mmol), potassium carbonate (158 mg, 1.14 mmol), 4-chloro-2-phenyl-quinazoline (111 mg, 0.46 mmol) and 1 mL of anhydrous dimethylformamide, fitted with a reflux condenser, and the stirred mixture was heated at 60°, under nitrogen, for 18 h. The mixture was cooled, diluted with ethyl acetate (75 mL) and washed with brine (2×25 mL). The combined organic extracts were dried over sodium sulfate, concentrated, and purified by silica gel chromatography (80–100% ethyl acetate/hexanes eluent gradient) to give 112 mg (63%) of the title compound as an off white solid. mp 185°–193°. FDMS: m/e=465. $\alpha[D]_{589}$=+49.59 (c=0.57, chloroform).

| Analysis | Calculated | Found |
|---|---|---|
| C | 74.81 | 73.56 |
| H | 5.84 | 5.94 |
| N | 9.02 | 8.95 |

EXAMPLE 173

(+)-(4aR)-(10bR)-4-methyl-8-(6-fluoro-2-quinolinylthio)-10b-methyl-1,2,3,4,4a,5,6,10b-octahydrobenzo[f]quinolin-3-one A 15 mL round bottom flask was charged with (+)-(4aR)-(10bR)-4methyl-8-mercapto-10b-methyl-1,2,3,4,4a,-5,6,10b-octahydrobenzo[f]quinolin-3-one (100 mg, 0.38 mmol), potassium carbonate (158 mg, 1.14 mmol), 2-chloro-6-fluoro-quinoline (84 mg, 0.46 mmol) and 1.5 mL of anhydrous dimethylformamide, fitted with a reflux condenser, and the stirred mixture was heated at 60°, under nitrogen, for 48 h. The mixture was cooled, diluted with ethyl acetate (75 mL) and washed with brine (2×25 mL). The combined organic extracts were dried over sodium sulfate, concentrated, and purified by silica gel chromatography (80% ethyl acetate/hexanes eluent) to give 96 mg (62%) of the title compound as a solid. mp 152°–155°. FDMS: m/e=406. $\alpha[D]_{589}$=+63.16 (c=0.61, chloroform).

| Analysis | Calculated | Found |
|---|---|---|
| C | 70.91 | 70.76 |
| H | 5.70 | 5.83 |
| N | 6.89 | 6.81 |

EXAMPLE 174

(+)-(4aR)-(10bR)-4-methyl-8-(8-fluoro-2-quinolinylthio)-10b-methyl-1,2,3,4,4a,5,6,10b-octahydrobenzo[f]quinolin-3-one A 15 mL round bottom flask was charged with (+)-(4aR)-(10bR)-4-methyl-8-mercapto-10b-methyl-1,2,3,4,4a,-5,6,10b-octahydrobenzo[f]quinolin-3-one (100 mg, 0.38 mmol), potassium carbonate (158 mg, 1.14 mmol), 2-chloro-8-fluoroquinoline (84 mg, 0.46 mmol) and 1.5 mL of anhydrous dimethylformamide, fitted with a reflux condenser, and the stirred mixture was heated at 60°, under nitrogen, for 18 h. The mixture was cooled, diluted with ethyl acetate (75 mL) and washed with brine (2×25 mL). The combined organic extracts were dried over sodium sulfate, concentrated, and purified by silica gel chromatography (80% ethyl acetate/hexanes eluent) to give 78 mg (50%) of the title compound as an amorphous foam. FDMS: m/e=406. $\alpha[D]_{589}$=+63.29 (c=0.56, chloroform).

| Analysis | Calculated | Found |
|---|---|---|
| C | 70.91 | 71.15 |
| H | 5.70 | 5.82 |
| N | 6.89 | 6.94 |

EXAMPLE 175

(+)-(4aR)-(10bR)-4-methyl-8-(4-thieno[3,2-c]pyridylthio)-10b-methyl-1,2,3,4,4a,5,6,10b-octahydrobenzo[f]quinolin-3-one A 15 mL round bottom flask was charged with (+)-(4aR)-(10bR)-4-methyl-8-mercapto-10b-methyl-1,2,3,4,4a,-5,6,10b-octahydrobenzo[f]quinolin-3-one (100 mg, 0.38 mmol), potassium carbonate (158 mg, 1.14 mmol), 4-chlorothieno[3,2-c]pyridine (78 mg, 0.46 mmol) and 1 mL of anhydrous dimethyl formamide, fitted with a reflux condenser, and the stirred mixture was heated at 60°, under nitrogen, for 18 h. The mixture was cooled, diluted with ethyl acetate (75 mL) and washed with brine (2×25 mL). The combined organic extracts were dried over sodium sulfate, concentrated, and purified by silica gel chromatography (80% ethyl acetate/hexanes eluent) to give 37 mg (25%) of the title compound as a white solid. mp 196°–197°. FDMS: m/e=394. $\alpha[D]_{589}$=+75.17 (c=0.57, chloroform).

| Analysis | Calculated | Found |
|---|---|---|
| C | 66.97 | 66.70 |
| H | 5.62 | 5.70 |
| N | 7.10 | 6.88 |

EXAMPLE 176

(+)-(4aR)-(10bR)-4-methyl-8-(10-oxo-10H-2-pyridazino[6,1-b]-quinazolinylthio)-10b-methyl-1,2,3,4,4a,5,6,10b-octahydro-benzo[f]quinolin-3-one A 15 mL round bottom flask was charged with (+)-(4aR)-(10bR)-4-methyl-8-mercapto-10b-methyl-1,2,3,4,4a,-5,6,10b-octahydrobenzo[f]quinolin-3-one (100 mg, 0.38 mmol), potassium carbonate (158 mg, 1.14 mmol), 2-chloro-10H-pyridazino[6,1-b]-quinazolin-10-one (107 mg, 0.46 mmol) and 1 mL of anhydrous dimethylformamide, fitted with a reflux condenser, and the stirred mixture was heated at 60°, under nitrogen, for 18 h. The mixture was cooled, diluted with ethyl acetate (75 mL) and washed with brine (2×25 mL). The combined organic extracts were dried over sodium sulfate, concentrated, and purified by silica gel chromatography (0–10% methanol/ethyl acetate eluent gradient) to give 103 mg (62%) of the title compound as an amorphous foam. mp 110°–114°. FDMS: m/e=456. α[D]$_{589}$=+54.77 (c=0.49, chloroform).

| Analysis | Calculated | Found |
|---|---|---|
| C | 68.40 | 68.22 |
| H | 5.30 | 5.31 |
| N | 12.27 | 12.01 |

EXAMPLE 177

(+)-(4aR)-(10bR)-4-methyl-8-(3-phenyl-1-isoquinolinylthio)-10b-methyl-1,2,3,4,4a,5,6,10b-octahydrobenzo[f]quinolin-3-one A 15 mL round bottom flask was charged with (+)-(4aR)-(10bR)-4-methyl-8-mercapto-10b-methyl-1,2,3,4,4a,-5,6,10b-octahydrobenzo[f]quinolin-3-one (86 mg, 0.33 mmol), potassium carbonate (158 mg, 1.14 mmol), 1-chloro-3-phenyl-isoquinoline (95 mg, 0.40 mmol) and 1 mL of anhydrous dimethylformamide, fitted with a reflux condenser, and the stirred mixture was heated at 60°, under nitrogen, for 18 h. The mixture was cooled, diluted with ethyl acetate (75 mL) and washed with brine (2×25 mL). The combined organic extracts were dried over sodium sulfate, concentrated, and purified by silica gel chromatography (80% ethyl acetate/hexanes eluent) to give 64 mg (42%) of the title compound as an off white solid. mp 183°–189°. FDMS: m/e=464. α[D]$_{589}$=+54.61 (c=0.53, chloroform).

| Analysis | Calculated | Found |
|---|---|---|
| C | 77.55 | 77.26 |
| H | 6.07 | 6.16 |
| N | 6.03 | 6.16 |

EXAMPLE 178

(+)-(4aR)-(10bR)-4-methyl-8-(3-methyl-2-quinolinylthio)-10b-methyl-1,2,3,4,4a,5,6,10b-octahydrobenzo[f]quinolin-3-one A 15 mL round bottom flask was charged with (+)-(4aR)-(10bR)-4-methyl-8-mercapto-10b-methyl-1,2,3,4,4a,-5,6,10b-octahydrobenzo[f]quinolin-3-one (37 mg, 0.14 mmol), potassium carbonate (158 mg, 1.14 mmol), 2-chloro-3-methyl-quinoline (30 mg, 0.17 mmol) and 1 mL of anhydrous dimethylformamide, fitted with a reflux condenser, and the stirred mixture was heated at 60°, under nitrogen, for 18 h. The mixture was cooled, diluted with ethyl acetate (75 mL) and washed with brine (2×25 mL). The combined organic extracts were dried over sodium sulfate, concentrated, and purified by silica gel chromatography (80 ethyl acetate/hexanes eluent) to give 9 mg (16%) of the title compound as an amorphous foam. mp 185°–193°. FDMS: m/e=402.

EXAMPLE 179

(+)-(4aR)-(10bR)-4-methyl-8-[3-phenyl-4-(4-methoxyphenyl)-2-quinolinylthio]-10b-methyl-1,2,3,4,4a,5,6,10b-octahydro-benzo[f]quinolin-3-one A 15 mL round bottom flask was charged with (+)-(4aR)-(10bR)-4-methyl-8-mercapto-10b-methyl-1,2,3,4,4a,5,6,10b-octahydrobenzo[f]quinolin-3-one (60 mg, 0.23 mmol), potassium carbonate (158 mg, 1.14 mmol), 2-chloro-3-phenyl-4-(4-methoxyphenyl)quinoline (95 mg, 0.27 mmol) and 1 mL of anhydrous dimethylformamide, fitted with a reflux condenser, and the stirred mixture was heated at 60°, under nitrogen, for 18 h. The mixture was cooled, diluted with ethyl acetate (75 mL) and washed with brine (2×25 mL). The combined organic extracts were dried over sodium sulfate, concentrated, and purified by silica gel chromatography (ethyl acetate eluent) to give 56 mg (43%) of the title compound as an off white solid. mp 239°–242°. FDMS: m/e=570. α[D]$_{589}$=+45.00 (c=1.40, chloroform).

| Analysis | Calculated | Found |
|---|---|---|
| C | 77.86 | 77.58 |
| H | 6.00 | 6.12 |
| N | 4.91 | 4.94 |

EXAMPLE 180

(+)-(4aR)-(10bR)-4-methyl-8-(3-[1,2-benzisothiazolyl]thio)-10b-methyl-1,2,3,4,4a,5,6,10b-octahydrobenzo[f]quinolin-3-one A 15 mL round bottom flask was charged with (+)-(4aR)-(10bR)-4-methyl-8-mercapto-10b-methyl-1,2,3,4,4a,5,6,10b-octahydrobenzo[f]quinolin-3-one (100 mg, 0.38 mmol), potassium carbonate (158 mg, 1.14 mmol), 3-chloro-1,2-benzisothiazole (78 mg, 0.46 mmol) and 1 mL of anhydrous dimethylformamide, fitted with a reflux condenser, and the stirred mixture was heated at 60°, under nitrogen, for 18 h. The mixture was cooled, diluted with ethyl acetate (75 mL) and washed with brine (2×25 mL). The combined organic extracts were dried over sodium sulfate, concentrated, and purified by silica gel chromatography (80–100% ethyl acetate/hexanes eluent gradient) to give 54 mg (36%) of the title compound as an amorphous foam. FDMS: m/e=394.

| Analysis | Calculated | Found |
|---|---|---|
| C | 66.97 | 67.05 |
| H | 5.62 | 5.83 |
| N | 7.10 | 7.03 |

EXAMPLE 181

(+)-(4aR)-(10bR)-4-methyl-8-(2-[4,6-diphenyl]pyridylthio)-10b-methyl-1,2,3,4,4a,5,6,10b-octahydrobenzo[f]quinolin-3-one A 15 mL round bottom flask was charged with (+)-(4aR)-(10bR)-4-methyl-8-mercapto-10b-methyl-1,2,3,4,4a,5,6,10b-octahydrobenzo[f]quinolin-3-one (78 mg, 0.30 mmol), potassium carbonate (158 mg, 1.14 mmol), 2-chloro-4,6-diphenylpyridine (95 mg, 0.36 mmol) and 1.5 mL of anhydrous dimethylformamide, fitted with a reflux condenser, and the stirred mixture was heated at 60°, under nitrogen, for 18 h. The mixture was cooled, diluted with ethyl acetate (75 mL) and washed with brine (2×25 mL). The combined organic extracts were dried over sodium sulfate, concentrated, and purified by silica gel chromatography (80% ethyl acetate/hexanes eluent) to give 40 mg (27%) of the title compound as an amorphous solid. FDMS: m/e=490. α[D]$_{589}$=−37.97 (c=0.39, chloroform).

EXAMPLE 182

(+)-(4aR)-(10bR)-4-methyl-8-(4-methoxy-2-benzothiazolylthio)-10b-methyl-1,2,3,4,4a,5,6,10b-octahydrobenzo[f]quinolin-3-one A 15 mL round bottom flask was charged with (+)-(4aR)-(10bR)-4-methyl-8-mercapto-10b-methyl-1,2,3,4,4a,5,6, 10b-octahydrobenzo[f]quinolin-3-one (100 mg, 0.38 mmol), potassium carbonate (158 mg, 1.14 mmol), 2-chloro-4-methoxybenzothiazole (92 mg, 0.46 mmol) and 1.5 mL of anhydrous dimethylformamide, fitted with a reflux condenser, and the stirred mixture was heated at 60°, under nitrogen, for 18 h. The mixture was cooled, diluted with ethyl acetate (75 mL) and washed with brine (4×25 mL). The combined organic extracts were dried over sodium sulfate, concentrated, and purified by silica gel chromatography (ethyl acetate eluent) to give 107 mg (66%) of the title compound as an off white solid. mp 200°–205°. FDMS: m/e=424. $\alpha[D]_{589}$=+60.56 (c=0.96, chloroform).

| Analysis | Calculated | Found |
|---|---|---|
| C | 65.07 | 64.43 |
| H | 5.70 | 5.55 |
| N | 6.60 | 7.81 |

EXAMPLE 183

(+)-(4aR)-(10bR)-4-methyl-8-(4-bromo-2-benzothiazolylthio)-10b-methyl-1,2,3,4,4a,5,6,10b-octahydrobenzo[f]quinolin-3-one A 15 mL round bottom flask was charged with (+)-(4aR)-(10bR)-4-methyl-8-mercapto-10b-methyl-1,2,3,4,4a,5,6,10b-octahydrobenzo[f]quinolin-3-one (100 mg, 0.38 mmol), potassium carbonate (158 mg, 1.14 mmol), 2-chloro-4-bromobenzothiazole (114 mg, 0.46 mmol) and 1 mL of anhydrous dimethylformamide, fitted with a reflux condenser, and the stirred mixture was heated at 60°, under nitrogen, for 18 h. The mixture was cooled, diluted with ethyl acetate (75 mL) and washed with brine (2×25 mL). The combined organic extracts were dried over sodium sulfate, concentrated, and purified by silica gel chromatography (ethyl acetate eluent) to give 142 mg (79%) of the title compound as an off white solid. mp 206°–210°. FDMS: m/e=474. $\alpha[D]_{589}$=+56.25 (c=0.59, chloroform).

| Analysis | Calculated | Found |
|---|---|---|
| C | 55.81 | 55.63 |
| H | 4.47 | 4.62 |
| N | 5.92 | 6.16 |

EXAMPLE 184

(+)-(4aR)-(10bR)-4-methyl-8-(4-phenyl-2-benzothiazolylthio)-10b-methyl-1,2,3,4,4a,5,6,10b-octahydrobenzo[f]quinolin-3-one A 15 mL round bottom flask was charged with (+)-(4aR)-(10bR)-4-methyl-8-mercapto-10b-methyl-1,2,3,4,4a,-5,6,10b-octahydrobenzo[f]quinolin-3-one (100 mg, 0.38 mmol), potassium carbonate (158 mg, 1.14 mmol), 2-chloro-4-phenyl-benzothiazole (113 mg, 0.46 mmol) and 1 mL of anhydrous dimethylformamide, fitted with a reflux condenser, and the stirred mixture was heated at 60°, under nitrogen, for 18 h. The mixture was cooled, diluted with ethyl acetate (75 mL) and washed with brine (4×25 mL). The combined organic extracts were dried over sodium sulfate, concentrated, and purified by silica gel chromatography (ethyl acetate eluent) to give 110 mg (61%) of the title compound as an amorphous foam. FDMS: m/e=470. $\alpha[D]_{589}$=+53.51 (c=0.66, chloroform).

| Analysis | Calculated | Found |
|---|---|---|
| C | 71.46 | 71.22 |
| H | 5.57 | 5.69 |
| N | 5.95 | 5.82 |

EXAMPLE 185

(+)-(4aR)-(10bR)-4-methyl-8-(4,7-dimethyl-2-benzothiazolylthio)-10b-methyl-1,2,3,4,4a,5,6,10b-octahydrobenzo[f]-quinolin-3-one A 15 mL round bottom flask was charged with (+)-(4aR)-(10bR)-4-methyl-8-mercapto-10b-methyl-1,2,3,4,4a,5,6,10b-octahydrobenzo[f]quinolin-3-one (100 mg, 0.38 mmol), potassium carbonate (158 mg, 1.14 mmol), 2-chloro-4,7-dimethylbenzothiazole (91 mg, 0.46 mmol) and 1 mL of anhydrous dimethylformamide, fitted with a reflux condenser, and the stirred mixture was heated at 60°, under nitrogen, for 18 h. The mixture was cooled, diluted with ethyl acetate (75 mL) and washed with brine (2×25 mL). The combined organic extracts were dried over sodium sulfate, concentrated, and purified by silica gel chromatography (80% ethyl acetate/hexanes eluent) to give 111 mg (69%) of the title compound as an amorphous foam. FDMS: m/e=422. $\alpha[D]_{589}$=+63.27 (c=0.95, chloroform).

EXAMPLE 186

(+)-(4aR)-(10bR)-4-methyl-8-(4-propyl-2-benzothiazolylthio)-10b-methyl-1,2,3,4,4a,5,6,10b-octahydrobenzo[f]quinolin-3-one A 15 mL round bottom flask was charged with (+)-(4aR)-(10bR)-4-methyl-3-mercapto-10b-methyl-1,2,3,4,4a,-5,6,10b-octahydrobenzo[f]quinolin-3-one (100 mg, 0.38 mmol), potassium carbonate (158 mg, 1.14 mmol), 2-chloro-4-propyl-benzothiazole (97 mg, 0.46 mmol) and 1 mL of anhydrous dimethylformamide, fitted with a reflux condenser, and the stirred mixture was heated at 60°, under nitrogen, for 18 h. The mixture was cooled, diluted with ethyl acetate (75 mL) and washed with brine (6×25 mL). The combined organic extracts were dried over sodium sulfate, concentrated, and purified by silica gel chromatography (80% ethyl acetate/hexanes eluent) to give 116 mg (70%) of the title compound as an amorphous solid. mp 109°–111°. FDMS: m/e=436. $\alpha[D]_{589}$=+45.00 (c=0.80, chloroform).

| Analysis | Calculated | Found |
|---|---|---|
| C | 68.77 | 68.50 |
| H | 6.46 | 6.57 |
| N | 6.42 | 6.44 |

EXAMPLE 187

(+)-(4aR)-(10bR)-4-methyl-8-(4-ethyl-2-benzothiazolylthio)-10b-methyl-1,2,3,4,4a,5,6,10b-octahydrobenzo[f]quinolin-3-one A 200 mL round bottom flask was charged with (+)-(4aR)-(10bR)-4-methyl-8-mercapto-10b-methyl-1,2,3,4,4a,-5,6,10b-octahydrobenzo[f]quinolin-3-one (1.36g, 5.20 mmol), potassium carbonate (2.16 g, 15.6 mmol), 2-chloro-4-ethyl-benzothiazole (1.23 g, 6.20 mmol) and 14 mL of anhydrous dimethylformamide, fitted with a reflux condenser, and the stirred mixture was heated at 60°, under nitrogen, for 18 h. The mixture was cooled, diluted with ethyl acetate (750 mL)

and washed with brine (6×250 mL). The combined organic extracts were dried over sodium sulfate, concentrated, and purified by silica gel chromatography (80% ethyl acetate/hexanes eluent) to give 1.51 g (69%) of the title compound as an amorphous foam. FDMS: m/e=422. $\alpha[D]_{589}$=+62.74 (c=0.67, chloroform).

| Analysis | Calculated | Found |
|---|---|---|
| C | 68.21 | 68.40 |
| H | 6.20 | 6.22 |
| N | 6.63 | 6.49 |

EXAMPLE 188

(+)-(4aR)-(10bR)-4-methyl-8-(4-trifluoromethoxy-2-benzo-thiazolylthio)-10b-methyl-1,2,3,4,4a,5,6,10b-octahydrobenzo[f]-quinolin-3-one A 15 mL round bottom flask was charged with (+)-(4aR)-(10bR)-4-methyl-8-mercapto-10b-methyl-1,2,3,4,4a,-5,6,10b-octahydrobenzo[f]quinolin-3-one (100 mg, 0.38 mmol), potassium carbonate (158 mg, 1.14 mmol), 2-chloro-4-trifluoromethoxybenzothiazole (117 mg, 0.46 mmol) and 1.5 mL of anhydrous dimethylformamide, fitted with a reflux condenser, and the stirred mixture was heated at 60°, under nitrogen, for 18 h. The mixture was cooled, diluted with ethyl acetate (75 mL) and washed with brine (4×25 mL). The combined organic extracts were dried over sodium sulfate, concentrated, and purified by silica gel chromatography (ethyl acetate eluent) to give 141 mg (77%) of the title compound as a white solid. mp 168°–173°. FDMS: m/e= 478. $\alpha[D]_{589}$=+57.89 (c=0.59, chloroform).

| Analysis | Calculated | Found |
|---|---|---|
| C | 57.73 | 57.50 |
| H | 4.42 | 4.52 |
| N | 5.85 | 5.78 |

EXAMPLE 189

(+)-(4aR)-(10bR)-4-methyl-8-[4,7-di(t-butyl)-2-benzothiazolylthio]-10b-methyl-1,2,3,4,4a,5,6,10b-octahydro-benzo[f]-quinolin-3-one A 15 mL round bottom flask was charged with (+)-(4aR)-(10bR)-4-methyl-8-mercapto-10b-methyl-1,2,3,4,4a,-5,6,10b-octahydrobenzo[f]quinolin-3-one (100 mg, 0.38 mmol), potassium carbonate (158 mg, 1.14 mmol), 2-chloro-4,7-di(t-butyl)benzothiazole (130 mg, 0.46 mmol) and 1.5 mL of anhydrous dimethylformamide, fitted with a reflux condenser, and the stirred mixture was heated at 60°, under nitrogen, for 18 h. The mixture was cooled, diluted with ethyl acetate (75 mL) and washed with brine (4×25 mL). The combined organic extracts were dried over sodium sulfate, concentrated, and purified by silica gel chromatography (80% ethyl acetate/hexanes eluent) to give 33 mg (17%) of the title compound as an amorphous foam. FDMS: m/e=506.

EXAMPLE 190

(+)-(4aR)-(10bR)-4-methyl-8-(4-methyl-7-trifluoromethyl-2-benzothiazolylthio)-10b-methyl-1,2,3,4,4a,5,6,10b-octahydrobenzo[f]quinolin-3-one A 15 mL round bottom flask was charged with (+)-(4aR)-(10bR)-4-methyl-8-mercapto-10b-methyl-1,2,3,4,4a,5,6,10b-octahydrobenzo[f]quinolin-3-one (100 mg, 0.38 mmol), potassium carbonate (158 mg, 1.14 mmol), 2-chloro-4-methyl-7-trifluoromethylbezothiazole (116 mg, 0.46 mmol) and 1.5 mL of anhydrous dimethyl formamide, fitted with a reflux condenser, and the stirred mixture was heated at 60°, under nitrogen, for 18 h. The mixture was cooled, diluted with ethyl acetate (75 mL) and washed with brine (4×25 mL). The combined organic extracts were dried over sodium sulfate, concentrated, and purified by silica gel chromatography (80% ethyl acetate/hexanes eluent) to give 94 mg (52%) of the title compound as an amorphous foam. mp 50°–54°. FDMS: m/e=476.

| Analysis | Calculated | Found |
|---|---|---|
| C | 60.49 | 60.79 |
| H | 4.86 | 5.14 |
| N | 5.88 | 5.75 |

EXAMPLE 191

(+)-(4aR)-(10bR)-8-(3-isoquinolinylmethylthio)-4,10b-dimethyl-1,2,3,4,4a,5,6,10b-octahydrobenzo[f]quinoline-3-one To a stirred solution of (4aR)-(10bR)-8-thio-4,10b-diemthyl-1,2,3,4,4a,5,6,10b-octahydrobenzo[f]quinoline-3-one (100 mg, 0.38 mmol) in dimethylformamide (2 mL) was added powdered potassium carbonate (158 mg, 1.14 mmol followed by 3-bromomethylisoquinoline (89 mg, 0.4 mmol). The mixture was purged with nitrogen and heated to 60° for 14 h. The mixture was cooled to ambient temperature and partitioned between water and ethyl acetate. The aqueous phase was back extracted with ethyl acetate and the combined organic phases were washed with saturated brine and dried over anhydrous sodium sulfate. Removal of solvent afforded crude product. Purification by flash chromatography on silica gel (0.5% aq ammonium hydroxide/ethyl acetate) followed by crystallization from ethyl acetate afforded product as a crystalline solid (91 mg), mp=129°–130°. m/e 402. OR (c=1.0, methanol) @ 589 nM, +64.2°, @ 365 nM, +226.7°.

| Analysis | Calculated | Found |
|---|---|---|
| C | 74.59 | 74.87 |
| H | 6.51 | 6.45 |
| N | 6.96 | 7.09 |

EXAMPLE 192

(+)-(4aR)-(10bR)-8-(2-benzothiazolylmethylthio)-4,10b-dimethyl-1,2,3,4,4a,5,6,10b-octahydrobenzo[f]quinoline-3-one To a stirred solution of (4aR)-(10bR)-8-thio-4,10b-dimethyl-1,2,3,4,4a,5,6,10b-octahydrobenzo[f]quinoline-3-one (100 mg, 0.38 mmol) in dimethylformamide (2 mL) was added powdered potassium carbonate (158 mg, 1.14 mmol) followed by 2-chloromethylbenzothiazole (73 mg, 0.4 mmol). The mixture was purged with nitrogen and heated to 60° for 14 h. The mixture was cooled to ambient temperature and partitioned between water and ethyl acetate. The aqueous phase was back extracted with ethyl acetate and the combined organic phases were washed with saturated brine and dried over anhydrous sodium sulfate. Removal of solvent afforded crude product. Purification by flash chromatography on silica gel (0.5% aq ammonium hydroxide/ethyl acetate) followed by crystallization from diethyl ether/ethyl acetate afforded product as a crystalline solid (55 mg), mp=78°–80°. m/e 408. OR (c=0.3, methanol) @ 589 nM, +66.3°.

| Analysis | Calculated | Found |
|---|---|---|
| C | 67.61 | 67.51 |
| H | 5.92 | 6.05 |
| N | 6.86 | 6.63 |

EXAMPLE 193

(4aR)-(10bR)-4,10b-dimethyl-8-(7-chloro-2-benzothiazolylthio)-1,2,3,4,4a,5,6,10b-octahydrobenzo[f]quinoline-3-one A 303 mg portion of 2,7-dichlorobenzothiazole and 316 mg of potassium carbonate were dissolved in 3 ml of anhydrous dimethylformamide. To the solution was added 400 mg of (4aR)-(10bR)-8-thio-4,10b-dimethyl-1,2,3,4,4a,5,6,10b-octahydrobenzo[f]quinoline-3-one dissolved in 6 ml of anhydrous dimethylformamide, and the mixture was warmed to 60° and stirred over night. The mixture was then diluted with 60 ml of ethyl acetate and washed 4 times with brine. The organic layer was dried over sodium sulfate, filtered and evaporated to obtain 638 mg of impure product, which was evaporated under high vacuum and purified by rotary chromatography on siliga gel, eluting with ethyl acetate, to obtain 195 mg of the desired product. mp 90°–91°. FDMS: m/e=+428.

| Analysis | Calculated | Found |
|---|---|---|
| C | 61.60 | 61.83 |
| H | 4.93 | 5.09 |
| N | 6.53 | 6.49 |

EXAMPLE 194

(4aR)-(10bR)-4,10b-dimethyl-8-(5-chloro-2-benzothiazolylthio)-1,2,3,4,4a,5,6,10b-octahydrobenzo[f]quinoline-3-one 400 mg of (4aR)-(10bR)-8-thio-4,10b-dimethyl-1,2,3,4,4a,5,6,10b-octahydrobenzo[f]-quinoline-3-one was reacted with 2,5-dichlorobenzothiazole as described in Example 193 to obtain 56 mg of the desired product. mp 179°–180°. FDMS: m/e=+428.

| Analysis | Calculated | Found |
|---|---|---|
| C | 61.60 | 61.30 |
| H | 4.93 | 4.89 |
| N | 6.53 | 6.15 |

EXAMPLE 195

(4aR)-(10bR)-8-diphenylmethylthio-4,10b-dimethyl-1,2,3,4,4a,5,6,10b-octahydrobenzo[f]-quinoline-3-one 500 mg of (4aR)-(10bR)-8-thio-4,10b-dimethyl-1,2,3,4,4a,5,6,10b-octahydrobenzo[f]-quinoline-3-one was dissolved in 12.5 ml of dimethylformamide, and to the solution was added 789 mg of potassium carbonate, followed by 405 μl of diphenyl chloromethane. The mixture was stirred at 60° for 18 hours, cooled and partitioned between ethyl acetate and water. The organic layer was washed 3 times with brine, dried over sodium sulfate and concentrated under vacuum to obtain 896 mg of crude product. That material was purified on a Chromatotron, eluting with ethyl acetate, and the product-containing fractions were recrystallized from ethyl acetate/hexane to obtain 146 mg of the desired product. mp 102°–104°. FDMS: m/e=+427. α[D]$_{589}$=60.28.

| Analysis | Calculated | Found |
|---|---|---|
| C | 78.65 | 78.65 |
| H | 6.84 | 6.72 |
| N | 3.28 | 3.47 |

The following preparation and examples illustrate the synthesis of compounds of the present invention through an intermediate having a boronic acid substituent on the benzoquinolinone nucleus.

Preparation 9

(+)-(4aR)-(10bR)-4-methyl-10b-methyl-1,2,3,4,4a,5,6,10b-octahydrobenzo[f]quinolin-3-one-8-boronic acid To a solution of (+)-(4aR)-(10bR)-4-methyl-8-bromo-10b-methyl-1,2,3,4,4a,5,6,10b-octahydrobenzo[f]-quinolin-3-one (5.0 g, 16.2 mmol) in 500 mL of anhydrous THF was added t-butyllithium (37.5 mL, 1.3M solution in cyclohexane) at −78°. The mixture was allowed to stir at −78° for 75 min, and a solution of triisopropyl borate (2.0 equiv.) in 12.5 mL of anhydrous THF was added dropwise. The mixture was stirred for an additional 45 min, then the cold bath was removed, and the mixture was allowed to warm to room temperature. The mixture was quenched with 5N hydrochloric acid (50 mL), and volatiles were removed on rotary evaporator. The mixture was then treated with 35 mL of 5N sodium hydroxide, and was extracted with THF (300 mL). The organic extract was dried over sodium sulfate, filtered, and concentrated. The resulting solid was heated in boiling ethyl acetate for 15 min, followed by filtration (while still hot), to yield 3.65 g (82%) of the title compound as a white solid. mp 200° (decomp.) α[D]$_{589}$=+72.27 (c=0.89, methanol).

| Analysis | Calculated | Found |
|---|---|---|
| C | 65.96 | 65.74 |
| H | 7.38 | 7.73 |
| N | 5.13 | 4.94 |

EXAMPLE 196

(+)-(4aR)-(10bR)-8-(3-quinolinyl)-10b-methyl-1,2,3,4,4a,-5,6,10b-octahydrobenzo[f]quinolin-3-one A 15 mL round bottom flask was charged with (+)-(4aR)-(10bR)-10b-methyl-1,2,3,4,4a,5,6,10b-octahydrobenzo[f]quinolin-3-one-8-boronic acid (168 mg, 0.65 mmol), tetrakis (triphenylphosphine)palladium(0) (23 mg, 0.02 mmol), 3-bromoquinoline (135 mg, 0.65 mmol), 0.65 mL of aqueous 2M sodium carbonate and 2 mL of THF, fitted with a reflux condenser, and the stirred mixture was heated at 80°, under nitrogen, for 24 h. The mixture was cooled, diluted with chloroform (75 mL) and washed with brine (2 ×25 mL). The combined organic extracts were dried over sodium sulfate, concentrated, and purified by silica gel chromatography (5% methanol/ethyl acetate eluent) to give 141 mg (63%) of the title compound as a white solid. mp 265°–266°. FDMS: m/e=342. α[D]$_{589}$=+88.70 (c=0.84, chloroform)

EXAMPLE 197

(+)-(4aR)-(10bR)-8-(4-[2,8-bistrifluoromethyl] quinolinyl)-10b-methyl-1,2,3,4,4a,5,6,10b-octahydrobenzo [f]quinolin-3-one A 15 mL round bottom flask was charged with (+)-(4aR) -(10bR)-10b-methyl-1,2,3,4,4a,5,6,10b-octahydrobenzo[f] quinolin-3-one-8-boronic acid (168 mg, 0.65 mmol), tetrakis (triphenylphosphine)palladium(0) (23 mg, 0.02 mmol), 4-bromo-2,8-bis(trifluoromethyl)quinoline (224 mg, 0.65 mmol), 0.65 mL of 2M sodium carbonate and 2 mL of THF, fitted with a reflux condenser, and the stirred mixture was heated at 80°, under nitrogen, for 24 h. The mixture was cooled, diluted with chloroform (75 mL) and washed with brine (2×25 mL). The combined organic extracts were dried over sodium sulfate, concentrated, and purified by silica gel chromatography (ethyl acetate eluent) to give 186 mg (60%) of the title compound as a white solid. mp 214°–215°. FDMS: m/e=478. $\alpha[D]_{589}$=+62.00 (c=1.10, chloroform)

EXAMPLE 198

(+)-(4aR)-(10bR)-8-(2-thiazolyl)-10b-methyl-1,2,3,4,4a,-5,6,10b-octahydrobenzo[f]quinolin-3-one A 15 mL round bottom flask was charged with (+)-(4aR) -(10bR)-10b-methyl-1,2,3,4,4a,5,6,10b-octahydrobenzo[f]-quinolin-3-one-8-boronic acid (168 mg, 0.65 mmol), tetrakis (triphenylphosphine)palladium(0) (23 mg, 0.02 mmol), 2-bromothiazole (107 mg, 0.65 mmol), 0.65 mL of 2M sodium carbonate and 2 mL of THF, fitted with a reflux condenser, and the stirred mixture was heated at 80°, under nitrogen, for 24 h. The mixture was cooled, diluted with chloroform (75 mL) and washed with brine (2 ×25 mL). The combined organic extracts were dried over sodium sulfate, concentrated, and purified by silica gel chromatography (5% methanol/ethyl acetate eluent) to give 64 mg (35%) of the title compound as a white solid. mp 206°–207°. FDMS: m/e=298. $\alpha[D]_{589}$=+101.7 (c=0.97, chloroform).

EXAMPLE 199

(+)-(4aR)-(10 bR)-8-(5-nitro-2-pyridinyl)-10b-methyl-1, 2,3,4,4a,5,6,10b-octahydrobenzo[f]quinolin-3-one A 15 mL round bottom flask was charged with (+)-(4aR) -(10bR)-10b-methyl-1,2,3,4,4a,5,6,10b-octahydrobenzo[f] quinolin-3-one-8-boronic acid (168 mg, 0.65 mmol), tetrakis (triphenylphosphine)palladium(0) (23 mg, 0.02 mmol), 2-bromo-5-nitropyridine (132 mg, 0.65 mmol), 0.65 mL of 2M sodium carbonate and 2 mL of THF, fitted with a reflux condenser, and the stirred mixture was heated at 80°, under nitrogen, for 24 h. The mixture was cooled, diluted with chloroform (75 mL) and washed with brine (2×25 mL). The combined organic extracts were dried over sodium sulfate, concentrated, and purified by silica gel chromatography (ethyl acetate eluent) to give 71 mg of the title compound as a white solid. mp 123°–124°. FDMS: m/e=337. $\alpha[D]_{589}$=+85.60 (c=0.61, chloroform).

EXAMPLE 200

(+)-(4aR)-(10bR)-4-methyl-8-(4-isoquinolinyl)-10b-methyl-1,2,3,4,4a,5,6,10b-octahydrobenzo[f]quinolin-3-one A 15 mL round bottom flask was charged with (+)-(4aR) -(10bR)-4-methyl-10b-methyl-1,2,3,4,4a,-5,6,10b-octahydrobenzo[f]quinolin-3-one-8-boronic acid (178 mg, 0.65 mmol), tetrakis(triphenylphosphine)palladium(0) (23 mg, 0.02 mmol), 4-bromoisoquinoline (135 mg, 0.65 mmol), 0.65 mL of sodium carbonate and 2 mL of THF, fitted with a reflux condenser, and the stirred mixture was heated at 80°, under nitrogen, for 24 h. An additional 23 mg of the palladium reagent was added, and the mixture was heated an additional 24 h. The mixture was cooled, diluted with chloroform (75 mL) and washed with brine (2 ×25 mL). The combined organic extracts were dried over sodium sulfate, concentrated, and purified by silica gel chromatography (ethyl acetate eluent) to give 110 mg (47%) of the title compound as an amorphous foam. FDMS: m/e=356. $\alpha[D]_{589}$=+67.82 (c=0.40, methanol).

| Analysis | Calculated | Found |
|---|---|---|
| C | 80.87 | 80.57 |
| H | 6.79 | 6.82 |
| N | 7.86 | 7.69 |

EXAMPLE 201

(+)-(4aR)-(10bR)-4-methyl-8-(3-quinolinyl)-10b-methyl-1,2,3,4,4a,5,6,10b-octahydrobenzo[f]quinolin-3-one A 15 mL round bottom flask was charged with (+)-(4aR) -(10bR)-4-methyl-10b-methyl-1,2,3,4,4a,5,6,10b-octahydrobenzo[f]quinolin-3-one-8-boronic acid (178 mg, 0.65 mmol), tetrakis(triphenylphosphine)palladium(0) (23 mg, 0.02 mmol), 3-bromoquinoline (135 mg, 0.65 mmol), 0.65 mL of 2M sodium carbonate solution and 2 mL of THF, fitted with a reflux condenser, and the stirred mixture was heated at 80°, under nitrogen, for 24 h. An additional 23 mg of the palladium reagent was added, and the mixture was heated an additional 24 h. The mixture was cooled, diluted with chloroform (75 mL) and washed with brine (2×25 mL). The combined organic extracts were dried over sodium sulfate, concentrated, and purified by silica gel chromatography (ethyl acetate eluent) to give 130 mg (56%) of the title compound as an amorphous solid. mp 180°–185°. FDMS: m/e=356. $\alpha[D]_{589}$=+80.22 (c=0.37, chloroform).

| Analysis | Calculated | Found |
|---|---|---|
| C | 80.87 | 80.65 |
| H | 6.79 | 6.52 |
| N | 7.86 | 7.68 |

EXAMPLE 202

(+)-(4aR)-(10bR)-4-methyl-8-(5-nitro-2-pyridinyl)-10b-methyl-1,2,3,4,4a,5,6,10b-octahydrobenzo[f]quinolin-3-one A 15 mL round bottom flask was charged with (+)-(4aR) -(10bR)-4-methyl-10b-methyl-1,2,3,4,4a,-5,6,10b-octahydrobenzo[f]quinolin-3-one-8-boronic acid (178 mg, 0.65 mmol), tetrakis(triphenylphosphine)palladium(0) (23 mg, 0.02 mmol), 2-bromo-5-nitropyridine (132 mg, 0.65 mmol), 0.65 mL of 2M aqueous sodium carbonate and 2 mL of THF, fitted with a reflux condenser, and the stirred mixture was heated at 80°, under nitrogen, for 24 h. The mixture was cooled, diluted with ethyl acetate (75 mL) and washed with brine (2×25 mL). The combined organic extracts were dried over sodium sulfate, concentrated, and purified by silica gel chromatography (ethyl acetate eluent) to give 148 mg (65%) of the title compound as an amorphous foam. mp 70°–80°. FDMS: m/e=351. $\alpha[D]_{589}$=+85.59 (c=0.48, chloroform).

| Analysis | Calculated | Found |
|---|---|---|
| C | 68.26 | 67.81 |
| H | 6.02 | 6.18 |
| N | 11.96 | 11.42 |

EXAMPLE 203

(+)-(4aR)-(10bR)-4-methyl-8-[2,8-bis(trifluoromethyl)-4-quinolinyl]-10b-methyl-1,2,3,4,4a,5,6,10b-octahydrobenzo[f]-quinolin-3-one A 15 mL round bottom flask was charged with (+)-(4aR)-(10bR)-4-methyl-10b-methyl-1,2,3,4,4a-,5,6,10b-octahydrobenzo[f]quinolin-3-one-8-boronic acid (178 mg, 0.65 mmol), tetrakis(triphenylphosphine)palladium(0) (23 mg, 0.02 mmol), 2,8-bis(trifluoromethyl)-4-bromoquinoline (224 mg, 0.65 mmol), 0.65 mL of 2M aqueous sodium carbonate and 2 mL of THF, fitted with a reflux condenser, and the stirred mixture was heated at 80°, under nitrogen, for 24 h. The mixture was cooled, diluted with ethyl acetate (75 mL) and washed with brine (2×25 mL). The combined organic extracts were dried over sodium sulfate, concentrated, and purified by silica gel chromatography (ethyl acetate eluent) to give 153 mg (48%) of the title compound as an amorphous foam. mp 100°–106°. FDMS: m/e=492. α[D]$_{589}$=+51.86 (c=0.47, chloroform)

| Analysis | Calculated | Found |
|---|---|---|
| C | 63.41 | 63.25 |
| H | 4.50 | 4.77 |
| N | 5.69 | 5.40 |

EXAMPLE 204

(+)-(4aR)-(10bR)-4-methyl-8-(4-methylsulfonylphenyl)-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo[f]quinolin-3-one-8-boronic acid (178 mg, 0.65 mmol), tetrakis (triphenylphosphine)palladium(0) (23 mg, 0.02 mmol), methyl 4-bromophenylsulfone (153 mg, 0.65 mmol), 0.65 mL of 2M aqueous sodium carbonate and 2 mL of THF, fitted with a reflux condenser, and the stirred mixture was heated at 80°, under nitrogen, for 24 h. The mixture was cooled, diluted with ethyl acetate (75 mL) and washed with brine (2×25 mL). The combined organic extracts were dried over sodium sulfate, concentrated, and purified by silica gel chromatography (ethyl acetate eluent) to give 137 mg (55%) of the title compound as a white solid. mp 229°. FDMS: m/e=383. α[D]$_{589}$=+28.24 (c=0.23, chloroform).

| Analysis | Calculated | Found |
|---|---|---|
| C | 68.90 | 69.10 |
| H | 6.57 | 6.65 |
| N | 3.65 | 3.89 |

EXAMPLE 205

(+)-(4aR)-(10bR)-4-methyl-8-(2,3,4,5,6-pentafluorophenyl)-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo[f]quinolin-3-one-8-boronic acid (178 mg, 0.65 mmol), tetrakis(triphenylphosphine)palladium(0) (23 mg, 0.02 mmol), 1-bromo-2,3,4,5,6-pentafluorobenzene (161 mg, 0.65 mmol), 0.65 mL of 2M aqueous sodium carbonate and 2 mL of THF, fitted with a reflux condenser, and the stirred mixture was heated at 80°, under nitrogen, for 24 h. The mixture was cooled, diluted with chloroform (75 mL) and washed with brine (2×25 mL). The combined organic extracts were dried over sodium sulfate, concentrated, and purified by silica gel chromatography (ethyl acetate eluent) to give 97 mg (38%) of the title compound as an amorphous foam. mp 92°–100°. FDMS: m/e=395. α[D]$_{589}$=+64.15 (c=0.42, chloroform).

EXAMPLE 206

(+)-(4aR)-(10bR)-4-methyl-8-(3,4,5-trifluorophenyl)-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,-5,6,10b-octahydrobenzo[f]quinolin-3-one-8-boronic acid (178 mg, 0.65 mmol), tetrakis(triphenylphosphine)palladium(0) (23 mg, 0.02 mmol), 1-bromo-3,4,5-trifluorobenzene (137 mg, 0.65 mmol), 0.65 mL of 2M aqueous sodium carbonate and 2 mL of THF, fitted with a reflux condenser, and the stirred mixture was heated at 80°, under nitrogen, for 24 h. The mixture was cooled, diluted with ethyl acetate (75 mL) and washed with brine (2×25 mL). The combined organic extracts were dried over sodium sulfate, concentrated, and purified by silica gel chromatography (ethyl acetate eluent) to give 117 mg (50%) of the title compound as an amorphous wax. FDMS: m/e=359 α[D]$_{589}$=+75.86 (c=0.47, chloroform).

| Analysis | Calculated | Found |
|---|---|---|
| C | 70.18 | 70.41 |
| H | 5.61 | 5.81 |
| N | 3.90 | 3.78 |

EXAMPLE 207

(+)-(4aR)-(10bR)-4-methyl-8-(1-oxo-5-indanyl)-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo[f]quinolin-3-one-8-boronic acid (178 mg, 0.65 mmol), tetrakis(triphenylphosphine)palladium(0) (23 mg, 0.02 mmol), 5-bromo-1-indanone (137 mg, 0.65 mmol), 0.65 mL of 2M aqueous sodium carbonate and 2 mL of THF, fitted with a reflux condenser, and the stirred mixture was heated at 80°, under nitrogen, for 24 h. The mixture was cooled, diluted with ethyl acetate (75 mL) and washed with brine (2×25 mL). The combined organic extracts were dried over sodium sulfate, concentrated, and purified by silica gel chromatography (ethyl acetate eluent) to give 91 mg (39%) of the title compound as a white solid. mp 175°–178°. FDMS: m/e=359. α[D]$_{589}$=+74.81 (c=0.53, chloroform).

| Analysis | Calculated | Found |
|---|---|---|
| C | 80.19 | 79.08 |
| H | 7.01 | 7.01 |
| N | 3.90 | 4.08 |

EXAMPLE 208

(+)-(4aR)-(10bR)-4-methyl-8-(2-fluoro-3-trifluoromethylphenyl)-10b-methyl-1,2,3,4,4a,5,6,10b-octahydrobenzo[f]-quinolin-3-one A 15 mL round bottom flask was charged with (+)-(4aR)-(10bR)-4-methyl-10b-methyl-1,2,3,4,4a,5,6,10b-octahydrobenzo[f]quinolin-3-one-8-boronic acid (178 mg, 0.65 mmol), tetrakis(triphenylphosphine)palladium(0) (23 mg, 0.02 mmol), 1-bromo-2-fluoro-3-trifluoromethylbenzene (158 mg, 0.65 mmol), 0.65 mL of 2M aqueous sodium carbonate and 2 mL of THF, fitted with a reflux condenser, and the stirred mixture was heated at 80°, under nitrogen, for 24 h. The mixture was cooled, diluted with ethyl acetate (75 mL) and washed with brine (2×25 mL). The combined organic extracts were dried over sodium sulfate, concentrated, and purified by silica gel chromatography (ethyl acetate eluent) to give 130 mg (51%) of the title compound as an oil. FDMS: m/e=391. α[D]$_{589}$=+68.49 (c=0.38, chloroform).

EXAMPLE 209

(+)-(4aR)-(10bR)-4-methyl-8-(3-[1-benzyl-4-piperidinylcarboxamido]phenyl)-10b-methyl-1,2,3,4,4a,5,6,10b-octahydrobenzo[f]quinolin-3-one A 15 mL round bottom flask was charged with (+)-(4aR)-(10bR)-4-methyl-(10b-methyl-1,2,3,4,4a,5,6,10b-octahydrobenzo[f]quinolin-3-one-8-boronic acid (178 mg, 0.65 mmol), tetrakis(triphenylphosphine)palladium(0) (23 mg, 0.02 mmol), 1-bromo-3-(1-benzyl-4-piperidinylcarboxamido)benzene (243 mg, 0.65 mmol), 0.65 mL of 2M aqueous sodium carbonate and 2 mL of THF, fitted with a reflux condenser, and the stirred mixture was heated at 80°, under nitrogen, for 24 h. The mixture was cooled, diluted with ethyl acetate (75 mL) and washed with brine (2×25 mL). The combined organic extracts were dried over sodium sulfate, concentrated, and purified by silica gel chromatography (5% methanol/ethyl acetate eluent) to give 148 mg (44%) of the title compound as an amorphous foam. FDMS: m/e=521. α[D]$_{589}$=+53.50 (c=0.45, chloroform).

| Analysis | Calculated | Found |
|---|---|---|
| C | 78.28 | 77.50 |
| H | 7.53 | 7.60 |
| N | 8.05 | 7.65 |

EXAMPLE 210

(+)-(4aR)-(10bR)-4-methyl-8-(2-fluoro-4-trifluoromethyl-phenyl)-10b-methyl-1,2,3,4,4a,5,6,10b-octahydrobenzo[f]-quinolin-3-one A 15 mL round bottom flask was charged with (+)-(4aR)-(10bR)-4-methyl-10b-methyl-1,2,3,4,4a,5,6,10b-octahydrobenzo[f]quinolin-3-one-8-boronic acid (178 mg, 0.65 mmol), tetrakis(triphenylphosphine)palladium(0) (23 mg, 0.02 mmol), 4-bromo-3-fluorobenzotrifluoride (158 mg, 0.78 mmol), 0.65 mL of sodium carbonate and 2 mL of THF, fitted with a reflux condenser, and the stirred mixture was heated at 80°, under nitrogen, for 48 h. The mixture was cooled, diluted with chloroform (75 mL) and washed with brine (2×25 mL). The combined organic extracts were dried over sodium sulfate, concentrated, and purified by silica gel chromatography (ethyl acetate eluent) to give 171 mg (67%) of the title compound as an amorphous solid. mp 72°–79°. FDMS: m/e=391. α[D]$_{589}$=+62.50 (c=0.48, chloroform).

| Analysis | Calculated | Found |
|---|---|---|
| C | 67.51 | 67.72 |
| H | 5.41 | 5.65 |
| N | 3.58 | 3.33 |

EXAMPLE 211

(+)-(4aR)-(10bR)-4-methyl-8-(2-fluoro-5-trifluoromethylphenyl)-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo [f]quinolin-3-one-8-boronic acid (178 mg, 0.65 mmol), tetrakis (triphenylphosphine)palladium(0) (23 mg, 0.02 mmol), 3-bromo-4-fluorobenzotrifluoride (158 mg, 0.65 mmol), 0.65 mL of 2M aqueous sodium carbonate and 2 mL of THF, fitted with a reflux condenser, and the stirred mixture was heated at 80°, under nitrogen, for 24 h. The mixture was cooled, diluted with ethyl acetate (75 mL) and washed with brine (2×25 mL). The combined organic extracts were dried over sodium sulfate, concentrated, and purified by silica gel chromatography (70% ethyl acetate/ hexanes eluent) to give 113 mg (44%) of the title compound as an oil. FDMS: m/e=391. α[D]$_{589}$=+55.84 (c=0.34, chloroform).

| Analysis | Calculated | Found |
|---|---|---|
| C | 67.51 | 67.73 |
| H | 5.41 | 5.62 |
| N | 3.58 | 3.31 |

EXAMPLE 212

(+)-(4aR)-(10bR)-4-methyl-8-(3-methylthiophenyl)-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo [f]quinolin-3-one-8-boronic acid (178 mg, 0.65 mmol), tetrakis (triphenylphosphine)palladium(0) (23 mg, 0.02 mmol), 3-methylthio-1-bromobenzene (132 mg, 0.65 mmol), 0.65 mL of 2M aqueous sodium carbonate and 2 mL of THF, fitted with a reflux condenser, and the stirred mixture was heated at 80°, under nitrogen, for 48 h. The mixture was cooled, diluted with chloroform (75 mL) and washed with brine (2×25 mL). The combined organic extracts were dried over sodium sulfate, concentrated, and purified by silica gel chromatography (ethyl acetate eluent) to give 110 mg (48%) of the title compound as an oily solid. FDMS: m/e=351. α[D]$_{589}$=+90.00 (c=0.17, chloroform).

| Analysis | Calculated | Found |
|---|---|---|
| C | 75.17 | 75.02 |
| H | 7.17 | 7.13 |
| N | 3.98 | 3.77 |

EXAMPLE 213

(+)-(4aR)-(10bR)-4-methyl-8-(4-carboxamidophenyl)-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo [f]quinolin-3-one-8-boronic acid (178 mg, 0.65 mmol), tetrakis(triphenylphosphine)palladium(0) (23 mg, 0.02 mmol), 4-carboxamido-1-bromobenzene (130 mg, 0.65 mmol), 0.65 mL of 2M sodium carbonate and 2 mL of THF, fitted with a reflux condenser, and the stirred mixture was heated at 80°, under nitrogen, for 24 h. The mixture was cooled, diluted with ethyl acetate (75 mL) and washed with brine (2×25 mL). The combined organic extracts were dried over sodium sulfate, concentrated, and purified by silica gel chromatography (0–10% methanol/ethyl acetate eluent gradient) to give 21 mg (9%) of the title compound as amorphous foam. mp 177°–189° (decomp.) FDMS: m/e=348.

EXAMPLE 214

(+)-(4aR)-(10bR)-4-methyl-8-[2-oxo-3-(N,N-diethylcarboxamido)-1-2H-benzopyran-6-yl)-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo [f]quinolin-3-one-8-boronic acid (178 mg, 0.65 mmol), tetrakis (triphenylphosphine)palladium(0) (23 mg, 0.02 mmol), 6-bromo-2-oxo-3-(N,N-diethylcarboxamido)-1-2H-benzopyran (211 mg, 0.65 mmol), 0.65 mL of 2M sodium carbonate and 2 mL of THF, fitted with a reflux condenser, and the stirred mixture was heated at 80°, under nitrogen, for 24 h. The mixture was cooled, diluted with ethyl acetate (75 mL) and washed with brine (2×25 mL). The combined organic extracts were dried over sodium sulfate, concentrated, and purified by silica gel chromatography (5% methanol/ethyl acetate eluent) to give 138 mg (45%) of the title compound as an amorphous foam. mp 120°–125°. FDMS: m/e=472. α[D]$_{589}$=+54.69 (c=0.49, chloroform).

| Analysis | Calculated | Found |
|---|---|---|
| C | 73.71 | 73.49 |
| H | 6.82 | 6.85 |
| N | 5.93 | 5.86 |

EXAMPLE 215

(+)-(4aR)-(10bR)-4-methyl-8-[2-(t-butylcarbonylamino)-5-pyridinyl]-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo [f]quinolin-3-one-8-boronic acid (178 mg, 0.65 mmol), tetrakis (triphenylphosphine)palladium(0) (23 mg, 0.02 mmol), 5-bromo-2-(t-butylcarbonylamino) pyridine (167 mg, 0.65 mmol), 0.65 mL of 2M aqueous sodium carbonate and 2 mL of THF, fitted with a reflux condenser, and the stirred mixture was heated at 80°, under nitrogen, for 24 h. The mixture was cooled, diluted with ethyl acetate (75 mL) and washed with brine (2×25 mL). The combined organic extracts were dried over sodium sulfate, concentrated, and purified by silica gel chromatography (ethyl acetate eluent) to give 84 mg (32%) of the title compound as a brown solid. mp 248°–250°. FDMS: m/e=405. α[D]$_{589}$=+70.74 (c=0.45, chloroform)

| Analysis | Calculated | Found |
|---|---|---|
| C | 74.04 | 74.31 |
| H | 7.70 | 7.70 |
| N | 10.36 | 9.85 |

EXAMPLE 216

(+)-(4aR)-(10bR)-4-methyl-8-(3-fluoro-5-trifluoromethylphenyl)-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo [f]quinolin-3-one-8-boronic acid (178 mg, 0.65 mmol), tetrakis (triphenylphosphine)palladium(0) (23 mg, 0.02 mmol), 1-bromo-3-fluoro-5-trifluoromethylbenzene (158 mg, 0.65 mmol), 0.65 mL of 2M aqueous sodium carbonate and 2 mL of THF, fitted with a reflux condenser, and the stirred mixture was heated at 80°, under nitrogen, for 24 h. The mixture was cooled, diluted with ethyl acetate (75 mL) and washed with brine (2×25 mL). The combined organic extracts were dried over sodium sulfate, concentrated, and purified by silica gel chromatography (ethyl acetate eluent) to give 145 mg (57%) of the title compound as an oil. FDMS: m/e=391. α[D]$_{589}$=+67.32 (c=0.55, chloroform).

| Analysis | Calculated | Found |
|---|---|---|
| C | 67.51 | 67.90 |
| H | 5.41 | 5.73 |
| N | 3.58 | 3.27 |

EXAMPLE 217

(+)-(4aR)-(10bR)-4-methyl-8-(5-nitro-2-thienyl)-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo [f]quinolin-3-one-8-boronic acid (178 mg, 0.65 mmol), tetrakis (triphenylphosphine)palladium(0) (23 mg, 0.02 mmol), 2-bromo-5-nitrothiophene (135 mg, 0.65 mmol), 0.65 mL of 2M aqueous sodium carbonate and 2 mL of THF, fitted with a reflux condenser, and the stirred mixture was heated at 80°, under nitrogen, for 24 h. The mixture was cooled, diluted with ethyl acetate (75 mL) and washed with brine (2×25 mL). The combined organic extracts were dried over sodium sulfate, concentrated, and purified by silica gel chromatography (ethyl acetate eluent) to give 118 mg (51%) of the title compound as a white solid. mp 147°–149°. FDMS: m/e=356. α[D]$_{589}$=+83.48 (c=0.54, chloroform).

| Analysis | Calculated | Found |
|---|---|---|
| C | 64.02 | 64.30 |
| H | 5.66 | 5.78 |
| N | 7.86 | 7.57 |

EXAMPLE 218

(+)-(4aR)-/10bR)-4-methyl-8-(5-chloro-2-thienyl)-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo [f]quinolin-3-one-8-boronic acid (178 mg, 0.65 mmol), tetrakis (triphenylphosphine)palladium(0) (23 mg, 0.02 mmol), 2-bromo-5-chlorothiophene (128 mg, 0.65 mmol), 0.65 mL of 2M aqueous sodium carbonate and 2 mL of THF, fitted with a reflux condenser, and the stirred mixture was heated at 80°, under nitrogen, for 24 h. The mixture was cooled, diluted with ethyl acetate (75 mL) and washed with brine (2×25 mL). The combined organic extracts were dried over sodium sulfate, concentrated, and purified by silica gel chromatography (ethyl acetate eluent) to give 125 mg (56%) of the title compound as an oil. FDMS: m/e=345. $\alpha[D]_{589}$=+74.03 (c=0.51, chloroform).

| Analysis | Calculated | Found |
|---|---|---|
| C | 66.98 | 67.39 |
| H | 5.83 | 5.90 |
| N | 4.05 | 3.86 |

EXAMPLE 219

(+)-(4aR)-(10bR)-4-methyl-8-(4-chloro-3-fluorophenyl)-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo [f]quinolin-3-one-8-boronic acid (178 mg, 0.65 mmol), tetrakis (triphenylphosphine)palladium(0) (23 mg, 0.02 mmol), 1-bromo-4-chloro-3-fluorobenzene (136 mg, 0.65 mmol), 0.65 mL of 2M sodium carbonate and 2 mL of THF, fitted with a reflux condenser, and the stirred mixture was heated at 80°, under nitrogen, for 24 h. The mixture was cooled, diluted with ethyl acetate (75 mL) and washed with brine (2×25 mL). The combined organic extracts were dried over sodium sulfate, concentrated, and purified by silica gel chromatography (ethyl acetate eluent) to give 125 mg (56%) of the title compound as an amorphous foam. FDMS: m/e=357. $\alpha[D]_{589}$=+74.28 (c=0.35, chloroform).

| Analysis | Calculated | Found |
|---|---|---|
| C | 70.48 | 70.54 |
| H | 5.91 | 6.04 |
| N | 3.91 | 3.81 |

EXAMPLE 220

(+)-(4aR)-(10bR)-4-methyl-8-(4-sulfonamidophenyl)-10b-Methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,6,10b-octahydrobenzo [f]quinolin-3-one-8-boronic acid (178 mg, 0.65 mmol), tetrakis(triphenylphosphine)palladium(0) (23 mg, 0.02 mmol), 4-bromobenzene sulfonamide (153 mg, 0.65 mmol), 0.65 mL of 2M sodium carbonate and 2 mL of THF, fitted with a reflux condenser, and the stirred mixture was heated at 80°, under nitrogen, for 24 h. The mixture was cooled, diluted with ethyl acetate (75 mL) and washed with brine (2×25 mL). The combined organic extracts were dried over sodium sulfate, concentrated, and purified by silica gel chromatography (ethyl acetate eluent) to give 34 mg (14%) of the title compound as a white solid. mp 200° (decomp.) FDMS: m/e=384. $\alpha[D]_{589}$=+201.8 (c=0.43, chloroform).

| Analysis | Calculated | Found |
|---|---|---|
| C | 65.50 | 65.83 |
| H | 6.29 | 6.46 |
| N | 7.29 | 7.52 |

EXAMPLE 221

(+)-(4aR)-(10bR)-4-methyl-8-[4-(4-chlorobutyryl)phenyl]-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo [f]quinolin-3-one-8-boronic acid (178 mg, 0.65 mmol), tetrakis(triphenylphosphine)palladium(0) (23 mg, 0.02 mmol), 4-bromo-γ-chlorobutyrophenone (170 mg, 0.65 mmol), 0.65 mL of 2M aqueous sodium carbonate and 2 mL of THF, fitted with a reflux condenser, and the stirred mixture was heated at 80°, under nitrogen, for 24 h. The mixture was cooled, diluted with ethyl acetate (75 mL) and washed with brine (2×25 mL). The combined organic extracts were dried over sodium sulfate, concentrated, and purified by silica gel chromatography (ethyl acetate eluent) to give 113 mg (42%) of the title compound an oil. FDMS: m/e=409. $\alpha[D]_{589}$=+60.00 (c=0.18, chloroform).

| Analysis | Calculated | Found |
|---|---|---|
| C | 73.25 | 72.91 |
| H | 6.88 | 6.80 |
| N | 3.42 | 3.33 |

EXAMPLE 222

(+)-(4aR)-(10bR)-4-methyl-8-(4-[(2-t-butylcarbonylamino]-5-thienyl]phenyl)-10b-methyl-1,2,3,4,4a,5,6,10b-octahydro-benzo[f]quinolin-3-one A 15 mL round bottom flask was charged with (+)-(4aR)-(10bR)-4-methyl-10b-methyl-1,2,3,4,4a,5,6,10b-octahydrobenzo [f]quinolin-3-one-8-boronic acid (178 mg, 0.65 mmol), tetrakis (triphenylphosphine)palladium(0) (23 mg, 0.02 mmol), 5-(4-bromophenyl)-2-(t-butylcarbonylamino)-thiophene (221 mg, 0.65 mmol), 0.65 mL of 2M aqueous sodium carbonate and 2 mL of THF, fitted with a reflux condenser, and the stirred mixture was heated at 80°, under nitrogen, for 24 h. The mixture was cooled, diluted with ethyl acetate (75 mL) and washed with brine (2×25 mL). The combined organic extracts were dried over sodium sulfate, concentrated, and purified by silica gel chromatography (ethyl acetate eluent) to give 88 mg (28%) of the title compound a brown solid. mp 240° (decomp.) FDMS: m/e=487. $\alpha[D]_{589}$=+61.73 (c=0.47, chloroform).

| Analysis | Calculated | Found |
|---|---|---|
| C | 71.43 | 71.62 |
| H | 6.82 | 7.00 |
| N | 8.62 | 8.05 |

EXAMPLE 223

(+)-(4aR)-(10bR)-4-methyl-8-(2,3-dioxo-5-indolinyl)-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo [f]quinolin-3-one-8-boronic acid (178 mg, 0.65 mmol), tetrakis (triphenylphosphine)palladium(0) (23 mg, 0.02 mmol), 5-bromoisatin hydrate (159 mg, 0.65 mmol), 0.65 mL of 2M sodium carbonate and 2 mL of THF, fitted with a reflux condenser, and the stirred mixture was heated at 80°, under nitrogen, for 24 h. The mixture was cooled, diluted with ethyl acetate (75 mL) and washed with brine (2×25 mL). The combined organic extracts were dried over sodium sulfate, concentrated, and purified by silica gel chromatography (5% methanol/ethyl acetate eluent) to give 36 mg (15%) of the title compound as a white solid. mp >250° FDMS: m/e=374. $\alpha[D]_{589}$=+75.33 (c=0.53, chloroform).

| Analysis | Calculated | Found |
|---|---|---|
| C | 73.78 | 73.29 |
| H | 5.92 | 5.98 |
| N | 7.48 | 7.22 |

EXAMPLE 224

(+)-(4aR)-(10bR)-4-methyl-8-(2-(2-dimethylaminoethyl)-1H-benzo<de>isoquinolin-6-yl-1,3-(2H)dione)-10b-methyl-1,2,3,4, 4a,5,6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo [f]quinolin-3-one-8-boronic acid (178 mg, 0.65 mmol), tetrakis (triphenylphosphine)palladium(0) (23 mg, 0.02 mmol), 6-bromo-2-(2-dimethylaminoethyl)-1H-benzo<de>isoquinolin-1,3-(2H)dione (226 mg, 0.65 mmol), 0.65 mL of aqueous sodium carbonate and 2 mL of THF, fitted with a reflux condenser, and the stirred mixture was heated at 80°, under nitrogen, for 48 h. The mixture was cooled, diluted with chloroform (75 mL) and washed with brine (2×25 mL). The combined organic extracts were dried over sodium sulfate, concentrated, and purified by silica gel chromatography (15% methanol/ethyl acetate eluent) to give 141 mg (44%) of the title compound as a white solid. mp 190°-192°. FDMS: m/e=495. $\alpha[D]_{589}$=+74.71 (c=0.53, chloroform).

| Analysis | Calculated | Found |
|---|---|---|
| C | 75.13 | 74.94 |
| H | 6.71 | 6.33 |
| N | 8.48 | 8.22 |

EXAMPLE 225

(+)-(4aR)-(10bR)-4-methyl-8-2aR,4S-1-benzoyl-4-dipropylamino-2,2a,3,4-tetrahydrobenz[cd]-1H-indol-7-yl)-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo [f]quinolin-3-one-8-boronic acid (178 mg, 0.65 mmol), tetrakis (triphenylphosphine)palladium(0) (23 mg, 0.02 mmol), 2aR,4S-1-benzoyl-4-dipropylamino-7-iodo-2,2a,3,4-tetrahydrobenz[cd]-1H-indole (317 mg, 0.65 mmol), 0.65 mL of 2M sodium carbonate and 2 mL of THF, fitted with a reflux condenser, and the stirred mixture was heated am 80°, under nitrogen, for 24 h. The mixture was cooled, diluted with washed with brine (75 mL) and washed with brine (2×25 mL). The combined organic extracts were dried over sodium sulfate, concentrated, and purified by silica gel chromatography (5% methanol/ethyl acetate eluent) to give 64 mg (17%) of the title compound as an amorphous foam. mp 110°-115°. FDMS: m/e=589. $\alpha[D]_{589}$=+80.14 (c=0.46, chloroform).

| Analysis | Calculated | Found |
|---|---|---|
| C | 79.42 | 79.58 |
| H | 8.03 | 8.06 |
| N | 7.12 | 6.73 |

EXAMPLE 226

(+)-(4aR)-(10bR)-4-methyl-8-(2aR,4S-1-benzoyl-4-amino-2,2a,3,4-tetrahydrobenz[cd]-1H-indol-7-yl)-10b-methyl-1,2,3,4, 4a,5,6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo [f]quinolin-3-one-8-boronic acid (178 mg, 0.65 mmol), tetrakis (triphenylphosphine)palladium(0) (23 mg, 0.02 mmol), 2aR,4S-1-benzoyl-4-amino-7-iodo-2,2a,3,4-tetrahydrobenz[cd]-1H-indole (263 mg, 0.65 mmol), 0.65 mL of 2M aqueous sodium carbonate and 2 mL of THF, fitted with a reflux condenser, and the stirred mixture was heated at 80°, under nitrogen, for 24 h. The mixture was cooled, diluted with ethyl acetate (75 mL) and washed with brine (2×25 mL). The combined organic extracts were dried over sodium sulfate, concentrated, and purified by silica gel chromatography (5% methanol/ethyl acetate eluent) to give 187 mg (57%) of the title compound as an amorphous foam. mp 134°-136°. FDMS: m/e=505.

EXAMPLE 227

(+)-(4aR)-(10bR)-4-methyl-8-(3,5-difluorophenyl)-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo [f]quinolin-3-one-8-boronic acid (178 mg, 0.65 mmol), tetrakis (triphenylphosphine)palladium(0) (23 mg, 0.02 mmol), 1-bromo-3,5-difluorobenzene (125 mg, 0.65 mmol), 0.65 mL of 2M aqueous sodium carbonate and 2 mL of THF, fitted with a reflux condenser, and the stirred mixture was heated at 80°, under nitrogen, for 24 h. The mixture was cooled, diluted with ethyl acetate (75 mL) and washed with brine (2×25 mL). The combined organic extracts were dried over sodium sulfate, concentrated, and purified by silica gel chromatography (70% ethyl acetate/hexanes eluent) to give 137 mg (62%) of the title compound as an oil. FDMS: m/e=341. $\alpha[D]_{589}$=+79.29 (c=0.28, chloroform).

| Analysis | Calculated | Found |
|---|---|---|
| C | 73.88 | 73.40 |
| H | 6.20 | 6.11 |
| N | 4.10 | 3.99 |

EXAMPLE 228

(+)-(4aR)-(10bR)-4-methyl-8-(2,6-difluorophenyl)-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo [f]quinolin-3-one-8-boronic acid (178 mg, 0.65 mmol), tetrakis (triphenylphosphine)palladium(0) (23 mg, 0.02 mmol), 1-bromo-2,6-difluorobenzene (125 mg, 0.65 mmol), 0.65 mL of 2M aqueous sodium carbonate and 2 mL of THF, fitted with a reflux condenser, and the stirred mixture was heated at 80°, under nitrogen, for 24 h. The mixture was cooled, diluted with ethyl acetate (75 mL) and washed with brine (2×25 mL). The combined organic extracts were dried over sodium sulfate, concentrated, and purified by silica gel chromatography (70% ethyl acetate/hexanes eluent) to give 98 mg (44%) of the title compound as an amorphous solid. mp 125°–130°. FDMS: m/e=341. $\alpha[D]_{589}$=+71.79 (c=0.58, chloroform).

| Analysis | Calculated | Found |
|---|---|---|
| C | 73.88 | 74.13 |
| H | 6.20 | 6.32 |
| N | 4.10 | 3.87 |

EXAMPLE 229

(+)-(4aR)-(10bR)-4-methyl-8-(2,5-difluorophenyl)-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo [f]quinolin-3-one-8-boronic acid (178 mg, 0.65 mmol), tetrakis (triphenylphosphine)palladium(0) (23 mg, 0.02 mmol), 1-bromo-2,5-difluorobenzene (125 mg, 0.65 mmol), 0.65 mL of 2M sodium carbonate and 2 mL of THF, fitted with a reflux condenser, and the stirred mixture was heated at 80°, under nitrogen, for 24 h. The mixture was cooled, diluted with ethyl acetate (75 mL) and washed with brine (2×25 mL). The combined organic extracts were dried over sodium sulfate, concentrated, and purified by silica gel chromatography (70% ethyl acetate/hexanes eluent) to give 105 mg (47%) of the title compound as an oil. FDMS: m/e=341. $\alpha[D]_{589}$=+70.96 (c=0.38, chloroform).

| Analysis | Calculated | Found |
|---|---|---|
| C | 73.88 | 74.01 |
| H | 6.20 | 6.43 |
| N | 4.10 | 3.76 |

EXAMPLE 230

(+)-(4aR)-(10bR)-4-methyl-8-(2,4,6-trifluorophenyl)-10b-methyl-1,2,3,4,4a,5 6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo [f]quinolin-3-one-8-boronic acid (178 mg, 0.65 mmol), tetrakis (triphenylphosphine)palladium(0) (23 mg, 0.02 mmol), 1-bromo-2,4,6-trifluorobenzene (137 mg, 0.65 mmol), 0.65 mL of 2M aqueous sodium carbonate and 2 mL of THF, fitted with a reflux condenser, and the stirred mixture was heated at 80°, under nitrogen, for 24 h. The mixture was cooled, diluted with ethyl acetate (75 mL) and washed with brine (2×25 mL). The combined organic extracts were dried over sodium sulfate, concentrated, and purified by silica gel chromatography (70% ethyl acetate/hexanes eluent) to give 116 mg (50%) of the title compound as an oil. FDMS: m/e=359. $\alpha[D]_{589}$=+68.65 (c=0.35, chloroform).

| Analysis | Calculated | Found |
|---|---|---|
| C | 70.18 | 70.15 |
| H | 5.61 | 5.86 |
| N | 3.90 | 3.69 |

EXAMPLE 231

(+)-(4aR)-(10bR)-4-methyl-8-(2,4-difluorophenyl)-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo [f]quinolin-3-one-8-boronic acid (178 mg, 0.65 mmol), tetrakis (triphenylphosphine)palladium(0) (23 mg, 0.02 mmol), 1-bromo-2,4-difluorobenzene (125 mg, 0.65 mmol), 0.65 mL of 2M aqueous sodium carbonate and 2 mL of THF, fitted with a reflux condenser, and the stirred mixture was heated at 80°, under nitrogen, for 24 h. The mixture was cooled, diluted with ethyl acetate 75 mL) and washed with brine (2×25 mL). The combined organic extracts were dried over sodium sulfate, concentrated, and purified by silica gel chromatography (70% ethyl acetate/hexanes eluent) to give 106 mg (48%) of the title compound as white solid. mp 108°–112°. FDMS: m/e=341. $\alpha[D]_{589}$=+82.90 c=0.52, chloroform)

| Analysis | Calculated | Found |
|---|---|---|
| C | 73.88 | 73.94 |
| H | 6.20 | 6.33 |
| N | 4.10 | 4.05 |

EXAMPLE 232

(+)-(4aR)-(10bR)-4-methyl-8-(2,3,4-trifluorophenyl)-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo [f]quinolin-3-one-8-boronic acid (178 mg, 0.65 mmol), tetrakis (triphenylphosphine)palladium(0) (23 mg, 0.02 mmol), 1-bromo-2,3,4-trifluorobenzene (137 mg, 0.65 mmol), 0.65 mL of 2M sodium carbonate and 2 mL of THF, fitted with a reflux condenser, and the stirred mixture was heated at 80°, under nitrogen, for 24 h. The mixture was cooled, diluted with ethyl acetate (75 mL) and washed with brine (2×25 mL). The combined organic extracts were dried over sodium sulfate, concentrated, and purified by silica gel chromatography (70% ethyl acetate/hexanes eluent) to give 100 mg (43%) of the title compound as a white solid. mp 100°–102°. FDMS: m/e=359. $\alpha[D]_{589}$=+7837 (c=0.33, chloroform).

111

| Analysis | Calculated | Found |
|---|---|---|
| C | 70.18 | 70.47 |
| H | 5.61 | 5.80 |
| N | 3.90 | 3.78 |

EXAMPLE 233

(+)-(4aR)-(10bR)-4-methyl-8-(4-[4-nitrobenzyl] thiophenyl)-10b-methyl-1,2,3,4,4a,5,6,10b-ocahydrobenzo [f]quinolin-3-one A 15 mL round bottom flask was charged with (+)-(4aR) -(10bR)-4-methyl-10b-methyl-1,2,3,4,4a,5,6,10b- octahydrobenzo [f]quinolin-3-one-8-boronic acid (178 mg, 0.65 mmol), tetrakis (triphenylphosphine)palladium(0) (23 mg, 0.02 mmol), 4-(4-nitrobenzylthio-1-bromobenzene (211 mg, 0.65 mmol), 0.65 mL of sodium carbonate and 2 mL of THF, fitted with a reflux condenser, and the stirred mixture was heated at 80°, under nitrogen, for 48 h. The mixture was cooled, diluted with chloroform (75 mL) and washed with brine (2×25 mL). The combined organic extracts were dried over sodium sulfate, concentrated, and purified by silica gel chromatography (ethyl acetate eluent) to give 166 mg (54%) of the title compound as an oily solid. FDMS: m/e=472. α[D]$_{589}$=+65.63 (c=0.41, chloroform).

| Analysis | Calculated | Found |
|---|---|---|
| C | 71.16 | 71.63 |
| H | 5.97 | 6.21 |
| N | 5.93 | 6.26 |

EXAMPLE 234

(+)-(4aR)-(10bR)-4-methyl-8-(2-(2-[1-morpholino]ethyl) -1H-benzo<de>isoquinolin-6-yl-1,3-(2H)dione)-10b- methyl-1,2,3,4,4a,5,6,10b-octahydrobenzo[f]quinolin-3-one A 15 mL round bottom flask was charged with (+)-(4aR) -(10bR)-4-methyl-10b-methyl-1,2,3,4,4a-5,6,10b- octahydrobenzo [f]quinolin-3-one-8-boronic acid (178mg, 0.65 mmol), tetrakis (triphenylphosphine)palladium(0) (23 mg, 0.02 mmol), 6-bromo-2-(2-[1-morpholino]ethyl)-1H- benzo<de>iso-quinoline-1,3-(2H)dione (253 mg, 0.65 mmol), 0.65 mL of aqueous sodium carbonate and 2 mL of THF, fitted with a reflux condenser, and the stirred mixture was heated at 80°, under nitrogen, for 48 h. The mixture was cooled, diluted with chloroform (75 mL) and washed with brine (2×25 mL). The combined organic extracts were dried over sodium sulfate, concentrated, and purified by silica gel chromatography (5% methanol/ethyl acetate eluent) to give 176 mg (50%) of the title compound as an amorphous solid. mp 100°–105°. FDMS: m/e=537. α[D]$_{589}$=+45.10 (c=0.53, chloroform).

| Analysis | Calculated | Found |
|---|---|---|
| C | 73.72 | 73.46 |
| H | 6.56 | 6.73 |
| N | 7.82 | 7.55 |

EXAMPLE 235

(+)-(4aR)-(10bR)-4-methyl-8-(4-pyridinyl)-10b-methyl- 1,2,3,4,4a,5,6,10b-octahydrobenzo[f]quinolin-3-one

112

A 15 mL round bottom flask was charged with (+)-(4aR) -(10bR)-4-methyl-10b-methyl-1,2,3,4,4a,5,6,10b- octahydrobenzo [f]quinolin-3-one-8-boronic acid (178 mg, 0.65 mmol), tetrakis (triphenylphosphine)palladium(0) (23 mg, 0.02 mmol), 4-bromopyridine hydrochloride (126 mg, 0.65 mmol), 1.30 mL of 2M sodium carbonate and 2 mL of THF, fitted with a reflux condenser, and the stirred mixture was heated at 80°, under nitrogen, for 24 h. The mixture was cooled, diluted with ethyl acetate (75 mL) and washed with brine (2×25 mL). The combined organic extracts were dried over sodium sulfate, concentrated, and purified by silica gel chromatography (5% methanol/ethyl acetate eluent) to give 85 mg (43%) of the title compound as an oil. FDMS: m/e=306.

| Analysis | Calculated | Found |
|---|---|---|
| C | 78.40 | 78.56 |
| H | 7.24 | 7.00 |
| N | 9.14 | 8.68 |

EXAMPLE 236

(+)-(4aR)-(10bR)-4-methyl-8-(1-p-toluenesulfonylindol- 5-yl)-10b-methyl-1,2,3,4,4a,5,6,10b-octahydrobenzo[f] quinolin-3-one A 15 mL round bottom flask was charged with (+)-(4aR) -(10bR)-4-methyl-10b-methyl-1,2,3,4,4a,5,6,10b- octahydrobenzo [f]quinolin-3-one-8-boronic acid (178 mg, 0.65 mmol), tetrakis (triphenylphosphine)palladium(0) (23 mg, 0.02 mmol), N-tosyl-5-bromoindole (228 mg, 0.65 mmol), 0.65 mL of sodium carbonate and 2 mL of THF, fitted with a reflux condenser, and the stirred mixture was beamed a 80°, under nitrogen, for 24 h. The mixture was cooled, diluted with ethyl acetate (75 mL) and washed with brine (2×25 mL). The combined organic extracts were dried over sodium sulfate, concentrated, and purified by silica gel chromatography (ethyl acetate eluent) to give 49 mg (15%) of the title compound as an amorphous foam. FDMS: m/e=498.

| Analysis | Calculated | Found |
|---|---|---|
| C | 72.26 | 71.04 |
| H | 6.06 | 6.32 |
| N | 5.62 | 4.94 |

EXAMPLE 237

(+)-(4aR)-(10bR)-4-methyl-8-(1-acetyl-7-nitroindolin- 5-yl )-10b-methyl-1,2,3,4,4a,5,6,10b-octahydrobenzo[f] quinolin-3-one A 15 mL round bottom flask was charged with (+)-(4aR) -(10bR)-4-methyl-10b-methyl-1,2,3,4,4a,5,6,10b- octahydrobenzo [f]quinolin-3-one-8-boronic acid (178 mg, 0.65 mmol), tetrakis (triphenylphosphine)palladium(0) (23 mg, 0.02 mmol), 1-acetyl-5-bromo-7-nitroindoline (185 mg, 0.65 mmol), 0.65 mL of 2M sodium carbonate and 2 mL of THF, fitted with a reflux condenser, and the stirred mixture was heated at 80°, under nitrogen, for 24 h. The mixture was cooled, diluted with ethyl acetate (75 mL) and washed with brine (2×25 mL). The combined organic extracts were dried over sodium sulfate, concentrated, and purified by silica gel chromatography (5% methanol/ethyl acetate eluent) to give 63 mg (22%) of the title compound a yellow solid. mp 235°–240°. FDMS: m/e=433. α[D]$_{589}$=+65.72 (c=0.99, chloroform).

| Analysis | Calculated | Found |
|---|---|---|
| C | 69.27 | 69.39 |
| H | 6.28 | 6.55 |
| N | 9.69 | 9.54 |

EXAMPLE 238

(+)-(4aR)-(10bR)-4-methyl-8-(1-acetylindolin-5-yl)-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo [f]quinolin-3-one-8-boronic acid (178 mg, 0.65 mmol), tetrakis (triphenylphosphine)palladium(0) (23 mg, 0.02 mmol), 1-acetyl-5-bromoindoline (156 mg, 0.65 mmol), 0.65 mL of 2M sodium carbonate and 2 mL of THF, fitted with a reflux condenser, and the stirred mixture was heated at 80°, under nitrogen, for 24 h. The mixture was cooled, diluted with chloroform (75 mL) and washed with brine (2×25 mL). The combined organic extracts were dried over sodium sulfate, concentrated, and purified by silica gel chromatography (5% methanol/ethyl acetate eluent) to give 67 mg (26%) of the title compound as a yellow solid. mp 197°–200°. FDMS: m/e=388. α[D]$_{589}$=+77.92 (c=0.36, chloroform).

| Analysis | Calculated | Found |
|---|---|---|
| C | 77.29 | 77.04 |
| H | 7.26 | 7.00 |
| N | 7.21 | 7.12 |

EXAMPLE 239

(+)-(4aR)-(10bR)-4-methyl-8-(8-quinolinyl)-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo [f]quinolin-3-one-8-boronic acid (178 mg, 0.65 mmol), tetrakis (triphenylphosphine)palladium(0) (23 mg, 0.02 mmol), 8-bromoquinoline (135 mg, 0.65 mmol), 0.65 mL of 2M sodium carbonate and 2 mL of THF, fitted with a reflux condenser, and the stirred mixture was heated at 80°, under nitrogen, for 24 h. The mixture was cooled, diluted with ethyl acetate (75 mL) and washed with brine (2×25 mL). The combined organic extracts were dried over sodium sulfate, concentrated, and purified by silica gel chromatography (ethyl acetate eluent) to give 88 mg (38%) of the title compound as a tan solid. mp 205°–207°. FDMS: m/e=356 α[D]$_{589}$=+76.28 (c=0.47, chloroform).

| Analysis | Calculated | Found |
|---|---|---|
| C | 80.87 | 80.66 |
| H | 6.79 | 6.69 |
| N | 7.86 | 7.76 |

EXAMPLE 240

(+)-(4aR)-(10bR)-4-methyl-8-(5-quinolinyl)-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo [f]quinolin-3-one-8-boronic acid (178 mg, 0.65 mmol), tetrakis (triphenylphosphine)palladium(0) (23 mg, 0.02 mmol), 5-bromoquinoline (135 mg, 0.65 mmol), 0.65 mL of 2M sodium carbonate and 2 mL of THF, fitted with a reflux condenser, and the stirred mixture was heated at 80°, under nitrogen, for 24 h. The mixture was cooled, diluted with ethyl acetate (75 mL) and washed with brine (2×25 mL). The combined organic extracts were dried over sodium sulfate, concentrated, and purified by silica gel chromatography (ethyl acetate eluent) to give 128 mg (55%) of the title compound as an amorphous foam. mp 100°–104°. FDMS: m/e=356. α[D]$_{589}$=+61.77 (c=0.35, chloroform).

| Analysis | Calculated | Found |
|---|---|---|
| C | 80.87 | 79.55 |
| H | 6.79 | 6.92 |
| N | 7.86 | 7.60 |

EXAMPLE 241

(+)-(4aR)-(10bR)-4-methyl-8-(5-isoquinolinyl)-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo[f]quinolin-3-one-8-boronic acid (178 mg, 0.65 mmol), tetrakis (triphenylphosphine)palladium(0) (23 mg, 0.02 mmol), 5-bromoisoquinoline (135 mg, 0.65 mmol), 0.65 mL of 2M sodium carbonate and 2 mL of THF, fitted with a reflux condenser, and the stirred mixture was heated at 80°, under nitrogen, for 24 h. The mixture was cooled, diluted with ethyl acetate (75 mL) and washed with brine (2×25 mL). The combined organic extracts were dried over sodium sulfate, concentrated, and purified by silica gel chromatography (5% methanol/ethyl acetate eluent) to give 98 mg (42%) of the title compound as an amorphous solid. mp 182°–184°. FDMS: m/e=356. α[D]$_{589}$=+57.25 (c=0.49, chloroform).

| Analysis | Calculated | Found |
|---|---|---|
| C | 80.87 | 80.28 |
| H | 6.79 | 6.86 |
| N | 7.86 | 7.43 |

EXAMPLE 242

(+)-(4aR)-(10bR)-4-methyl-8-(2-pyridinyl)-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo[f]quinolin-3-one-8-boronic acid (178 mg, 0.65 mmol), tetrakis (triphenylphosphine)palladium(0) (23 mg, 0.02 mmol), 2-bromopyridine (103 mg, 0.65 mmol), 0.65 mL of 2M sodium carbonate and 2 mL of THF, fitted with a reflux condenser, and the stirred mixture was heated at 80°, under nitrogen, for 24 h. The mixture was cooled, diluted with ethyl acetate (75 mL) and washed with brine (2×25 mL). The combined organic extracts were dried over sodium sulfate, concentrated, and purified by silica gel chromatography (ethyl acetate eluent) to give 98 mg (49%) of the title compound as an oil. FDMS: m/e=306. α[D]$_{589}$=+83.48 c=0.38, chloroform).

| Analysis | Calculated | Found |
|---|---|---|
| C | 78.40 | 77.73 |
| H | 7.24 | 6.96 |
| N | 9.14 | 9.07 |

EXAMPLE 243

(+)-(4aR)-(10bR)-4-methyl-8-(2,5-difluoro-4-nitrophenyl)-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo[f]quinolin-3-one-8-boronic acid (178 mg, 0.65 mmol), tetrakis (triphenylphosphine)palladium(0) (23 mg, 0.02 mmol), 1-bromo-2,5-difluoro-4-nitrobenzene (155 mg, 0.65 mmol), 0.65 mL of aqueous 2M sodium carbonate solution and 2 mL of THF, fitted with a reflux condenser, and the stirred mixture was heated at 80°, under nitrogen, for 24 h. An additional 23 mg of the palladium reagent was added, and the mixture was heated an additional 24 h. The mixture was cooled, diluted with chloroform (75 mL) and washed with brine (2×25 mL). The combined organic extracts were dried over sodium sulfate, concentrated, and purified by silica gel chromatography (ethyl acetate eluent) to give 128 mg (51%) of the title compound as an amorphous solid. mp 130°–140°. FDMS: m/e=386. α[D]$_{589}$=+73.44 (c=0.53, chloroform).

| Analysis | Calculated | Found |
|---|---|---|
| C | 65.28 | 66.70 |
| H | 5.22 | 5.69 |
| N | 7.25 | 7.64 |

EXAMPLE 244

(+)-(4aR)-(10bR)-4-methyl-8-(6-quinolinyl)-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo[f]quinolin-3-one-8-boronic acid (178 mg, 0.65 mmol), tetrakis (triphenylphosphine)palladium(0) (23 mg, 0.02 mmol), 6-bromoquinoline (135 mg, 0.65 mmol), 0.65 mL of 2M sodium carbonate and 2 mL of THF, fitted with a reflux condenser, and the stirred mixture was heated at 80°, under nitrogen, for 24 h. The mixture was cooled, diluted with ethyl acetate (75 mL) and washed with brine (2×25 mL). The combined organic extracts were dried over sodium sulfate, concentrated, and purified by silica gel chromatography (5% methanol/ethyl acetate eluent) to give 107 mg (46%) of the title compound as an amorphous solid. mp 185°–190°. FDMS: m/e=356. α[D]$_{589}$=+78.73 (c=0.56, chloroform).

| Analysis | Calculated | Found |
|---|---|---|
| C | 80.87 | 80.13 |
| H | 6.79 | 6.74 |
| N | 7.86 | 6.99 |

EXAMPLE 245

(+)-(4aR)-(10bR)-4-methyl-8-(1-hydroxy-5-indanyl)-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo[f]quinolin-3-one-8-boronic acid (178 mg, 0.65 mmol), tetrakis (triphenylphosphine)palladium(0) (23 mg, 0.02 mmol), 5-bromo-1-hydroxyindane (138 mg, 0.65 mmol), 0.65 mL of aqueous 2M sodium carbonate solution and 2 mL of THF, fitted with a reflux condenser, and the stirred mixture was heated at 80°, under nitrogen, for 16 h. The mixture was cooled, diluted with chloroform (75 mL) and washed with brine (2×25 mL). The combined organic extracts were dried over sodium sulfate, concentrated, and purified by silica gel chromatography (ethyl acetate eluent) to give 79 mg (34) of the title compound as an amorphous solid. mp 185°–190°. FDMS: m/e=361. α[D]$_{589}$=+77.38 (c=0.35, chloroform).

| Analysis | Calculated | Found |
|---|---|---|
| C | 79.74 | 79.01 |
| H | 7.53 | 7.53 |
| N | 3.87 | 3.79 |

EXAMPLE 246

(+)-(4aR)-(10bR)-4-methyl-8-[2-(4-[N-benzyl]piperidinyl)-1H-benzo<de>isoquinolin-6-yl-1,3-(2H)dione]-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,6,6,10b-octahydrobenzo[f]quinolin-3-one-8-boronic acid (178 mg, 0.65 mmol), tetrakis (triphenylphosphine)palladium(0) (23 mg, 0.02 mmol), 6-bromo-2-(4-[N-benzyl]piperidinyl)-1H-benzo<de>iso-quinoline-1,3-(2H)dione (292 mg, 0.65 mmol), 0.65 mL of aqueous sodium carbonate and 2 mL of THF, fitted with a reflux condenser, and the stirred mixture was heated at 80°, under nitrogen, for 48 h. The mixture was cooled, diluted with chloroform (75 mL) and washed with brine (2×35 mL). The combined organic extracts were dried over sodium sulfate, concentrated, and purified by silica gel chromatography (ethyl acetate eluent) to give 197 mg (51%) of the title compound as an amorphous foam. FDMS: m/e=597. α[D]$_{589}$=+51.09 (c=0.58, chloroform).

| Analysis | Calculated | Found |
|---|---|---|
| C | 78.36 | 76.08 |
| H | 6.58 | 6.80 |
| N | 7.03 | 6.40 |

EXAMPLE 247

(+)-(4aR)-(10bR)-4-methyl-8-(2-quinolinyl)-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo[f]quinolin-3-one-8-boronic acid (178 mg, 0.65 mmol), tetrakis (triphenylphosphine)palladium(0) (23 mg, 0.02 mmol), 2-bromoquinoline (135 mg, 0.65 mmol), 0.65 mL of 2M sodium carbonate and 2 mL of THF, fitted with a reflux condenser, and the stirred mixture was heated at 80°, under nitrogen, for 24 h. The mixture was cooled, diluted with ethyl acetate (75 mL) and washed with brine (2×25 mL). The combined organic extracts were dried over sodium sulfate, concentrated, and purified by silica gel chromatography (ethyl acetate eluent) to give 126 mg (54%) of the title compound as an amorphous foam. mp 140°–145°. FDMS: m/e=356. α[D]$_{589}$=+74.01 (c=0.46, chloroform).

| Analysis | Calculated | Found |
|---|---|---|
| C | 80.87 | 80.56 |
| H | 6.79 | 6.88 |
| N | 7.86 | 7.45 |

EXAMPLE 248

(+)-(4aR)-(10bR)-4-methyl-8-(2-oxo-1-benzopyran-6-yl)-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo[f]quinolin-3-one-8-boronic acid (178 mg, 0.65 mmol), tetrakis (triphenylphosphine)palladium(0) (23 mg, 0.02 mmol), 6-bromocoumarin (146 mg, 0.65 mmol), 0.65 mL of 2M aqueous sodium carbonate and 2 mL of THF, fitted with a reflux condenser, and the stirred mixture was heated at 80°, under nitrogen, for 24 h. The mixture was cooled, diluted with ethyl acetate (75 mL) and washed with brine (2×25 mL). The combined organic extracts were dried over sodium sulfate, concentrated, and purified by silica gel chromatography (ethyl acetate eluent) to give 108 mg (40%) of the title compound an amorphous solid. mp 180° (decomp.) FDMS: m/e=373. α[D]$_{589}$=+40.48 (c=0.42, chloroform).

| Analysis | Calculated | Found |
|---|---|---|
| C | 77.19 | 76.90 |
| H | 6.21 | 6.48 |
| N | 3.75 | 4.02 |

EXAMPLE 249

(+)-(4aR)-(10bR)-4-methyl-8-(6-benzothiazolyl)-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo[f]quinolin-3-one-8-boronic acid(178 mg, 0.65 mmol), tetrakis (triphenylphosphine)palladium(0) (23 mg, 0.02 mmol), 6-bromobenzothiazole (139 mg, 0.65 mmol), 0.65 mL of 2M aqueous sodium carbonate and 2 mL of THF, fitted with a reflux condenser, and the stirred mixture was heated at 80°, under nitrogen, for 24 h. The mixture was cooled, diluted with chloroform (75 mL) and washed with brine (2×25 mL). The combined organic extracts were dried over sodium sulfate, concentrated, and purified by silica gel chromatography (20% ethyl acetate/hexanes eluent) to give 106 mg (47%) of the title compound as an amorphous solid. mp 183°–187°. FDMS: m/e=362. α[D]$_{589}$=+87.80 (c=0.55, chloroform).

| Analysis | Calculated | Found |
|---|---|---|
| C | 72.90 | 72.63 |
| H | 6.12 | 6.30 |
| N | 7.73 | 7.49 |

EXAMPLE 250

(+)-(4aR)-10bR)-4-methyl-8-(1-[t-butoxycarbonyl]-5-indolyl)-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo[f]quinolin-3-one-8-boronic acid (178 mg, 0.65 mmol), tetrakis (triphenylphosphine)palladium(0) (23 mg, 0.02 mmol), 1-(t-butoxycarbonyl)-5-bromoindole (193 mg, 0.65 mmol), 0.65 mL of 2M sodium carbonate and 2 mL of THF, fitted with a reflux condenser, and the stirred mixture was heated at 80°, under nitrogen, for 24 h. The mixture was cooled, diluted with chloroform (75 mL) and washed with brine (2×25 mL). The combined organic extracts were dried over sodium sulfate, concentrated, and purified by silica gel chromatography (5% methanol/ethyl acetate eluent) to give 113 mg (39%) of the title compound as an amorphous foam. FDMS: m/e=445. α[D]$_{589}$=+68.17 (c=0.47, chloroform).

| Analysis | Calculated | Found |
|---|---|---|
| C | 75.65 | 75.82 |
| H | 7.25 | 7.28 |
| N | 6.30 | 5.88 |

EXAMPLE 251

(+)-(4aR)-(10bR)-4-methyl-8-(2-benzoxazolyl)-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo[f]quinolin-3-one-8-boronic acid (178 mg, 0.65 mmol), tetrakis (triphenylphosphine)palladium(0) (23 mg, 0.02 mmol), 2-chlorobenzoxazole (110 mg, 0.65 mmol), 0.65 mL of 2M sodium carbonate solution and 2 mL of THF, fitted with a reflux condenser, and the stirred mixture was heated at 80°, under nitrogen, for 18 h. Additional palladium reagent (23 mg) was added, and the mixture was heated an additional 48 h. The mixture was cooled, diluted with chloroform (75 mL) and washed with brine (2×25 mL). The combined organic extracts were dried over sodium sulfate, concentrated, and purified by silica gel chromatography (90–100% ethyl acetate/hexanes eluent) to give 45 mg (20%) of the title compound as an amorphous foam. FDMS: m/e=346.

EXAMPLE 252

(+)-(4aR)-(10bR)-4-methyl-8-(2-benzothiazolyl)-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo[f]quinolin-3-one-8-boronic acid (178 mg, 0.65 mmol), tetrakis (triphenylphosphine)palladium(0) (23 mg, 0.02 mmol), 2-chlorobenzothiazole (110 mg, 0.65 mmol), 0.65 mL of aqueous 2M sodium carbonate solution and 2 mL of THF, fitted with a reflux condenser, and the stirred mixture was heated at 80°, under nitrogen, for 18 h. The mixture was cooled, diluted with chloroform (75 mL) and washed with brine (2×25 mL). The combined organic extracts were dried over sodium sulfate, concentrated, and purified by silica gel chromatography (ethyl acetate eluent) to give 107 mg (45%) of the title compound as an amorphous solid. mp 207°–212°. FDMS: m/e=362. α[D]$_{589}$=+88.83 (c=0.60, chloroform).

| Analysis | Calculated | Found |
|---|---|---|
| C | 72.90 | 72.03 |
| H | 6.12 | 6.06 |
| N | 7.73 | 7.20 |

EXAMPLE 253

(+)-(4aR)-(10bR)-4-methyl-8-(2-pyrazinyl)-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo[f]quinolin-3-one-8-boronic acid (178 mg, 0.65 mmol), tetrakis (triphenylphosphine)palladium(0) (23 mg, 0.02 mmol), 2-chloropyrazine (74 mg, 0.65 mmol), 0.65 mL of 2M sodium carbonate solution and 2 mL of THF, fitted with a reflux condenser, and the stirred mixture was heated at 80°, under nitrogen, for 18 h. The mixture was cooled, diluted with chloroform (75 mL) and washed with brine (2×25 mL). The combined organic extracts were dried over sodium sulfate, concentrated, and purified by silica gel chromatography (ethyl acetate eluent) to give 132 mg (66%) of the title compound as an amorphous foam. FDMS: m/e=308. $\alpha[D]_{589}$=+89.71 (c=0.34, chloroform).

| Analysis | Calculated | Found |
|---|---|---|
| C | 74.24 | 73.97 |
| H | 6.89 | 6.55 |
| N | 13.67 | 13.50 |

EXAMPLE 254

(+)-(4aR)-(10bR)-4-methyl-8-(2-pyrimidinyl)-10b-methyl 1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo[f]quinolin-3-one-8-boronic acid (187 mg, 0.65 mmol), tetrakis (triphenylphosphine)palladium(0) (23 mg, 0.02 mmol), 2-chloropyrimidine(74 mg, 0.65 mmol), 0.65 mL of 2M sodium carbonate solution and 2 mL of THF, fitted with a reflux condenser, and the stirred mixture was heated at 80°, under nitrogen, for 15 h. An additional 23 mg of the palladium reagent was added, and let stir an additional 16 h. The mixture was cooled, diluted with chloroform (75 mL) and washed with brine (2×25 mL). The combined organic extracts were dried over sodium sulfate, concentrated, and purified by silica gel chromatography ethyl acetate eluent) to give 102 mg (51%) of the title compound as an amorphous foam. mp 160°–162°. FDMS: m/e=307. $\alpha[D]_{589}$=+95.71 (c=0.28, chloroform).

| Analysis | Calculated | Found |
|---|---|---|
| C | 74.24 | 73.29 |
| H | 6.89 | 6.88 |
| N | 13.67 | 13.52 |

EXAMPLE 255

(+)-(4aR)-(10bR)-4-methyl-8-(2-quinoxalinyl)-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo[f]quinolin-3-one-8-boronic acid (187 mg, 0.65 mmol), tetrakis (triphenylphosphine)palladium(0) (23 mg, 0.02 mmol), 2-chloroquinoxaline (107 mg, 0.65 mmol), 0.65 mL of 2M sodium carbonate solution and 2 mL of THF, fitted with a reflux condenser, and the stirred mixture was heated at 80°, under nitrogen, for 16 h. Added an additional 23 mg of the palladium reagent, and let stir an additional 16 h. The mixture was cooled, diluted with chloroform (75 mL) and washed with brine (2×25 mL). The combined organic extracts were dried over sodium sulfate, concentrated, and purified by silica gel chromatography (ethyl acetate eluent) to give 156 mg (67%) of the title compound as a foam. mp 129°–135°. FDMS: m/e=357. $\alpha[D]_{589}$=+72.94 (c=0.63, chloroform).

EXAMPLE 256

(+)-(4aR)-(10bR)-4-methyl-8-(2-benzimidazolyl)-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,-5,6,10b-octahydrobenzo[f]quinolin-3-one-8-boronic acid (187 mg, 0.65 mmol), tetrakis (triphenylphosphine)palladium(0) (23 mg, 0.02 mmol), 2-chlorobenzimidazole (104 mg, 0.68 mmol), 0.65 mL of 2M sodium carbonate solution and 2 mL of THF, fitted with a reflux condenser, and the stirred mixture was heated at 80°, under nitrogen, for 24 h. An additional 23 mg of the palladium reagent was added, and let stir an additional 16 h. The mixture was cooled, diluted with chloroform (75 mL) and washed with brine (2×25 mL). The combined organic extracts were dried over sodium sulfate, concentrated, and purified by silica gel chromatography (0–5% methanol/ethyl acetate eluent gradient) to give 57 mg (25%) of the title compound as an amorphous foam. mp 183°–186°. FDMS: m/e=345.

| Analysis | Calculated | Found |
|---|---|---|
| C | 76.49 | 75.99 |
| H | 6.71 | 6.35 |
| N | 12.16 | 11.69 |

EXAMPLE 257

(+)-(4aR)-(10bR)-4-methyl-8-(3-indazolyl)-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo[f]quinolin-3-one-8-boronic acid (178 mg, 0.65 mmol), tetrakis (triphenylphosphine)palladium(0) (23 mg, 0.02 mmol), N-(tBOC)-3-chloroindazole (172 mg, 0.68 mmol), 0.65 mL of sodium carbonate and 2 mL of THF, fitted with a reflux condenser, and the stirred mixture was heated at 80°, under nitrogen, for 18 h. An additional portion of palladium reagent (0.04 mmol) was added and continued heating for an additional 24 h. The mixture was cooled, diluted with chloroform (75 mL), and washed with brine (2×25 mL). The combined organic extracts were dried over sodium sulfate, concentrated, and purified by silica gel chromatography (80–100% ethyl acetate/hexanes gradient eluent) to give 49 mg (11%) of the title compound as an amorphous foam. FDMS: m/e=345.

EXAMPLE 258

(+)-(4aR)-(10bR)-4-methyl-8-(2-[3-phenyl]tetrazolyl)-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo[f]quinolin-3-one-8-boronic acid (178 mg, 0.65 mmol), tetrakis(triphenylphosphine)palladium(0) (23 mg, 0.02 mmol), 2-chloro-3-phenyltetrazole (129 mg, 0.72 mmol), 0.65 mL of 2M sodium carbonate solution and 2 mL of THF, fitted with a reflux condenser, and the stirred mixture was heated at 80°, under nitrogen, for 18 h. The mixture was cooled, diluted with ethyl acetate (75 mL) and washed with brine (2×25 mL). The combined organic extracts were dried over sodium sulfate, concentrated, and purified by silica gel chromatography (ethyl acetate eluent) to give 69 mg (28%) of the title compound as an amorphous foam. mp 85°–90°. FDMS: m/e=373. α[D]$_{589}$=+84.79 (c=0.65, chloroform).

| Analysis | Calculated | Found |
|---|---|---|
| C | 70.76 | 70.61 |
| H | 6.21 | 5.97 |
| N | 18.75 | 18.63 |

EXAMPLE 259

(+)-(4aR)-(10bR)-4-methyl-8-(2-[5-trifluoromethyl]pyridinyl)-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,-5,6,10b-octahydrobenzo[f]quinolin-3-one-8-boronic acid (178 mg, 0.65 mmol), tetrakis (triphenylphosphine)palladium(0) (23 mg, 0.02 mmol), 2-chloro-5-trifluoromethylpyridine (131 mg, 0.72 mmol), 0.65 mL of 2M sodium carbonate and 2 mL of THF, fitted with a reflux condenser, and the stirred mixture was heated at 80°, under nitrogen, for 24 h. The mixture was cooled, diluted with ethyl acetate (75 mL) and washed with brine (2×25 mL). The combined organic extracts were dried over sodium sulfate, concentrated, and purified by silica gel chromatography (ethyl acetate eluent) to give 141 mg (58%) of the title compound as an amorphous foam. mp 65°–68°. FDMS: m/e=374. α[D]$_{589}$=+81.90 (c=0.84, chloroform).

| Analysis | Calculated | Found |
|---|---|---|
| C | 67.37 | 67.12 |
| H | 5.65 | 5.68 |
| N | 7.48 | 7.23 |

EXAMPLE 260

(+)-(4aR)-10bR)-4-methyl-8-(2-naphtho<1,2-d>thiazolyl)-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo[f]quinolin-3-one-8-boronic acid (178 mg, 0.65 mmol), tetrakis (triphenylphosphine)palladium(0) (23 mg, 0.02 mmol), 2-chloronaphtho<1,2-d>thiazole (158 mg, 0.72 mmol), 0.65 mL of 2M sodium carbonate solution and 2 mL of THF, fitted with a reflux condenser, and the stirred mixture was heated at 80°, under nitrogen, for 24 h. Added an additional 23 mg of the palladium reagent and 50 mg of the chloride, and let stir an additional 24 h. The mixture was cooled, diluted with chloroform (75 mL) and washed with brine (2×25 mL). The combined organic extracts were dried over sodium sulfate, concentrated, and purified by silica gel chromatography (ethyl acetate eluent) to give 192 mg (72%) of the title compound as an amorphous solid. mp 105°–107°. FDMS: m/e=412. α[D]$_{589}$=+86.44 (c=0.70, chloroform).

| Analysis | Calculated | Found |
|---|---|---|
| C | 75.70 | 75.46 |
| H | 5.86 | 5.58 |
| N | 6.79 | 6.55 |

EXAMPLE 261

(+)-(4aR)-(10bR)-4-methyl-8-(2-[4-fluoro]benzothiazolyl)-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo[f]quinolin-3-one-8-boronic acid (178 mg, 0.65 mmol), tetrakis (triphenylphosphine)palladium(0) (46 mg, 0.04 mmol), 2-chloro-4-fluorobenzothiazole (154 mg, 0.82 mmol), 0.65 mL of 2M sodium carbonate solution and 2 mL of THF, fitted with a reflux condenser, and the stirred mixture was heated at 80°, under nitrogen, for 48 h. The mixture was cooled, diluted with chloroform (75 mL) and washed with brine (2×25 mL). The combined organic extracts were dried over sodium sulfate, concentrated, and purified by silica gel chromatography (ethyl acetate eluent) to give 181 mg (73%) of the title compound as an amorphous foam. mp 170°–190°. FDMS: m/e=380. α[D]$_{589}$=+92.40 (c=0.50, chloroform).

| Analysis | Calculated | Found |
|---|---|---|
| C | 69.45 | 69.68 |
| H | 5.56 | 5.80 |
| N | 7.36 | 7.07 |

EXAMPLE 262

(+)-(4aR)-(10bR)-4-methyl-8-(2-[4-chloro]benzothiazolyl)-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo[f]quinolin-3-one-8-boronic acid (178 mg, 0.65 mmol), tetrakis (triphenyphosphine)palladium(0) (46 mg, 0.04 mmol), 2,4-dichlorobenzothiazole (265 mg, 1.30 mmol), 0.65 mL of aqueous 2M sodium carbonate solution and 2 mL of THF, fitted with a reflux condenser, and the stirred mixture was heated at 80°, under nitrogen, for 48 h. The mixture was cooled, diluted with chloroform (75 mL) and washed with brine (2×25 mL). The combined organic extracts were dried over sodium sulfate, concentrated, and purified by silica gel chromatography (ethyl acetate eluent) to give 177 mg (69%) of the title compound as an amorphous solid. mp 206°–209°. m/e=396. α[D]$_{589}$=+91.10 (c=0.81, chloroform).

| Analysis | Calculated | Found |
|---|---|---|
| C | 66.57 | 66.77 |
| H | 5.33 | 5.48 |
| N | 7.06 | 6.97 |

EXAMPLE 263

(+)-(4aR)-(10bR)-4-methyl-8-(2-[5,6-dichloro]benzothiazolyl)-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo[f]quinolin-3-one-8-boronic acid (178 mg, 0.65 mmol), tetrakis (triphenylphosphine)palladium(0) (69 mg, 0.06 mmol), 2,5,6-trichlorobenzothiazole (110 mg, 1.13 mmol), 0.65 mL of 2M sodium carbonate solution and 2 mL of THF, fitted with a reflux condenser, and the stirred mixture was heated at 80°, under nitrogen, for 72 h. The mixture was cooled, diluted with chloroform (75 mL) and washed with brine (2×25 mL). The combined organic extracts were dried over sodium sulfate, concentrated, and purified by silica gel chromatography (ethyl acetate eluent) to give 113 mg (40%) of the title compound as an amorphous foam. FDMS: m/e=431. $\alpha[D]_{589}$=+79.41 (c=0.79, chloroform).

| Analysis | Calculated | Found |
|---|---|---|
| C | 61.26 | 60.99 |
| H | 4.67 | 4.82 |
| N | 6.49 | 6.31 |

EXAMPLE 264

(+)-(4aR)-(10bR)-4-methyl-8-(2-[4-isopropyl]benzothiazolyl)-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,-5,6,10b-octahydrobenzo[f]quinolin-3-one-8-boronic acid (110 mg, 0.39 mmol), tetrakis (triphenylphosphine)palladium(0) (23 mg, 0.04 mmol), 2-chloro-4-isopropylbenzothiazole (110 mg, 0.39 mmol), 0.65 mL of 2M sodium carbonate solution and 2 mL of THF, fitted with a reflux condenser, and the stirred mixture was heated at 80°, under nitrogen, for 48 h. The mixture was cooled, diluted with chloroform (75 mL) and washed with brine (2×25 mL). The combined organic extracts were dried over sodium sulfate, concentrated, and purified by silica gel chromatography (ethyl acetate eluent) to give 94 mg (36%) of the title compound as an amorphous solid. mp 170°–180°. FDMS: m/e=404.

EXAMPLE 265

(+)-(4aR)-(10bR)-4-methyl-8-(2-[6-chloro]benzothiazolyl)-10b-methyl-1,2,3,4,4a,5,6,10b-octahydrobenzo[f]quinolin-3-one A 15 mL round bottom flask was charged with (+)-(4aR)-(10bR)-4-methyl-10b-methyl-1,2,3,4,4a,5,6,10b-octahydrobenzo[f]quinolin-3-one-8-boronic acid (178 mg, 0.65 mmol), tetrakis (triphenylphosphine)palladium(0) (23 mg, 0.02 mmol), 2,6-dichloro benzothiazole (110 mg, 0.65 mmol), 0.65 mL of 2M sodium carbonate solution and 2 mL of THF, fitted with a reflux condenser, and the stirred mixture was heated at 80°, under nitrogen, for 18 h. The mixture was cooled, diluted with chloroform (75 mL) and washed with brine (2×25 mL). The combined organic extracts were dried over sodium sulfate, concentrated, and purified by silica gel chromatography (80–100% ethyl acetate/hexanes eluent gradient) to give 100 mg (39%) of the title compound as a white solid. mp 123°–125°. FDMS: m/e=396. $\alpha[D]_{589}$=+73.63 (c=1.26, methanol).

| Analysis | Calculated | Found |
|---|---|---|
| C | 66.57 | 66.32 |
| H | 5.33 | 5.52 |
| N | 7.06 | 7.01 |

The following preparation and example illustrate the synthesis of compounds of the present invention wherein the X group is an oxygen atom.

Preparation 10

(+)-(4aR)-(10bR)-4-methyl-8-hydroxy-10b-methyl-1,2,3,4,4a,5,6,10b-octahydrobenzo[f]quinolin-3-one To a suspension of (+)-(4aR)-(10bR)-4-methyl-10b-methyl-1,2,3,4,4a,5,6,10b-octahydrobenzo[f]-quinolin-3-one-8-boronic acid (1.0 g, 3.7 mmol) in 30 mL of THF was added 3N sodium hydroxide (6 mL) followed by 6.0 mL of 30% hydrogen peroxide at −30°. The cold bath was removed, and the mixture was stirred at room temperature for 2.5 h. Six mL of saturated aqueous sodium sulfite solution was added, followed by 5N hydrochloric acid until solution was acidic. Volatiles were removed via rotary evaporation, and the crude solid was heated in ethyl acetate and filtered to give 441 mg (53%) of the title compound as an amorphous solid. FDMS m/e=245.

EXAMPLE 266

(+)-(4aR)-(10bR)-4-methyl-8-(2-quinolinyloxy)-10b-methyl-1,2,3,4,4a,5,6,10b-octahydrobenzo[f]quinolin-3-one A 50 mL round bottom flask was charged with (+)-(4aR)-(10bR)-4-methyl-8-hydroxy-10b-methyl-1,2,3,4,4a,-5,6,10b-octahydrobenzo[f]quinolin-3-one (300 mg, 1.22 mmol), tetrabutylammonium chloride (339 mg, 1.22 mmol), 2-chloroquinoline (200 mg, 1.22 mmol), 4 mL of 50% sodium hydroxide solution, and 4 mL of toluene, fitted with a reflux condenser, and the stirred mixture was heated at 100°, under nitrogen, for 24 h. The mixture was cooled, diluted with water (50 mL) and extracted with chloroform (3×100 mL). The combined organic extracts were dried over sodium sulfate, concentrated, and purified by silica gel chromatography (60% ethyl acetate/hexanes eluent; followed by an additional chromatography on a short silica column, eluting with 10% ethyl acetate/dichloromethane) to give 52 mg (11%) of the title compound as a white solid. mp 172°–174°. FDMS: m/e=372. $\alpha[D]_{589}$=+67.74 (c=0.43, chloroform).

| Analysis | Calculated | Found |
|---|---|---|
| C | 77.39 | 77.32 |
| H | 6.49 | 6.70 |
| N | 7.52 | 7.25 |

The following preparation and examples illustrate syntheses of compounds of the invention wherein the group X incorporates an amino group, and the synthesis uses a starting material having an amino substituent on the benzoquinolinone nucleus.

Preparation 11

(4aR)-(10bR)-8-formamido-4,10b-dimethyl-1,2,3,4,4a,5,6,10b-octahydrobenzo[f]quinoline-3-one In a sealable, heavy-walled pyrex tube equipped with teflon stirring bar was placed (4aR)-(10bR)-8-bromo-4,10b-dimethyl-1,2,3,4,4a,5,6,10b-octahydrobenzo[f]quinoline-3-one (500 mg, 1.6 mmol), copper(I) iodide (340 mg, 1.8 mmol), powdered potassium carbonate (500 mg, 3.6 mmol) and formamide (40 mL). The mixture was purged with nitrogen for 10 minutes and the tube sealed. The mixture was heated to 125° for 18 h. After cooling to ambient temperature, the tube was opened and the contents partitioned between water (250 mL) and ethyl acetate (250 mL). The aqueous phase was extracted with ethyl acetate (2×100 mL) and the combined organic phase was dried over anhydrous magnesium sulfate and concentrated to afford crude 8-formamido intermediate product (220 mg) which was utilized without further purification. m/e 272.

The crude intermediate product was dissolved in ethyl acetate (50 mL), 5N hydrochloric acid solution (10 mL) was added and the solution stirred at ambient temperature for 2.5 h. The mixture was made basic with aqueous ammonium hydroxide solution and extracted with ethyl acetate (2×50 mL). The combined organic phase was dried over anhydrous magnesium sulfate and concentrated to afford crude product (90 mg) which was utilized without further purification. m/e 244.

EXAMPLE 267

(+)-(4aR)-(10bR)-4,10b-dimethyl-8-benzoylamino-1,2,3,4,4a,-5,6,10b-octahydrobenzo[f]quinolin-3-one A 200 mg portion of (4aR)-(10bR)-4,10b-dimethyl-8-amino-1,2,3,4,4a,5,6,10b-octahydrobenzo[f]quinolin-3-one was dissolved in 50 mL of THF and a slight excess of benzoyl chloride was added. The mixture was stirred at ambient temperature for 3 h, and volatiles were then removed under vacuum. The resulting oil was triturated with diethyl ether, and the resulting solids were purified by chromatography on silica gel, eluting with 50% methanol/ethyl acetate. A yield of 104 mg of solid product was obtained from the column and found to be the desired product, m.p. 220°–222°. FDMS: m/e=348. $\alpha[D]_{589}$=+75.53°

| Analysis | Calculated | Found |
|---|---|---|
| C | 75.83 | 75.62 |
| H | 6.24 | 6.97 |
| N | 8.04 | 7.98 |

EXAMPLE 268

(+)-(4aR)-(10bR)-4,10b-dimethyl-8-(3-nitrobenzoylamino)-amino)-1,2,3,4,4a,5,6,10b-octahydrobenzo[f]quinolin-3-one A 620 mg portion of (4aR)-(10bR)-4,10b-dimethyl-8-amino-1,2,3,4,4a,5,6,10b-octahydrobenzo[f]quinolin-3-one was dissolved in 100 ml of THF, and an equivalent amount of 3-nitrobenzoyl chloride (500 mg) was added. The reaction mixture was stirred for 4 h, and was then evaporated to dryness under vacuum. The residue was purified by chromatography on silica gel, eluting with 10% methanol in ethyl acetate, and the product-containing fractions were evaporated and the resulting solid was crystallized from dichloromethane/hexane to obtain 595 mg of the desired product, m.p. 240°–242°. FDMS: m/e=393. $\alpha[D]_{589}$=+75.79°.

| Analysis | Calculated | Found |
|---|---|---|
| C | 67.16 | 66.92 |
| H | 5.89 | 5.86 |
| N | 10.68 | 10.45 |

EXAMPLE 269

(4aR)-(10bR)-4,10b-dimethyl-8-(4-nitrobenzoylamino)-1,2,3,4,4a,5,6,10b-octahydrobenzo[f]quinolin-3-one The same procedure used in Example 268 was repeated, starting with 4-nitrobenzoyl chloride, to obtain 38.2 mg of the desired product, m.p. 269°–270°. FDMS: m/e=393.

| Analysis | Calculated | Found |
|---|---|---|
| C | 67.16 | 66.88 |
| H | 5.89 | 5.82 |
| N | 10.68 | 10.59 |

EXAMPLE 270

(4aR)-(10bR)-4,10b-dimethyl-8-(3-aminobenzoylamino)-1,2,3,4,4a,5,6,10b-octahydrobenzo[f]quinolin-3-one A 200 mg portion of the product of Example 268 was dissolved in ethyl acetate and methanol. Twenty ml of 20% aqueous titanium trichloride was added, the flask was evacuated and the mixture was stirred at ambient temperature for 16 h. The mixture was then made basic with ammonium hydroxide, resulting in an exotherm and the formation of a dark solid. Water was added to break up the solid, and the mixture was extracted with dichloromethane. The remaining reaction mixture was filtered, and the solid filter cake was washed with dichloromethane. The organic layers were collected, dried and concentrated under vacuum. The residue was recrystallized from dichloromethane/hexane to obtain 190 mg of the desired product. It was purified by chromatography over silica gel, eluting with ethyl acetate going to 10% methanol/ethyl acetate, and recrystallized again from dichloromethane/hexane to obtain 80.5 mg of purified product, m.p. 154°–156°. FDMS: m/e=363.

| Analysis | Calculated | Found |
|---|---|---|
| C | 72.70 | 73.00 |
| H | 6.93 | 7.03 |
| N | 11.56 | 11.61 |

EXAMPLE 271

(4aR)-(10bR)-4,10b-dimethyl-8-(4-aminobenzoylamino)-1,2,3,4,4a,5,6,10b-octahydrobenzo[f]quinolin-3-one A 420 mg portion of the product of Example 269 was reduced as described in Example 270 above to obtain 30.6 mg of the desired product. FDMS: m/e=363.

| Analysis | Calculated | Found |
|---|---|---|
| C | 66.07 | 65.84 |
| H | 6.55 | 6.72 |
| N | 10.51 | 10.46 |

EXAMPLE 272

(+)-(4aR)-(10bR)-4-methyl-8-(3-diphenylmethylaminophenyl)-10b-methyl-1,2,3,4,4a,5,6,10b-octahydrobenzo[f]quinolin-3-one To a solution of (+)-(4aR)-(10bR)-4-methyl-8-(3-aminophenyl)-10b-methyl-1,2,3,4,4a,5,6,10b-octahydrobenzo[f]quinolin-3-one (22 mg, 0.07 mmol), in 0.25 mL of dichloromethane was added benzophenone imine (1 eq), followed by 1 drop of 1N hydrochloric acid. The mixture was stirred at room temperature for 1 h, concentrated, and 0.5 mL of methanol and sodium cyanoborohydride (0.14 mmol) followed by two drops of glacial acetic acid was added, and the mixture was stirred for 16 h, diluted with ethyl acetate, rinsed with saturated sodium bicarbonate solution, and brine. The organic layer was dried over sodium sulfate, concentrated and chromatographed on silica gel (ethyl acetate eluent) to give, after trituration of the resulting oil from ether/hexanes, 28 mg (83%) of the title compound as a white solid. mp 109°–111°. FDMS: m/e= 486. α[D]₅₈₉=+46.90 (c=0.49, methanol).

| Analysis | Calculated | Found |
|---|---|---|
| C | 83.91 | 83.62 |
| H | 7.04 | 7.14 |
| N | 5.76 | 5.51 |

EXAMPLE 273

(+)-(4aR)-(10bR)-4-methyl-8-(3-[benzoylamino]phenyl)-10b-methyl-1,2,3,4,4a,5,6,10b-octahydrobenzo[f]quinolin-3-one A 15 mL round bottom flask was charged with (+)-(4aR)-(10bR)-4-methyl-8-(3-aminophenyl)-10b-methyl-1,2,3,4,4a,-5,6,10b-octahydrobenzo[f]quinolin-3-one (50 mg, 0.16 mmol), N,N-dimethylaminopyridine (3 mg, 0.024 mmol), benzoic acid (21 mg, 0.18 mmol), and 0.4 mL of dichloromethane. 1-(3-dimethylaminopropyl)-3-ethyl carbodiimide (EDCI) hydrochloride (120 mg, 0.64 mmol) was added in one portion, and the mixture was stirred at room temperature for 10 min. The mixture was diluted with dichloromethane, and the organic phase was washed with water followed by brine. The organic phase was dried over sodium sulfate, concentrated, and chromatographed on silica gel (0–50% methanol/ethyl acetate eluent gradient) to give 50 mg (76%) of the title compound as an amorphous foam. mp 257°–262° (decomp.) FDMS m/e=424. α[D]₅₈₉=+62.50 (c=0.61, chloroform).

| Analysis | Calculated | Found |
|---|---|---|
| C | 79.22 | 79.62 |
| H | 6.65 | 6.50 |
| N | 6.60 | 6.70 |

EXAMPLE 274

(+)-(4aR)-(10bR)-4-methyl-8-(3-[pivaloylamino]phenyl)-10methyl-1,2,3,4,4a,5,6,10b-octahydrobenzo[f]quinolin-3-one A 15 mL round bottom flask was charged with (+)-(4aR)-(10bR)-4-methyl-8-(3-aminophenyl)-10b-methyl 1,2,3,4,4a,-5,6,10b octahydrobenzo[f]quinolin-3-one (31 mg, 0.097 mmol), N,N-dimethylaminopyridine (3 mg, 0.024 mmol), 1 mL of pyridine and 0.5 mL of dichloromethane. The solution was cooled to 0°, and excess pivaloyl chloride (0.086 mL, 0.69 mmol) was added. The stirred mixture was allowed to warm to room temperature over 2 h. The mixture was diluted with chloroform, and washed with 5% aqueous hydrochloric acid solution, water, 5% aqueous sodium hydroxide solution, water, and the combined organic extracts were dried over sodium sulfate, concentrated and chromatographed on silica gel (ethyl acetate eluent) to give 25 mg (64%) of the title compound as a yellow solid. mp 95°–98°. FDMS m/e=404. α[D]₅₈₉=+62.50 (c=0.16, chloroform).

The following group of examples demonstrates typical synthesis of compounds having X groups which are alkyl, alkenyl, and alkynyl.

EXAMPLE 275

(+)-(4aR)-(10bR)-4-methyl-8-(3-phenylpropyl )-10b-methyl-1,2,3,4,4a,5,6,10b-octahydrobenzo[f]quinolin-3-one To a solution of allylbenzene (106 mg, 0.89 mmol) in 0.5 mL of THF was added 9-BBN (0.89 mmol, 1 equiv) in THF, at 0°. Let stir for 1 h, warming to 5°. To the mixture was added (+)-(4aR)-(10bR)-8-bromo-10b-methyl-1,2,3,4,4a,5,6,10b-octahydrobenzo[f]quinolin-3-one (250 mg, 0.812 mmol), triphenyl phosphine (42 mg, 0.16 equiv.), tetrakis (triphenylphosphine) palladium(0) (19 mg, 0.02 equiv.), 1 mL of 3N sodium hydroxide solution and an additional 1 mL of THF. The resulting mixture was heated at 80° for 18 h, cooled, and ethanolamine was added, followed by ethyl acetate. The resulting organic phase was washed with brine, dried over sodium sulfate, concentrated, and purified by silica gel chromatography (50–100% ethyl acetate/hexanes eluent gradient) to give 160 mg (59%) of the title compound as an oil. FDMS m/e=347.

EXAMPLE 276

(+)-(4aR)-(10bR)-4-methyl-8-(2-[2-naphthyl]ethyl)-10b-methyl-1,2,3,4,4a,5,6,10b-octahydrobenzo[f]quinolin-3-one To a solution of 2-vinylnaphthalene (138 mg, 0.89 mmol) in 0.5 mL of THF was added 9-BBN (0.89 mmol, 1 equiv) in THF, at 0°. Let stir for 1 h, warming to 5°. To the mixture was added (+)-(4aR)-(10bR)-4-H-8-bromo-10b-methyl-1,2,3,4,4a,5,6,10b-octahydrobenzo[f]quinolin-3-one (250 mg, 0.812 mmol), triphenyl phosphine, (42 mg, 0.16 equiv.), tetrakis (triphenylphosphine)palladium(0) (19 mg, 0.02 equiv), 1 mL of 3N sodium hydroxide solution and an additional 1 mL of THF. The resulting mixture was heated at 80° for 18 h, cooled, and ethanolamine was added, followed by ethyl acetate. The resulting organic phase was washed with brine, dried over sodium sulfate, concentrated, and purified by silica gel chromatography (50–100% ethyl acetate/hexanes eluent gradient) to give 186 mg (60%) of the title compound as a tan solid. mp 109°–110°. FDMS m/e= 383. α[D]₅₈₉=+46.45 (c=0.66, chloroform).

Preparation 12

(4aR)-(10bR)-4,10b-dimethyl-8-allyl-1,2,3,4,4a,5, 6,10b-octahydrobenzo[f]quinolin-3-one A 9 g portion of (4aR)-(10bR)-4,10b-dimethyl-8-bromo-1,2,3,4,4a,5,6,10b-octahydrobenzo[f]quinolin-3-one was combined with 11.1 g of tri-n-butyl-2-propenylstannane and 1.69 g of tetrakis(triphenylphosphene)palladium in 40 mL of acetonitrile in a sealable tube. Argon was bubbled through the mixture, the cap replaced, and the reaction heated at 90° for 18 h. Upon cooling, the mixture was filtered and the filtrate was concentrated under vacuum. The residue was triturated with diethyl ether to obtain 4.23 g of crystalline product, and a second crop of 1.31 g of product was also obtained. mp 144°–146°. FDMS 255 M+. Calcd for $C_{17}H_{21}N_1O_2$:

| Analysis | Calculated | Found |
|---|---|---|
| C | 79.96 | 79.69 |
| H | 8.29 | 8.22 |
| N | 5.49 | 5.73 |

Preparation 13

(4aR)-(10bR)-4,10b-dimethyl-8-carboxymethyl-1,2,3,4,4a,-5,6,10b-octahydrobenzo[f]quinolin-3-one A 158 mg portion of the product of Preparation 12 was dissolved in 4 mL of acetonitrile, and a solution of 378 mg of sodium periodate in 4 mL of water was added, followed by 18 mg of ruthenium trichloride. The mixture was stirred at ambient temperature for 18 h, and diluted with dichloromethane. The organic layer was removed, and the aqueous layer extracted with dichloromethane. The organic layers were combined, washed with water, dried, filtered and evaporated to a brown foam. The residue was dissolved in dichloromethane and extracted with saturated aqueous sodium bicarbonate to which a few milliliters of 10% aqueous sodium carbonate had been added. The basic aqueous extract was made acid with hydrochloric acid, and extracted with dichloro-methane. The organic layer was then dried and evaporated under vacuum to obtain 51 mg of a solid, which was recrystallized from ethyl acetate/hexane to obtain the desired product in purified form. mp 200°–202°;

| Analysis | Calculated | Found |
|---|---|---|
| C | 71.06 | 71.22 |
| H | 7.37 | 7.36 |
| N | 4.87 | 5.00 |

EXAMPLE 277

(4aR)-(10bR)-4,10b-dimethyl-8-phenylaminocarbonylmethyl-1,2,3,4,4a,5,6,10b-octahydrobenzo[f]quinolin-3-one A 200 mg portion of the product of Preparation 13 was dissolved in 5 mL of dimethylformamide, and 135 mg of 1,1-carbonyldiimidazole was added. The reaction mixture was blanketed with nitrogen, and was stirred at ambient temperature for 4 h, at which time 0.1 mL of aniline was added. The solution was then stirred briefly, and concentrated under vacuum. The residue was dissolved in dichloromethane and washed with 1N hydrochloric acid, 10% sodium sulfate, water and brine. The solution was then dried, filtered and evaporated to obtain 220 mg of crude product. It was purified by chromatography on a silica gel column, eluting with 3% isopropanol in chloroform. The product-containing fractions were combined, evaporated and recrystallized from ethyl acetate to obtain the desired product in pure form. mp 192°–195°. FDMS 362 M+;

| Analysis | Calculated | Found |
|---|---|---|
| C | 76.21 | 75.98 |
| H | 7.23 | 7.03 |
| N | 7.73 | 7.81 |

EXAMPLE 278

(4aR)-(10bR)-4,10b-dimethyl-8-(2-thiophenyl)-1,2,3,4,4a,-5,6,10b-octahydrobenzo[f]quinolin-3-one Five hundred mg of (4aR)-(10bR)-4,10b-dimethyl-8-bromo-1,2,3,4,4a,5,6,10b-octahydrobenzo[f]quinolin-3-one was combined with 730 mg of 2-(tri-n-butylstannyl)thiophene and 100 mg of bis(triphenylphosphene)palladium chloride in 6 mL of acetonitrile in a screw capped sealable tube. The mixture was flushed with argon for 5 minutes, capped and heated at 90° for 20 h. Upon cooling, the mixture was filtered and the filtrate was concentrated in vacuum. The residue was purified by chromatography on a silica gel column, eluting with ethyl acetate, and the isolated product was recrystallized from ethyl acetate/hexane/chloroform to obtain 167 mg of the desired product. mp 193°–195°. FDMS 311.

| Analysis | Calculated | Found |
|---|---|---|
| C | 73.27 | 73.32 |
| H | 6.80 | 6.94 |
| N | 4.50 | 4.55 |

EXAMPLE 279

(4aR)-(10bR)-4,10b-dimethyl-8-(2-phenylethenyl)-1,2,3,4,4a,5,6,10b-octahydrobenzo[f]quinolin-3-one Five hundred mg of (4aR)-(10bR)-4,10b-dimethyl-8-bromo-1,2,3,4,4a,5,6,10b-octahydrobenzo[f]quinolin-3-one, 4 mg of palladium acetate, 20 mg of tri-o-tolylphosphine, 0.34 mL of triethylamine and 5 mL of dimethylformamide were placed in a screw capped sealable tube with a stir bar. The mixture was warmed to 60° and then 200 mg of styrene was added and the vessel was flushed with argon. The vessel was then capped and heated at 120° for 24 h. The reaction mixture was cooled, diluted with ethyl acetate and filtered and the filtrate was concentrated under vacuum. The residue was dissolved in chloroform and washed twice with water. The organic layer was dried, filtered and evaporated under vacuum to obtain 400 mg of residue, which was recrystallized from ethyl acetate to obtain the desired product. m.p. 173°–175°. FDMS m/e=331.

| Analysis | Calculated | Found |
|---|---|---|
| C | 83.34 | 83.12 |
| H | 7.60 | 7.64 |
| N | 4.23 | 4.14 |

EXAMPLE 280

(4aR)-(10bR)-4,10b-dimethyl-8-(2-phenylethyl)-1,2,3,4,4a,5,6,10b-octahydrobenzo[f]quinolin-3-one A 150 mg portion of the product of Example 279 was hydrogenated on a Parr apparatus at 40 p.s.i. in 50 mL of ethanol containing 5 mL of dimethylformamide and 20 mg of 10% palladium/carbon catalyst. When the starting material had been consumed, the mixture was filtered and the filtrate was concentrated under vacuum. The residue was purified by chromatography on silica gel, eluting with 90% ethyl acetate/hexane to obtain a product which was recrystallized from ethyl acetate/hexane to produce the desired product. m.p. 109°–111°.

| Analysis | Calculated | Found |
| --- | --- | --- |
| C | 82.84 | 83.02 |
| H | 8.16 | 8.10 |
| N | 4.20 | 4.06 |

EXAMPLE 281

(4aR)-(10bR)-4,10b-dimethyl-8-(2-[4-isoquinolinyl]ethenyl)-1,2,3,4,4a,5,6,10b-octahydrobenzo[f]quinolin-3-one A 508 mg portion of (4aR)-(10bR)-4,10b-dimethyl-8-bromo-1,2,3,4,4a,6,10b-octahydrobenzo[f]quinolin-3-one, 4 mg of palladium acetate, 20 mg of tri-o-tolylphosphine, 0.34 mL of triethylamine and 5 mL of dimethylformamide were combined in a sealable tube with a stir bar, and the mixture was warmed to 50° under argon. An 0.26 g portion of 4-ethenylisoquinoline was added. Then the vessel was blanketed with argon and sealed and the mixture was heated with stirring at 120° for 20 hours. It was then cooled, and concentrated under vacuum and the residue was purified by chromatography on silica gel, eluting with 5% isopropanol in chloroform. An 0.29 g portion of an oil was obtained, which was recrystallized from ethyl acetate/hexane to obtain the desired product in crystalline form. mp 183°–185°; FDMS 382 M+.

| Analysis | Calculated | Found |
| --- | --- | --- |
| C | 81.64 | 81.43 |
| H | 6.85 | 6.94 |
| N | 7.32 | 7.22 |

EXAMPLE 282

(4aR)-(10bR)-4,10b-dimethyl-8-(2-[3-quinolinyl]ethenyl)-1,2,3,4,4a,5,6,10b-octahydrobenzo[f]quinolin-3-one A 290 mg portion of 3-ethenylquinoline was used in a process otherwise similar to that of Example 281 to obtain the title product. mp 181°–183°. FDMS 382.

| Analysis | Calculated | Found |
| --- | --- | --- |
| C | 81.64 | 81.89 |
| H | 6.85 | 6.71 |
| N | 7.32 | 7.55 |

EXAMPLE 283

(4aR)-(10bR)-4,10b-dimethyl-8-(2-[2-quinolinyl]ethenyl)-1,2,3,4,4a,5,6,10b-ocahydrobenzo[f]quinolin-3-one The process of Example 281 was substantially repeated, using 0.34 g of 2-ethenylquinoline as the starting material to obtain the title product. mp 233°–236°. FDMS 382.

| Analysis | Calculated | Found |
| --- | --- | --- |
| C | 81.64 | 81.42 |
| H | 6.85 | 7.00 |
| N | 7.32 | 7.57 |

EXAMPLE 284

(4aR)-(10bR)-4,10b-dimethyl-8-(2-phenylethynyl)-1,2,3,4,4a,5,6,10b-octahydrobenzo[f]quinolin-3-one A 1 g portion of (4aR)-(10bR)-4,10b-dimethyl-8-bromo-1,2,3,4,4a,5,6,10b-octahydrobenzo[f]quinolin-3-one was reacted with 0.4 mL of phenylacetylene in a process substantially similar to that of Example 281 to obtain the desired title product in pure form. mp 205°–208°. FDMS 329.

| Analysis | Calculated | Found |
| --- | --- | --- |
| C | 83.85 | 84.07 |
| H | 7.04 | 7.05 |
| N | 4.25 | 4.27 |

EXAMPLE 285

(4aR)-(10bR)-4,10b-dimethyl-8-(2-phenylethenyl)-1,2,3,4,4a,5,6,10b-octahydrobenzo[f]quinolin-3-one A 300 mg portion of the product of Example 284 was hydrogenated over palladium/barium sulfate catalyst in 25 mL of pyridine at 15 psi hydrogen pressure at ambient temperature for 1 h. The mixture was then filtered and concentrated under vacuum, and the residue was purified by chromatography on silica gel, eluting with 75% ethyl acetate/hexane. The product thereby obtained was further purified on a Chromatatron, eluting with 5% isopropanol in chloroform to obtain the desired product in the form of a yellow oil. High resolution mass spectroscopy showed the correct molecular ion of 332.201440.

EXAMPLE 286

(4aR)-(10bR)-8-benzoyl-4,10b-dimethyl-1,2,3,4,4a,5,6,10b-octahydrobenzo[f]quinolin-3-one A. To a solution of (4aR)-(10bR)-10b-methyl-8-bromo-1,2,3,4,4a,5,6,10b-octahydrobenzo[f]quinolin-3-one in 25 mL of THF at −78° under an atmosphere of nitrogen was added 330 µL of a 1.4M solution of methyllithium in diethyl ether (0.46 mmol). The reaction mixture turned bright yellow, and after 10 min, 470 µl of a 1.7M solution of t-butyllithium in pentane (0.80 mmol) was added. The reaction mixture was stirred for 10 min before the addition of benzaldehyde (80 µL, 0.79 mmol) as a single aliquot. The reaction was warmed to room temperature and stirred for 30 min before partitioning between diethyl ether and 1N hydrochloric acid. The ether layer was dried over sodium sulfate, filtered and evaporated under reduced pressure to afford 0.1818 g crude product. The material was purified on a Chromatotron (2 mm plate, dry loaded with chloroform, eluted with 5% methanol/chloroform) to give 106 mg of desired product. A portion of this material was triturated with diethyl ether to yield a white solid. mp 116°–118. FDMS: m/e=321. α[D]$_{589}$=100.39

| Analysis | Calculated | Found |
|---|---|---|
| C | 78.47 | 78.45 |
| H | 7.21 | 7.26 |
| N | 4.36 | 4.21 |

B. To a solution of the alcohol prepared as described above (395 mg, 1.2 mmol) in 40 mL of acetone at 0° was added dropwise 1 mL (2.54 mmol) of a 2.54M solution of Jones Reagent. The reaction mixture was stirred at 0° for 15 min. before the addition of 2 mL of isopropanol to quench the excess reagent. The mixture was partitioned between ethyl acetate and brine. The aqueous layer was extracted with chloroform. The combined organic layers were washed with water (100 mL), dried (sodium sulfate), filtered and evaporated under reduced pressure to afford crude product. This material was purified on a chromatotron (2 mm plate, dry loaded with chloroform, eluted with 5% methanol/chloroform) to give 166 mg of desired product (42% yield). This material was methylated using the standard potassium t-butoxide/methyl iodide in t-butanol method to afford 170 mg crude product. This material was purified on a chromatotron (2 mm plate, eluted with ethyl acetate) to give 113 mg of desired white solid (65% yield); mp 173°–175°. FDMS: m/e=334. $\alpha[D]_{589}$=80.39 (c=0.5 in chloroform).

| Analysis | Calculated | Found |
|---|---|---|
| C | 79.25 | 79.49 |
| H | 6.95 | 7.07 |
| N | 4.20 | 4.30 |

EXAMPLE 287

(4aR)-(10bR)-8-benzyl-4,10b-dimethyl-1,2,3,4,4a,5,6,10b-octahydrobenzo[f]quinolin-3-one A solution of the hydroxymethyl compound prepared in part A of the example above, in 80 mL of ethanol with 23.5 mg of 10% Pd/C catalyst, was shaken under an atmosphere of 40 psi of hydrogen for 24 h. Reaction was not complete and an additional 29 mg of 10% Pd/C was added. After an additional 48 h, the mixture was filtered through celite and concentrated under reduced pressure to yield 141 mg of crude product which was methylated using he standard potassium t-butoxide/methyl iodide in t-butanol method co afford 120 mg of desired product. This material was purified on a Chromatotron (2 mm plate, eluted with 1% isopropanol in ethyl acetate) to give 87 mg of white solid. This material was further purified by recrystallization from a 10:1 mixture of hexane:ethyl acetate to afford 30 mg of product. mp 99°–101° C. FDMS: m/e=319 $\alpha[D]_{589}$=77.08

| Analysis | Calculated | Found |
|---|---|---|
| C | 82.72 | 82.68 |
| H | 7.89 | 7.87 |
| N | 4.38 | 4.33 |

EXAMPLE 288

(4aR)-(10bR)-8-(2-chlorobenzoyl)-4,10b-dimethyl-1,2,3,4,4a,-5,6,10b-octahydrobenzo[f]quinolin-3-one To a solution of (4aR)-(10bR)-10b-methyl-8-bromo-1,2,3,4,4a,5,6,10b-octahydrobenzo[f]quinolin-3-one in 50 mL of THF at −78° under an atmosphere of nitrogen was added 2.25 mL of a 1.4M solution of methyllithium in diethyl ether (3.15 mmol). After 10 min, 3.34 mL of a 1.7M solution of t-butyllithium in pentane (5.68 mmol) was added. The reaction mixture was stirred for 10 min before the addition of 2-chlorobenzaldehyde (870 mL, 7.72 mmol) as a single aliquot. The reaction was warmed to room temperature and stirred for 2 h before partitioning between ethyl acetate and 1N hydrochloric acid. The organic layer was dried, filtered and evaporated under reduced pressure to afford 1.7 g of crude product. The material was purified on a Chromatotron (4 mm plane, dry loaded with chloroform, eluted with 5% methanol/chloroform) to give 435.5 mg of desired product (47% yield): mp 105°–115°. FDMS: m/e=355, 357.

| Analysis | Calculated | Found |
|---|---|---|
| C | 70.88 | 70.87 |
| H | 6.23 | 6.25 |
| N | 3.94 | 3.92 |

To a solution of the alcohol prepared as described above (211.7 mg, 0.6 mmol) in 25 mL of acetone at 0° was added dropwise 0.5 mL (1.27 mmol) of a 2.54M solution of Jones Reagent. The reaction mixture was stirred at 0° for 30 min before the addition of 2 mL of isopropanol to quench the excess reagent. The mixture was partitioned between chloroform and brine. The organic layer was dried, filtered and evaporated under reduced pressure to afford crude product. This material was purified on a Chromatotron (2 mm plate, dry loaded with chloroform, eluted with 5% methanol/chloroform to give 81.0 mg of desired product.

This material was methylated using the standard potassium t-butoxide/methyl iodide in t-butanol method to afford 160 mg crude product. This material was purified on a Chromatotron (2 mm plate, eluted with 2% methanol/ethyl acetate) followed by a second Chromatotron run (2 mm plate, eluted with 5% methanol/chloroform) to give 61 mg of white foam after concentration from diethyl ether (65%) yield: mp 65°–70°.

EXAMPLE 289

(4aR)-(10bR)-8-phenylthiomethyl-10b-methyl-1,2,3,4,4a,5,6,10b-octahydrobenzo[f]quinolin-3-one A. To a solution of (4aR)-(10bR)-10b-methyl-8-bromo-1,2,3,4,4a,5,6,10b-octahydrobenzo[f]quinolin-3-one in 60 mL of THF at −78° under an atmosphere of nitrogen was added 2.9 mL of a 1.4M solution of methyllithium in diethyl ether (4.1 mmol). After 20 min, 4.8 mL of a 1.7M solution of t-butyllithium in pentane (8.2 mmol) was added. The reaction mixture was stirred for 45 min before the addition of dimethylformamide (0.63 mL, 8.1 mmol). The reaction was warmed to room temperature before partitioning between ethyl acetate and 1N hydrochloric acid. The organic layer was washed with additional 1N hydrochloric acid, saturated sodium bicarbonate, brine and then dried (sodium sulfate), filtered and evaporated under reduced pressure to afford 665 mg desired product (80% crude yield). This material was taken on without further purification.

B. To a solution of the aldehyde prepared above (665 mg, 2.73 mmol) in 50 mL of absolute ethanol was added 2 equivalents of sodium borohydride (207 mg, 5.4 mmol). The reaction mixture was stirred at room temperature for 18 h before the addition of 50 mL of 1N hydrochloric acid. After stirring for 1.5 h, ethyl acetate was added and the material concentrated to remove ethanol. The residual aqueous layer was extracted with ethyl acetate and the organic layer was washed with brine, dried (sodium sulfate), and concentrated under reduced pressure to afford 436 mg of crude product. This material was purified on a Chromatotron (eluted with 3% methanol/chloroform) to give 310 mg of desired white solid (46% yield): mp 176°–177°. FDMS: m/e=245. α[D]$_{589}$=120.08 (c=0.5 in methanol).

| Analysis | Calculated | Found |
|---|---|---|
| C | 73.44 | 73.73 |
| H | 7.81 | 7.96 |
| N | 5.71 | 5.82 |

C. To a solution of the alcohol prepared as described above (462.3 mg, 1.88 mmol) in 40 mL of anhydrous acetonitrile was added 0.8 mL of neat trimethylsilyl iodide (5.6 mmol). After 30 minutes, the reaction mixture was concentrated and the residue partitioned between ethyl acetate and saturated thiosulfate. The organic layer was washed with brine, dried (sodium sulfate) and concentrated under reduced pressure to yield 664 mg of crude product. This material was purified on a Chromatotron (4 mm plate, eluted with 3% methanol/chloroform) to give 597 mg of desired solid (89% yield): mp 215°–217°. FDMS: m/e=355, 228 (m–1). α[D]$_{589}$=99.12 (c=0.5 in methanol). Material was taken on without further purification.

D. To a solution of the iodide prepared as described above (249.4 mg, 0.70 mmol) in 25 mL of THF was added a solution of 145 μL of phenylmercaptan (1.4 mmol) and 210 82 L of DBU (1.4 mmol) in 5 mL of THF. After stirring at room temperature for 2 days, the reaction mixture was partitioned between 1N hydrochloric acid and ethyl acetate. The organic layer was washed sequentially with 1N hydrochloric acid, 1N sodium hydroxide, and brine before being dried (sodium sulfate) and concentrated under reduced pressure to yield 293 mg of crude product. This material was purified on a Chromatotron (4 mm plate, eluted with 3% methanol/chloroform) followed by recrystallization from ethyl acetate to give 166 mg of desired white solid (70% yield): mp 187°–189°. FDMS: m/e=337. α[D]$_{589}$=82.27 (c=0.5 in methanol).

| Analysis | Calculated | Found |
|---|---|---|
| C | 74.74 | 74.97 |
| H | 6.87 | 7.11 |
| N | 4.15 | 4.29 |

EXAMPLE 290

(4aR)-10bR)-8-(2-benzothiazolyl)thiomethyl-10b-methyl-1,2,3,4,4a,5,6,10b-octahydrobenzo[f]quinolin-3-one To a solution of the iodomethyl compound prepared in Step C of Example 289 in 25 mL of THF was added a solution of 252 mg of 2-mercaptobenzothiazole (1.5 mmol) and 226 mL of diazabicycloundecane (DBU) (1.5 mmol) in 5 ml of THF. After stirring at room temperature for 2 days, the reaction mixture was partitioned between 1N hydrochloric acid and ethyl acetate. The organic layer was washed sequentially with 1N hydrochloric acid, 1N sodium hydroxide, and brine before being dried (sodium sulfate) and concentrated under reduced pressure to yield 382 mg of crude product. This material was purified on a Chromatotron (4 mm plate, eluted with 3% methane/chloroform) followed by recrystallization from ethyl acetate to give 193 mg of desired white solid. mp 201°–202°. FDMS: m/e=394. α[D]$_{589}$=75.70

| Analysis | Calculated | Found |
|---|---|---|
| C | 66.97 | 67.23 |
| H | 5.62 | 5.82 |
| N | 7.10 | 7.22 |

EXAMPLE 291

(+)-(4aR)-(10bR)-8-phenylcarboxamido-10b-methyl-1,2,3,4,4a,-5,6,10b-octahydrobenzo[f]quinoline-3-one In a flame-dried 3-neck round bottom flask equipped with magnetic stirrer and nitrogen inlet was dissolved (4aR)-(10bR)-8-bromo-10b-methyl-1,2,3,4,4a,5,6,10b-octahydrobenzo[f]quinoline-3-one (500 mg, 1.7 mmol), in anhydrous THF (50 mL). The solution was cooled to –78° and treated with ethereal methyllithium (1.3 mL, 1.4M, 1.8 mmol) added dropwise over 2 min. After further stirring for 15 min., a solution of t-butyllithium (2.1 mL, 1.7M in pentane, 3.6 mmol) was added dropwise. Following complete addition, the suspension was treated with phenylisocyanate (418 μL, 3.6 mmol) in a single portion. The mixture was warmed to ambient temperature and acidified with 1N hydrochloric acid solution. The mixture was extracted with ethyl acetate and the organic phase washed with brine and dried over anhydrous magnesium sulfate. Removal of solvent and chromatography of the crude product on silica gel 0.5% aqueous ammonium hydroxide/ethyl acetate as eluent) and crystallization from ethyl acetate afforded product as tan solid. m/e 334, OR (c=1.0, MeOH) @589 nM, +100.1°, @365 nM, +308.4°.

| Analysis | Calculated | Found |
|---|---|---|
| C | 75.42 | 75.22 |
| H | 6.63 | 6.76 |
| N | 8.38 | 8.25 |

EXAMPLE 292

(+)-(4aR)-(10bR)-4-methyl-8-(3-diphenylmethylaminomethylphenyl)-10b-methyl-1,2,3,4,4a,5,6,10b-octahydrobenzo[f]quinolin-3-one To a suspension of (+)-(4aR)-(10bR)-4-methyl-8-3-formylphenyl)-10b-methyl-1,2,3,4,4a,5,6,10b-octahydrobenzo[f]quinolin-3-one (30 mg, 0.09 mmol), in 0.75 mL of methanol was added benzhydryl amine (0.09 mmol), sodium cyanoborohydride (0.09 mmol) and 2 drops of glacial acetic acid (mixture became homogeneous; pH =4). The reaction was stirred at room temperature for 60 h. The mixture was diluted with ethyl acetate, saturated aqueous sodium bicarbonate solution was added, and the resulting mixture was extracted repeatedly with ethyl acetate. The combined organic extracts were dried over sodium sulfate, concentrated, and purified by silica gel chromatography (ethyl acetate eluent), followed by trituration of the resulting oil with ether/hexanes, to give 36 mg (80%) of the title compound as a white solid. mp 55°–57°. FDMS: m/e=500. α[D]$_{589}$=+48.40 (c=0.64, methanol).

| Analysis | Calculated | Found |
|---|---|---|
| C | 83.96 | 83.42 |
| H | 7.25 | 6.92 |
| N | 5.60 | 5.62 |

Biological Testing

Representative compounds of the present invention have been tested in standardized biological test methods in order to determine their activity as inhibitors of Type I 5AR.

Activity of the compounds wherein $R^4$ and $X-R^5$ are absent is shown in U.S. Pat. No. 5,239,075. The activities which are tabulated at columns 65–66 of that patent are against Type I 5AR, although it is not so explicitly stated.

The following test methods are adapted to routine use and may be followed conveniently by the skilled reader.

Methodology of Human Type I Steroid 5α-Reductase Assays

Preparation of Type I 5α-Reductase from Human Scalp:

Scalp punch biopsies from graft recipient sites were obtained, following the proper Informed Consent and Institutional Review Board guidelines, from human hair transplant procedures immediately after surgery and were frozen on dry ice and stored at −80° C. Approximately 60–75 punches from multiple surgical procedure were used to generate an enzyme preparation. The subcutaneous tissue was cut away and discarded. The skin was frozen with liquid nitrogen and pulverized to powder. The powder was homogenized in 30 mL of ice-cold buffer (20 mM Tris-HCl, pH 7.5) using a Brinkmann Polytron (Westbury, N.Y.) with a PTA 10-S probe and a setting of 7. The homogenization procedure consisted of four 15 second pulses. Connective tissue was cleared from the probe with forceps between pulses. The homogenate was then filtered through cheese cloth and the filtrate centrifuged at 100,000× g for one hour in a Beckman L8–60M ultracentrifuge. The pellet was resuspended by homogenization with a Dounce homogenizer using the same buffer solution. An aliquot was taken for protein determination by the Lowry method, Lowry, et al., Protein Measurement with the Folin Phenol Reagent, *J. Biol. Chem.*, 193, 265–75 (1951). Aliquots of the enzyme preparation were stored at −80° until use.

Human 5α-Reductase Homogenate Assay:

This enzyme assay is based on the conversion of [$^3$H]-testosterone to [$^3$H]-5α-dihydrotestosterone (DHT) and other 5α-reduced metabolites. While about 70% of the 5α-reduced metabolites formed in these assays was DHT, androstanedione was formed at about 30%. Essentially no androsterone was detected. In a total volume of 1.0 mL, the Type I assay contained 2.6 µCi [$^3$H]-testosterone (50 nM), 500 µM of reduced nicotine adenine dinucleotide phosphate, 100 mM Tris-HCl pH 7.5, (in Type II assays, 40 mM sodium acetate at pH 5.5 is used instead of Tris-HCl) and test compounds as indicated. Test compounds were added in 20 µL of dimethylsulfoxide (20 µL of dimethylsulfoxide was added to blanks and controls). The reaction was initiated by the addition of 0.5 mg of Type I 5α-reductase. The reaction mixture was incubated at 25° for 180 min, and terminated by the addition of 1 mL ice-cold stopping solution. The stopping solution contained 40 µM each of non-radioactive testosterone, DHT, androstenedione, androstanedione, androsterone, androstan-3β,17β- diol, and androstan-3α, 17β-diol. The samples were prepared for high performance liquid chromatography by solid phase extraction. Disposable solid matrix extraction columns (C-18 reversed phase, 6 mL, 500 mg; Bond Elut™ from Analytichem International; Harbor City, Calif.) were conditioned by washing with 5 mL of methanol followed by 5 mL of deionized water. The reaction mixtures were then applied to the columns. The columns were subsequently washed with 5 mL of acetone:water (1:4), followed by 0.3 mL of methanol. The samples were then eluted with 3 mL of methanol and collected in 20 mL scintillation vials. Three mL of water was then added to each scintillation vial. The solutions were then transferred to tubes and centrifuged for 30 min at 1000× g to remove any particulate material before chromatography. The [$^3$H]-testosterone substrate and its metabolites were separated by chromatography using a C-18 reversed phase column (Beckman Ultrasphere 5 µm spherical 80A pore, part no. 235329, 4.6 mm i.d.×25 mm length) with an isocratic mobile phase (46 water:46 methanol:8 tetrahydrofuran by volume). The column temperature was maintained at 35° and the flow rate was 1.5 mL/min. A 400 µL aliquot was injected onto the column and radioactivity was determined using a Beckman 171 in-line flow radioisotope detector in conjunction with Rainin Dynamax™ software and a Macintosh computer. The flow rate of the Atomflow™ scintillation fluid was 4.5 mL/min.

While in most instances the compounds listed below have been tested at various concentrations, only the test results at 0.3 µM concentration are shown here, in order to reduce the bulk of the following table. The data are reported as percent inhibition of Type I 5AR produced by each compound at that concentration, compared to control reaction mixtures.

TABLE I

| Compound of Example No. | Type I |
|---|---|
| 5 | 44 |
| 6 | 11 |
| 7 | 49 |
| 8 | 22 |
| 9 | 3 |
| 10 | 22 |
| 11 | 87 |
| 12 | 16 |
| 13 | 11 |
| 14 | 37 |
| 15 | 23 |
| 16 | 14 |
| 17 | 29 |
| 18 | 7 |
| 19 | 59 |
| 20 | 22 |
| 21 | 27 |
| 22 | — |
| 23 | 59 |
| 24 | 88 |
| 25 | 83 |
| 26 | 86 |
| 27 | 92 |
| 28 | 65 |
| 29 | 78 |
| 30 | 19 |
| 31 | 84 |
| 32 | 71 |
| 33 | 55 |
| 34 | 13 |
| 35 | 17 |
| 36 | 41 |
| 37 | 72 |
| 38 | 84 |
| 39 | 81 |
| 40 | 90 |
| 41 | 88 |
| 42 | — |

TABLE I-continued

| Compound of Example No. | Type I |
|---|---|
| 43 | 68 |
| 44 | — |
| 45 | 11 |
| 46 | 3 |
| 47 | — |
| 48 | — |
| 49 | 96 |
| 50 | 95, 94 |
| 51 | 91 |
| 52 | 68 |
| 53 | 100, 66 |
| 54 | — |
| 55 | 68 |
| 56 | 92 |
| 57 | — |
| 58 | 65 |
| 59 | — |
| 60 | — |
| 61 | 53 |
| 62 | 45 |
| 63 | — |
| 64 | 81 |
| 65 | 79 |
| 66 | 67 |
| 67 | 22 |
| 68 | 31 |
| 69 | 84 |
| 70 | — |
| 71 | 80 |
| 72 | 16 |
| 73 | 87 |
| 74 | 16 |
| 75 | 63 |
| 76 | 83 |
| 77 | 88 |
| 78 | — |
| 79 | — |
| 80 | 76 |
| 81 | 92 |
| 82 | 85 |
| 83 | — |
| 84 | 88 |
| 85 | — |
| 86 | 66 |
| 87 | 83 |
| 88 | 96 |
| 89 | — |
| 90 | — |
| 91 | 87 |
| 92 | — |
| 93 | — |
| 94 | — |
| 95 | 95 |
| 96 | 89 |
| 97 | — |
| 98 | 76 |
| 99 | 88 |
| 100 | 96 |
| 101 | 75 |
| 102 | 92 |
| 103 | 81 |
| 104 | 89 |
| 105 | 92 |
| 106 | 73 |
| 107 | 80 |
| 108 | 100 |
| 109 | 97 |
| 110 | 97 |
| 111 | 44 |
| 112 | 64 |
| 113 | 70 |
| 114 | 55 |
| 115 | 31 |
| 116 | — |
| 117 | 46 |
| 118 | 25 |

TABLE I-continued

| Compound of Example No. | Type I |
|---|---|
| 119 | 84 |
| 120 | 93 |
| 121 | — |
| 122 | — |
| 123 | 10 |
| 124 | 23 |
| 125 | 64 |
| 126 | 85 |
| 127 | — |
| 128 | 82 |
| 129 | 91 |
| 130 | 83 |
| 131 | 57 |
| 132 | 87 |
| 133 | 77 |
| 134 | 97 |
| 135 | 92 |
| 136 | 100 |
| 137 | 90 |
| 138 | 88 |
| 139 | 30 |
| 140 | — |
| 141 | — |
| 142 | 22 |
| 143 | 63 |
| 144 | 90 |
| 145 | 85 |
| 146 | 13 |
| 147 | 35 |
| 148 | 2 |
| 149 | 58 |
| 150 | 67 |
| 151 | 31 |
| 152 | 47 |
| 153 | 49 |
| 154 | 56 |
| 155 | 58 |
| 156 | 71 |
| 157 | 88 |
| 158 | 78 |
| 159 | 87, 87 |
| 160 | 61 |
| 161 | 71 |
| 162 | 79 |
| 163 | 80 |
| 164 | 85, 87 |
| 165 | 61 |
| 166 | 50 |
| 167 | 62 |
| 168 | 85 |
| 169 | 75 |
| 170 | — |
| 171 | 43 |
| 172 | 55 |
| 173 | 65 |
| 174 | 82 |
| 175 | 58 |
| 176 | 25 |
| 177 | 58 |
| 178 | — |
| 179 | 61 |
| 180 | 59 |
| 181 | 63 |
| 182 | 63 |
| 183 | 89 |
| 184 | 73 |
| 185 | 88 |
| 186 | 90 |
| 187 | 93 |
| 188 | 88 |
| 189 | 84 |
| 190 | 76 |
| 191 | 65 |
| 192 | 80 |
| 193 | — |
| 194 | — |

TABLE I-continued

| Compound of Example No. | Type I |
|---|---|
| 195 | 90 |
| 196 | 11 |
| 197 | — |
| 198 | — |
| 199 | — |
| 200 | 59 |
| 201 | 69 |
| 202 | 41 |
| 203 | 8 |
| 204 | 34 |
| 205 | 100 |
| 206 | 97, 100 |
| 207 | 45 |
| 208 | 77 |
| 209 | 24 |
| 210 | 81 |
| 211 | 70 |
| 212 | 73 |
| 213 | 64 |
| 214 | 26 |
| 215 | 84 |
| 216 | 78 |
| 217 | 93 |
| 218 | 84 |
| 219 | 91 |
| 220 | 67 |
| 221 | 95 |
| 222 | 86 |
| 223 | 36 |
| 224 | 71 |
| 225 | 47 |
| 226 | 16 |
| 227 | 97 |
| 228 | 77 |
| 229 | 97 |
| 230 | 86 |
| 231 | 80 |
| 232 | 94 |
| 233 | 95 |
| 234 | 83 |
| 235 | 28 |
| 236 | 84 |
| 237 | 33 |
| 238 | 72 |
| 239 | 42 |
| 240 | 55 |
| 241 | 65 |
| 242 | 5 |
| 243 | 88 |
| 244 | 51 |
| 245 | 54 |
| 246 | 92 |
| 247 | 60 |
| 248 | 54 |
| 249 | 69 |
| 250 | 83 |
| 251 | 69 |
| 252 | 89 |
| 253 | 5 |
| 254 | 37 |
| 255 | 71 |
| 256 | 38 |
| 257 | 36 |
| 258 | 27 |
| 259 | 31 |
| 260 | 84 |
| 261 | 86 |
| 262 | 91 |
| 263 | 56 |
| 264 | 90 |
| 265 | 78 |
| 266 | 57 |
| 267 | 34 |
| 268 | — |
| 269 | 8 |
| 270 | 18 |

TABLE I-continued

| Compound of Example No. | Type I |
|---|---|
| 271 | — |
| 272 | 86 |
| 273 | — |
| 274 | 34 |
| 275 | 75 |
| 276 | 92 |
| 277 | 42 |
| 278 | — |
| 279 | 85 |
| 280 | 97, 100 |
| 281 | 75 |
| 282 | 75 |
| 283 | 87 |
| 284 | 86 |
| 285 | 93 |
| 286 | 53 |
| 287 | 82 |
| 288 | 19 |
| 289 | 23 |
| 290 | 25 |
| 291 | — |
| 292 | 86 |

The methods of treatment of the present invention are mechanistically founded on the outstanding activity of the compounds of Formula I in inhibiting the conversion of testosterone to $5\alpha$-dihydrotestosterone by Type I $5\alpha$-reductase.

Inhibition of Bone Loss

Fracture rate as a consequence of bone loss is inversely correlated with bone mineral density. However, changes in bone density occur slowly, and are measured meaningfully only over many months or years. It is possible, however, to demonstrate that the formula I compounds with or without the coadministration of a bone antiresorptive or anabolic agent, have positive effects on bone mineral density and bone loss by measuring various quickly responding biochemical parameters that reflect changes in skeletal metabolism. Typically, patients are treated for a period of from 8 weeks to 3 years. Blood and urine are collected before, during and at the conclusion of treatment. Estrogen administration and placebo may serve as the positive and negative controls, respectively.

The patients are either healthy postmenopausal (surgical or natural) women, age 45–65 who would be considered candidates for estrogen replacement therapy for potential bone loss, or patients of the same age group or older who have shown clinical signs of bone loss (e.g., shortened stature).

Patients who have received any of the following medications at the beginning of the study are systematically excluded from the study; vitamin D, corticosteroids, hypolipidemics, thiazides, antigout agents, salicylates, phenothiazines, sulfonates, tetracyclines, neomycin, and antihelmintics. Patients who have received any estrogen, progestin, or androgen treatment more recently than three months prior to the beginning of the study; patents who have ever received calcitonin, fluoride, or bisphosphonate therapy; patients who have diabetes mellitus; patients who have a cancer history anytime within the previous five years; patients with any undiagnosed or abnormal genital bleeding; patients with active, or a history of, thromboembolic disorders; patients who have impaired liver or kidney function; patients who have abnormal thyroid function; patients who are poor medical or psychiatric risks; or patients who consume an excess of alcohol or abuse drugs.

Patients in the estrogen treatment group, when used, receive 0.625 mg/day and the test groups for compounds of formula I receive dosages from 0.1 mg to 50 mg, preferably 1 mg to 20 mg per day, all groups receiving oral capsule formulations. Coadministration of a bone antiresorptive agent or an anabolic agent with the administration of a formula I compound also are tested. Coadministration is either concurrent or sequential.

The study is a double-blind design. The investigators and the patients do not know the treatment group to which the patient is assigned.

A baseline examination of each patient includes quantitative measurement of urinary calcium, creatinine, hydroxyproline, and pyridinoline crosslinks. Blood samples are measured for serum levels of osteocalcin, bone-specific alkaline phosphatase, raloxifene, and raloxifene metabolites. Baseline measurements also include examination of the uterus including uterine biopsy.

During subsequent visits to the investigating physician, measurements of the above parameters in response to treatment are repeated.

Subsequent longer term studies can incorporate the direct measurement of bone density by the use of a photon absorptiometry and the measurement of fracture rates associated with therapy.

In all of the above patients and methods of treatment, the benefit is obtained and the inhibition of bone loss activity through the inhibition of conversion of testosterone to 5α-dihydrotestosterone in bone cells. The mechanism of efficacy is the inhibition in such cells of the activity of Type I 5α-reductase.

The term "an effective amount" is used in the present document to describe the dose of a compound of Formula I, an antiresorptive agent and an anabolic agent, and is defined as the dose which provides effective treatment or prevention to the patient.

Antiresportive agents are those agents which are known in the art to inhibit the resorption of bone and include, for example, estrogen in which estrogens include steroidal compounds having estrogenic activity such as, for example, 17β-estradiol, estrone, conjugated estrogen (Premarin®), equine estrogen, 17β-ethynyl estradiol, and the like. Bisphosphonate compounds such as alendronate sodium [4-amino-1-hydroxybutlidine(diphosphoris acid) monosodium salt, trihydrate, and the like, and antiestrogenic compounds such as raloxifene (see, e.g., U.S. Pat. No. 5,393,763) clomiphene, zuclomiphene, enclomiphene, nafoxidene, CI-680, CI-628, CN-55,945-27, Mer-25, U-11, 555A, U-100A, and salts thereof, and the like (see, e.g., U.S. Pat. Nos. 4,729,999 and 4,894,373).

Bone anabolic agents are those agents which are known in the art to build bone by increasing the production of the bone protein matrix. Such anabolic agents include, for example, the various forms of parathyroid hormone (PTH) such as naturally occurring PTH (1-84), PTH (1-34), analogs thereof, and the like.

The administration of compounds of formula I in order to practice the present methods of therapy is carried out by administering an effective amount of the chosen compound to the patient in need of such treatment or prophylaxis. The need for a prophylactic administration according to the methods of the present invention is determined via the use of well known risk factors. The effective amount of an individual compound is determined, in the final analysis, by the physician in charge of the case, but depends on factors such as the exact disease to be treated, the severity of the disease and other diseases or conditions from which the patient suffers, the chosen route of administration, other drugs and treatments which the patient may concomitantly require, and other factors in the physician's judgment. It will be observed that the compounds are active at very low concentrations, and hence at low dosage levels, thereby allowing effective bone loss inhibition with slight probability of side effects or cross-reactions with other treatments or drugs. Accordingly, a typical daily dose of a compound of formula I is in the range of from about 0.02 mg to about 100 mg per day. More preferred ranges of daily dosage are from about 0.1 mg to about 50 mg, and, more particularly, from about 1 mg to about 20 mg per day. The compounds may be administered in a single daily dose, or the daily dose may be administered in portions at intervals through the day, as is preferred in the judgment of the physician.

Daily dosage ranges for bone antiresorptive and anabolic agents are those which are known in the art. The compounds of the methods of the present invention can be administered by a variety of routes including oral, rectal, transdermal, subcutaneous, intravenous, intramuscular, and intranasal, and such compounds are preferably formulated prior to administration. Therefore, another embodiment of the present invention is a pharmaceutical formulation comprising an effective amount of a compound of Formula I or a pharmaceutically acceptable salt thereof, a bone antiresorptive or anabolic agent, and a pharmaceutically acceptable carrier, diluent or excipient therefor.

The active ingredient in such formulations comprises from 1% to 99% by weight of the formulation. By "pharmaceutically acceptable" it is meant the carrier, diluent ore excipient must be compatible with the other ingredients of the formulation and not deleterious to the recipient thereof.

The present pharmaceutical formulations are prepared by known procedures using well known and readily available ingredients. In making the composition of the present invention, the active ingredient(s) will usually be admixed with a carrier which may be in the form of a capsule, sachet, paper, or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions solutions, syrups, aerosols, (as a solid or in a liquid medium), soft and hard gelatin capsules, suppositories, sterile injectable solutions, sterile packaged powders, and the like.

The following formulation examples are illustrative only and are not intended to limit the scope of the invention in any way. "Active ingredient," of course, means a compound according to Formula I or a pharmaceutically acceptable salt thereof.

Formulation 1

Hard gelatin capsules are prepared using the following ingredients.

|  | Quantity (mg/capsule) |
| --- | --- |
| Example 136 | 20 |
| Starch, dried | 400 |
| Magnesium stearate | 10 |
| Total | 430 mg |

Formulation 2

A tablet is prepared using the ingredients below:

|  | Quantity (mg/capsule) |
|---|---|
| Example 280 | 40 |
| Cellulose, microcrystalline | 600 |
| Silicon dioxide, fumed | 10 |
| Stearate acid | 5 |
| Total | 655 mg |

The components are blended and compressed to form tablets each weighing 665 mg.

Formulation 3

|  |  |
|---|---|
| Compound A | 10 mg |
| Starch | 70 mg |
| Microcrystalline cellulose | 60 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinyl-pyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 4

Capsules, each containing 80 mg of active ingredient, are made as follows:

|  |  |
|---|---|
| (−)-(4aR)-(10bR)-8-chloro-4-methyl-1,2,3,4,5,6,10b-octahydrobenzo[f]-quinolin-3-one | 80 mg |
| Starch | 58 mg |
| Microcrystalline cellulose | 58 mg |
| Magnesium stearate | 4 mg |
| Total | 200 mg |

The active ingredient, cellulose, starch, and magnesium stearate are blended, passed through a No. 45 mesh U.S. sieve, and filled into hard gelatin capsules in 200 mg quantities.

Formation 5

Suppositories, each containing 25 mg of active ingredient per dose, are made as follows:

|  |  |
|---|---|
| (+)-(4aR)-(10bR)-8-chloro-4,10b-dimethyl-1,2,3,4,4a,5,6,10b-octahydrobenzo[f]quinolin-3-one | 25 mg |
| Saturated fatty acid glycerid | 2,000 mg |
| Total | 2,025 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 6

Suspensions, each containing 50 mg of active ingredient per 5 ml dose, are made as follows:

|  |  |
|---|---|
| 8-chloro-4,10b-dimethyl-1,2,3,4,4a,5,6,10b-octahydrobenzo[f]quinolin-3-one | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic ad solution, flavor and color are diluted with a portion of the water and added, with stirring. Sufficient water is then added to produce the required volume.

Formulation 7

An intravenous formulation may be prepared as follows:

|  |  |
|---|---|
| (+)-(4aR)-(10bR)-8,9-dichloro-4,10b-dimethyl-1,2,3,4,4a,5,6,10b-octahydrobenzo[f]quinolin-3-one | 10 mg |
| Isotonic saline | 1,000 ml |

The solution of the above ingredients generally is administered intravenously to a subject at a rate of 1 ml per minute.

Formulation 8

Combination Capsule I

| Ingredient | Quantity (mg/capsule) |
|---|---|
| (−)-(4aR)-(10bR)-8-chloro-4-methyl-1,2,3,4,4a,5,6,10b-octahydrobenzo[f]-quinolin-3-one | 80 |
| Premarin | 1 |
| Avicel pH 101 | 50 |
| Starch 1500 | 117.50 |
| Silicon Oil | 2 |
| Tween 80 | 0.50 |
| Cab-O-Sil | 0.25 |

Formulation 9

Combination Capsule II

| Ingredient | Quantity (mg/capsule) |
|---|---|
| (−)-(4aR)-(10bR)-8-chloro-4-methyl-1,2,3,4,4a,5,6,10b-octahydrobenzo[f]-quinolin-3-one | 80 |
| Raloxifene | 10–250 |
| Avicel pH 101 | 50 |
| Starch 1500 | 117.50 |
| Silicon Oil | 2 |
| Tween 80 | 0.50 |
| Cab-O-Sil | 0.25 |

Formulation 10

Combination Capsule III

| Ingredient | Quantity (mg/capsule) |
|---|---|
| (−)-(4aR)-(10bR)-8-chloro-4-methyl-1,2,3,4,4a,5,6,10b-octahydrobenzo[f]-quinolin-3-one | 80 |
| Alendronate | 0.1–250 |
| Avicel pH 101 | 50 |
| Starch 1500 | 117.50 |
| Silicon Oil | 2 |
| Tween 80 | 0.50 |
| Cab-O-Sil | 0.25 |

Formulation 11

Combination Capsule IV

| Ingredient | Quantity (mg/capsule) |
|---|---|
| (−)-(4aR)-(10bR)-8-chloro-4-methyl-1,2,3,4,4a,5,6,10b-octahydrobenzo[f]-quinolin-3-one | 80 |
| PTH (1-84 or 1-34) | 0.1–1000 |
| Avicel pH 101 | 50 |
| Starch 1500 | 117.50 |
| Silicon Oil | 2 |
| Tween 80 | 0.50 |
| Cab-O-Sil | 0.25 |

We claim:

1. A pharmaceutical composition comprising a compound of formula I

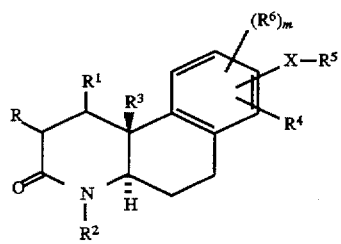

wherein

R and $R^1$ both represent hydrogen or combine to form a bond;

$R^2$ represents hydrogen or $C_1$–$C_3$ alkyl;

$R^3$ represents hydrogen, methyl or ethyl; either $R^4$ and X—$R^5$ have the following definitions, $(R^6)_m$ is absent, and $R^3$ does not represent hydrogen; or $(R^6)_m$ has the following definition, $R^4$ and X—$R^5$ are absent, and $R^3$ does not represent ethyl;

$R^4$ and —X—$R^5$ each occupies one of the 7-, 8- and 9-positions;

$R^4$ represents hydrogen, halo, methyl or ethyl;

X represents $C_1$–$C_4$ alkyl, $C_2$–$C_4$ alkenyl, $C_2$–$C_4$ alkynyl, a bond —SO—, —SO$_2$—, —CO—Y—(CH$_2$)$_n$—, —Y—CO—(CH$_2$)$_n$, —CO—, —Z—(CH$_2$)$_n$—, or —SO$_3$—; wherein X groups which are not symmetrical may be in either orientation;

Y represents —S—, —O—, or —NH—;

Z represents —O— or —S—;

n represents 0–3;

$R^5$ represents phenyl, naphthalenyl, pyridinyl, pyrazinyl, pyridazinyl, pyrimidinyl, anthracenyl, acenaphthalenyl, thiazolyl, benzimidazolyl, indazolyl, thiophenyl, phenanthrenyl, quinolinyl, fluorenyl, isoquinolinyl, indanyl, benzopyranyl, indolyl, benzisoquinolinyl, benzindolyl, benzothiazolyl, benzothiophenyl, quinoxalinyl, benzoxazolyl, tetrazolyl, naphthothiazolyl, quinazolinyl, thiazolopyridinyl, pyridazinoquinazolinyl, benzisothiazolyl, benzodioxolyl, benzodioxinyl, diphenylmethyl or triphenylmethyl;

the above $R^5$ groups are unsubstituted or substituted with 1–3 groups chosen from the group consisting of halo, trifluoromethyl, trifluoroethoxy, $C_1$–$C_4$ alkyl, trifluoromethoxy, hydroxy, $C_1$–$C_3$ alkoxy, nitro, $C_1$–$C_3$ alkylthio, $C_1$–$C_6$ alkanoyl, phenyl, oxo, phenoxy, phenylthio, $C_1$–$C_3$ alkylsulfinyl, $C_1$–$C_3$ alkylsulfonyl, cyano, amino, $C_1$–$C_3$ alkylamino, diphenylmethylamino, triphenylmethylamino, benzyloxy, benzylthio, (mono-halo, nitro or CF$_3$) benzyl(oxy or thio), di($C_1$–$C_3$ alkyl, $C_3$–$C_6$ cycloalkyl, or $C_4$–$C_8$ cycloalkylalkyl)amino, (mono-$C_1$–$C_3$ alkyl, $C_1$–$C_3$ alkoxy or halo)-(phenyl, phenoxy, phenylthio, phenylsulfonyl or phenoxysulfonyl), $C_2$–$C_6$ alkanoylamino, benzoylamino, diphenylmethylamino ($C_1$–$C_3$ alkyl), aminocarbonyl, $C_1$–$C_3$ alkylaminocarbonyl, di($C_1$–$C_3$ alkyl)aminocarbonyl, halo-$C_1$–$C_6$ alkanoyl, aminosulfonyl, $C_1$–$C_3$ alkylaminosulfonyl, di($C_1$–$C_3$ alkyl)aminosulfonyl, phenyl(oxy or thio) ($C_1$–$C_3$ alkyl), (halo, $C_1$–$C_3$ alkyl or $C_1$–$C_3$ alkoxy)phenyl(oxy or thio) ($C_1$–$C_3$ alkyl), benzoyl, or (amino, $C_1$–$C_3$ alkylamino or di($C_1$–$C_3$ alkyl)amino) ($C_1$–$C_3$ alkyl);

or an above $R^5$ group is substituted with a morpholino ($C_1$–$C_3$ alkyl) group, a phenyl($C_1$–$C_3$ alkyl)piperidinyl group, a phenyl($C_1$–$C_3$ alkyl)-piperidinylaminocarbonyl group, a $C_2$–$C_6$ alkanoyl-aminothiophenyl group, or a (amino, $C_1$–$C_3$ alkylamino or di($C_1$–$C_3$ alkyl)amino) naphthalenylsulfonylamino group;

or $R^5$ is a perhalophenyl group;

m represents 1–2;

$R^6$ represents hydrogen, halogen, NO$_2$, cyano, CF$_3$, $C_1$–$C_6$ alkyl, $C_1$–$C_6$ alkoxy, carboxy, $C_1$–$C_6$ alkoxycarbonyl, amino, $C_1$–$C_4$ alkylamino, $C_1$–$C_4$ dialkylamino, amido, $C_1$–$C_4$ alkylamido, $C_1$–$C_4$ dialkylamido, mercapto, $C_1$–$C_6$ alkylthio, $C_1$–$C_6$ alkylsulfinyl, $C_1$–$C_6$ alkylsulfonyl, or a group —A—$R^7$ where A is $C_1$–$C_6$ alkylene $C_2$–$C_6$ alkenylene or $C_2$–$C_6$ alkynylene; and $R^7$ represents halogen, hydroxy, CF$_3$, $C_1$–$C_6$ alkoxy, carboxy, $C_1$–$C_6$ alkoxycarbonyl, amino, $C_1-C_4$ alkylamino, $C_1-C_4$ dialkylamino, amido, $C_1-C_4$ alkylamido, $C_1-C_4$ dialkylamido, $C_1-C_4$ alkylsulfonylamino, aminosulfonyl or $C_1-C_4$ alkylaminosulfonyl;

or a pharmaceutically acceptable salt thereof, and an effective amount of a bone antiresorptive agent, in combination with a pharmaceutically acceptable carrier, diluent, or excipient.

2. A pharmaceutical composition according to claim 1 wherein said bone antiresorptive agent is estrogen, raloxifene, or alendronate.

3. A pharmaceutical composition comprising a compound of formula I

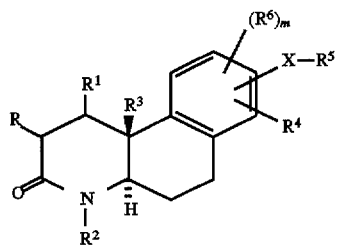

wherein

R and $R^1$ both represent hydrogen or combine to form a bond;

$R^2$ represents hydrogen or $C_1-C_3$ alkyl;

$R^3$ represents hydrogen, methyl or ethyl; either $R^4$ and X—$R^5$ have the following definitions, $(R^6)_m$ is absent, and $R^3$ does not represent hydrogen; or $(R^6)_m$ has the following definition, $R^4$ and X—$R^5$ are absent, and $R^3$ does not represent ethyl;

$R^4$ and —X—$R^5$ each occupies one of the 7-, 8- and 9-positions;

$R^4$ represents hydrogen, halo, methyl or ethyl;

X represents $C_1-C_4$ alkyl, $C_2-C_4$ alkenyl, $C_2-C_4$ alkynyl, a bond, —SO—, —SO$_2$—, —CO—Y—$(CH_2)_n$, —Y—CO—$(CH_2)_n$, —CO—, —Z —$(CH_2)_n$—, or —SO$_3$—; wherein X groups which are not symmetrical may be in either orientation;

Y represents —S—, —O—, or —NH—;

Z represents —O— or —S—;

n represents 0–3;

$R^5$ represents phenyl, naphthalenyl, pyridinyl, pyrazinyl, pyridazinyl, pyrimidinyl, anthracenyl, acenaphthalenyl, thiazolyl, benzimidazolyl, indazolyl, thiophenyl, phenanthrenyl, quinolinyl, fluorenyl, isoquinolinyl, indanyl, benzopyranyl, indolyl, benzisoquinolinyl, benzindolyl, benzothiazolyl, benzothiophenyl, quinoxalinyl, benzoxazolyl, tetrazolyl, naphthothiazolyl, quinazolinyl, thiazolopyridinyl, pyridazinoquinazolinyl, benzisothiazolyl, benzodioxolyl, benzodioxinyl, diphenylmethyl or triphenylmethyl;

the above $R^5$ groups are unsubstituted or substituted with 1–3 groups chosen from the group consisting of halo, trifluoromethyl, trifluoroethoxy, $C_1-C_4$ alkyl, trifluoromethoxy, hydroxy, $C_1-C_3$ alkoxy, nitro, $C_1-C_3$ alkylthio, $C_1-C_6$ alkanoyl, phenyl, oxo, phenoxy, phenylthio, $C_1-C_3$ alkylsulfinyl, $C_1-C_3$ alkylsulfonyl, cyano, amino, $C_1-C_3$ alkylamino, diphenylmethylamino, triphenylmethylamino, benzyloxy, benzylthio, (mono-halo, nitro or $CF_3$) benzyl(oxy or thio), di($C_1-C_3$ alkyl, $C_3-C_6$ cycloalkyl, or $C_4-C_8$ cycloalkylalkyl)amino, (mono-$C_1-C_3$ alkyl, $C_1-C_3$ alkoxy or halo)-(phenyl, phenoxy, phenylthio, phenylsulfonyl or phenoxysulfonyl), $C_2-C_6$ alkanoylamino, benzoylamino, diphenylmethylamino ($C_1-C_3$ alkyl), aminocarbonyl, $C_1-C_3$ alkylaminocarbonyl, di($C_1-C_3$ alkyl)aminocarbonyl, halo-$C_1-C_6$ alkanoyl, aminosulfonyl, $C_1-C_3$ alkylaminosulfonyl, di($C_1-C_3$ alkyl)aminosulfonyl, phenyl(oxy or thio) ($C_1-C_3$ alkyl), (halo, $C_1-C_3$ alkyl or $C_1-C_3$ alkoxy)phenyl(oxy or thio) ($C_1-C_3$ alkyl), benzoyl, or (amino, $C_1-C_3$ alkylamino or di($C_1-C_3$ alkyl)amino) ($C_1-C_3$ alkyl);

or an above $R^5$ group is substituted with a morpholino ($C_1-C_3$ alkyl) group, a phenyl ($C_1-C_3$ alkyl)piperidinyl group, a phenyl ($C_1-C_3$ alkyl)-piperidinylaminocarbonyl group, a $C_2-C_6$ alkanoylaminothiophenyl group, or a (amino, $C_1-C_3$ alkylamino or di(C–$C_3$ alkyl)amino) naphthalenylsulfonylamino group;

or $R^5$ is a perhalophenyl group;

m represents 1–2;

$R^6$ represents hydrogen, halogen, $NO_2$, cyano, $CF_3$, $C_1-C_6$ alkyl, $C_1-C_6$ alkoxy, carboxy, $C_1-C_6$ alkoxycarbonyl, amino, $C_1-C_4$ alkylamino, $C_1-C_4$ dialkylamino, amido, $C_1-C_4$ alkylamido, $C_1-C_4$ dialkylamido, mercapto, $C_1-C_6$ alkylthio, $C_1-C_6$ alkylsulfinyl, $C_1-C_6$ alkylsulfonyl, or a group —A—$R^7$ where A is $C_1-C_6$ alkylene $C_2-C_6$ $C_6$ alkenylene or $C_2-C_6$ alkynylene; and $R^7$ represents halogen, hydroxy, $CF_3$, $C_1-C_6$ alkoxy, carboxy, $C_1-C_6$ alkoxycarbonyl, amino, $C_1-C_4$ alkylamino, $C_1-C_4$ dialkylamino, amido, $C_1-C_4$ alkylamido, $C_1-C_4$ dialkylamido, $C_1-C_4$ alkylsulfonylamino, aminosulfonyl or $C_1-C_4$ alkylaminosulfonyl;

or a pharmaceutically acceptable salt thereof, and an effective amount of a bone anabolic agent, in combination with a pharmaceutically acceptable carrier, diluent, or excipient.

4. A pharmaceutical composition according to claim 3 wherein said bone anabolic agent is parathyroid hormone (1–84) or (1–34).

5. A pharmaceutical composition comprising (−)-(4aR)-(10bR)-8-chloro-4-methyl-1,2,3,4,4a,5,6,10b-octahydrobenzo[f]-quinolin-3-one, or a pharmaceutically acceptable salt thereof, and raloxifene or a pharmaceutically acceptable sale thereof, in combination with a pharmaceutically acceptable carrier, diluent or excipient.

* * * * *